(12) United States Patent
Backes et al.

(10) Patent No.: US 10,131,668 B2
(45) Date of Patent: Nov. 20, 2018

(54) SUBSTITUTED IMIDAZO[1,5-A]PYRAZINES FOR MODULATION OF IRE1

(71) Applicants: The Regents of the University of California, Oakland, CA (US); University of Washington Through Its Center For Commercialization, Seattle, WA (US)

(72) Inventors: Bradley J. Backes, San Francisco, CA (US); Dustin J. Maly, Seattle, WA (US); Scott A. Oakes, San Francisco, CA (US); Feroz R. Papa, San Francisco, CA (US); Gayani Perera, Negegoda (LK); Likun Wang, San Francisco, CA (US)

(73) Assignees: The Regents of the University of California, Oakland, CA (US); University of Washington Through Its Center For Commercialization, Seattle, WA (US)

( * ) Notice: Subject to any disclaimer, the term of this patent is extended or adjusted under 35 U.S.C. 154(b) by 0 days.

(21) Appl. No.: 14/670,088

(22) Filed: Mar. 26, 2015

(65) Prior Publication Data
US 2016/0024094 A1   Jan. 28, 2016

Related U.S. Application Data

(63) Continuation of application No. PCT/US2013/062039, filed on Sep. 26, 2013.

(60) Provisional application No. 61/706,037, filed on Sep. 26, 2012, provisional application No. 61/783,965, filed on Mar. 14, 2013, provisional application No. 61/831,088, filed on Jun. 4, 2013.

(51) Int. Cl.
*A61K 31/4985* (2006.01)
*C07D 487/04* (2006.01)

(52) U.S. Cl.
CPC ................ *C07D 487/04* (2013.01)

(58) Field of Classification Search
CPC .......................... A61K 31/4985; C07D 487/04
USPC .......................................... 514/249; 544/350
See application file for complete search history.

(56) References Cited

U.S. PATENT DOCUMENTS

| | | | |
|---|---|---|---|
| 4,704,381 A | 11/1987 | Schaumann et al. |
| 4,861,760 A | 8/1989 | Mazuel et al. |
| 4,911,920 A | 3/1990 | Jani et al. |
| 5,010,175 A | 4/1991 | Rutter et al. |
| 5,212,162 A | 5/1993 | Missel et al. |
| 5,240,941 A | 8/1993 | Bruneau |
| 5,288,514 A | 2/1994 | Ellman |
| 5,310,731 A | 5/1994 | Olsson et al. |
| 5,364,862 A | 11/1994 | Spada et al. |
| 5,403,841 A | 4/1995 | Lang et al. |
| 5,420,419 A | 5/1995 | Wood |
| 5,428,125 A | 6/1995 | Hefner, Jr. et al. |
| 5,442,039 A | 8/1995 | Hefner, Jr. et al. |
| 5,506,347 A | 4/1996 | Erion et al. |
| 5,539,083 A | 7/1996 | Cook et al. |
| 5,561,134 A | 10/1996 | Spada et al. |
| 5,563,257 A | 10/1996 | Zilch et al. |
| 5,593,853 A | 1/1997 | Chen et al. |
| 5,593,997 A | 1/1997 | Dow et al. |
| 5,646,128 A | 7/1997 | Firestein et al. |
| 5,652,366 A | 7/1997 | Spada et al. |
| 5,654,307 A | 8/1997 | Bridges et al. |
| 5,665,721 A | 9/1997 | Bhagwat et al. |
| 5,674,998 A | 10/1997 | Boyer et al. |
| 5,686,455 A | 11/1997 | Adams et al. |
| 5,736,554 A | 4/1998 | Spada et al. |
| 5,747,235 A | 5/1998 | Farid et al. |
| 5,756,711 A | 5/1998 | Zilch et al. |
| 5,763,596 A | 6/1998 | Boyer et al. |
| 5,763,597 A | 6/1998 | Ugarkar et al. |
| 5,763,885 A | 6/1998 | Murphy et al. |
| 5,795,977 A | 8/1998 | Ugarkar et al. |
| 5,824,492 A | 10/1998 | Hiles et al. |
| 5,858,753 A | 1/1999 | Chantry et al. |
| 5,914,488 A | 6/1999 | Sone |
| 5,919,808 A | 7/1999 | Petrie et al. |
| 5,922,753 A | 7/1999 | Petrie et al. |
| 5,948,776 A | 9/1999 | Petrie et al. |
| 5,965,573 A | 10/1999 | Petrie et al. |
| 5,977,061 A | 11/1999 | Holy et al. |
| 5,981,533 A | 11/1999 | Traxler et al. |
| 5,985,589 A | 11/1999 | Chantry et al. |
| 5,990,169 A | 11/1999 | Petrie et al. |
| 5,994,358 A | 11/1999 | Petrie et al. |
| 6,001,839 A | 12/1999 | Calderwood et al. |

(Continued)

FOREIGN PATENT DOCUMENTS

| | | |
|---|---|---|
| CA | 1338379 | 6/1996 |
| CN | 101602768 | 12/2009 |

(Continued)

OTHER PUBLICATIONS

Jordan, V. C. Nature Reviews: Drug Discovery, 2, 2003, 205.*
Hackam, et al. JAMA, 296(14), 2006, 1731-1732.*
Wang, et al. Nature Chemical Biology, 8(12), 2012, 982-989.*
West et al., "Activation of the PI3K/Akt pathway and chemotherapeutic resistance," Drug Resistance Updates, 5, 2002, 234-248.

(Continued)

*Primary Examiner* — Douglas M Willis
(74) *Attorney, Agent, or Firm* — Zachary L. Terranova; Mintz, Levin, Cohn, Ferris, Glovsky and Popeo, P.C.

(57) ABSTRACT

Described herein, inter alia, are compositions and methods of using the same for modulating the activity of Ire1 using for example, substituted imidazopyrazine compounds.

20 Claims, 78 Drawing Sheets

Specification includes a Sequence Listing.

(56) References Cited

U.S. PATENT DOCUMENTS

| | | |
|---|---|---|
| 6,057,305 A | 5/2000 | Holy et al. |
| 6,084,095 A | 7/2000 | Bridges et al. |
| 6,093,737 A | 7/2000 | Anthony et al. |
| 6,127,121 A | 10/2000 | Meyer, Jr. et al. |
| 6,153,631 A | 11/2000 | Petrie et al. |
| 6,191,170 B1 | 2/2001 | Medina |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,323,201 B1 | 11/2001 | Carson et al. |
| 6,342,514 B1 | 1/2002 | Petrie et al. |
| 6,350,741 B1 | 2/2002 | Golec et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,455,534 B2 | 9/2002 | Bridges et al. |
| 6,472,153 B1 | 10/2002 | Dempcy et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,583,161 B1 | 6/2003 | Medina |
| 6,613,798 B1 | 9/2003 | Porter et al. |
| 6,630,495 B1 | 10/2003 | Cooke et al. |
| 6,632,789 B1 | 10/2003 | June |
| 6,645,989 B2 | 11/2003 | Adams et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,667,300 B2 | 12/2003 | Sadhu et al. |
| 6,690,583 B1 | 2/2004 | Bergstedt et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,800,620 B2 | 10/2004 | Sadhu et al. |
| 6,849,420 B2 | 2/2005 | Vanhasebroeck et al. |
| 6,849,713 B2 | 2/2005 | Zhang et al. |
| 6,852,727 B2 | 2/2005 | Goulet et al. |
| 6,906,103 B2 | 6/2005 | Zhang et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 7,026,461 B1 | 4/2006 | Shokat |
| 7,041,676 B2 | 5/2006 | McDonald et al. |
| 7,049,116 B2 | 5/2006 | Shokat |
| 7,049,312 B1 | 5/2006 | Rafferty et al. |
| 7,064,218 B2 | 6/2006 | Dyatkina et al. |
| 7,071,355 B2 | 7/2006 | Leban et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,157,487 B2 | 1/2007 | Nakayama et al. |
| 7,166,293 B2 | 1/2007 | Teng et al. |
| 7,208,601 B2 | 4/2007 | Mjalli et al. |
| 7,217,794 B2 | 5/2007 | Abdel-Meguid et al. |
| 7,244,741 B2 | 7/2007 | Simon et al. |
| 7,247,736 B2 | 7/2007 | Leban et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,329,765 B2 | 2/2008 | Burli et al. |
| 7,332,497 B2 | 2/2008 | Hirst et al. |
| 7,348,427 B2 | 3/2008 | Burli et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,459,462 B2 | 12/2008 | Simon et al. |
| 7,459,472 B2 | 12/2008 | Mjalli et al. |
| 7,470,721 B2 | 12/2008 | Durden |
| 7,501,538 B2 | 3/2009 | Mjalli et al. |
| 7,534,797 B2 | 5/2009 | Arnold et al. |
| 7,541,373 B2 | 6/2009 | Polisetti et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,608,594 B2 | 10/2009 | Blagg et al. |
| 7,615,552 B2 | 11/2009 | Ono et al. |
| 7,622,451 B2 | 11/2009 | Blagg et al. |
| 7,648,987 B2 * | 1/2010 | Crew .................. C07D 487/04 514/249 |
| 7,678,803 B2 | 3/2010 | Huang et al. |
| 7,700,607 B2 | 4/2010 | Hu et al. |
| 7,745,485 B2 | 6/2010 | Durden |
| 7,858,666 B2 | 12/2010 | Patterson et al. |
| 7,932,260 B2 | 4/2011 | Fowler et al. |
| 8,697,709 B2 | 4/2014 | Dar et al. |
| 8,980,899 B2 | 3/2015 | Korennykh et al. |
| 9,321,772 B2 | 4/2016 | Dar et al. |
| 2001/0019829 A1 | 9/2001 | Nelson |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0146690 A1 | 10/2002 | Meyer et al. |
| 2002/0147160 A1 | 10/2002 | Bhat et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat et al. |
| 2003/0083268 A1 | 5/2003 | Burli et al. |
| 2003/0109248 A1 | 6/2003 | Lewis |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer, Jr. et al. |
| 2003/0153752 A1 | 8/2003 | Hirst et al. |
| 2003/0166929 A1 | 9/2003 | Snow et al. |
| 2003/0180924 A1 | 9/2003 | Desimone et al. |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0208800 A1 | 11/2003 | Eby |
| 2003/0212113 A1 | 11/2003 | Dyatkina et al. |
| 2003/0232849 A1 | 12/2003 | Noe et al. |
| 2003/0235822 A1 | 12/2003 | Lokhov et al. |
| 2004/0039035 A1 | 2/2004 | Collins et al. |
| 2004/0043388 A1 | 3/2004 | Come et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0102423 A1 | 5/2004 | MacLaughlan et al. |
| 2004/0102437 A1 | 5/2004 | Takami et al. |
| 2004/0110717 A1 | 6/2004 | Carroll et al. |

(56) References Cited

U.S. PATENT DOCUMENTS

| | | |
|---|---|---|
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0170622 A1 | 9/2004 | Glimcher et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0215579 A1 | 9/2005 | Simon et al. |
| 2005/0239809 A1 | 10/2005 | Watts et al. |
| 2005/0239820 A1 | 10/2005 | Borzilleri et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2006/0019988 A1 | 1/2006 | McDonald et al. |
| 2006/0035912 A1 | 2/2006 | Marx et al. |
| 2006/0069034 A1 | 3/2006 | Burli et al. |
| 2006/0079538 A1 | 4/2006 | Hallahan et al. |
| 2006/0084654 A1 | 4/2006 | Beck et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0235031 A1 | 10/2006 | Arnold et al. |
| 2006/0276470 A1 | 12/2006 | Jackson et al. |
| 2006/0287295 A1 | 12/2006 | Barlaam et al. |
| 2007/0015773 A1 | 1/2007 | Bergeron et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0142405 A1 | 6/2007 | Dong et al. |
| 2007/0224672 A1 | 9/2007 | Leban et al. |
| 2007/0249598 A1 | 10/2007 | Wang et al. |
| 2007/0270452 A1 | 11/2007 | Blagg et al. |
| 2008/0014200 A1 | 1/2008 | Arnold et al. |
| 2008/0032960 A1 | 2/2008 | Knight et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0030023 A1 | 1/2009 | Harada et al. |
| 2009/0053192 A1 | 2/2009 | Milian et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270567 A1 | 10/2009 | Small et al. |
| 2009/0286768 A1 | 11/2009 | Crew et al. |
| 2009/0312319 A1 | 12/2009 | Ren et al. |
| 2009/0312406 A1 | 12/2009 | Hsieh et al. |
| 2009/0325967 A1 | 12/2009 | Fairhurst et al. |
| 2010/0009963 A1 | 1/2010 | Knight et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0105630 A1 | 4/2010 | Blagg |
| 2010/0190749 A1 | 7/2010 | Ren et al. |
| 2011/0046165 A1 | 2/2011 | Ren et al. |
| 2011/0124641 A1 | 5/2011 | Ren et al. |
| 2011/0144134 A1 | 6/2011 | Shokat et al. |
| 2011/0172228 A1 | 7/2011 | Ren et al. |
| 2011/0224223 A1 | 9/2011 | Shokat et al. |
| 2011/0269779 A1 | 11/2011 | Wilson et al. |
| 2011/0281866 A1 | 11/2011 | Ren et al. |
| 2011/0301144 A1 | 12/2011 | Knight et al. |
| 2012/0059000 A1 | 3/2012 | Ren et al. |
| 2012/0065154 A1 | 3/2012 | Tanaka et al. |
| 2012/0294930 A1 | 11/2012 | Ren et al. |
| 2012/0322814 A1 | 12/2012 | Korennykh et al. |
| 2012/0329776 A1 | 12/2012 | Ren et al. |
| 2013/0116247 A1 | 5/2013 | Zeng et al. |
| 2013/0303599 A1 | 11/2013 | Koong et al. |
| 2016/0354377 A1 | 12/2016 | Dar et al. |
| 2017/0165259 A1 | 6/2017 | Maly et al. |

FOREIGN PATENT DOCUMENTS

| | | |
|---|---|---|
| EP | 773023 A1 | 5/1997 |
| EP | 1020445 B1 | 8/2008 |
| EP | 2 548 877 A1 | 1/2013 |
| GB | 812366 | 4/1959 |
| GB | 937725 | 9/1963 |
| JP | 61109797 | 5/1986 |
| JP | 5256693 | 10/1993 |
| JP | 8295667 | 11/1996 |
| JP | 9143163 | 6/1997 |
| JP | 10-506624 | 6/1998 |
| JP | 10206995 | 8/1998 |
| JP | 2000072773 A | 3/2000 |
| JP | 2001-1516353 A | 9/2001 |
| JP | 2002037787 A | 2/2002 |
| JP | 2002131859 | 5/2002 |
| JP | 2002131859 A2 | 5/2002 |
| JP | 2002-526500 A | 8/2002 |
| JP | 2002-527359 A | 8/2002 |
| JP | 2003-509428 A | 3/2003 |
| JP | 2003073357 A | 3/2003 |
| JP | 2003073357 A2 | 3/2003 |
| JP | 2004-514405 A | 5/2004 |
| JP | 2004-161716 A | 6/2004 |
| JP | 2004161716 A | 6/2004 |
| JP | 2004-531513 A | 10/2004 |
| JP | 2005-501811 A | 1/2005 |
| JP | 2006-512356 A | 4/2006 |
| JP | 2007-511596 A | 5/2007 |
| JP | 2007-520559 A | 7/2007 |

(56) References Cited

FOREIGN PATENT DOCUMENTS

| | | |
|---|---|---|
| JP | 2008-500330 A | 1/2008 |
| JP | 2008-533172 A | 8/2008 |
| WO | WO-83/01446 A1 | 4/1983 |
| WO | WO-91/17161 A1 | 11/1991 |
| WO | WO-91/19735 A1 | 12/1991 |
| WO | WO-92/00091 A1 | 1/1992 |
| WO | WO-92/14733 A1 | 9/1992 |
| WO | WO-93/16091 A1 | 8/1993 |
| WO | WO-93/16092 A1 | 8/1993 |
| WO | WO-93/18035 A1 | 9/1993 |
| WO | WO-93/20242 A1 | 10/1993 |
| WO | WO-93/22443 A1 | 11/1993 |
| WO | WO-94/013677 A1 | 6/1994 |
| WO | WO-94/017803 A1 | 8/1994 |
| WO | WO-95/29673 A1 | 11/1995 |
| WO | WO-95/32984 A1 | 12/1995 |
| WO | WO-96/05309 A2 | 2/1996 |
| WO | WO-96/05309 A3 | 2/1996 |
| WO | WO-96/040706 A1 | 12/1996 |
| WO | WO-97/00271 A1 | 1/1997 |
| WO | WO-97/15658 A1 | 5/1997 |
| WO | WO-97/28133 A1 | 8/1997 |
| WO | WO-97/28161 A1 | 8/1997 |
| WO | WO-98/41525 A1 | 9/1998 |
| WO | WO-98/52611 A1 | 11/1998 |
| WO | WO-98/57952 A1 | 12/1998 |
| WO | WO-2000/017202 A1 | 3/2000 |
| WO | WO-2000/017203 A1 | 3/2000 |
| WO | WO-2000/042042 A2 | 7/2000 |
| WO | WO-2001/002369 A2 | 1/2001 |
| WO | WO-2001/002369 A3 | 1/2001 |
| WO | WO-2001/16114 A2 | 3/2001 |
| WO | WO-2001/16114 A3 | 3/2001 |
| WO | WO-2001/019829 A2 | 3/2001 |
| WO | WO-2001/019829 A3 | 3/2001 |
| WO | WO-2001/25238 A2 | 4/2001 |
| WO | WO-2001/25238 A3 | 4/2001 |
| WO | WO-2001/031063 A1 | 5/2001 |
| WO | WO-2001/038584 A2 | 5/2001 |
| WO | WO-2001/038584 A3 | 5/2001 |
| WO | WO-2001/55140 A1 | 8/2001 |
| WO | WO-2001/056988 A1 | 8/2001 |
| WO | WO-2001/072751 A1 | 10/2001 |
| WO | WO-2001/72778 A2 | 10/2001 |
| WO | WO-2001/72778 A3 | 10/2001 |
| WO | WO-2001/81346 A2 | 11/2001 |
| WO | WO-2001/81346 A3 | 11/2001 |
| WO | WO-2002/06192 A1 | 1/2002 |
| WO | WO-2002/030944 A2 | 4/2002 |
| WO | WO-2002/030944 A3 | 4/2002 |
| WO | WO-2002/057425 A2 | 7/2002 |
| WO | WO-2002/057425 A3 | 7/2002 |
| WO | WO-2002/076986 A1 | 10/2002 |
| WO | WO-2002/080926 A1 | 10/2002 |
| WO | WO-2002/083143 A1 | 10/2002 |
| WO | WO-2002/088025 A1 | 11/2002 |
| WO | WO-2002/090334 A1 | 11/2002 |
| WO | WO-2003/000187 A2 | 1/2003 |
| WO | WO-2003/000187 A3 | 1/2003 |
| WO | WO-2003/016275 A1 | 2/2003 |
| WO | WO-2003/020880 A2 | 3/2003 |
| WO | WO-2003/020880 A3 | 3/2003 |
| WO | WO-2003/024969 A1 | 3/2003 |
| WO | WO-2003/035075 A1 | 5/2003 |
| WO | WO-2003/059884 A1 | 7/2003 |
| WO | WO-2003/082341 A1 | 10/2003 |
| WO | WO-2003/106426 A1 | 12/2003 |
| WO | WO-2004/006906 A2 | 1/2004 |
| WO | WO-2004/006906 A3 | 1/2004 |
| WO | WO-2004/018058 A2 | 3/2004 |
| WO | WO-2004/018058 A3 | 3/2004 |
| WO | WO-2004/022562 A1 | 3/2004 |
| WO | WO-2004/031177 A1 | 4/2004 |
| WO | WO-2004/039774 A2 | 5/2004 |
| WO | WO-2004/039774 A3 | 5/2004 |
| WO | WO-2004/056830 A1 | 7/2004 |
| WO | WO-2004/087053 A2 | 10/2004 |
| WO | WO-2004/087053 A3 | 10/2004 |
| WO | WO-2004/100868 A2 | 11/2004 |
| WO | WO-2004/100868 A3 | 11/2004 |
| WO | WO-2004/111014 A1 | 12/2004 |
| WO | WO-2005/002585 A1 | 1/2005 |
| WO | WO-2005/007085 A2 | 1/2005 |
| WO | WO-2005/007085 A3 | 1/2005 |
| WO | WO-2005/012323 A2 | 2/2005 |
| WO | WO-2005/012323 A3 | 2/2005 |
| WO | WO-2005/016348 A1 | 2/2005 |
| WO | WO-2005/016349 A1 | 2/2005 |
| WO | WO-2005/016528 A2 | 2/2005 |
| WO | WO-2005/016528 A3 | 2/2005 |
| WO | WO-2005/021533 A1 | 3/2005 |
| WO | WO-2005/037836 A2 | 4/2005 |
| WO | WO-2005/044181 A2 | 5/2005 |
| WO | WO-2005/044181 A3 | 5/2005 |
| WO | WO-2005/047289 A1 | 5/2005 |
| WO | WO-2005/061460 A1 | 7/2005 |
| WO | WO-2005/063258 A1 | 7/2005 |
| WO | WO-2005/067901 A2 | 7/2005 |
| WO | WO-2005/067901 A3 | 7/2005 |
| WO | WO-2005/074603 A2 | 8/2005 |
| WO | WO-2005/074603 A3 | 8/2005 |
| WO | WO-2005/097800 A1 | 10/2005 |
| WO | WO-2005/105760 A1 | 11/2005 |
| WO | WO-2005/112935 A1 | 12/2005 |
| WO | WO-2005/113556 A1 | 12/2005 |
| WO | WO-2005/117889 A1 | 12/2005 |
| WO | WO-2005/120511 A1 | 12/2005 |
| WO | WO-2006/030032 A1 | 3/2006 |
| WO | WO-2006/038865 A1 | 4/2006 |
| WO | WO-2006/050501 A2 | 5/2006 |
| WO | WO-2006/050501 A3 | 5/2006 |
| WO | WO-2006/050946 A1 | 5/2006 |
| WO | WO-2006/068760 A2 | 6/2006 |
| WO | WO-2006/068760 A3 | 6/2006 |
| WO | WO-2006/089106 A2 | 8/2006 |
| WO | WO-2006/089106 A3 | 8/2006 |
| WO | WO-2006/102079 A1 | 9/2006 |
| WO | WO-2006/108107 A1 | 10/2006 |
| WO | WO-2006/112666 A1 | 10/2006 |
| WO | WO-2006/114064 A2 | 11/2006 |
| WO | WO-2006/114064 A3 | 11/2006 |
| WO | WO-2006/114065 A2 | 11/2006 |
| WO | WO-2006/114065 A3 | 11/2006 |
| WO | WO-2006/114180 A1 | 11/2006 |
| WO | WO-2007/002293 A2 | 1/2007 |
| WO | WO-2007/002293 A3 | 1/2007 |
| WO | WO-2007/006547 A1 | 1/2007 |
| WO | WO-2007/020046 A1 | 2/2007 |
| WO | WO-2007/025090 A2 | 3/2007 |
| WO | WO-2007/025090 A3 | 3/2007 |
| WO | WO-2007/061737 A2 | 5/2007 |
| WO | WO-2007/061737 A3 | 5/2007 |
| WO | WO-2007/064993 A2 | 6/2007 |
| WO | WO-2007/064993 A3 | 6/2007 |
| WO | WO-2007/066189 A2 | 6/2007 |
| WO | WO-2007/066189 A3 | 6/2007 |
| WO | WO-2007/075554 A2 | 7/2007 |
| WO | WO-2007/075554 A3 | 7/2007 |
| WO | WO-2007/079164 A2 | 7/2007 |
| WO | WO-2007/079164 A3 | 7/2007 |
| WO | WO-2007/095223 A2 | 8/2007 |
| WO | WO-2007/095223 A3 | 8/2007 |
| WO | WO-2007/101224 A2 | 9/2007 |
| WO | WO-2007/101224 A3 | 9/2007 |
| WO | WO-2007/103308 A2 | 9/2007 |
| WO | WO-2007/103308 A3 | 9/2007 |
| WO | WO-2007/106503 A2 | 9/2007 |
| WO | WO-2007/112005 A2 | 10/2007 |
| WO | WO-2007/112005 A3 | 10/2007 |
| WO | WO-2007/114926 A2 | 10/2007 |
| WO | WO-2007/114926 A3 | 10/2007 |
| WO | WO-2007/121453 A2 | 10/2007 |
| WO | WO-2007/121453 A3 | 10/2007 |
| WO | WO-2007/121920 A2 | 11/2007 |

(56) References Cited

FOREIGN PATENT DOCUMENTS

| | | |
|---|---|---|
| WO | WO-2007/121920 A3 | 11/2007 |
| WO | WO-2007/121924 A2 | 11/2007 |
| WO | WO-2007/121924 A3 | 11/2007 |
| WO | WO-2007/124854 A1 | 11/2007 |
| WO | WO-2007/125310 A2 | 11/2007 |
| WO | WO-2007/125310 A3 | 11/2007 |
| WO | WO-2007/125315 A2 | 11/2007 |
| WO | WO-2007/125315 A3 | 11/2007 |
| WO | WO-2007/126841 A2 | 11/2007 |
| WO | WO-2007/126841 A3 | 11/2007 |
| WO | WO-2007/134828 A1 | 11/2007 |
| WO | WO-2007/135380 A2 | 11/2007 |
| WO | WO-2007/135380 A3 | 11/2007 |
| WO | WO-2007/135398 A1 | 11/2007 |
| WO | WO-2008/025755 A1 | 3/2008 |
| WO | WO-2008/037477 A1 | 4/2008 |
| WO | WO-2008/047821 A1 | 4/2008 |
| WO | WO-2008/063625 A2 | 5/2008 |
| WO | WO-2008/063625 A3 | 5/2008 |
| WO | WO-2008/064018 A1 | 5/2008 |
| WO | WO-2008/079028 A1 | 7/2008 |
| WO | WO-2008/082487 A2 | 7/2008 |
| WO | WO-2008/082487 A3 | 7/2008 |
| WO | WO-2008/094737 A2 | 8/2008 |
| WO | WO-2008/094737 A3 | 8/2008 |
| WO | WO-2008/112715 A2 | 9/2008 |
| WO | WO-2008/112715 A3 | 9/2008 |
| WO | WO-2008/118454 A2 | 10/2008 |
| WO | WO-2008/118454 A3 | 10/2008 |
| WO | WO-2008/118455 A1 | 10/2008 |
| WO | WO-2008/118468 A1 | 10/2008 |
| WO | WO-2008/125014 A1 | 10/2008 |
| WO | WO-2008/125207 A1 | 10/2008 |
| WO | WO-2008/127226 A2 | 10/2008 |
| WO | WO-2008/127226 A3 | 10/2008 |
| WO | WO-2008/136457 A1 | 11/2008 |
| WO | WO-2008/141140 A1 | 11/2008 |
| WO | WO-2008/141145 A1 | 11/2008 |
| WO | WO-2008/154484 A1 | 12/2008 |
| WO | WO-2009/000412 A1 | 12/2008 |
| WO | WO-2009/004621 A1 | 1/2009 |
| WO | WO-2009/010925 A2 | 1/2009 |
| WO | WO-2009/010925 A3 | 1/2009 |
| WO | WO-2009/023718 A2 | 2/2009 |
| WO | WO-2009/023718 A3 | 2/2009 |
| WO | WO-2009/044707 A1 | 4/2009 |
| WO | WO-2009/050506 A2 | 4/2009 |
| WO | WO-2009/050506 A3 | 4/2009 |
| WO | WO-2009/062118 A2 | 5/2009 |
| WO | WO-2009/062118 A3 | 5/2009 |
| WO | WO-2009/064802 A2 | 5/2009 |
| WO | WO-2009/064802 A3 | 5/2009 |
| WO | WO-2009/088986 A1 | 7/2009 |
| WO | WO-2009/088990 A1 | 7/2009 |
| WO | WO-2009/091939 A1 | 7/2009 |
| WO | WO-2009/100406 A2 | 8/2009 |
| WO | WO-2009/100406 A3 | 8/2009 |
| WO | WO-2009/117157 A1 | 9/2009 |
| WO | WO-2010/009207 A1 | 1/2010 |
| WO | WO-2010/019210 A2 | 2/2010 |
| WO | WO-2010/019210 A3 | 2/2010 |
| WO | WO-2010/036380 A1 | 4/2010 |
| WO | WO-2010/039534 A1 | 4/2010 |
| WO | WO-2010/045542 A2 | 4/2010 |
| WO | WO-2010/045542 A3 | 4/2010 |
| WO | WO-2001/19829 A2 | 3/2011 |
| WO | WO-2001/19829 A3 | 3/2011 |
| WO | WO-2011/044157 A1 | 4/2011 |
| WO | WO-2011/047384 A2 | 4/2011 |
| WO | WO-2011/047384 A3 | 4/2011 |
| WO | WO-2011/094628 A1 | 8/2011 |
| WO | WO-2011/127070 A2 | 10/2011 |
| WO | WO-2011/127070 A3 | 10/2011 |
| WO | WO-2012/064774 A1 | 5/2012 |
| WO | WO-2013/010380 A1 | 1/2013 |
| WO | WO-2013/010868 A1 | 1/2013 |
| WO | WO-2013/077921 A2 | 5/2013 |
| WO | WO-2013/077921 A3 | 5/2013 |
| WO | WO-2014/052669 A1 | 4/2014 |
| WO | WO-2016/004254 A1 | 1/2016 |

OTHER PUBLICATIONS

International Preliminary Report on Patentability and Written Opinion dated Mar. 4, 2014 for International Application No. PCT/US2012/053542, 10 pages.

"Report of the Expert Committee on the Diagnosis and Classification of Diabetes Mellitus", Diabetes Care (1992) 2(Suppl 1):S5-S19.

Abbott, L. et al. (Mar. 1, 2007, e-published Dec. 15, 2006). "Discovery of thienopyridines as Src-family selective Lck inhibitors," Bioorg Med Chem Lett 17(5):1167-1171.

Abdel-Mohsen, S.A., "Synthesis, reactions and antimicrobial activity of 2-amino-4-(8-quinolino1-5-y1)-1-(p-toly1)-pyrrole-3-carbonitrile", Bull. Korean Chem. Soc. 2005 26(5):719-728.

Ames et al., "Heterocyclic Synthesis from o-Halogen-acids. Part II. Thienopyridinones and Thienopyranones from 3-bromothiophene-2-and 4-Bromothiophene-3-Carboxylic Acids", Journal of the Chemical Society, Perkin Transactions 1, Jan., 14:1390-1395 (1975).

Andrews, R.C., et al. "Effects of the 11β-Hydroxysteroid Dehydrogenase Inhibitor Carbenoxolone on Insulin Sensitivity in Men with Type 2 Diabetes", J. Clin. Endocrinol. Metab. (2003) 88(1):285¬291.

Aragon, Anthony D. et al., Microarray based analysis of temperature and oxidative stress induced messenger RNA in Schistosoma mansoni, Molecular & Biochemical Parasitology 162:134¬141, 2008

Aragon, Tomas et al., " Messenger RNA targeting to endoplasmic reticulum stress signaling sites", Nature 457(7230):736-740, 2009.

Arnold, et al. "Pyrrolo[2,3-d]pyrimidines containing an extended 5-substituent as potent and selective inhibitors of Ick I", Bioorg. & Med. Chem. Lett (2000) 10:2167-70.

Banker, G.S., et al. Modern Pharmaceutics, 3ed, Marcel Dekker, New York, 1996, pp. 451-596.

Barf, T. et al. "Arylsulfonamidothiazoles as a New Class of Potential Antidiabetic Drugs. Discovery of Potent and Selective Inhibitors of the 11β-Hydroxysteroid Dehydrogenase Type 1", J. Med. Chem. (2002) 45(18):3813-3815.

Barnes, P.J., et al. "Efficacy and Safety of Inhaled Corticosteroids in Asthma", Am. Rev. Respir. Dis. (1993) 148:S1-26.

Basotest®, "Test Kit for the Quantitative Determination of the Degranulation of Basophilic Granulocytes in Heparinized Human Whole Blood", [www.biocarta.com/TDS/10-0500.pdf], Retreived from the Internet Nov. 29, 2011, 10 pages.

Beeram, M. et al., "Akt-induced endocrine therapy resistance is reversed by inhibition of mTOR signaling", Annals of Oncology 18:1323-1328, 2007.

Bell, G., et al. "Glucokinase Mutations Insulin Secretion, and Diabetes Mellitus", Annu. Rev. Physiol., (1996) 58:171-186.

Berge, Stephen M. et al., "Pharmaceutical Salts", Journal of Pharmaceutical Sciences Berge et al., "Pharmaceutical Salts", Journal of Pharmaceutical Sciences 66(1):1-19, 1977.

Bhat, G. A., et al., "Pyrazolopyrimidine nucleosides. 12. Synthesis and biological activity of certain pyrazolo[3,4-d]pyrimidine nucleosides related to adenosine," J. Med. Chem. vol. 24, No. 10, (1981), pp. 1165-1172.

Bishop, A.C. et al. "Generation of monospecific nanomolar tyrosine kinase inhibitors via a chemical genetic approach", Journal of the American Chemical Society, American Chemical Society, Washington, DC, US, vol. 121, No. 4, 1999, pp. 627-631.

Bishop, Anthony C. et al., "Design of allele-specific inhibitors to probe protein kinase signalling", Current Biology 8:257-266, 1998.

Blethrow, Justin et al., "Design and Use of Analog-Sensitive Protein Kinases", Current Protocols in Molecular Biology 18.11.1-18.11.19, 2004.

Bohren, K.M., et al. "Expression, Crystallization and Preliminary Crystallographic Analysis of Human Carbonyl Reductase", J. Mol. Biol. (1994) 224:659-664.

(56) References Cited

OTHER PUBLICATIONS

Campora, et al. Binuclear complexes of nickel bridged by hydrocarbon ligands. Isocyanide insertion chemistry and amide formation by intramolecular coupling of acyl and imidoyl functionalities. Organometallics. Jan. 1992;11(1):11-13.

Campora, et al. Isocyanide insertion chemistry. Synthesis and structural characterization of bridging imidoyl complexes of nickel and amide formation by intramolecular coupling of acyl and imidoyl functionalities. Organometallics. Oct. 1993;12(10):4025-31.

Carrasco, Daniel R. et al., "The Differentiation and Stress Response Factor XBP-1 Drives Multiple Myeloma Pathogenesis", Cancer Cell 11:349-360, 2007.

Chaisuparat, et al. Dual Inhibition of P13K(alpha) and mTOR as an Alternative Treatment for Kaposi's Sarcoma. Cancer Research. 2008;68:8361.

Chappelow, et al. Neovascular Age-Related Macular Degeneration: Potential Therapies. Drugs. 2008;68(8):1029-1036.

Cox, B., et al. "Human Colorectal Cancer Cells Efficiently Conjugate the Cyclopentenone Prostaglandin, Prostaglandin J2 to Glutathione", Biochim. Bioghys. Acta (2002) 1584:37-45.

Cox, Jeffery S. et al., "A Novel Mechanism for Regulating Activity of a Transcription Factor That Controls the Unfolded Protein Response", Cell 87:391-404, 1996.

Credle, Joel J. et al., "On the mechanism of sensing unfolded protein in the endoplasmic reticulum", Proceedings of the National Academy of Sciences 102(52):18773-18784, 2005.

Davis, et al. The Preparation of Substituted 1(2H)-Isoquinolinones from Dilithiated 2-Methyl-N-arylbenzamides, 2-Methyl-N-(arylmethyl)-benzamides, or 2-Methylbenzoic Acid, 2,2-Dimethylhydrazide. Synthetic Communications. Sep. 1997;27(17):2961-9.

Diederich, S., et al. "In the Search for Specific Inhibitors of Human 11p-Hydroxysteroid-Dehydrogenases (11(3-HSDs): Chenodeoxycholic Acid Selectively Inhibits 11p-HSD-I", Eur. J. Endocrinol. (2000) 142:200-207.

Dijksman, et al. 271. 1 : 2-Dihydro-2-thianaphthalene derivatives. Part I. Preparation and reactions of 1 : 2-dihydro-1-keto-2-thianaphthalenes. J. Chem. Soc. 1951:1213-18.

Ding, S., et al. "A Combinatorial Scaffold Approach Toward Kinase-Directed Heterocycle Libraries", J. Am. Chem. Soc. (2002) 124(8):1594-1596.

Ding, S., et al. "A Concise and Traceless Linker Strategy Toward Combinatorial Libraries of 2,6,9-Substituted Purines", J. Org. Chem. (2001) 66:8273-8276.

Ding, S., et al. "Resin-Capture and Release Strategy Toward Combinatorial Libraries of 2,6,9-Substituted Purines", J. Comb. Chem.(2002) 4:183-186.

Donati. Emerging Therapies for Neovascular Age-Related Macular Degeneration: State of the Art. Ophthalmologica. 2007;221:366-377.

Doody, Gina M. et al., "BLIMP-1 is a target of cellular stress and downstream of the unfolded protein response", European Journal of Immunology 36:1572-1582, 2006.

European Examination Report dated Sep. 14, 2011 for EP Application No. 07873406.8, 4 pages.

European search report and search opinion dated Oct. 26, 2011 for Application No. 9700424.6, 5 pages.

European Search Report dated Mar. 1, 2010 for EP Application No. 07873406.8, 5 pages.

European Search Report dated Feb. 4, 2011 for EP Application No. 05857011.0, 5 pages.

Examination Report for GB Application No. GB0819947.3 dated Oct. 27, 2010, 2 pages.

Extended European Search Report from corresponding European Application No. 09700784.3 dated Oct. 28, 2011, 6 pages.

Extended European Search Report from corresponding European Application No. 12175020.2 dated Jan. 1, 2013, 7 pages.

Extended European Search Report from corresponding European Application No. 12175019.4 dated Apr. 4, 2013, 12 pages.

Fajans, S., et al."Maturity Onset Diabetes of the Young (MODY)", Diabet. Med. (1996) 13:S90-S95.

Feinstein, M.B., et al. "Regulation of the Action of Hydrocotisone in Airway Epithelial Cells by 116-Hydroxysteroid Dehydrogenase", Am. J. Respir. Cell. Mol. Biol. (1999) 21:403-408.

Feldman, M.E. et al. , "Active site inhibitors of mTOR target rapamycin-resistant outputs of rnTORC1 and mTORC2", PLOS Biology 7(2):371-383, Feb. 2009.

Fingl, E., et al. "General Principles", The Pharmacological Basis of Therapeutics, Fifth Edition (1975), Ch. 1, 1-46.

Forrest, G.L., et al. "Carbonyl Reductase", Chem. Biol. Interact. (2000) 129:21-40.

Forrest, G.L., et al. "Induction of a Human Carbonyl Reductase Gene Located on Chromosome 21", Biochim. Biophys. Acta. (1990) 1048:149-155.

Franzen, R. "The Suzuki, the Heck, and the Stille reaction—three versative methods for the introduction of new C—C bonds on solid support", Can J. Chem. (2000) 78:957-962.

Funder, J.W., et al. "Mineralocorticoid Action: Target Tissue Specificity Is Enzyme, Not Receptor, Mediated", Science (1998) 242:583-585.

Garber, M.E., et al. "Diversity of Gene Expression in Adenocarcinoma of the Lung", Proc. Nat. Acad. Sci. USA (2001) 98(24):13784-13789.

Gonzalez, B., et al. "Protection against Daunorubicin Cytotoxicity by Expression of a Cloned Human Carbonyl Reductase cDNA in K562 Leukemia Cells", Cancer Res. (1995) 55:4646-4650.

Gonzalez, Tania N. et al., "Ire1p: A Kinase and Site-Specific Endoribonuclease", Methods in Molecular Biology 160:25-36, 2001.

Graupera, et al. Angiogenesis selectively requires the p110 isoform of P13K to control endothelial cell migration. Nature. 2008;453:662-666.

Haase, A.,et al. "Detection of Viral Nucleic Acids by in Situ Hybridization", Methods in Virology (1984) VII:189-226.

Hanefeld, U., et al. "One-pot Synthesis of Tetrasubstituted Pyrazoles Proof of Regiochemistry", J. Chem. Soc. Perkin Trans. (1996) 1:1545-1552.

Hellwinkel, et al. Heterocyclensynthesen mit MF/A1203-Basensystemen: 2-Arylbenzofurane and 2,3-Diarylisochinolin-1(2H)-one. Synthesis. 1995;1995(9)1135-41.

International Preliminary Report on Patentability and Written Opinion dated Jan. 1, 2011 for International Application No. PCT/US2009/049969, 7 pages.

International Preliminary Report on Patentability and Written Opinion dated May 22, 2007 for International Application No. PCT/US2005/042524, 12 pages.

International Preliminary Report on Patentability and Written Opinion dated Nov. 4, 2008 for International Application No. PCT/US2007/008355, 7 pages.

International Preliminary Report on Patentability and Written Opinion dated Oct. 8, 2008 for International Application No. PCT/US2007/008395, 6 pages.

International Preliminary Report on Patentability from International Application No. PCT/US2009/000042 dated Jul. 6, 2010, 9 pages.

International Preliminary Report on Patentability and Written Opinion dated Apr. 17, 2012 for International Application No. PCT/US2010/053072, 5 pages.

International search report and written opinion dated Aug. 22, 2011 for PCT/US2011/037412, 2 pages.

International search report and written opinion dated Nov. 20, 2009 for PCT/US2009/005380, 9 pages.

International search report dated Nov. 2, 2010 for PCT Application No. PCT/US10/02020, 8 pages.

International search report dated Mar. 11, 2009 for PCT Application No. PCT/US2009/00038, 1 page.

International search report dated Mar. 23, 2009 for PCT Application No. PCT/US2009/00042, 2 pages.

International Search Report dated Apr. 5, 2006 for international Application No. PCT/FR2005/051073, 3 pages.

International Search Report dated Aug. 27, 2008 for International Application No. PCT/US07/08395, 4 pages.

International Search report dated Jul. 4, 2011 for International Application No. PCT/US2010/053072, 5 pages.

International Search Report dated Mar. 15, 2010 for International Application No. PCT/US2009/049969, 4 pages.

(56) References Cited

OTHER PUBLICATIONS

International Search Report dated Oct. 2, 2006 for International Application No. PCT/US05/042524, 7 pages.
International Search Report dated Sep. 25, 2008 for International Application No. PCT/US07/08355, 1 page.
International Search Report dated Jun. 28, 2010 for International Application No. PCT/US2009/060985, 5 pages.
International Preliminary Report on Patentability and Written Opinion for International Application No. PCT/US2009/060985, 5 pages.
International Search Report dated Jan. 29, 2014, for PCT Application No. PCT/US2013/062039, filed Sep. 26, 2013, 4 pages.
Written Opinion dated Jan. 29, 2014, for PCT Application No. PCT/US2013/062039, filed Sep. 26, 2013, 7 pages.
International Search Report dated Sep. 23, 2015 for PCT Application No. PCT/US2015/038906, filed Jul. 1, 2015, 3 pages.
Written Opinion dated Sep. 23, 2015 for PCT Application No. PCT/US2015/038906, filed Jul. 1, 2015, 7 pages.
Ishiyama, T., et al. "A Stoichiometric Aromatic C—H Borylation Catalyzed by Iridium(I)/2,2'-Bipyridine Complexes at Room Temperature", Angew. Chem. Int. Ed. (2002) 41(16):3056-3058.
Ishiyama, T., et al. "Mild Iridium-Catalyzed Borylation of Arenes. High Turnover Numbers, Room Temperature Reactions, and Isolation of a Potential Intermediate", J. Am. Chem. Soc. (2002) 124(3):390-391.
Kajita, et al. Nickel-catalyzed decarbonylative addition of phthalimides to alkynes. J Am Chem Soc. May 14, 2008;130(19):6058-9.
Kallberg, Y., et al. "Short-Chain Dehydrogenase/Reductase (Sdr) Relationships: a Large Family with Eight Clusters Common to Human, Animal, and Plant Genomes", Protein Sci. (2002) 11:636-641.
Kallberg, Y., et al. "Short-Chain Dehydrogenases/Reductases (SDRs)", Eur. J. Biochem. (2002) 269:4409-4417.
Kim, M. et al., "Activation and function of the mTORC1 pathway in mast cells", The Journal of Immunology 180:4586-4595, Apr. 2008.
Kimata, Yukio et al., "Two regulatory steps of ER-stress sensor Ire 1 involving its cluster formation and interaction with unfolded proteins", The Journal of Cell Biology 179(1):75-86, 2007.
Knight, et al. "A Pharmacological Map of the P13-K Family Defines a Role for p110a in Insulin Signaling", Cell (2006) 125:733-747.
Koong, Albert C. et al., "Targeting XBP-1 as a Novel Anti-Cancer Strategy", Cancer Biology & Therapy 5(7):756-759, 2006.
Kost et al., "Recyclization of 3-Alkyl-and 1,3-Dialkylisoquinolinium Salts to Naphthylamines", Chemistry of Heterocyclic Compounds, Jan., 16(9):965-970 (1981).
Kraybill, B.C. et al. "Inhibitor scaffolds as new allele specific kinase substrates", Journal of the American Chemical Society, American Chemical Society, Washington, DC, US, vol. 124, No. 41, Oct. 16, 2002, pp. 12118-12128.
Kreutzberger, A. et al., "5-substituierte 4-aminopyrimidine durch aminomethinylierung von acetonitrilen", Justus Liebigs Annalen der Chemie 4:537-544, 1977.
Kudo, Takashi et al., "The Unfolded Protein Response Is Involved in the Pathology of Alzheimer's Disease", New York Academy of Sciences 977:349-355, 2002.
Kumar et al., "Keten Dithioacetals. Part II. Reaction of 3-Cyano-4-Methylthio-2(1H)-pyridones with Hydazine and Guanidine: Synthesis of Novel Substituted and Fused Pyrazolo[4,3-c]pyridone and Pyrido[4,3-d]pyrimidine Derivatives", Journal of the Chemical Society, Perkin Transactions 1, Chemical Society, Letchworth, Jan., 8:857-862 (1978).
Kundu, et al. Palladium-Catalysed Heteroannulation with Terminal Alkynes: a Highly Regio-and Stereoselective Synthesis of (Z)-3-Aryl(alkyl)idene Isoindolin-1-ones1. Tetrahedron. Jun. 30, 2000;56(27):4777-92.
Kwok, B.H., et al. "The Anti-Inflammatory Natural Product Parthenolide from the Medicinal Herb Feverfew Directly Binds to and Inhibits IkB Kinase", Chem. Biol. (2001) 8:759-766.
Lee, et al. All roads lead to mTOR: integrating inflammation and tumor angiogenesis. Cell Cycle. 2007;6(24):3011-3014.

Lee, Kenneth P.K. et al., "Structure of the Dual Enzyme Ire1 Reveals the Basis for the Catalysis and Regulation in Nonconventional RNA Splicing", Cell 132:89-100, 2008.
Lin, Jonathan H. et al., "IRE1 Signaling Affects Cell Fate During the Unfolded Protein Response", Science 318:944-949 (2007).
Majumder, et al. mTOR inhibition reverses Akt-dependent prostate intraepithelial neoplasia through regulation of apoptotic and HIF-1-dependent pathways. Nature Medicine. 2004;10:594-601.
Ma, Yanjun et al., "The role of the unfolded protein response in tumour development: friend or foe?", Nature Reviews Cancer 4:966-977, 2004.
Mayer, T.U., et al. "Small Molecule Inhibitor of Mitotic Spindle Bipolarity Identified in a Pheontype-Based Screen", Science (1999) 286:971-974.
Mellinghoff, et al. TORward AKTually useful mouse models. Nature Medicine. 2004;10:579¬580.
Miyaura, N., et al., "Palladium-Catalyzed Cross-Coupling Reactions of Organoboron Compounds," Chem. Rev. (1995) 95(7):2457-2483.
Modi, et at. Isoquinolones: Part IV—Synthesis of 3-Methyl, 3-Formyl & Other 3-Substituted N-Arylisoquinolones, Indian J. Chem. 1979; 18B:304-306.
Moon, H.S., et al. "A Novel Microtubule Destabilizing Entity from Orthogonal Synthesis of Triazine Library and Zebrafish Embryo Screening", J. Am. Chem. Soc. (2002) 124:11608-11609.
Naidoo, Nirinjini et al., "Sleep deprivation induces the unfolded protein response in mouse cerebral cortex", Journal of Neurochemistry 92:1150-1157, 2005.
Nakanishi, M., et al. "Cloning and Sequence Analysis of a cDNA Encoding Tetrameric Carbonyl Reductase of Pig Lung", Biochem. Biophys. Acta (1993) 194(3):1311-1316.
Nemazanyi, et al. 3-Amino-4-aryl-1(2H)-isoquinolones. Chemistry of Heterocyclic Compounds. Mar. 1991;27(3):307-8.
Niswender, C.M., et al. "Protein Engineering of Protein Kinase A Catalytic Subunits Results in the Acquisition of Novel Inhibitor Sensitivity", The Journal of Biological Chemistry (2002) 277(32):28916-28922.
Nobel, C.S.I., et al. "Purification of Full-Length Recombinant Human and Rat Type 1 1113-hydroxysteroid Dehydrogenases with Retained Oxidoreductase Activities", Protein Expr. Purif. (2002) 26:349-356.
Oda, et al. PIK3CA Cooperates with Other Phosphatidylinositol 3'-Kinase Pathway Mutations to Effect Oncogenic Transformation. Cancer Research. 2008;68:8127.
Oppermann, U.C., et al. "Forms and Functions of Human SDR Enzymes", Chem. Biol. Interact. (2001) 130-132(1-3):699-705.
Ozaki, et al. Studies on 4 (1H)-Quinazolinones. IV. Convenient Syntheses of 12-Methyl-6H-isoquino [2,1-a] quinazolin-6-one and 6-Methyl-13H-quinazolino [3,4-a] quinazolin-13-one. Chem. Pharm. Bull. Jun. 25, 1984;32(6):2160-4.
Ozol, et al. Autoxidative transformations of 2-substituted 3-alkyl-4-hydroxy-1-oxo-1, 2-dihydroisoquinolines. Chemistry of Heterocyclic Compounds. Jun. 1978;14(6):644-8.
Papa, Feroz R. et al., "Bypassing a Kinase Activity with an ATP-Competitive Drug", Science 302:1533-1537, 2003.
Patel, et al. Immunopathological aspects of age-related macular degeneration. Seminars in Immunopathology. 2008;30(2):97-110.
Persson, C.G. "Glucocorticoids for Asthma—Early Contributions", Pulm. Pharmacol. (1989) 2:163-166.
Petrie et al., "A novel biotinylated adenylate analogue derived from pyrazolo[3,4-d]pyrimidine for labeling DNA probes," Bioconj. Chem. vol. 2, No. 6, (1991), pp. 441-446.
Pudlo, J.S., et al. "Synthesis, Antiproliferative, and Antiviral Activity of Certain 4-Substituted and 4,5 Disubstituted 7[1,3-Dihydroxy-2-propoxy)methyl]pyrrolo[2,3-d]pyrimidines", J. Med. Chem. (1990) 33:1984-1992.
Robertson, R.P. "Eicosandoids and Human Disease", Harrison's Principles of Internal Medicine, Isselbacher K.J., et al. (eds.), McGraw-Hill, New York City (1994) 1:431-435.
Romero, D.G., et al. "Cloning and Expression of the Bovine 11p-hydroxysteroid Dehydrogenase Type-2", J. Steroid Biochm. Mol. Biol. (2000) 72:231-237.

(56) References Cited

OTHER PUBLICATIONS

Shamu, Caroline E. et al., "Oligomerization and phosphorylation of the Ire1p kinase during intracellular signaling from the endoplasmic reticulum to the nucleus", The EMBO Journal 15(12):3028-3039, 1996.
Singer, R.H., et al. "Optimization of in situ Hybridization Using Isotopic and Non-Isotopic Detection Methods", Biotechniques (1986) 4(3):230-250.
Soldan, M., et al. "Induction of Daunorubicin Carbonyl Reducing Enzymes by Daunorubicin in Sensitive and Resistant Pancreas Carcinoma Cells", Biochem. PharmacoL (1996) 51:117-123.
Stanoeva et al. Homophthalic anhydrides and their application to the synthesis of heterocyclic compounds (review). Chemistry of Heterocyclic Compounds. Dec. 1984;20(12);1305-15.
Supplementary European Examination Report dated Sep. 20, 2011 for EP Application No. 07754845.1, 4 pages.
Supplementary European Search Report dated Feb. 24, 2010 for EP Application No. 07754845, 4 pages.
Supplementary European Search Report dated Feb. 16, 2010 for EP Application No. 07754845.1, 4 pages.
Takeuchi, H. et al., "Synergistic augmentation of reapamycin-induced autophagy in malignant glioma cells by phosphatidylinositol 3-kinase/protein kinase B inhibitors", Cancer Research 65(8):3336-3346, Apr. 15, 2005.
Tanaka, M., et al. "An Unbiased Cell Morphology-Based Screen for New, Biologically Active Small Molecules", PLoS Biology (2005) 3(5):0764-0776.
Tseng, Ping-Hui et al., "Synergistic interactions between imatinib mesylate and the novel phosphoinositide-dependent kinase-1 inhibitor OSU-03012 in overcoming imatinib mesylate resistance", Blood 105:4021-4027, 2005.
Ugarkar, B.G., et al. "Adenosine Kinase Inhibitors. 2. Synthesis, Enzyme Inhibition, and Antiseizure Activity of Diaryltubercidin Analogues", J. Med. Chem. (2000) 43:2894-2905.
Vasilevsky et al., "Study of the Heterocyclization of vic-Substituted Hydrazides of Acetylenylpyrazolecarboxylic Acids into N-Amino Pyrazolopyridinones", Journal of Heterocyclic Chemistry, Nov., 39(6):1229-1233 (2002).
Vasilevsky et al., "Unexpected results in the heterocyclization of 5-acetylenylpyrazole-4-carboxylic acid hydrazides under the influence of CuCI: formatin of a diazepinone and dehydrodimerization into the corresponding bis(pyrazolo [4,3-d] [1,2] diazepinone)", Tetrahedron Letters, Jan., 46(26): 4457-4459 (2005).
Walker et al., "Structural Determinants of Phosphoinositide 3-Kinase Inhibition by Wortmannin, LY294002, Quercetin, Myricetin, and Staurosporine", Molecular Cell 2000, 6(4):909-919.
White, P.C., et al. "11p-Hydroxysteroid Dehydrogenase and the Syndrome of Apparent Mineralocorticoid Excess", Endocr. Rev. (1997) 18(1):135-156.
Widler, L., et al. "7-Alkyl- and 7-Cycloalkyl-5-aryl-pyrrolo[2,3-d]pyrimidines—Potent Inhibitors of the Tyrosine Kinase c-Src," Bioorganic & Medicinal Chemistry Letters (2001) 11(6):849-852.
Wolff, M. E. Burger's Medicinal Chemistry, 5ed, Part 1, John Wiley & Sons, 1995, pp. 975-977.
Wymann, et al., "Wortmannin Inactivates Phosphoinositide 3-Kinase by Covalent Modification of Lys-802, a Residue Involved in the Phosphate Transfer Reaction", Molecular and Cellular Biology 1996, 16(4):1722-1733.
Yaguchi, et al., "A novel phosphatidylinositol 3-kinase inhibitor, ZSTK474 exterted antitumor activity against human tumor xenografts by oral administration", Proc. Amer. Assoc. Cancer Res. 2005, 46:1691 (Abstract).
Yaguchi, et al. Antitumor activity of ZSTK474, a new phosphatidylinositol 3-kinase inhibitor. J. Natl. Cancer. Inst. 2006; 98(8): 545-556. Abstract only.
Yoshida, Hiderou et al., "XBP1 mRNA Is Induced by ATF6 and Spliced by IRE1 in Response to ER Stress to Produce a Highly Active Transcription Factor", Cell 107:881-891, 2001.
Zhang, Xuewu et al., "An Allosteric Mechanism for Activation of the Kinase Domain of Epidermal Growth Factor Receptor", Cell 125:1137-1149, 2006.
Zheng, Yi et al., "Hepatitis C Virus Non-structural Protein NS4B Can Modulate an Unfolded Protein Response", The Journal of Microbiology 43(6):529-536, 2005.
Korean Intellectual Property Office, PCT/US2009/060985 International Search Report and Written Opinion, dated Jun. 28, 2010, 14 pages.
Read D. et al., Genetics, 2005. 171(3): p. 1057-81.
Read D., E.A. Bach, and R.L. Cagan, Mol Cell Biol, 2004. 24(15): p. 6676-89.
Sheridan, R.P., "The Most Common Chemical Replacements in Drug-Like Compounds". J. Chem. Inf. Comput. Sci. 2002, 42:103-108.
S.M. Wilhelm et al., Cancer Res, 2004. 64(19): p. 7099-109.
Sun, L. et al., J Med Chem, 2003. 46(7): p. 1116-9.
Verbeek, N.H. et al., J Clin Endocrinol Metab, 2011. 96(6): p. E991-5.
Vidal, M. et al., Cancer Res, 2005. 65(9): p. 3538-41.
Vidal, M., D.E. Larson, and R.L. Cagan, Dev Cell, 2006. 10(1): p. 33-44.
Vidal, M. et al., Cancer Res, 2007. 67(21): p. 10278-85).
Liu, Y. And N.S. Gray, Nat Chem Biol, 2006. 2(7): p. 358-64.
Knight, Z.A. et al., Nat. Rev. Cancer, 10(2): p. 130-7, 2010.
Durante, C. et al., Expert Opin Investig Drugs ,2011. 20(3): p. 407-413.
Gedaly, R. et al., Anticancer Res. 30(12): p. 4951-8, 2010.
Cannon, J.G., "Analog Design", Burger's Medicinal Chemistry and Drug Discovery, Fifth Edition, vol. 1: Principles and Practice, 1995, pp. 783-802.
Carlomagno, F. et al., Cancer Res, 2002. 62(24): p. 7284-90).
Carracedo, A. et al., J Clin Invest, 2008. 118(9): p. 3065-74.
Dar et al., "Small Molecule Recognition of c-Src via the Imatinib 1-35-Binding Conformation", Chemistry &Biology, vol. 15, 2008, 1015-1022.
Wells, S.A., Jr. et al., J Clin Oncol, 2010. 28(5): p. 767-72.
Wells SA, R.B., Gagel RF et al., JClin Oncol (Meeting Abstracts), 2010. 28(Suppl): p. 5503.
Wang, L. et al. (Dec. 2012, e-published Oct. 21, 2012). "Divergent allosteric control of the IRE1α endoribonuclease using kinase inhibitors," Nat Chem Biol 8(12):982-989.
Lala, P.K. et al. (Mar. 1998). "Role of nitric oxide in tumor progression: lessons from experimental tumors," Cancer Metastasis Rev 17(1):91-106.
Golub, T.R. et al. (Oct. 15, 1999). "Molecular classification of cancer: class discovery and class prediction by gene expression monitoring," Science 286(5439):531-537.
Medline Plus (2007). "Cancer", retrieved from <http:www.nlm.nih.gov/medlineplus/cancer.html> Jul. 6, 2007, 10 pages.
Ali, M. M. et al. Structure of the Ire1 autophosphorylation complex and implications for the unfolded protein response. EMBO J. 30, 894-905 (2011).
Calfon, M. et al. IRE1 couples endoplasmic reticulum load to secretory capacity by processing the XBP-1 mRNA. Nature 415, 92-96 (2002).
Cross, B. C. et al. The molecular basis for selective inhibition of unconventional mRNA splicing by an IRE1-binding small molecule. Proc Natl Acad Sci U S A 109, E869-878 (2012).
Gardner, B. M. & Walter, P. Unfolded proteins are Ire1-activating ligands that directly induce the unfolded protein response. Science 333, 1891-1894 (2011).
Han, D. et al. A kinase inhibitor activates the IRE1alpha RNase to confer cytoprotection against ER stress. Biochem. Biophys. Res. Commun. 365, 777-783 (2008).
Han, D. et al. IRE1alpha kinase activation modes control alternate endoribonuclease outputs to determine divergent cell fates. Cell 138, 562-575, (2009).
Hollien, J. et al. Journal of Cell Biology The Journal of Cell Biology Aug. 2009, 186 (3) 323-331.
Korennykh, A. V. et al. The unfolded protein response signals through high-order assembly of Ire1. Nature 457, 687-693 (2009).

(56) References Cited

OTHER PUBLICATIONS

Korennykh, A. V. et al. Cofactor-mediated conformational control in the bifunctional kinase/RNase Ire1. BMC Biol. 9, 48 (2011).

Lerner, A. G. et al. Cell metabolism 16, 250-264, (2012).

Ranjitkar, P., Brock, A. M. & Maly, D. J. Affinity reagents that target a specific inactive form of protein kinases. Chem. Biol. 17, 195-206 (2010).

Upton, J. P. et al. Science 338, 818-822, (2012).

Zhou, J. et al. The crystal structure of human IRE1 luminal domain reveals a conserved dimerization interface required for activation of the unfolded protein response. Proc. Natl. Acad. Sci. USA 103, 14343-14348 (2006).

Jordan, V.C. (Mar. 2003). "Tamoxifen: a most unlikely pioneering medicine," *Nat Rev Drug Discov* 2(3):205-213.

Hackam, D.G. et al. (Oct. 11, 2006). "Translation of research evidence from animals to humans," JAMA 296(14):1731-1732.

Tufani, O. et al. (Feb. 21, 2017, e-published Jan. 30, 2017). "Targeting IRE1 with small molecules counteracts progression of atherosclerosis," *Proc Natl Acad Sci USA* 114(8):E1395-E1404).

Dorwald, F. Zaragoza. Side Reactions in Organic Synthesis: A Guide to Successful Synthesis Design, Weinheim:WILEY-VCH Verlag GmbH & Co. KGaA, 2005, Preface.

Mulvihill, M.J. et al. (Feb. 1, 2008, e-published Oct. 23, 2007). "Novel 2-phenylquinolin-7-yl-derived imidazo[1,5-a]pyrazines as potent insulin-like growth factor-I receptor (IGF-IR) inhibitors," *Bioorg Med Chem* 16(3):1359-1375.

Mulvihill, M.J. et al. (2007). "1,3-Disubstituted-imidazo[1,5-a]pyrazines as insulin-like growth-factor-I receptor (IGF-IR) inhibitors," *Bioorg Med Chem Lett* 17(4):1091-1097.

CAS RN 1349063-44-0, entered STN Dec. 5, 2011.

CAS RN 1348561-65-8; entered STN Dec. 4, 2011.

CAS RN 1025939-56-3, entered STN Jun. 6, 2008.

Aragon, Anthony D. et al., "Characterization of Differentiated Quiescent and Nonquiescent Cells in Yeast Stationary-Phase Cultures", Molecular Biology of the Cell 19:1271-1280, 2008.

\* cited by examiner d

GP118     GP117

GP146

A

B c d

GP146(NMe)
IC$_{50}$ = > 80 μM

GP146(Am)
IC$_{50}$ = 30 μM a b

Forumla (A)

a b f g a b c d a b c d a b c

B
XBP-1 site 1: TGAGTCC G/C AGCACTCA
XBP-1 site 2: GACCTCT G/C AGCAGGTC
pre-miR-17 site 1: TCAAAGT G/C TTACAGTG
pre-miR-17 site 2: GATATGT G/C ATCTACTG
pre-miR-17 site 3: ATCTACT G/C AGTGAAGG

A

D
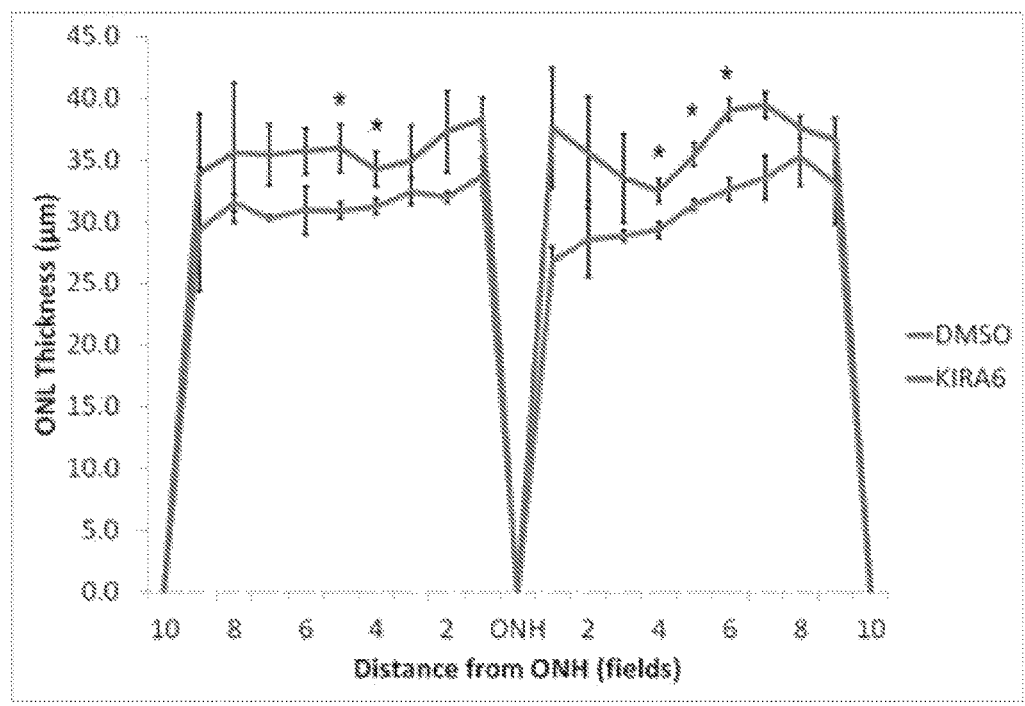
E
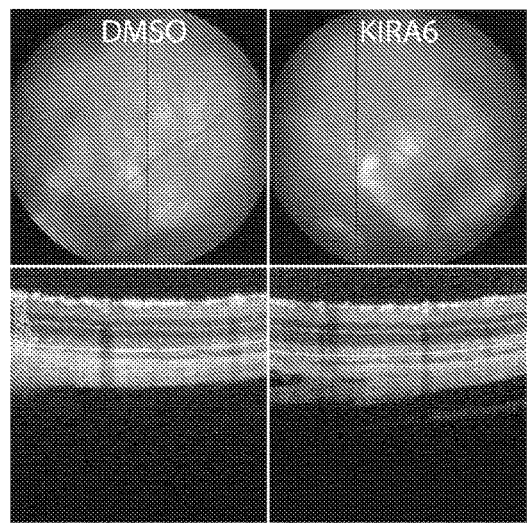
FIG. 39 con't

SUBSTITUTED IMIDAZO[1,5-A]PYRAZINES FOR MODULATION OF IRE1

CROSS-REFERENCES TO RELATED APPLICATIONS

This application claims the benefit of U.S. Provisional Patent Application Nos. 61/706,037, filed Sep. 26, 2012; 61/783,965, filed Mar. 14, 2013; and 61/831,088, filed Jun. 4, 2013, which are all incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant nos. OD001925, DK080955, GM086858, OD001926, awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 48536-547N01US_ST25.TXT, created on Sep. 9, 2015, 24,427 byte, machine format IBM-PC, MS-Windows operating system, is hereby incorporated by reference.

BACKGROUND

Cells often experience conditions during which the workload on the endoplasmic reticulum ("ER") protein folding machinery exceeds its capability. Such cells are said to be experiencing "ER stress." ER stress can result from secretory work overload, expression of folding-defective secretory proteins, deprivation of nutrients or oxygen, changes in luminal calcium concentration, and deviation from resting redox state. Sophisticated cellular surveillance and quality control systems work to maintain ER homeostasis under such perturbations. Under ER stress, secretory proteins accumulate in unfolded forms within the organelle to trigger a set of intracellular signaling pathways called the unfolded protein response (UPR). UPR signaling increases transcription of genes encoding chaperones, oxidoreductases, lipid-biosynthetic enzymes, and ER-associated degradation (ERAD) components (Travers, K. J. et al. *Cell* 101, 249-258 (2000)).

In some instances, the ER stressed state remains too great, and cannot be remedied through the UPR's homeostatic outputs. In these situations, the UPR switches strategies and actively triggers apoptosis (Zhang, K. & Kaufman, R. J. *Neurology* 66, S102-109 (2006)); we have named this destructive signaling state the Terminal UPR (signature events of the Terminal UPR are described herein). Apoptosis of irremediably stressed cells is an extreme, yet definitive, quality control strategy that protects multicellular organisms from exposure to immature and damaged secretory proteins. So at the cost of losing some cells, multicellular organisms may benefit temporarily from Terminal UPR-induced apoptosis. However, many deadly human diseases occur if too many cells die through this process. Conversely, many human diseases such as diabetes mellitus and retinopathies proceed from unchecked cell degeneration under ER stress (Merksamer, P. I., and Papa, F. R., *J Cell Sci* 123, 1003-1006 (2010); Papa, F. R. *Cold Spring Harbor perspectives in medicine* 2, a007666 (2012); Shore, G. C., Papa, F. R., and Oakes, S. A., *Curr Opin Cell Biol* 23, 143-149 (2011)). Type 2 diabetes may be a prototype of cell degenerative diseases caused by UPR-mediated apoptosis under irremediable ER stress. These same principles appear to be at play in type 1 diabetes, wherein immune attack on islet β-cells elevates ER workload and causes ER stress in remaining cells. A deeper fundamental and mechanistic understanding of the etiology and pathogenesis of diabetes mellitus may lead to increasing opportunities for the development of novel and effective therapies. Terminal UPR signaling is central to these conditions as shown through experimental data and uses of proprietary compounds that defeat the consequences of terminal UPR signaling in ER stress-challenged β-cells to afford significant cytoprotection.

IRE1α and IRE1β are ER-transmembrane proteins that become activated when unfolded proteins accumulate within the organelle. IRE1α is the more widely expressed and well-studied family member. The bifunctional kinase/endoribonuclease IRE1α controls entry into the terminal UPR. IRE1α senses unfolded proteins through an ER lumenal domain that becomes oligomerized during stress (Zhou, J. et al. *Proceedings of the National Academy of Sciences of the United States of America* 103, 14343-14348 (2006); Credle, J. J. et al. *Proc Natl Acad Sci USA* 102, 18773-18784 (2005); Aragon, T. et al. *Nature* (2008); Aragon, T. et al. *Nature* 457, 736-740 (2009)). On its cytosolic face, IRE1α possesses bifunctional kinase/RNase activities. Oligomerization juxtaposes IRE1α's kinase domains, which consequently trans-autophosphorylate. Kinase autophosphorylation activates the RNase activity, which cleaves XBP1 mRNA at specific sites to excise an intron. Religation of IRE1α-cleaved XBP1 mRNA shifts the open reading frame; translation of spliced XBP1 mRNA produces a transcription factor called XBP1s (s=spliced) (Calfon, M. et al. *Nature* 415, 92-96, (2002); Yoshida, H. *Cell* 107, 881-891 (2001)). XBP1s's target genes encode products that enhance ER protein folding and quality control (Lee, A. H. et al., *Molecular and cellular biology* 23, 7448-7459 (2003)). Thus, IRE1α promotes adaptation via XBP1s.

Under irremediable ER stress, positive feedback signals emanate from the UPR and become integrated and amplified at key nodes to trigger apoptosis. IRE1α is a key initiator of these pro-apoptotic signals. IRE1α employs auto-phosphorylation as a "timer." Remediable ER stress causes low-level, transient auto-phosphorylation that confines RNase activity to XBP1 mRNA splicing. However, sustained kinase autophosphorylation causes IRE1α's RNase to acquire relaxed specificity, causing it to endonucleolytically degrade thousands of ER-localized mRNAs in close proximity to IRE1α (Han, D. et al. *Cell* 138, 562-575, (2009); Hollien, J. et al. *Journal of Cell Biology*. These mRNAs encode secretory proteins being co-translationally translocated (e.g., insulin in β cells). As mRNA degradation continues, transcripts encoding ER-resident enzymes also become depleted, thus destabilizing the entire ER protein-folding machinery. Once IRE1α's RNase becomes hyperactive, adaptive signaling through XBP1 splicing becomes eclipsed by ER mRNA destruction, which pushes cells into apoptosis.

A terminal UPR signature tightly controlled by IRE1α's hyperactive RNase activity causes (1) widespread mRNA degradation at the ER membrane that leads to mitochondrial apoptosis (Han, D. et al. *Cell* 138, 562-575, (2009)), (2) induction of the pro-oxidant thioredoxin-interacting protein (TXNIP), which activates the NLRP3 inflammasome to produce maturation and secretion of interleukin-1β, and consequent sterile inflammation in pancreatic islets leading to diabetes (Lerner, A. G. et al. *Cell metabolism* 16, 250-264, (2012)), and (3) degradation of pre-miRNA 17, leading to translational upregulation and cleavage of pre-mitochondrial caspase 2 (Upton, J. P. et al. *Science* 338, 818-822, (2012)) and stabilization of the mRNA encoding TXNIP (Lerner, A. G. et al. *Cell metabolism* 16, 250-264, (2012)).

Retinitis pigmentosa (RP) is a clinically and genetically heterogeneous group of inherited retinal disorders characterized by diffuse progressive dysfunction and loss of rod and cone photoreceptors, and retinal pigment epithelium. There are no approved therapies to offer the over 100,000 Americans who currently suffer from RP. As RP is a leading cause of irreversible vision loss, new therapeutic approaches for this condition would be expected to have significant cost-saving benefits for health care systems.

A great deal of evidence suggests that the accumulation of misfolded proteins within the ER is a central causative mechanism in many forms of RP. When the protein-folding capacity of the ER is overwhelmed, cells experience "ER stress" and actively commit programmed cell death. For example, mutations in rhodopsin are the most common cause of RP in the US and lead to a defective rhodopsin protein that misfolds and accumulates in the ER to cause high levels ER stress.

Disclosed herein, inter alia, are solutions to these and other problems in the art.

BRIEF SUMMARY

Provided herein, inter alia, are novel ATP-competitive small molecule kinase inhibitors of IRE1α that prevent oligomerization and/or allosterically inhibit its RNase activity.

In an aspect is provided a compound, or a pharmaceutically acceptable salt thereof, having the formula:

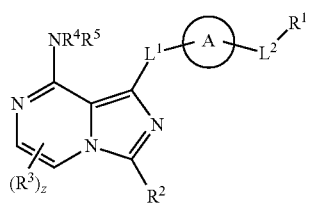

(I)

wherein, ring A is substituted or unsubstituted cycloalkylene, substituted or unsubstituted heterocycloalkylene, substituted or unsubstituted arylene, or substituted or unsubstituted heteroarylene; $L^1$ is a bond or unsubstituted $C_1$-$C_5$ alkylene; $L^2$ is a bond, $-NR^{6a}-$, $-O-$, $-S-$, $-C(O)-$, $-S(O)-$, $-S(O)_2-$, $-NR^{6a}C(O)-$, $-C(O)(CH_2)_{z2}-$, $-C(O)NR^{6b}-$, $-NR^{6a}C(O)O-$, $-NR^{6a}C(O)NR^{6b}-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^1$ is hydrogen, oxo, halogen, $-CX_3$, $-CN$, $-SO_2Cl$, $-SO_nR^{10}$, $-SO_vNR^7R^8$, $-NHNH_2$, $-ONR^7R^8$, $-NHC=(O)NR^7R^8$, $-NHC=(O)NHNH_2$, $-NHC=(O)NR^7R^8$, $-N(O)_m$, $-NR^7R^8$, $-C(O)R^9$, $-C(O)-OR^9$, $-C(O)NR^7R^8$, $-OR^{10}$, $-NR^7SO_nR^{10}$, $-NR^7C=(O)R^9$, $-NR^7C(O)OR^9$, $-NR^7OR^9$, $-OCX_3$, $-OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, oxo, halogen, $-CX^a_3$, $-CN$, $-SO_2Cl$, $-SO_{n1}R^{10a}$, $-SO_{v1}NR^{7a}R^{8a}$, $-NHNH_2$, $-ONR^{7a}R^{8a}$, $-NHC=(O)NHNH_2$, $-NHC=(O)NR^{7a}R^{8a}$, $-N(O)_{m1}$, $-NR^{7a}R^{8a}$, $-C(O)R^{9a}$, $-C(O)OR^{9a}$, $-C(O)NR^{7a}R^{8a}$, $-OR^{10a}$, $-NR^{7a}SO_{n1}R^{10a}$, $-NR^{7a}C=(O)R^{9a}$, $-NR^{7a}C(O)OR^{9a}$, $-NR^{7a}OR^{9a}$, $-OCX^a_3$, $-OCHX^a_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently hydrogen, oxo, halogen, $-CX^b_3$, $-CN$, $-SO_2Cl$, $-SO_{n2}R^{10b}$, $-SO_{v2}NR^{7b}R^{8b}$, $-NHNH_2$, $-ONR^{7b}R^{8b}$, $-NHC=(O)NHNH_2$, $-NHC=(O)NR^{7b}R^{8b}$, $-N(O)_{m2}$, $-NR^{7b}R^{8b}$, $-C(O)R^{9b}$, $-C(O)-OR^{9b}$, $-C(O)NR^{7b}R^{8b}$, $-OR^{10b}$, $-NR^{7b}SO_{n2}R^{10b}$, $-NR^{7b}C=(O)R^{9b}$, $-NR^{7b}C(O)OR^{9b}$, $-NR^{7b}OR^{9b}$, $-OCX^b_3$, $-OCHX^b_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ and $R^5$ are independently hydrogen or unsubstituted $C_1$-$C_6$ alkyl; $R^7$, $R^8$, $R^9$, $R^{10}$, $R^{6a}$, $R^{7a}$, $R^{8a}$, $R^{9a}$, $R^{10a}$, $R^{6b}$, $R^{7b}$, $R^{8b}$, $R^{9b}$, and $R^{10b}$ are independently hydrogen, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCF_3$, $-OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{7a}$ and $R^{8a}$ substituents bonded to the same nitrogen atom may optionally be joined to form a substituted or unsubstituted heterocycloalkyl or substituted or unsubstituted heteroaryl; $R^{7b}$ and $R^{8b}$ substituents bonded to the same nitrogen atom may optionally be joined to form a substituted or unsubstituted heterocycloalkyl or substituted or unsubstituted heteroaryl; each occurrence of the symbols n, n1, and n2 is independently an integer from 0 to 4; each occurrence of the symbols m, m1, m2, v, v1, and v2 is independently an integer from 1 to 2; the symbol z is an integer from 0 to 2; the symbol z2 is an integer from 1 to 4; and each occurrence of the symbols X, $X^a$, and $X^b$ is independently a halogen.

In another aspect is provided a pharmaceutical composition including a pharmaceutically acceptable excipient and a compound, or pharmaceutically acceptable salt thereof, as described herein (e.g. formula I, formula II, formula III, aspect, embodiment, example, figure, table, or claim).

In an aspect is provided a method of treating a disease in a patient in need of such treatment, the method including administering a therapeutically effective amount of a compound described herein (e.g. formula I, formula II, formula III, aspect, embodiment, example, figure, table, or claim), or a pharmaceutically acceptable salt thereof, to the patient, wherein the disease is a neurodegenerative disease, demyelinating disease, cancer, eye disease, fibrotic disease, or diabetes.

In an aspect is provided a method of modulating the activity of an Ire1 protein, the method including contacting the Ire1 protein with an effective amount of a compound described herein (e.g. formula I, formula II, formula III, aspect, embodiment, example, figure, table, or claim), or a pharmaceutically acceptable salt thereof.

In another aspect, the present disclosure provides compounds having the formula (A):

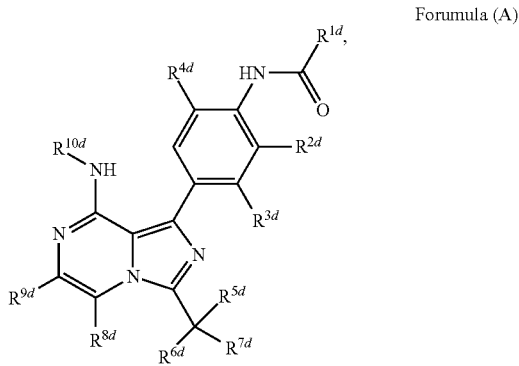

Forumula (A)

(also illustrated in FIG. 7) and pharmaceutically acceptable salts thereof, wherein $R^{1d}$, $R^{2d}$, $R^{3d}$, $R^{4d}$, $R^{5d}$, $R^{6d}$, $R^{7d}$, $R^{8d}$, $R^{9d}$, and $R^{10d}$, are each independently $C_{2-6}$ alkyl, $C_{1-6}$ haloalkyl, —$C_{1-4}$ alkyl-$R^{12d}$, $C_{2-6}$ alkenyl, $C_{2-6}$ alkynyl, $C_{3-8}$ cycloalkyl, monocyclic heterocyclyl, monocyclic heteroaryl, or phenyl, aryl, wherein the cycloalkyl, heterocyclyl, heteroaryl, and phenyl groups are each optionally substituted with one or two $R^{11d}$ groups; each $R^{11d}$ is independently $C_{1-6}$ alkyl, $C_{1-6}$ haloalkyl, —C(O)$R^d$, —C(O)O$R^d$, —C(O)N$R^d_2$, S(O)$_2$N$R^d_2$, or —S(O)$_2R^d$; and $R^{12d}$ is —O$R^d$, —S$R^d$, —N$R^d_2$, —C(O)$R^d$, —C(O)O$R^d$, —C(O)N$R^d_2$, —S(O)$_2R^d$, —OC(O)$R^d$, OC(O)O$R^d$, OC(O)N$R^d_2$, —N($R^d$)C(O)$R^d$, —N($R^d$)C(O)O$R^d$, —N($R^d$)C(O)N$R^d_2$, phenyl, monocyclic heteroaryl, $C_{3-8}$ cycloalkyl, or monocyclic heterocyclyl, wherein the aryl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, —O$R^d$, —S$R^d$, —N$R^d_2$, —C(O)$R^d$, C(O)O$R^d$, —C(O)N$R^d_2$, —S(O)$_2R^d$, —OC(O)$R^d$, —OC(O)O$R^d$, OC(O)N$R^d_2$, N($R^d$)C(O)$R^d$, —N($R^d$)C(O)O$R^d$, or —N($R^d$)C(O)N$R^d_2$; and each $R^d$ is independently hydrogen, $C_{1-6}$ alkyl, $C_{2-6}$ alkenyl, $C_{1-6}$ haloalkyl, $C_{3-8}$ cycloalkyl, heterocyclyl, aryl, aryl$C_{1-6}$ alkyl, heteroaryl, or heteroaryl$C_{1-6}$ alkyl wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —O$R^{Od}$, S$R^{Od}$, N$R^{Od}$2, C(O)$R^{Od}$, C(O)O$R^{Od}$, —C(O)N($R^{Od}$)2, S(O)2$R^{Od}$, —OC(O)$R^{Od}$, —OC(O)O$R^{Od}$, OC(O)N($R^{Od}$)2, N($R^{Od}$)C(O)$R^{Od}$, —N($R^{Od}$)C(O)O$R^{Od}$, or N($R^{Od}$)C(O)N($R^{Od}$)2, wherein each $R^{Od}$ is independently hydrogen or $C_{1-6}$ alkyl, each $R^d$ is independently hydrogen, or $C_{1-6}$ alkyl.

In another aspect, $R^{2d}$ and $R^{3d}$ are together a phenyl, monocyclic heteroaryl, $C_{3-8}$ cycloalkyl, or monocyclic heterocyclyl, wherein the aryl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, —O$R^d$, —S$R^d$, —N$R^d_2$, —C(O)$R^d$, C(O)O$R^d$, —C(O)N$R^d_2$, —S(O)$_2R^d$, —OC(O)$R^d$, —OC(O)O$R^d$, OC(O)N$R^d_2$, N($R^d$)C(O)$R^d$, —N($R^d$)C(O)O$R^d$, or —N($R^d$)C(O)N$R^d_2$; wherein each $R^d$ is independently hydrogen, $C_{1-6}$ alkyl, $C_{2-6}$ alkenyl, $C_{1-6}$ haloalkyl, $C_{3-8}$ cycloalkyl, heterocyclyl, aryl, aryl$C_{1-6}$ alkyl, heteroaryl, or heteroaryl$C_{1-6}$ alkyl wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —O$R^{Od}$, SR$^{Od}$, NR$^{Od}$2, C(O)R$^{Od}$, C(O)OR$^{Od}$, —C(O)N(R$^{Od}$)2, S(O)2R$^{Od}$, —OC(O)R$^{Od}$, —OC(O)OR$^{Od}$, OC(O)N(R$^{Od}$)2, N(R$^{Od}$)C(O)R$^{Od}$, —N(R$^{Od}$)C(O)OR$^{Od}$, or N(R$^{Od}$)C(O)N(R$^{Od}$)2, wherein each $R^{Od}$ is independently hydrogen or $C_{1-6}$ alkyl, each $R^d$ is independently hydrogen, or $C_{1-6}$ alkyl.

In yet another aspect, $R^{1d}$ is —O$R^d$, —S$R^d$, —N$R^d_2$, —C(O)$R^d$, —C(O)O$R^d$, —C(O)N$R^d_2$, —N($R^d$)C(O)$R^d$, —N($R^d$)C(O)O$R^d$, —N($R^d$)C(O)N$R^d_2$, phenyl, monocyclic heteroaryl, $C_{3-8}$ cycloalkyl, or monocyclic heterocyclyl, wherein the aryl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, —O$R^d$, —S$R^d$, —N$R^d_2$, —C(O)$R^d$, C(O)O$R^d$, —C(O)N$R^d_2$, —S(O)$_2R^d$, —OC(O) $R^d$, —OC(O)O$R^d$, OC(O)N$R^d_2$, N($R^d$)C(O)$R^d$, —N($R^d$)C(O)O$R^d$, or —N($R^d$)C(O)N$R^d_2$.

In one aspect, the present disclosure is directed to compositions and methods for activating IRE1α RNase activity using human and murine IRE1α.

In another aspect, the present disclosure is directed to compositions and methods for inhibiting human and murine IRE1α RNase activity using compounds: GP117 (KIRA2), GP118 (KIRA1), GP146 (KIRA3), GP146 (NMe), GP146 (Am), Formula B, Formula (A), compounds shown FIGS. 7 and 8, and other derivative compounds disclosed herein The present disclosure may also be directed to pharmaceutical compositions comprising any of the compounds disclosed herein.

In an additional aspect, the present disclosure provides a compound having Formula (B),

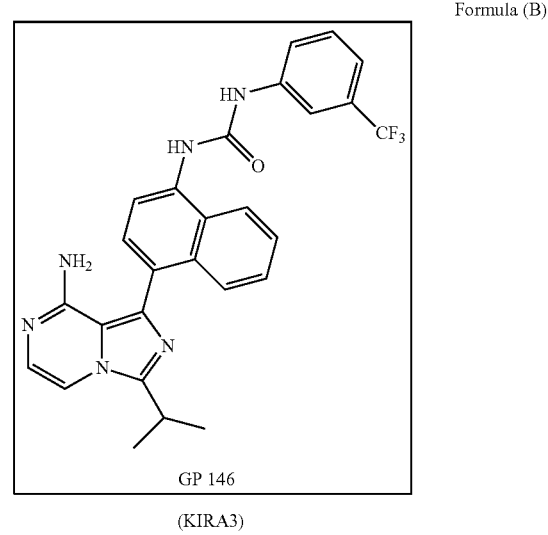

Formula (B)

GP 146
(KIRA3)

and pharmaceutically acceptable salts thereof.

In still another aspect, the present disclosure provides those compounds illustrated in FIG. 8, and pharmaceutically acceptable salts thereof.

In another aspect, the present disclosure provides methods for treating disorders associated with deregulated UPR signaling comprising providing to a patient in need of such treatment a therapeutically effective amount of either (i) any of the compounds disclosed herein, or (ii) a pharmaceutical composition comprising any of the compounds disclosed herein and a pharmaceutically acceptable excipient, carrier, or diluent.

In another aspect, the present disclosure provides methods for treating disorders associated with deregulated UPR signaling comprising providing to a patient in need of such treatment a therapeutically effective amount of either a compound of formula (B), the compound illustrated in FIG. 7 and any described derivatives, and those compounds illustrated in FIG. 8 or any of the described or illustrated derivatives thereof, or (ii) a pharmaceutical composition comprising a compound of formula (B) or any of the derivatives thereof described herein and a pharmaceutically acceptable excipient, carrier, or diluent, wherein the compound of formula (B) is

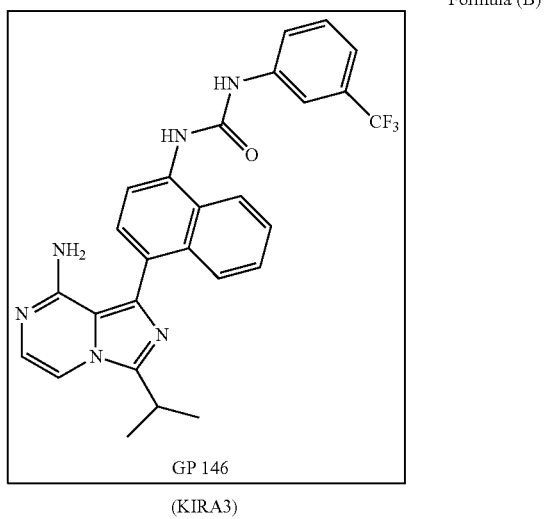

Formula (B)

GP 146
(KIRA3)

BRIEF DESCRIPTION OF THE DRAWINGS

(FIG. 31C): SEQ ID NO:16.

DETAILED DESCRIPTION

Figure 36:
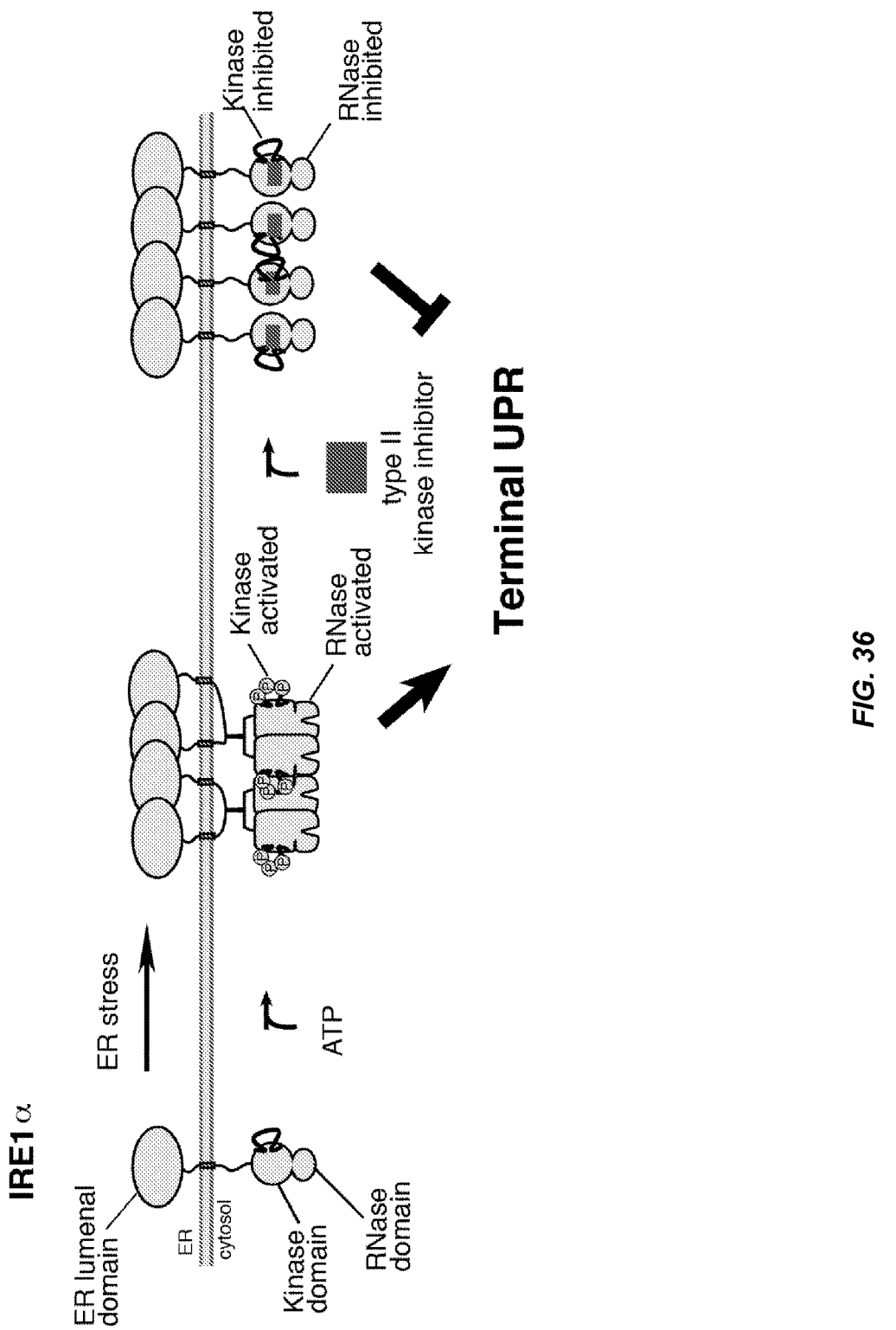
FIG. 36. Inhibiting the Terminal UPR by attenuating IRE1α's RNAse with kinase inhibitors (KIRAs).
Figure 37:
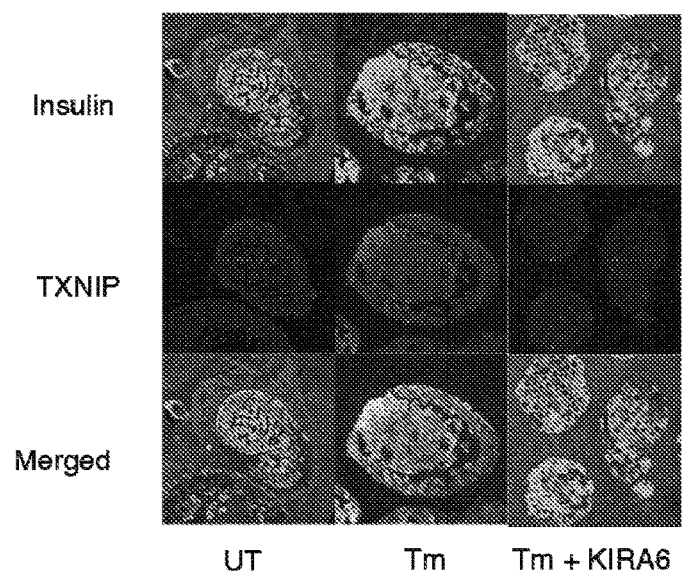
FIG. 37. KIRA6 shuts down all critical terminal UPR events in pancreatic islet beta cells experiencing ER stress; inhibition of pro-inflammatory signaling through TXNIP and Interleukin 1-beta.
Figure 37:
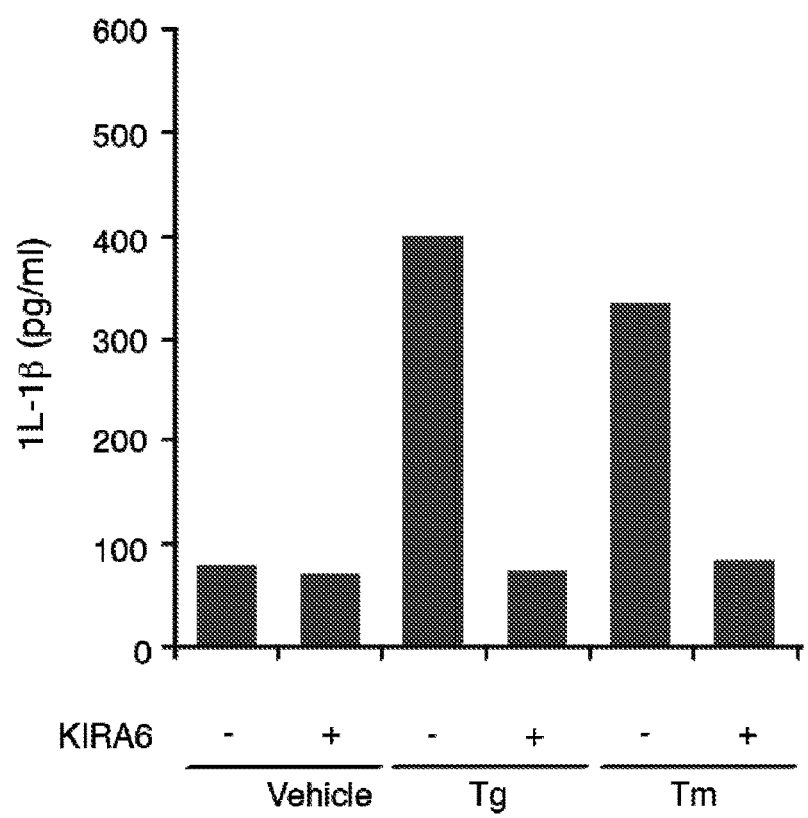
Figure 38:
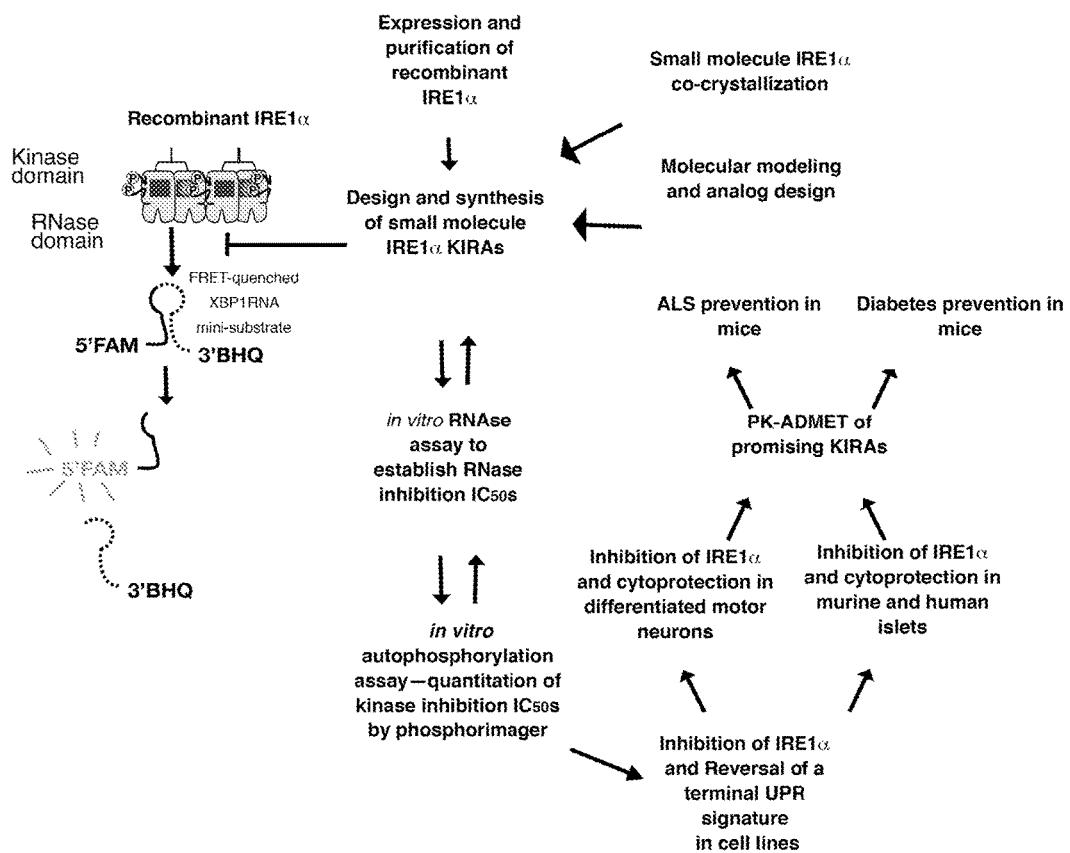
FIG. 38. Testing cascade to improve potency, selectivity, and efficacy of IRE1α KIRAs.
Figure 39:
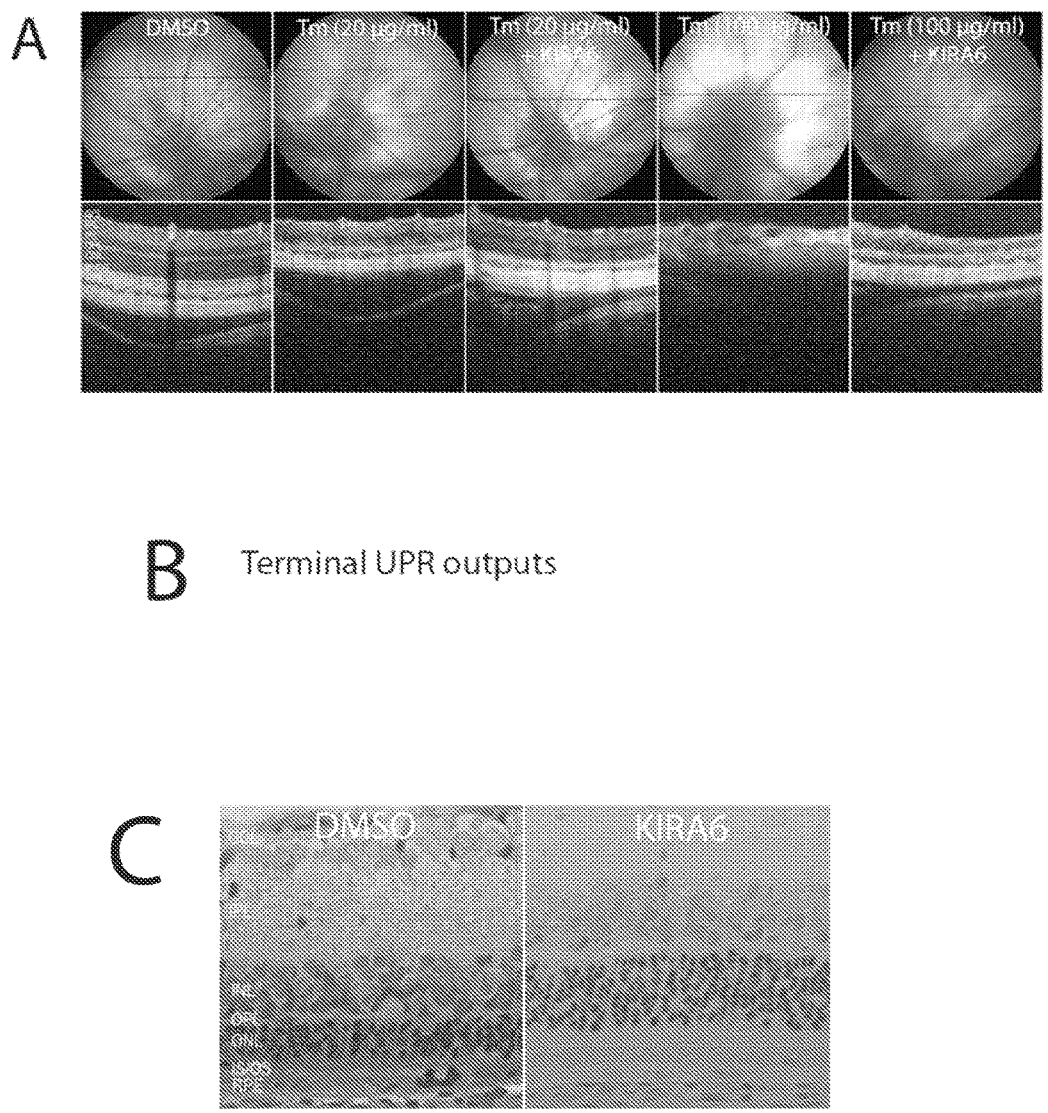
FIG. 39: KIRA6 protects viability and preserves function of retinal photoreceptors during tunicamycin- and mutant rhodopsin-induced stress. (A) Fundus and OCT images of Sprague-Dawley rats injected intravitreally with tunicamycin+/−10 μM KIRA6. (B) Fundus and OCT images of P23H-1 rats at P40 injected intravitreally with DMSO or 10 μM KIRA6. (C) Histological sections of retinas from P23H-1 rats at P30 after intravitreal injection of DMSO or 10 μM KIRA6. (D) Quantification of outer nuclear layer (ONL) thickness (n=2) of P23H-1 rats at P30; higher thickness line is KIRA6 and lower line is DMSO. (E) Fundus and OCT images of P23H-1 rats at P40 after intravitreal injection of DMSO or 10 μM KIRA6. (F) Scotopic series of ERG measurements with indicated light intensities (top) and a photopic single flash ERG measurement (+20 dB) (bottom).
Figure 39:
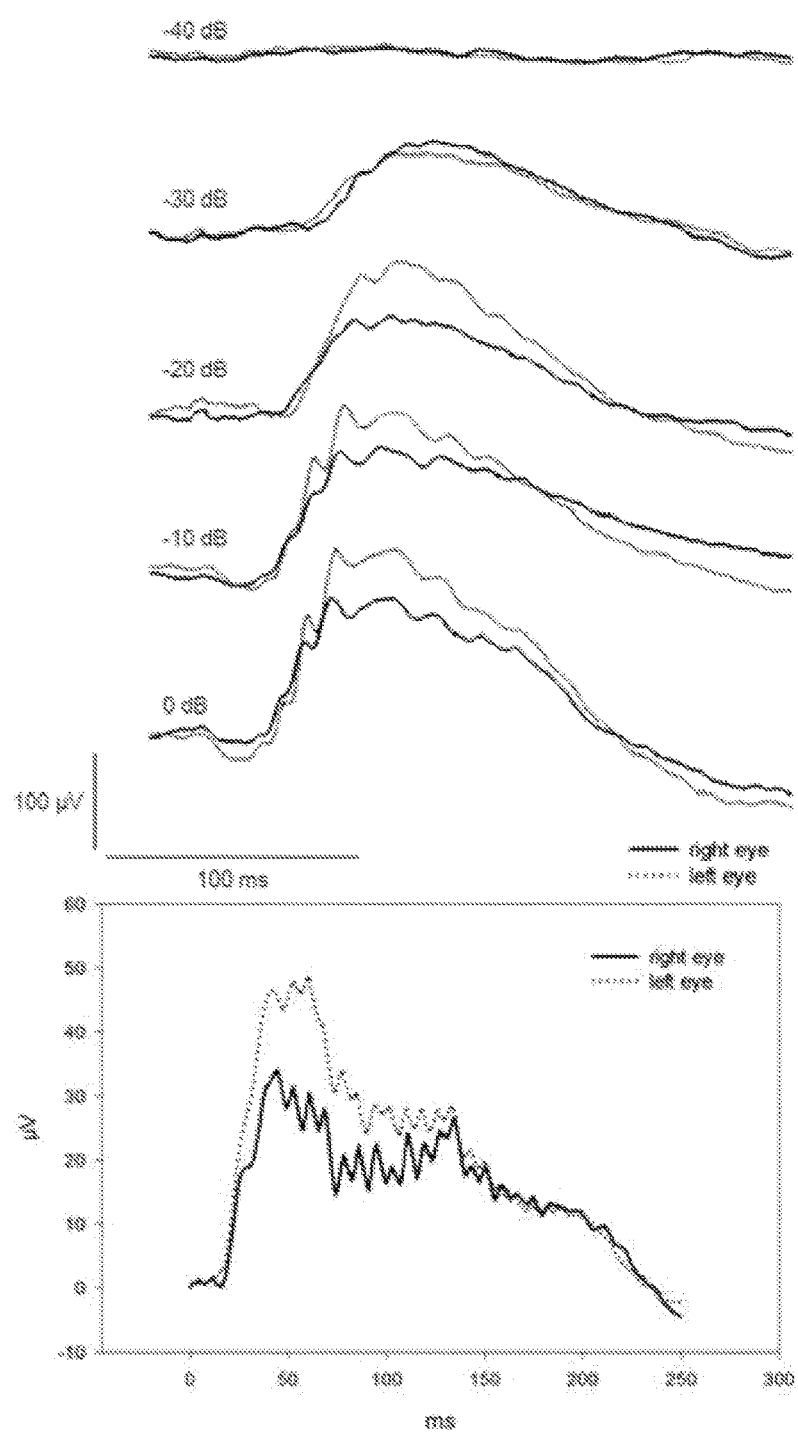
Figure 40:
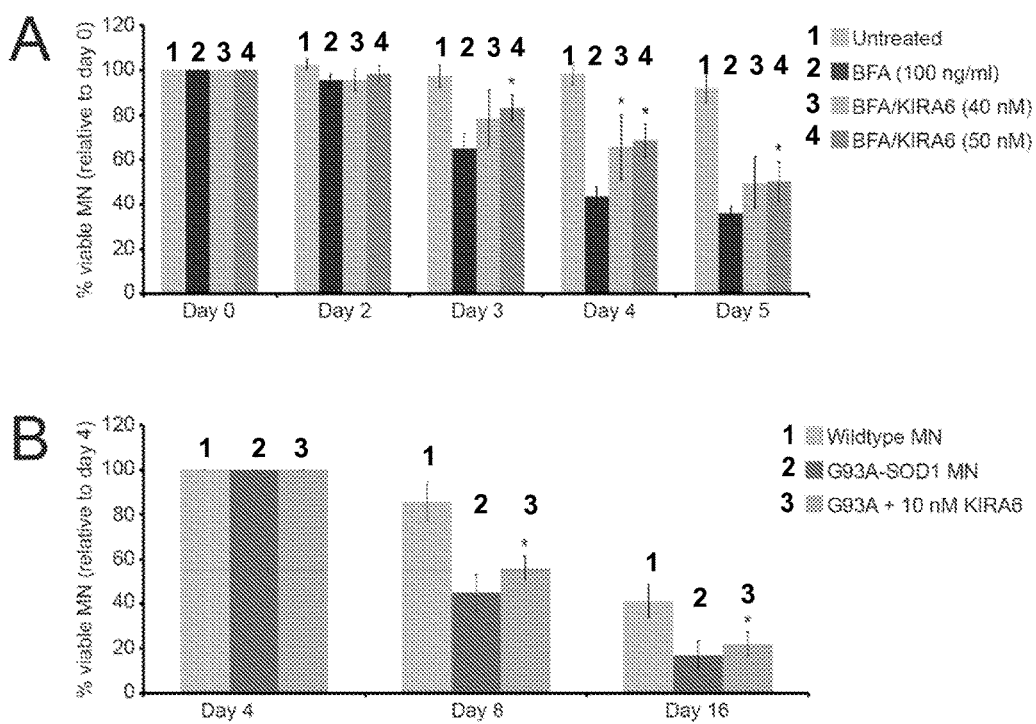
FIG. 40. Survival curves of murine embryonic stem cell (ESC)-derived motor neurons. A. Wild-type (WT) Hb9:GFP ESCs were differentiated into GFP+ motor neurons (MNs) and subsequently treated with brefeldin A (BFA) with or without KIRA6 at the indicated concentrations. B. G93A-SOD1/Hb9:GFP ESCs were differentiated into GFP+MNs and treated with KIRA6 at the indicated concentrations; MNs derived from WT Hb9:GFP ESCs served as a control. p-values: * <0.05. MutSOD1 leads to a form of familial amyotrophic lateral sclerosis.

Activation of IRE1α's RNase is normally dependent on kinase autophosphorylation (Tirasophon, W. et al. *Genes Dev* 12, 1812-1824 (1998)), but an allosteric relationship between these two domains exists, which allows nucleotides (ADP and ATP) and small molecule inhibitors that stabilize an active ATP-binding site conformation to directly activate the RNase without autophosphorylation (Papa, F. R. et al. *Science* 302, 1533-1537 (2003); Han, D. et al. *Biochemical and biophysical research communications* 365, 777-783, (2008); Korennykh, A. V. et al. *BMC biology* 9, 48, (2011)). Furthermore, a particular class of kinase inhibitors (called type II) stabilize an inactive ATP-binding site conformation of IRE1α and are able to potently inhibit its RNase activity by breaking high-order oligomerization state (FIGS. 1A and 36) (Wang, L. et al. *Nature chemical biology* 8, 982-989, (2012)). These compounds are herein labeled—KIRAs—for kinase-inhibiting RNase-attenuators.

Distinct classes of ATP-competitive kinase inhibitors divergently modulate the RNase activity of IRE1α. A co-crystal structure of yeast IRE1 bound with APY29—a predicted type I kinase inhibitor—shows that the kinase catalytic domain is in an active conformation, which is a conformation typically adopted by protein kinases when bound to ATP and other type I inhibitors (FIG. 1*a*) (Korennykh, A. V. et al. *Nature* 457, 687-693 (2009); Korennykh, A. V. et al. *BMC Biol.* 9, 48 (2011)). Moreover, two additional co-crystal structures of yeast IRE1 and human IRE1α bound with ADP show that the kinase domain is similarly in an active conformation (Ali, M. M. et al. *EMBO J.* 30, 894-90, (2011); Lee, K. P. et al. *Cell* 132, 89-100 (2008)). By stabilizing IRE1α's kinase in the active conformation, these type I inhibitors act as ligands that allosterically activate its adjacent RNase domain. It might be possible to stabilize IRE1α's kinase domain in an alternative conformation, and in so doing disable its RNase activity. Use of a class of small molecule kinase inhibitors that have been described to selectively stabilize the inactive conformation of the ATP-binding site (type II inhibitors) for a variety of kinases; examples include the clinically-approved drugs imatinib and sorafenib (Liu, Y. & Gray, N. S. *Nat. Chem. Biol.* 2, 358-364 (2006); Wan, P. T. et al. *Cell* 116, 855-867 (2004); Schindler, T. et al. *Science* 289, 1938-1942 (2000)), provides support for this approach. The inactive ATP-binding site conformation stabilized by type II inhibitors is characterized by outward movement of the catalytically-important Asp-Phe-Gly (DFG) motif, and is therefore called the DFG-out conformation (FIG. 1*a*) (Liu, Y. & Gray, N. S. *Nat. Chem. Biol.* 2, 358-364 (2006); Ranjitkar, P. et al. *Chem. Biol.* 17, 195-206 (2010)). In contrast, in all three co-crystal structures of IRE 1 in an active conformation mentioned previously, the kinase domain adopts the DFG-in conformation (Korennykh, A. V. et al. *Nature* 457, 687-693 (2009); Ali, M. M. et al. *EMBO J.* 30, 894-90, (2011); Lee, K. P. et al. *Cell* 132, 89-100 (2008)).

Under high endoplasmic reticulum (ER) stress, hyperactivation of intracellular signaling pathways termed the unfolded protein response (UPR) triggers cell death. Signature events of this "Terminal UPR" are controlled by IRE1α, an ER bifunctional kinase/endoribonuclease (RNase), which, when oligomerized, endonucleolytically degrades ER-localized mRNAs and repressive micro-RNA precursors to trigger apoptosis. Ire1α somatic mutations found in human cancers disable oligomerization and apoptotic function of its RNase. Using these instructive results from human biology, ATP-competitive kinase inhibitors were developed—termed KIRAs (Kinase Inhibiting RNase Attenuators)—that allosterically reduce IRE1α oligomerization and RNase activity. One such kinase inhibitor, KIRA6, inhibits all IRE1α outputs, and preserves cell viability and function under ER stress. In rat models of retinal degeneration caused by ER stress, intravitreal KIRA6 prevents photoreceptor loss.

A. DEFINITIONS

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—. Terms used herein may be preceded and/or followed by a single dash, "—", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents having a superscript "d" (e.g. R$^d$) are intended to be read "left to right" unless a dash indicates otherwise. For example, C$_1$ C$_6$alkoxycarbonyloxy and OC(O)C$_1$ C$_6$alkyl indicate the same functionality; similarly arylalkyl and alkylaryl indicate the same functionality.

The term "saturated" as used herein means the referenced chemical structure does not contain any multiple carbon carbon bonds. For example, a saturated cycloalkyl group as defined herein includes cyclohexyl, cyclopropyl, and the like.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butyryl, and the higher homologs and isomers. An alkoxy is an alkyl attached to the remainder of the molecule via an oxygen linker (—O—). In embodiments, an alkyl is a straight or branched chain hydrocarbon containing from 1 to 10 carbon atoms, unless otherwise specified. In embodiments, an alkyl is an alkenyl, wherein the term "alkenyl" is used in accordance with its plain ordinary meaning. In embodiments, an alkenyl is a straight or branched chain hydrocarbon containing from 2 to 10 carbons, unless otherwise specified, and containing at least one carbon carbon double bond. Examples of alkenyl include, but are not limited to, ethenyl, 2 propenyl, 2 methyl 2 propenyl, 3 butenyl, 4 pentenyl, 5 hexenyl, 2 heptenyl, 2 methyl 1 heptenyl, 3 decenyl, and 3,7 dimethylocta 2,6 dienyl. In embodiments, an alkyl is an alkynyl, wherein the term "alkynyl" is used in accordance with its plain ordinary meaning. In embodiments, an alkynyl is a straight or branched chain hydrocarbon group containing from 2 to 10 carbon atoms and containing at least one carbon carbon triple bond. Examples of alkynyl include, but are not limited, to acetylenyl, 1 propynyl, 2 propynyl, 3 butynyl, 2 pentynyl, and 1 butynyl.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—O$CH_3$ and $CH_2$—O—Si($CH_3$)$_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form ($CH_2$)$_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3 dioxanyl, 1,3 dioxolanyl, 1,3 dithiolanyl, 1,3 dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1 dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3 dihydrobenzofuran 2 yl, 2,3 dihydrobenzofuran 3 yl, indolin 1 yl, indolin 2 yl, indolin 3 yl, 2,3 dihydrobenzothien 2 yl, decahydroquinolinyl, decahydroisoquinolinyl, octahydro 1H indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively, such as for example a divalent radical of indoline. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

In embodiments, an aryl is a phenyl (i.e., monocyclic aryl), a bicyclic ring system containing at least one phenyl ring or an aromatic bicyclic ring containing only carbon atoms in the aromatic bicyclic ring system or a multicyclic aryl ring system, provided that the bicyclic or multicyclic aryl ring system does not contain a heteroaryl ring when fully aromatic. In embodiments, the bicyclic aryl can be azulenyl, naphthyl, or a phenyl fused to a monocyclic cycloalkyl, a monocyclic cycloalkenyl, or a monocyclic heterocyclyl. In embodiments, the bicyclic aryl may be attached to the parent molecular moiety through any carbon atom contained within the phenyl portion of the bicyclic system, or any carbon atom with the napthyl or azulenyl ring. In embodiments, the fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden 1 yl, dihydroinden 2 yl, dihydroinden 3 yl, dihydroinden 4 yl, 2,3 dihydroindol 4 yl, 2,3 dihydroindol 5 yl, 2,3 dihydroindol 6 yl, 2,3 dihydroindol 7 yl, inden 1 yl, inden 2 yl, inden 3 yl, inden 4 yl, dihydronaphthalen 2 yl, dihydronaphthalen 3 yl, dihydronaphthalen 4 yl, dihydronaphthalen 1 yl, 5,6,7,8 tetrahydronaphthalen 1 yl, 5,6,7,8 tetrahydronaphthalen 2 yl, 2,3 dihydrobenzofuran 4 yl, 2,3 dihydrobenzofuran 5 yl, 2,3 dihydrobenzofuran 6 yl, 2,3 dihydrobenzofuran 7 yl, benzo[d][1,3]dioxol 4 yl, benzo[d][1,3]dioxol 5 yl, 2H chromen 2 on 5 yl, 2H chromen 2 on 6 yl, 2H chromen 2 on 7 yl, 2H chromen 2 on 8 yl, isoindoline 1,3 dion 4 yl, isoindoline 1,3 dion 5 yl, inden 1 on 4 yl, inden 1 on 5 yl, inden 1 on 6 yl, inden 1 on 7 yl, 2,3 dihydrobenzo[b][1,4]dioxan 5 yl, 2,3 dihydrobenzo[b][1,4]dioxan 6 yl, 2H benzo[b][1,4]oxazin3(4H) on 5 yl, 2H benzo[b][1,4]oxazin3(4H) on 6 yl, 2H benzo[b][1,4]oxazin3(4H) on 7 yl, 2H benzo[b][1,4]oxazin3(4H) on 8 yl, benzo[d]oxazin 2(3H) on 5 yl, benzo[d]oxazin 2(3H) on 6 yl, benzo[d]oxazin 2(3H) on 7 yl, benzo[d]oxazin 2(3H) on 8 yl, quinazolin 4(3H) on 5 yl, quinazolin 4(3H) on 6 yl, quinazolin 4(3H) on 7 yl, quinazolin 4(3H) on 8 yl, quinoxalin 2(1H) on 5 yl, quinoxalin 2(1H) on 6 yl, quinoxalin 2(1H) on 7 yl, quinoxalin 2(1H) on 8 yl, benzo[d]thiazol 2(3H) on 4 yl, benzo[d]thiazol 2(3H) on 5 yl, benzo[d]thiazol 2(3H) on 6 yl, and, benzo[d]thiazol 2(3H) on 7 yl. In embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia. In embodiments, multicyclic aryl groups are a phenyl ring (base ring) fused to either (i) one ring system selected from the group consisting of a bicyclic aryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic cycloalkyl, a monocyclic or bicyclic cycloalkenyl, and a monocyclic or bicyclic heterocyclyl, provided that when the base ring is fused to a bicyclic cycloalkyl, bicyclic cycloalkenyl, or bicyclic heterocyclyl, then the base ring is fused to the base ring of the bicyclic cycloalkyl, bicyclic cycloalkenyl, or bicyclic heterocyclyl. In embodiments, the multicyclic aryl may be attached to the parent molecular moiety through any carbon atom contained within the base ring. In certain embodiments, multicyclic aryl groups are a phenyl ring (base ring) fused to either (i) one ring system selected from the group consisting of a bicyclic aryl, a bicyclic cycloalkyl, a bicyclic cycloalkenyl, and a bicyclic heterocyclyl; or (ii) two other ring systems independently selected from the group consisting of a phenyl, a monocyclic cycloalkyl, a monocyclic cycloalkenyl, and a monocyclic heterocyclyl, provided that when the base ring is fused to a bicyclic cycloalkyl, bicyclic cycloalkenyl, or bicyclic heterocyclyl, then the base ring is fused to the base ring of the bicyclic cycloalkyl, bicyclic cycloalkenyl, or bicyclic heterocyclyl. Examples of multicyclic aryl groups include but are not limited to anthracen-9-yl and phenanthren-9-yl.

In embodiments, the term "heteroaryl," as used herein, means a monocyclic, bicyclic, or a multicyclic heteroaryl ring system. In embodiments, the monocyclic heteroaryl can be a 5 or 6 membered ring. In embodiments, the 5 membered ring consists of two double bonds and one, two, three or four nitrogen atoms and optionally one oxygen or sulfur atom. In embodiments, the 6 membered ring consists of three double bonds and one, two, three or four nitrogen atoms. In embodiments, the 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. In embodiments, the bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. In embodiments, the fused cycloalkyl or heterocyclyl portion of the bicyclic heteroaryl group is optionally substituted with one or two groups which are independently oxo or thia. In embodiments, when the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. In embodiments, when the bicyclic heteroaryl is a monocyclic heteroaryl fused to a phenyl ring or a monocyclic heteroaryl, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6 dihydroquinolin 2 yl, 5,6 dihydroisoquinolin 1 yl, furopyridinyl, indazolyl, indolyl, isoquinolinyl, naphthyridinyl, quinolinyl, purinyl, 5,6,7,8 tetrahydroquinolin 2 yl, 5,6,7,8 tetrahydroquinolin 3 yl, 5,6,7,8 tetrahydroquinolin 4 yl, 5,6,7,8 tetrahydroisoquinolin 1 yl, thienopyridinyl, 4,5,6,7 tetrahydrobenzo[c][1,2,5] oxadiazolyl, and 6,7 dihydrobenzo[c][1,2,5]oxadiazol 4(5H) onyl. In embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia. In embodiments, the multicyclic heteroaryl group is a monocyclic heteroaryl ring (base ring) fused to either (i) one ring system selected from the group consisting of a bicyclic aryl, a bicyclic heteroaryl, a bicyclic heterocyclyl, a bicyclic cycloalkenyl, and a bicyclic cycloalkyl; or (ii) two ring systems selected from the group consisting of a phenyl, a bicyclic aryl, a monocyclic or bicyclic heteroaryl, a monocyclic or bicyclic heterocyclyl, a monocyclic or bicyclic cycloalkenyl, and a monocyclic or bicyclic cycloalkyl. In embodiments, the multicyclic heteroaryl group is connected to the parent molecular moiety through any carbon atom or nitrogen atom contained within the base ring. In embodiments, multicyclic heteroaryl groups are a monocyclic heteroaryl ring (base ring) fused to either (i) one ring system selected from the group consisting of a bicyclic aryl, a bicyclic heteroaryl, a bicyclic heterocyclyl, a bicyclic cycloalkenyl, and a bicyclic cycloalkyl; or (ii) two ring systems selected from the group consisting of a phenyl, a monocyclic heteroaryl, a monocyclic heterocyclyl, a monocyclic cycloalkenyl, and a monocyclic cycloalkyl. Examples of multicyclic heteroaryls include, but are not limited to 5H-[1,2,4]triazino[5,6-b]indol-5-yl, 2,3,4,9-tetrahydro-1H-carbazol-9-yl, 9H-pyrido[3,4-b]indol-9-yl, 9H-carbazol-9-yl, acridin-9-yl, A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom. The term "thia" as used herein means a =S group.

The term "alkylsulfonyl," as used herein, means a moiety having the formula —S(O)$_2$—R', where R' is a substituted or unsubstituted alkyl group as defined above. R' may have a specified number of carbons (e.g., "$C_1$-$C_4$ alkylsulfonyl").

The term "arylalkyl" and "alkylaryl" as used herein, means an aryl group, as defined herein, appended to the parent molecular moiety through an alkyl group, as defined herein. Representative examples of arylalkyl include, but are not limited to, benzyl, 2 phenylethyl, 3 phenylpropyl, and 2 naphth 2 ylethyl.

The term "heteroarylalkyl" and "alkylheteroaryl" as used herein, means a heteroaryl, as defined herein, appended to the parent molecular moiety through an alkyl group, as defined herein. Representative examples of heteroarylalkyl include, but are not limited to, fur 3 ylmethyl, 1H imidazol 2 ylmethyl, 1H imidazol 4 ylmethyl, 1 (pyridin 4 yl)ethyl, pyridin 3 ylmethyl, pyridin 4 ylmethyl, pyrimidin 5 ylmethyl, 2 (pyrimidin 2 yl)propyl, thien 2 ylmethyl, and thien 3 ylmethyl.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R''')=NR'''', —NR—C(NR'R")=NR'", —S(O)R', —S(O)$_2$R', —S(O)$_2$NR'R", —NRSO$_2$R', NR'NR"R'", ONR'R", NR'C=(O)NR"NR'"R'''', —CN, —NO$_2$, in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O) NR'R", —NR"C(O)R', —NR'—C(O)NR"R'", —NR"C(O)$_2$R', —NR—C(NR'R"R''')=NR'''', —NR—C(NR'R")=NR'", —S(O)R', —S(O)$_2$R', —S(O)$_2$NR'R", —NRSO$_2$R', NR'NR"R'", ONR'R", NR'C=(O)NR"NR'"R'''', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 9 membered heteroarylene. In some embodiments, the compound is a chemical species set forth in the Examples section below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-12, ($^{125}$I), or carbon-14 ($^{14}$C). All isotopic variations of the compounds of the present invention, whether radioactive or not, are encompassed within the scope of the present invention.

The symbol "⌇" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat cancer (e.g. multiple myeloma, cancers of secretory cells), neurodegenerative diseases, demyelinating diseases, eye diseases, fibrotic diseases, or diabetes (type I or type II). For example certain methods herein treat cancer by decreasing or reducing or preventing the occurrence, growth, metastasis, or progression of cancer; treat neurodegeneration by improving mental wellbeing, increasing mental function, slowing the decrease of mental function, decreasing dementia, delaying the onset of dementia, improving cognitive skills, decreasing the loss of cognitive skills, improving memory, decreasing the degradation of memory, or extending survival; treat demyelinating diseases by reducing a symptom of demyelinating diseases or reducing the loss of myelin or increasing the amount of myelin or increasing the level of myelin; treat diabetes by decreasing a symptom of diabetes or decreasing loss of insulin producing cells or decreasing loss of pancreatic cells or reducing insulin insensitivity; treat cancer by decreasing a symptom of cancer, or treat neurodegeneration by treating a symptom of neurodegeneration. Symptoms of cancer (e.g. multiple myeloma, cancers of secretory cells), neurodegenerative diseases, demyelinating diseases, eye diseases, fibrotic diseases, or diabetes would be known or may be determined by a person of ordinary skill in the art. The term "treating" and conjugations thereof, include prevention of an injury, pathology, condition, or disease (e.g. preventing the development of one or more symptoms of cancer, neurodegenerative diseases, demyelinating diseases, and/or diabetes).

An "effective amount" is an amount sufficient to accomplish a stated purpose (e.g. achieve the effect for which it is administered, treat a disease, reduce enzyme activity, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist (inhibitor) required to decrease the activity of an enzyme or protein relative to the absence of the antagonist. An "activity increasing amount," as used herein, refers to an amount of agonist (activator) required to increase the activity of an enzyme or protein relative to the absence of the agonist. A "function disrupting amount," as used herein, refers to the amount of antagonist (inhibitor) required to disrupt the function of an enzyme or protein relative to the absence of the antagonist. A "function increasing amount," as used herein, refers to the amount of agonist (activator) required to increase the function of an enzyme or protein relative to the absence of the agonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g cancer (e.g. multiple myeloma, cancers of secretory cells), neurodegenerative diseases, demyelinating diseases, eye diseases, fibrotic diseases, or diabetes) means that the disease (e.g cancer (e.g. multiple myeloma, cancers of secretory cells), neurodegenerative diseases, demyelinating diseases, eye diseases, fibrotic diseases, or diabetes) is caused by (in whole or in part), or a symptom of the disease is caused by (in whole or in part) the substance or substance activity or function. For example, a symptom of a disease or condition associated with an increase in Ire1 (e.g. Ire1α) activity may be a symptom that results (entirely or partially) from an increase in Ire1 (e.g. Ire1α) activity (e.g increase in Ire1 (e.g. Ire1α) phosphorylation or activity of phosphorylated Ire1 (e.g. Ire1α) or activity of Ire1 (e.g. Ire1α) or increase in activity of an Ire1 (e.g. Ire1α) signal transduction or signalling pathway, Ire1 (e.g. Ire1α) RNase activity). As used herein, what is described as being associated with a disease, if a causative agent, could be a target for treatment of the disease. For example, a disease associated with increased Ire1 (e.g. Ire1α) activity or Ire1 (e.g. Ire1α) pathway activity (e.g. phosphorylated Ire1 (e.g. Ire1α) activity or pathway), may be treated with an agent (e.g. compound as described herein) effective for decreasing the level of activity of Ire1 (e.g. Ire1α) activity or Ire1 (e.g. Ire1α) pathway or phosphorylated Ire1 (e.g. Ire1α) activity or pathway. For example, a disease associated with phosphorylated Ire1 (e.g. Ire1α), may be treated with an agent (e.g. compound as described herein) effective for decreasing the level of activity of phosphorylated Ire1 (e.g. Ire1α) or a downstream component or effector of phosphorylated Ire1 (e.g. Ire1α). For example, a disease associated with Ire1 (e.g. Ire1α), may be treated with an agent (e.g. compound as described herein) effective for decreasing the level of activity of Ire1 (e.g. Ire1α) or a downstream component or effector of Ire1 (e.g. Ire1α).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme (e.g. Ire1 (e.g. Ire1α) or phosphorylated Ire1 (e.g. Ire1α) or component of Ire1 (e.g. Ire1α) pathway or component of phosphorylated Ire1 (e.g. Ire1α) pathway). In some embodiments contacting includes allowing a compound described herein to interact with a protein or enzyme that is involved in a signaling pathway (e.g. Ire1 (e.g. Ire1α) protein or Ire1 (e.g. Ire1α) pathway).

As defined herein, the term "inhibition", "inhibit", "inhibiting" and the like in reference to a protein-inhibitor (e.g. antagonist) interaction means negatively affecting (e.g. decreasing) the activity or function of the protein relative to the activity or function of the protein in the absence of the inhibitor. In some embodiments inhibition refers to reduction of a disease or symptoms of disease. In some embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein. In some embodiments, inhibition refers to a decrease in the activity of a signal transduction pathway or signaling pathway (e.g. Ire1 (e.g. Ire1α) or phosphorylated Ire1 (e.g. Ire1α) or Ire1 (e.g. Ire1α) pathway or phosphorylated Ire1 (e.g. Ire1α) pathway or pathway activated by Ire1 (e.g. Ire1α) phosphorylation). Thus, inhibition may include, at least in part, partially or totally decreasing stimulation, decreasing or reducing activation, or inactivating, desensitizing, or down-regulating signal transduction or enzymatic activity or the amount of a protein increased in a disease (e.g. level of Ire1 (e.g. Ire1α) activity or protein or level or activity of a component of an Ire1 (e.g. Ire1α) pathway or level of phosphorylated Ire1 (e.g. Ire1α) activity or protein or level or activity of a component of a phosphorylated Ire1 (e.g. Ire1α) pathway, wherein each is associated with cancer (e.g. multiple myeloma, or cancers of secretory cells), neurodegenerative diseases, demyelinating diseases, eye diseases, fibrotic diseases, or diabetes) Inhibition may include, at least in part, partially or totally decreasing stimulation, decreasing or reducing activation, or deactivating, desensitizing, or down-regulating signal transduction or enzymatic activity or the amount of a protein (e.g. Ire1 (e.g. Ire1α), phosphorylated Ire1 (e.g. Ire1α), protein downstream in a pathway from Ire1 (e.g. Ire1α), protein downstream in a pathway activated by phosphorylated Ire1 (e.g. Ire1α)) that may modulate the level of another protein or increase cell survival (e.g. decrease in phosphorylated Ire1 (e.g. Ire1α) pathway activity may increase cell survival in cells that may or may not have an increase in phosphorylated Ire1 (e.g. Ire1α) pathway activity relative to a non-disease control or decrease in Ire1 (e.g. Ire1α) pathway activity may increase cell survival in cells that may or may not have a increase in Ire1 (e.g. Ire1α) pathway activity relative to a non-disease control).

As defined herein, the term "activation", "activate", "activating" and the like in reference to a protein-activator (e.g. agonist) interaction means positively affecting (e.g. increasing) the activity or function of the protein (e.g. Ire1 (e.g. Ire1α), phosphorylated Ire1 (e.g. Ire1α), component of pathway including Ire1 (e.g. Ire1α), or component of pathway including phosphorylated Ire1 (e.g. Ire1α)) relative to the activity or function of the protein in the absence of the activator (e.g. compound described herein). In some embodiments, activation refers to an increase in the activity of a signal transduction pathway or signaling pathway (e.g. Ire1 (e.g. Ire1α) or phosphorylated Ire1 (e.g. Ire1α) pathway). Thus, activation may include, at least in part, partially or totally increasing stimulation, increasing or enabling activation, or activating, sensitizing, or up-regulating signal transduction or enzymatic activity or the amount of a protein decreased in a disease (e.g. level of Ire1 (e.g. Ire1α) activity or level of protein or activity decreased by phosphorylation of Ire1 (e.g. Ire1α) or protein associated with cancer (e.g. multiple myeloma, or cancers of secretory cells), neurodegenerative diseases, demyelinating diseases, eye diseases, fibrotic diseases, or diabetes). Activation may include, at least in part, partially or totally increasing stimulation, increasing or enabling activation, or activating, sensitizing, or up-regulating signal transduction or enzymatic activity or the amount of a protein (e.g. Ire1 (e.g. Ire1α), protein downstream of Ire1 (e.g. Ire1α), protein activated or upregulated by Ire1 (e.g. Ire1α), protein activated or upregulated by phosphorylation of Ire1 (e.g. Ire1α)) that may modulate the level of another protein or increase cell survival (e.g. increase in Ire1 (e.g. Ire1α) activity may increase cell survival in cells that may or may not have a reduction in Ire1 (e.g. Ire1α) activity relative to a non-disease control).

The term "modulator" refers to a composition that increases or decreases the level of a target molecule or the function of a target molecule. In some embodiments, a modulator of Ire1 (e.g. Ire1α) or Ire1 (e.g. Ire1α) pathway or phosphorylation of Ire1 (e.g. Ire1α) or pathway activated by phosphorylation of Ire1 (e.g. Ire1α) is a compound that reduces the severity of one or more symptoms of a disease associated with Ire1 (e.g. Ire1α) or Ire1 (e.g. Ire1α) pathway (e.g. disease associated with an increase in the level of Ire1 (e.g. Ire1α) activity or protein or Ire1 (e.g. Ire1α) pathway activity or protein or Ire1 (e.g. Ire1α) phosphorylation or pathway activated by Ire1 (e.g. Ire1α) phosphorylation, for example cancer (e.g. multiple myeloma, or cancers of secretory cells), neurodegenerative diseases, demyelinating diseases, eye diseases, fibrotic diseases, or diabetes) or a disease that is not caused by Ire1 (e.g. Ire1α) or Ire1 (e.g. Ire1α) pathway but may benefit from modulation of Ire1 (e.g. Ire1α) or Ire1 (e.g. Ire1α) pathway activity (e.g. decreasing in level or level of activity of Ire1 (e.g. Ire1α) or Ire1 (e.g. Ire1α) pathway). In embodiments, a modulator of Ire1 (e.g. Ire1α) or Ire1 (e.g. Ire1α) pathway (e.g. phosphorylated Ire1 (e.g. Ire1α) or phosphorylated Ire1 (e.g. Ire1α) pathway) is an anti-cancer agent. In embodiments, a modulator of Ire1 (e.g. Ire1α) or Ire1 (e.g. Ire1α) pathway (e.g phosphorylated Ire1 (e.g. Ire1α) or phosphorylated Ire1 (e.g. Ire1α) pathway) is a neuroprotectant. In embodiments, a modulator of Ire1 (e.g. Ire1α) or Ire1 (e.g. Ire1α) pathway (e.g. phosphorylated Ire1 (e.g. Ire1α) or phosphorylated Ire1 (e.g. Ire1α) pathway) is an anti-demyelinating agent. In embodiments, a modulator of Ire1 (e.g. Ire1α) or Ire1 (e.g. Ire1α) pathway is a memory enhancing agent. In embodiments, a modulator of Ire1 (e.g. Ire1α) or Ire1 (e.g. Ire1α) pathway (e.g. phosphorylated Ire1 (e.g. Ire1α) or phosphorylated Ire1 (e.g. Ire1α) pathway) is an anti-diabetic agent.

In embodiments, a modulator of Ire1 (e.g. Ire1α) or Ire1 (e.g. Ire1α) pathway (e.g. phosphorylated Ire1 (e.g. Ire1α) or phosphorylated Ire1 (e.g. Ire1α) pathway) is an anti-eye disease agent. In embodiments, a modulator of Ire1 (e.g. Ire1α) or Ire1 (e.g. Ire1α) pathway (e.g. phosphorylated Ire1 (e.g. Ire1α) or phosphorylated Ire1 (e.g. Ire1α) pathway) is an anti-fibrosis agent.

"Patient" or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In some embodiments, a patient is human. In some embodiments, a patient is an ape. In some embodiments, a patient is a monkey. In some embodiments, a patient is a mouse. In some embodiments, a patient is an experimental animal. In some embodiments, a patient is a rat. In some embodiments, a patient is a test animal. In some embodiments, a patient is a newborn animal. In some embodiments, a patient is a newborn human. In some embodiments, a patient is a juvenile animal. In some embodiments, a patient is a juvenile human. In some embodiments, a patient is a newborn mammal. In some embodiments, a patient is an elderly animal. In some embodiments, a patient is an elderly human. In some embodiments, a patient is an elderly mammal. In some embodiments, a patient is a geriatric patient.

"Disease" or "condition" refer to a state of being or health status of a patient or subject capable of being treated with a compound, pharmaceutical composition, or method provided herein. In some embodiments, the disease is a disease related to (e.g. caused by) an increase in the level of Ire1 (e.g. Ire1α), Ire1 (e.g. Ire1α) phosphorylation, Ire1 (e.g. Ire1α) RNase activity, or Ire1 (e.g. Ire1α) pathway activity, or pathway activated by phosphorylation of Ire1 (e.g. Ire1α). In some embodiments, the disease is a disease related to (e.g. caused by) neurodegeneration. In some embodiments, the disease is a disease related to (e.g. caused by) neural cell death. In some embodiments, the disease is a disease related to (e.g. caused by) cell death. In some embodiments, the disease is a disease related to (e.g. caused by) pancreatic cell death. In some embodiments, the disease is a disease related to (e.g. caused by) insulin-producing cell death. In some embodiments, the disease is a disease related to (e.g. caused by) loss of myelin. In some embodiments, the disease is a disease related to (e.g. caused by) reduction in myelin. In some embodiments, the disease is a disease related to (e.g. caused by) an increase in the level of Ire1 (e.g. Ire1α) activity (e.g. RNase activity), Ire1 (e.g. Ire1α) phosphorylation, Ire1 (e.g. Ire1α) pathway activity, or phosphorylated Ire1 (e.g. Ire1α) pathway activity. In some embodiments, the disease is cancer (e.g. multiple myeloma or cancers of secretory cells). In some embodiments, the disease is a neurodegenerative disease. In some embodiments, the disease is a demyelinating disease. In some embodiments, the disease is diabetes. In some embodiments, the disease is an interstitial lung disease (ILD). In some embodiments, the disease is idiopathic pulmonary fibrosis (IPF). In some embodiments, the disease is a fibrotic disease. In some embodiments, the disease is an eye disease (e.g., disease causing vision impairment).

Examples of diseases, disorders, or conditions include, but are not limited to, cancer (e.g. multiple myeloma or cancers of secretory cells), neurodegenerative diseases, demyelinating diseases, eye diseases, fibrotic diseases, and diabetes. In some instances, "disease" or "condition" refers to cancer. In some further instances, "cancer" refers to human cancers and carcinomas, sarcomas, adenocarcinomas, lymphomas, leukemias, melanomas, etc., including solid and lymphoid cancers, kidney, breast, lung, bladder, colon, ovarian, prostate, pancreas, stomach, brain, head and neck, skin, uterine, testicular, glioma, esophagus, liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), and/or multiple myeloma.

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include multiple myeloma, blood cancers, lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, or melanoma. Additional examples include, cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the term "neurodegenerative disease" refers to a disease or condition in which the function of a subject's nervous system becomes impaired (e.g. relative to a control subject who does not have the neurodegenerative disease). Examples of neurodegenerative diseases that may be treated with a compound, pharmaceutical composition, or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Strussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoff's disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, Wolfram Syndrome, transverse myelitis, Charcot-Marie-Tooth (CMT) disease, or Tabes dorsalis. Examples of neurodegenerative diseases that may be treated with a compound, pharmaceutical composition, or method described herein include retinitis pigmentosa, amyotrophic lateral sclerosis, retinal degeneration, macular degeneration, Parkinson's Disease, Alzheimer Disease, Huntington's Disease, Prion Disease, Creutzfeldt-Jakob Disease, or Kuru.

As used herein, the term "demyelinating disease" refers to a disease or condition is which the myelin sheath of a subject's neurons is or becomes impaired (e.g. relative to a control subject who does not have the demyelinating disease). Examples of demyelinating disease that may be treated with a compound, pharmaceutical composition, or method described herein include Wolfram Syndrome, Pelizaeus-Merzbacher Disease, Transverse Myelitis, Charcot-Marie-Tooth Disease, and Multiple Sclerosis.

As used herein, the term "diabetes" or "diabetes mellitus" refers to a disease or condition is which a subject has high blood sugar. Examples of diabetes that may be treated with a compound, pharmaceutical composition, or method described herein include type I diabetes (type I diabetes mellitus), which is characterized by the subject's failure to produce insulin or failure to produce sufficient insulin for the subject's metabolic needs; type II diabetes (type II diabetes mellitus), which is characterized by insulin resistance (i.e. the failure of the subject (e.g. subject's cells) to use insulin properly; and gestational diabetes, which is high blood sugar during pregnancy. In embodiments, diabetes is type I diabetes. In embodiments, diabetes is type II diabetes. In embodiments, diabetes is gestational diabetes. In embodiments, diabetes is a disease or condition in which a subject has high blood sugar as determined by an A1C test (e.g. 6.5% or greater), fasting plasma glucose test (e.g. 126 mg/dL or greater), or oral glucose tolerance test (e.g. 200 mg/dL or greater). In embodiments, the diabetes is associated with Wolfram Syndrome.

As used herein, the term "eye disease" or "disease causing vision impairment" refers to a disease or condition is which the function of a subject's eye or eyes is impaired (e.g. relative to a subject without the disease). Examples of eye diseases that may be treated with a compound, pharmaceutical composition, or method described herein include retinitis pigmentosa, retinal degeneration, macular degeneration, and Wolfram Syndrome.

As used herein, the term "fibrosis" refers to the formation of excess fibrous connective tissue. The term "fibrotic disease" refers to a disease or condition caused by aberrant fibrosis or a disease or condition in which a symptom is aberrant fibrosis (e.g. relative to a control subject without the disease). Examples of fibrotic diseases that may be treated with a compound, pharmaceutical composition, or method described herein include idiopathic pulmonary fibrosis (IPF), myocardial infarction, cardiac hypertrophy, heart failure, cirrhosis, acetaminophen (Tylenol) liver toxicity, hepatitis C liver disease, hepatosteatosis (fatty liver disease), and hepatic fibrosis.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, mannitol, gum acacia, calcium phosphate, alginates, tragacanth, calcium silicate, microcrystalline cellulose, cellulose, syrup, and methyl cellulose, colors, and the like. The formulations can additionally include: lubricating agents such as talc, magnesium stearate, and mineral oil; wetting agents; emulsifying and suspending agents; preserving agents such as methyl and propylhydroxy benzoates; sweetening agents; and flavoring agents. The compositions described herein can be formulated so as to provide quick, sustained or delayed release of the active ingredient after administration to the patient by employing procedures known in the art. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means administration by any route, including systemic, local, oral administration, administration as a suppository, topical contact, intravenous, parenteral, intraperitoneal, intramuscular, intralesional, intrathecal, intracranial, intranasal or subcutaneous administration, topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), transmucosal (e.g., buccal, sublingual, palatal, gingival, nasal, vaginal, rectal, or transdermal), ocular, or the implantation of a slow-release device, e.g., a mini-osmotic pump, to a subject. Parenteral administration includes, e.g., intravenous, intraarterial, intramuscular, intra-arteriole, intradermal, subcutaneous, intraperitoneal, intrathecal, intraventricular, and intracranial. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Methods for ocular delivery can include topical administration (eye drops), subconjunctival, periocular or intravitreal injection or introduction by balloon catheter or ophthalmic inserts surgically placed in the conjunctival sac. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent, chemotherapeutic, treatment for an eye disease, treatment for fibrosis, treatment for a demyelinating disease, diabetes treatment, or treatment for a neurodegenerative disease). The compound of the invention can be administered alone or can be coadministered to the patient. The compositions (e.g. compounds) described herein can also be formulated in combination with one or more additional active ingredients which can include any pharmaceutical agent such as anti viral agents, vaccines, antibodies, immune enhancers, immune suppressants, anti inflammatory agents and the like. Coadministration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g. Ire1 (e.g. Ire1 α) or component of Ire1 (e.g. Ire1 α) signal transduction pathway or component of phosphorylated Ire1 (e.g. Ire1 α) pathway), and/or reducing, eliminating, or slowing the progression of disease symptoms (e.g. symptoms of cancer (e.g. multiple myeloma or cancers of secretory cells), neurodegenerative diseases, demyelinating diseases, eye diseases, fibrotic diseases, or diabetes). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer (e.g. multiple myeloma or cancers of secretory cells), neurodegenerative diseases, demyelinating diseases, eye diseases, fibrotic diseases, or diabetes), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer (e.g. multiple myeloma or cancers of secretory cells), neurodegenerative diseases, demyelinating diseases, eye diseases, fibrotic diseases, or diabetes, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer (e.g. multiple myeloma or cancers of secretory cells), neurodegenerative diseases, demyelinating diseases, or diabetes, such as surgery.

The term "Ire1" or "Ire1α" or "ERN1" refers to the protein "Serine/threonine-protein kinase/endoribonuclease IRE1" a.k.a. "Endoplasmic reticulum to nucleus signaling 1". In embodiments, "Ire1" or "Ire1α" or "ERN1" refers to the human protein. Included in the term "Ire1" or "Ire1α" or "ERN1" are the wildtype and mutant forms of the protein. In embodiments, "Ire1" or "Ire1α" or "ERN1" refers to the protein associated with Entrez Gene 2081, OMIM 604033, UniProt O75460, and/or RefSeq (protein) NM 001433. In embodiments, the reference numbers immediately above refer to the protein, and associated nucleic acids, known as of the date of filing of this application. In embodiments, "Ire1" or "Ire1α" or "ERN1" refers to the wildtype human protein. In embodiments, "Ire1" or "Ire1α" or "ERN1" refers to the wildtype human nucleic acid.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK inhibitors, alkylating agents, antimetabolites, plant alkaloids, topoisomerase inhibitors, antitumor antibiotics, platinum-based compounds, adrenocortical suppressants, epipodophyllotoxins, antibiotics, enzymes, inhibitors of mitogen-activated protein kinase signaling, antibodies, doxorubicin, vincristine, etoposide, gemcitabine, imatinib (Gleevec®), agents that arrest cells in the G2-M phases and/or modulate the formation or stability of microtubules (e.g. Taxol™ (i.e. paclitaxel), steroids, aromatase inhibitors, gonadotropin-releasing hormone agonists (GnRH), adrenocorticosteroids, progestins, estrogens, antiestrogens, androgens, antiandrogens, immunotoxins, radioimmunotherapy, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the compounds described herein can be co-administered with conventional immunotherapeutic agents including, but not limited to, immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

"Anti-diabetic agent" or "antidiabetic agent" is used in accordance with its plain ordinary meaning and refers to a composition (e.g. compound, drug, antagonist, inhibitor, modulator) having the ability to lower blood glucose levels in a subject. In some embodiments, an anti-diabetic agent is an agent identified herein having utility in methods of treating diabetes. In some embodiments, an anti-diabetic agent is an agent approved by the FDA or similar regulatory agency of a country other than the USA, for treating diabetes. Examples of anti-diabetic agents include, but are not limited to, insulin, insulin sensitizers (e.g. biguanides (e.g. metformin, phenformin, or buformin), thiazolidinediones (e.g. rosiglitazone, pioglitazone, troglitazone)), secretagogues (e.g. sulfonylureas (e.g. tolbutamide, acetohexamide, tolazamide, chlorpropamide, glipizide, glyburide, glibenclamide, glimepiride, gliclazide, glycopyramide, gliquidone), meglitinides (e.g. repaglinide, nateglinide)), alpha-glucosidase inhibitors (e.g. miglitol, acarbose, voglibose), peptide analog antidiabetic agents (e.g. incretins (glucagon-like peptide-1, gastric inhibitory peptide), glucagon-like peptide agonists (e.g. exenatide, liraglutide, taspoglutide), gastric inhibitoty peptide analogs, or dipeptidyl peptidase-4 inhibitors (e.g. vildagliptin, sitagliptin, saxagliptin, linagliptin, allogliptin, septagliptin), amylin agonist analogues (e.g. pramlintide).

B. COMPOSITIONS

In an aspect is provided a compound, or a pharmaceutically acceptable salt thereof, having the formula:

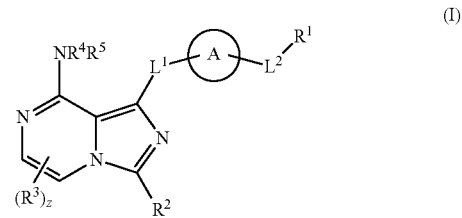

(I)

wherein, ring A is substituted or unsubstituted cycloalkylene, substituted or unsubstituted heterocycloalkylene, substituted or unsubstituted arylene, or substituted or unsubstituted heteroarylene; $L^1$ is a bond or unsubstituted $C_1$-$C_5$ alkylene; $L^2$ is a bond, —NR$^{6a}$—, —O—, —S—, —C(O)—,
—S(O)—, —S(O)$_2$—, —NR$^{6a}$C(O)—, —C(O)(CH$_2$)$_{z2}$—, —C(O)NR$^{6b}$—, —NR$^{6a}$C(O)O—,
—NR$^{6a}$C(O)NR$^{6b}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^1$ is hydrogen, oxo, halogen, —CX$_3$, —CN, —SO$_2$Cl, —SO$_n$R$^{19}$, —SO$_v$NR$^7$R$^8$, —NHNH$_2$, —ONR$^7$R$^8$, —NHC═(O)NHNH$_2$, —NHC═(O)NR$^7$R$^8$, —N(O)$_m$, —NR$^7$R$^8$, —C(O)R$^9$, —C(O)—OR$^9$, —C(O)NR$^7$R$^8$, —OR$^{10}$, —NR$^7$SO$_n$R$^{10}$, —NR$^7$C═(O)R$^9$, —NR$^7$C(O)OR$^9$, —NR$^7$OR$^9$, —OCX$_3$, —OCHX$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^2$ is hydrogen, oxo, halogen, —CX$^a$$_3$, —CN, —SO$_2$Cl, —SO$_{n1}$R$^{10a}$, —SO$_{v1}$NR$^{7a}$R$^{8a}$, —NHNH$_2$, —ONR$^{7a}$R$^{8a}$, —NHC═(O)NHNH$_2$, —NHC═(O)NR$^{7a}$R$^{8a}$, —N(O)$_{m1}$, —NR$^{7a}$R$^{8a}$, —C(O)R$^{9a}$, —C(O)OR$^{9a}$, —C(O)NR$^{7a}$R$^{8a}$, —OR$^{10a}$, —NR$^{7a}$SO$_{n1}$R$^{10a}$, —NR$^{7a}$C═(O)R$^{9a}$, —NR$^{7a}$C(O)OR$^{9a}$, —NR$^{7a}$OR$^{9a}$, —OCX$^a$$_3$, —OCHX$^a$$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^3$ is independently hydrogen, oxo, halogen, —CX$^b$$_3$, —CN, —SO$_2$Cl, —SO$_2$R$^{10b}$, —SO$_{v2}$NR$^{7b}$R$^{8b}$, —NHNH$_2$, —ONR$^{7b}$R$^{8b}$, —NHC═(O)NHNH$_2$, —NHC═(O)NR$^{7b}$R$^{8b}$, —N(O)$_{m2}$, —NR$^{7b}$R$^{8b}$, —C(O)R$^{9b}$, —C(O)—OR$^{9b}$, —C(O)NR$^{7b}$R$^{8b}$, —OR$^{10b}$, —NR$^{7b}$SO$_{n2}$R$^{10b}$, —NR$^{7b}$C═(O)R$^{9b}$, —NR$^{7b}$C(O)OR$^{9b}$, —NR$^{7b}$OR$^{9b}$, —OCX$^b$$_3$, —OCHX$^b$$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^4$ and R$^5$ are independently hydrogen or unsubstituted C$_1$-C$_6$ alkyl; R$^7$, R$^8$, R$^9$, R$^{10}$, R$^{6a}$, R$^{7a}$, R$^{8a}$, R$^{9a}$, R$^{10a}$, R$^{6b}$, R$^{7b}$, R$^{8b}$, R$^{9b}$ and R$^{10b}$ are independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, ONH$_2$, —NHC═(O)NHNH$_2$, —NHC═(O)NH$_2$, —NHSO$_2$H, —NHC═(O)H, —NHC(O)OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^7$ and R$^8$ substituents bonded to the same nitrogen atom may optionally be joined to form a substituted or unsubstituted heterocycloalkyl or substituted or unsubstituted heteroaryl; R$^{7a}$ and R$^{8a}$ substituents bonded to the same nitrogen atom may optionally be joined to form a substituted or unsubstituted heterocycloalkyl or substituted or unsubstituted heteroaryl; R$^{7b}$ and R$^{8b}$ substituents bonded to the same nitrogen atom may optionally be joined to form a substituted or unsubstituted heterocycloalkyl or substituted or unsubstituted heteroaryl; each occurrence of the symbols n, n1, and n2 is independently an integer from 0 to 4; each occurrence of the symbols m, m1, m2, v, v1, and v2 is independently an integer from 1 to 2; the symbol z is an integer from 0 to 2; the symbol z2 is an integer from 1 to 4; and each occurrence of the symbols X, X$^a$, and X$^b$ is independently a halogen.

In embodiments, ring A is substituted or unsubstituted monocyclic cycloalkylene, substituted or unsubstituted monocyclic heterocycloalkylene, substituted or unsubstituted monocyclic arylene, or substituted or unsubstituted monocyclic heteroarylene. In embodiments, ring A is substituted monocyclic cycloalkylene, substituted monocyclic heterocycloalkylene, substituted monocyclic arylene, or substituted monocyclic heteroarylene. In embodiments, ring A is unsubstituted monocyclic cycloalkylene, unsubstituted monocyclic heterocycloalkylene, unsubstituted monocyclic arylene, or unsubstituted monocyclic heteroarylene.

In embodiments, ring A is substituted or unsubstituted C$_3$-C$_8$ cycloalkylene, substituted or unsubstituted 3 to 8 membered heterocycloalkylene, substituted or unsubstituted C$_6$-C$_{10}$ arylene, or substituted or unsubstituted 5 to 10 membered heteroarylene. In embodiments, ring A is substituted C$_3$-C$_8$ cycloalkylene, substituted 3 to 8 membered heterocycloalkylene, substituted C$_6$-C$_{10}$ arylene, or substituted 5 to 10 membered heteroarylene. In embodiments, ring A is unsubstituted C$_3$-C$_8$ cycloalkylene, unsubstituted 3 to 8 membered heterocycloalkylene, unsubstituted C$_6$-C$_{10}$ arylene, or unsubstituted 5 to 10 membered heteroarylene. In embodiments, ring A is substituted or unsubstituted C$_3$-C$_6$ cycloalkylene, substituted or unsubstituted 3 to 6 membered heterocycloalkylene, substituted or unsubstituted C$_6$-C$_{10}$ arylene, or substituted or unsubstituted 5 to 9 membered heteroarylene. In embodiments, ring A is substituted C$_3$-C$_6$ cycloalkylene, substituted 3 to 6 membered heterocycloalkylene, substituted C$_6$-C$_{10}$ arylene, or substituted 5 to 9 membered heteroarylene. In embodiments, ring A is unsubstituted C$_3$-C$_6$ cycloalkylene, unsubstituted 3 to 6 membered heterocycloalkylene, unsubstituted C$_6$-C$_{10}$ arylene, or unsubstituted 5 to 9 membered heteroarylene.

In embodiments, ring A is substituted or unsubstituted arylene or substituted or unsubstituted heteroarylene. In embodiments, ring A is substituted or unsubstituted C$_6$-C$_{10}$ arylene. In embodiments, ring A is unsubstituted naphthalenyl (i.e. divalent naphthalene moiety). In embodiments, ring A is substituted naphthalenyl. In embodiments, ring A is unsubstituted phenylene (divalent benzene moiety or benzene-di-yl). In embodiments, ring A is substituted phenylene (divalent benzene moiety or benzene-di-yl).

In embodiments, ring A is R$^{41}$-substituted or unsubstituted cycloalkylene, R$^{41}$-substituted or unsubstituted heterocycloalkylene, R$^{41}$-substituted or unsubstituted arylene, or R$^{41}$-substituted or unsubstituted heteroarylene. In embodiments, ring A is substituted with 1 to 6 optionally different R$^{41}$ substituents. In embodiments, ring A is substituted with 1 R$^{41}$ substituent. In embodiments, ring A is substituted with 2 optionally different R$^{41}$ substituents. In embodiments, ring A is substituted with 3 optionally different R$^{41}$ substituents. In embodiments, ring A is substituted with 4 optionally different R$^{41}$ substituents. In embodiments, ring A is substituted with 5 optionally different R$^{41}$ substituents. In embodiments, ring A is substituted with 6 optionally different R$^{41}$ substituents.

R$^{41}$ is independently oxo, halogen, —CF$_3$, —CN, —OH, —NH$_2$, —COOH, —CONH$_2$, —NO$_2$, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCF$_3$, —OCHF$_2$, R$^{42}$-substituted or unsubstituted alkyl, R$^{42}$-substituted or unsubstituted heteroalkyl, R$^{42}$-substituted or unsubstituted cycloalkyl, R$^{42}$-substituted or unsubstituted heterocycloalkyl, R$^{42}$-substituted or unsubstituted aryl, or R$^{42}$-substituted or unsubstituted heteroaryl. In embodiments, R$^{41}$ is —OCH$_3$.

R$^{42}$ is independently oxo, halogen, —CF$_3$, —CN, —OH, —NH$_2$, —COOH, —CONH$_2$, —NO$_2$, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCF$_3$, —OCHF$_2$, R$^{43}$-substituted or unsubstituted alkyl, R$^{43}$-substituted or unsubstituted heteroalkyl, R$^{43}$-substituted or unsubstituted cycloalkyl, R$^{43}$-substituted or unsubstituted heterocycloalkyl, $R^{43}$-substituted or unsubstituted aryl, or $R^{43}$-substituted or unsubstituted heteroaryl.

In embodiments, $R^1$ is hydrogen, oxo, halogen, —$CX_3$, —$SO_2Cl$, —$SO_nR^{10}$, —$SO_vNR^7R^8$, —$NHNH_2$, —$ONR^7R^8$, —NHC=(O)NHNH$_2$, —NHC=(O)NR$^7$R$^8$, —N(O)$_m$, —NR$^7$R$^8$, —C(O)R$^9$, —C(O)—OR$^9$, —C(O)NR$^7$R$^8$, —OR$^{10}$, —NR$^7$SO$_n$R$^{10}$, —NR$^7$C=(O)R$^9$, —NR$^7$C(O)OR$^9$, —NR$^7$OR$^9$, —OCX$_3$, or —OCHX$_2$.

In embodiments, $R^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^1$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^1$ is hydrogen, substituted alkyl, substituted heteroalkyl, substituted cycloalkyl, substituted heterocycloalkyl, substituted aryl, or substituted heteroaryl. In embodiments, $R^1$ is hydrogen, unsubstituted alkyl, unsubstituted heteroalkyl, unsubstituted cycloalkyl, unsubstituted heterocycloalkyl, unsubstituted aryl, or unsubstituted heteroaryl. In embodiments, $R^1$ is hydrogen. In embodiments, $R^1$ is hydrogen and $L^2$ is —NHC(O)—.

In embodiments, $R^1$ is hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^1$ is hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 9 membered heteroaryl.

In embodiments, $R^1$ is substituted or unsubstituted cycloalkyl, substituted or unsubstituted heterocycloalkyl, substituted or unsubstituted aryl, or substituted or unsubstituted heteroaryl. In embodiments, $R^1$ is substituted or unsubstituted aryl or substituted or unsubstituted heteroaryl. In embodiments, $R^1$ is substituted phenyl. In embodiments, $R^1$ is unsubstituted phenyl. In embodiments, $R^1$ is phenyl substituted with —$CF_3$ or halogen. In embodiments, $R^1$ is phenyl meta-substituted with —$CF_3$. In embodiments, $R^1$ is phenyl meta-substituted with —F. In embodiments, $R^1$ is phenyl meta-substituted with —Cl. In embodiments, $R^1$ is phenyl meta-substituted with —Br. In embodiments, $R^1$ is phenyl meta-substituted with —I. In embodiments, $R^1$ is phenyl meta-substituted with —$CH_3$. In embodiments, $R^1$ is —OPh, —$CH_2Ph$, —$OCH_2Ph$, —NHC(O)H, or —CHO. In embodiments, $R^1$ is phenyl meta-substituted with —$CCl_3$. In embodiments, $R^1$ is phenyl para-substituted with —$CF_3$, —Cl, —$OCF_3$, —$CH_3$, —F, —$OCH_3$, —OPh, —$CH_2Ph$, or —CHO. In embodiments, $R^1$ is phenyl meta-substituted with —$CF_3$, —Cl, —$OCF_3$, —$CH_3$, —F, —$OCH_3$, —OPh, —$CH_2Ph$, or —CHO. In embodiments, $R^1$ is phenyl ortho-substituted with —$CF_3$, —Cl, —$OCF_3$, —$CH_3$, —F, —$OCH_3$, —OPh, —$CH_2Ph$, or —CHO. In embodiments, $R^1$ is aryl meta-substituted with —$CF_3$, —Cl, —$OCF_3$, —$CH_3$, —F, —$OCH_3$, —OPh, —$CH_2Ph$, or —CHO. In embodiments, $R^1$ is aryl ortho-substituted with —$CF_3$, —Cl, —$OCF_3$, —$CH_3$, —F, —$OCH_3$, —OPh, —$CH_2Ph$, or —CHO. In embodiments, $R^1$ is aryl para-substituted with —$CF_3$, —Cl, —$OCF_3$, —$CH_3$, —F, —$OCH_3$, —OPh, —$CH_2Ph$, or —CHO. In embodiments, $R^1$ is aryl substituted with —$CF_3$, —Cl, —$OCF_3$, —$CH_3$, —F, —$OCH_3$, —OPh, —$CH_2Ph$, or —CHO. In embodiments, $R^1$ is heteroaryl substituted with —$CF_3$, —Cl, —$OCF_3$, —$CH_3$, —F, —$OCH_3$, —OPh, —$CH_2Ph$, or —CHO. In embodiments, $R^1$ is phenyl substituted with —$CF_3$, —Cl, —$OCF_3$, —$CH_3$, —F, —$OCH_3$, —OPh, —$CH_2Ph$, or —CHO. In embodiments, $R^1$ is 5 to 6 membered heteroaryl substituted with —$CF_3$, —Cl, —$OCF_3$, —$CH_3$, —F, —$OCH_3$, —OPh, —$CH_2Ph$, or —CHO. In embodiments, $R^1$ is unsubstituted cyclohexyl. In embodiments, $R^1$ is substituted cyclohexyl. In embodiments, $R^1$ is unsubstituted cyclopenyl. In embodiments, $R^1$ is substituted cyclopenyl. In embodiments, $R^1$ is unsubstituted cyclobutyl. In embodiments, $R^1$ is substituted cyclobutyl. In embodiments, $R^1$ is unsubstituted cyclopropyl. In embodiments, $R^1$ is substituted cyclopropyl.

In embodiments, $R^1$ is a substituted or unsubstituted heteroaryl selected from the group consisting of pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, and quinolyl.

In some embodiments of the compounds provided herein, $R^1$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)NHNH$_2$, —NHC=(O)NH$_2$, —$NHSO_2H$, —NHC=(O)H, —NHC(O)—OH, —NHOH, —$OCF_3$, —$OCHF_2$, $R^{11}$-substituted or unsubstituted alkyl, $R^{11}$-substituted or unsubstituted heteroalkyl, $R^{11}$-substituted or unsubstituted cycloalkyl, $R^{11}$-substituted or unsubstituted heterocycloalkyl, $R^{11}$-substituted or unsubstituted aryl, or $R^{11}$-substituted or unsubstituted heteroaryl. In embodiments, $R^1$ is substituted with 1 to 6 optionally different $R^{11}$ substituents. In embodiments, $R^1$ is substituted with 1 $R^{11}$ substituent. In embodiments, $R^1$ is substituted with 2 optionally different $R^{11}$ substituents. In embodiments, $R^1$ is substituted with 3 optionally different $R^{11}$ substituents. In embodiments, $R^1$ is substituted with 4 optionally different $R^{11}$ substituents. In embodiments, $R^1$ is substituted with 5 optionally different $R^{11}$ substituents. In embodiments, $R^1$ is substituted with 6 optionally different $R^{11}$ substituents. In embodiments, $R^1$ is substituted with 7 optionally different $R^{11}$ substituents. In embodiments, $R^1$ is phenyl substituted with 1 to 5 optionally different $R^{11}$ substituents. In embodiments, $R^1$ is phenyl substituted with 1 $R^{11}$ substituent. In embodiments, $R^1$ is phenyl substituted with 2 optionally different $R^{11}$ substituents. In embodiments, $R^1$ is phenyl substituted with 3 optionally different $R^{11}$ substituents. In embodiments, $R^1$ is phenyl substituted with 4 optionally different $R^{11}$ substituents. In embodiments, $R^1$ is phenyl substituted with 5 optionally different $R^{11}$ substituents. In embodiments, $R^1$ is aryl substituted with 1 to 6 optionally different $R^{11}$ substituents. In embodiments, $R^1$ is aryl substituted with 1 $R^{11}$ substituent. In embodiments, $R^1$ is aryl substituted with 2 optionally different $R^{11}$ substituents. In embodiments, $R^1$ is aryl substituted with 3 optionally different $R^{11}$ substituents. In embodiments, $R^1$ is aryl substituted with 4 optionally different $R^{11}$ substituents. In embodiments, $R^1$ is aryl substituted with 5 optionally different $R^{11}$ substituents. In embodiments, $R^1$ is aryl substituted with 6 optionally different $R^{11}$ substituents. In embodiments, $R^1$ is aryl substituted with 7 optionally different $R^{11}$ substituents. In embodiments, $R^1$ is heteroaryl substituted with 1 to 6 optionally different $R^{11}$ substituents. In embodiments, $R^1$ is heteroaryl substituted with 1 $R^{11}$ substituent. In embodiments, $R^1$ is heteroaryl substituted with 2 optionally different $R^{11}$ substituents. In embodiments, $R^1$ is heteroaryl substituted with 3 optionally different $R^{11}$ substituents. In embodiments, $R^1$ is heteroaryl substituted with 4 optionally different $R^{11}$ substituents. In embodiments, $R^1$ is heteroaryl substituted with 5 optionally different $R^{11}$ substituents. In embodiments, $R^1$ is heteroaryl substituted with 6 optionally different $R^{11}$ substituents. In embodiments, $R^1$ is heteroaryl substituted with 7 optionally different $R^{11}$ substituents.

$R^{11}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl. In embodiments, $R^{11}$ is —$CCl_3$, —$CF_3$, —Cl, —$OCF_3$, —$CH_3$, —F, —$OCH_3$, —OPh, —$CH_2Ph$, or CHO.

$R^{12}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{13}$-substituted or unsubstituted alkyl, $R^{13}$-substituted or unsubstituted heteroalkyl, $R^{13}$-substituted or unsubstituted cycloalkyl, $R^{13}$-substituted or unsubstituted heterocycloalkyl, $R^{13}$-substituted or unsubstituted aryl, or $R^{13}$-substituted or unsubstituted heteroaryl.

In embodiments, $R^2$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^2$ is hydrogen, substituted alkyl, substituted heteroalkyl, substituted cycloalkyl, substituted heterocycloalkyl, substituted aryl, or substituted heteroaryl. In embodiments, $R^2$ is hydrogen, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^2$ is hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^2$ is hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 9 membered heteroaryl.

In embodiments, $R^2$ is substituted or unsubstituted alkyl. In embodiments, $R^2$ is substituted or unsubstituted $C_1$-$C_6$ alkyl. In embodiments, $R^2$ is unsubstituted $C_1$-$C_6$ alkyl. In embodiments, $R^2$ is unsubstituted methyl. In embodiments, $R^2$ is unsubstituted ethyl. In embodiments, $R^2$ is unsubstituted propyl (e.g. n-propyl or isopropyl). In embodiments, $R^2$ is unsubstituted isopropyl. In embodiments, $R^2$ is unsubstituted butyl (e.g. n-butyl, sec-butyl, isobutyl, or tert-butyl). In embodiments, $R^2$ is unsubstituted tert-butyl. In embodiments, $R^2$ is unsubstituted iso-butyl. In embodiments, $R^2$ is unsubstituted pentyl (e.g. n-pentyl, tert-pentyl, neopentyl, isopentyl, sec-pentyl, or 3-pentyl). In embodiments, $R^2$ is unsubstituted cyclopropyl. In embodiments, $R^2$ is unsubstituted cyclobutyl. In embodiments, $R^2$ is unsubstituted cyclopentyl. In embodiments, $R^2$ is unsubstituted cyclohexyl.

In some embodiments, $R^2$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{14}$-substituted or unsubstituted alkyl, $R^{14}$-substituted or unsubstituted heteroalkyl, $R^{14}$-substituted or unsubstituted cycloalkyl, $R^{14}$-substituted or unsubstituted heterocycloalkyl, $R^{14}$-substituted or unsubstituted aryl, or $R^{14}$-substituted or unsubstituted heteroaryl.

$R^{14}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{15}$-substituted or unsubstituted alkyl, $R^{15}$-substituted or unsubstituted heteroalkyl, $R^{15}$-substituted or unsubstituted cycloalkyl, $R^{15}$-substituted or unsubstituted heterocycloalkyl, $R^{15}$-substituted or unsubstituted aryl, or $R^{15}$-substituted or unsubstituted heteroaryl.

$R^1$, is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, or $R^{16}$-substituted or unsubstituted heteroaryl.

In embodiments, $R^3$ is independently hydrogen, oxo, halogen, —$CX^b_3$, —CN, —$SO_2Cl$, —$SO_n2R^{10b}$, —$SO_{v2}NR^{7b}R^{8b}$, —$NHNH_2$, —$ONR^{7b}R^{8b}$, —NHC=(O)$NHNH_2$, —NHC=(O)$NR^{7b}R^{8b}$, —$N(O)_{m2}$, —$NR^{7b}R^{8b}$, —C(O)$R^{9b}$, —C(O)—$OR^{9b}$, —C(O)$NR^{7b}R^{8b}$, —$OR^{10b}$, —$NR^{7b}SO_{n2}R^{10b}$, —$NR^{7b}C$=(O)$R^{9b}$, —$NR^{7b}C(O)OR^{9b}$, —$NR^{7b}OR^{9b}$, —$OCX^b_3$, or —$OCHX^b_2$. In embodiments, $R^3$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^3$ is independently hydrogen, substituted alkyl, substituted heteroalkyl, substituted cycloalkyl, substituted heterocycloalkyl, substituted aryl, or substituted heteroaryl. In embodiments, $R^3$ is independently hydrogen, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^3$ is independently hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^3$ is independently hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 9 membered heteroaryl.

In embodiments, $R^3$ is independently hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^3$ is independently hydrogen. In embodiments, $R^3$ is independently halogen.

In some embodiments, $R^3$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{17}$-substituted or unsubstituted alkyl, $R^{17}$-substituted or unsubstituted heteroalkyl, $R^{17}$-substituted or unsubstituted cycloalkyl, $R^{17}$-substituted or unsubstituted heterocycloalkyl, $R^{17}$-substituted or unsubstituted aryl, or $R^{17}$-substituted or unsubstituted heteroaryl.

$R^{17}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{18}$-substituted or unsubstituted alkyl, $R^{18}$-substituted or unsubstituted heteroalkyl, $R^{18}$-substituted or unsubstituted cycloalkyl, $R^{18}$-substituted or unsubstituted heterocycloalkyl, $R^{18}$-substituted or unsubstituted aryl, or $R^{18}$-substituted or unsubstituted heteroaryl.

$R^{18}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl.

In embodiments, $R^4$ and $R^5$ are independently hydrogen. In embodiments, $R^4$ and $R^5$ are independently unsubstituted $C_1$-$C_6$ alkyl. In embodiments, $R^4$ and $R^5$ are independently unsubstituted $C_1$-$C_5$ alkyl. In embodiments, $R^4$ and $R^5$ are independently unsubstituted $C_1$-$C_4$ alkyl. In embodiments, $R^4$ and $R^5$ are independently unsubstituted $C_1$-$C_3$ alkyl. In embodiments, $R^4$ and $R^5$ are independently unsubstituted $C_1$-$C_2$ alkyl. In embodiments, $R^4$ and $R^5$ are independently unsubstituted methyl.

In embodiments, $L^1$ is a bond. In embodiments, $L^1$ is unsubstituted $C_1$-$C_5$ alkylene. In embodiments, $L^1$ is unsubstituted $C_1$-$C_4$ alkylene. In embodiments, $L^1$ is unsubstituted $C_1$-$C_3$ alkylene. In embodiments, $L^1$ is unsubstituted $C_1$-$C_2$ alkylene. In embodiments, $L^1$ is unsubstituted methylene.

In embodiments, $L^2$ is a bond. In embodiments, $L^2$ is —$NR^{6a}$—. In embodiments, $L^2$ is —O—. In embodiments, $L^2$ is —S—. In embodiments, $L^2$ is C(O)—. In embodiments, $L^2$ is —S(O)—. In embodiments, $L^2$ is —$S(O)_2$—. In embodiments, $L^2$ is —$C(O)(CH_2)_{z2}$—. In embodiments, $L^2$ is —$NR^{6a}C(O)$—. In embodiments, $L^2$ is —$C(O)NR^{6b}$—. In embodiments, $L^2$ is —$NR^{6a}C(O)O$—. In embodiments, $L^2$ is —$NR^{6a}C(O)NR^{6b}$—. In embodiments, $L^2$ is —NH—. In embodiments, $L^2$ is —NHC(O)—. In embodiments, $L^2$ is —C(O)NH—. In embodiments, $L^2$ is —NHC(O)NH—. In embodiments, $L^2$ is —$NHC(O)OCH_2$—. In embodiments, $L^2$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^2$ is —$C(O)(CH_2)$—. In embodiments, $L^2$ is —$C(O)(CH_2)_2$—. In embodiments, $L^2$ is —$C(O)(CH_2)_3$—. In embodiments, $L^2$ is —$C(O)(CH_2)_4$—.

In embodiments, $L^2$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^2$ is substituted alkylene, substituted heteroalkylene, substituted cycloalkylene, substituted heterocycloalkylene, substituted arylene, or substituted heteroarylene. In embodiments, $L^2$ is unsubstituted alkylene, unsubstituted heteroalkylene, unsubstituted cycloalkylene, unsubstituted heterocycloalkylene, unsubstituted arylene, or unsubstituted heteroarylene.

In embodiments, $L^2$ is substituted or unsubstituted $C_1$-$C_8$ alkylene, substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^2$ is substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted $C_6$-$C_{10}$ arylene, or substituted or unsubstituted 5 to 9 membered heteroarylene.

In some embodiments, $L^2$ is independently $R^{44}$-substituted or unsubstituted alkylene, $R^{44}$-substituted or unsubstituted heteroalkylene, $R^{44}$-substituted or unsubstituted cycloalkylene, $R^{44}$-substituted or unsubstituted heterocycloalkylene, $R^{44}$-substituted or unsubstituted arylene, or $R^{44}$-substituted or unsubstituted heteroarylene.

$R^{44}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{45}$-substituted or unsubstituted alkyl, $R^{45}$-substituted or unsubstituted heteroalkyl, $R^{45}$-substituted or unsubstituted cycloalkyl, $R^{45}$-substituted or unsubstituted heterocycloalkyl, $R^{45}$-substituted or unsubstituted aryl, or $R^{45}$-substituted or unsubstituted heteroaryl.

$R^4$, is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{46}$-substituted or unsubstituted alkyl, $R^{46}$-substituted or unsubstituted heteroalkyl, $R^{46}$-substituted or unsubstituted cycloalkyl, $R^{46}$-substituted or unsubstituted heterocycloalkyl, $R^{46}$-substituted or unsubstituted aryl, or $R^{46}$-substituted or unsubstituted heteroaryl.

In embodiments, $R^{6a}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{6a}$ is hydrogen, substituted alkyl, substituted heteroalkyl, substituted cycloalkyl, substituted heterocycloalkyl, substituted aryl, or substituted heteroaryl. In embodiments, $R^{6a}$ is hydrogen, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{6a}$ is hydrogen. In embodiments, $R^{6a}$ is unsubstituted methyl. In embodiments, $R^{6a}$ is unsubstituted ethyl. In embodiments, $R^{6a}$ is unsubstituted propyl.

In embodiments, $R^{6a}$ is hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^{6a}$ is hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 9 membered heteroaryl.

In some embodiments of the compounds provided herein, $R^{6a}$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{26a}$-substituted or unsubstituted alkyl, $R^{26a}$-substituted or unsubstituted heteroalkyl, $R^{26a}$-substituted or unsubstituted cycloalkyl, $R^{26a}$-substituted or unsubstituted heterocycloalkyl, $R^{26a}$-substituted or unsubstituted aryl, or $R^{26a}$-substituted or unsubstituted heteroaryl.

$R^{26a}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{27a}$-substituted or unsubstituted alkyl, $R^{27a}$-substituted or unsubstituted heteroalkyl, $R^{27a}$-substituted or unsubstituted cycloalkyl, $R^{27a}$-substituted or unsubstituted heterocycloalkyl, $R^{27a}$-substituted or unsubstituted aryl, or $R^{27a}$-substituted or unsubstituted heteroaryl.

$R^{27a}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{28a}$-substituted or unsubstituted alkyl, $R^{28a}$-substituted or unsubstituted heteroalkyl, $R^{28a}$-substituted or unsubstituted cycloalkyl, $R^{28a}$-substituted or unsubstituted heterocycloalkyl, $R^{28a}$-substituted or unsubstituted aryl, or $R^{28a}$-substituted or unsubstituted heteroaryl.

In embodiments, $R^{6b}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{6b}$ is hydrogen, substituted alkyl, substituted heteroalkyl, substituted cycloalkyl, substituted heterocycloalkyl, substituted aryl, or substituted heteroaryl. In embodiments, $R^{6b}$ is hydrogen, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{6b}$ is hydrogen. In embodiments, $R^{6b}$ is unsubstituted methyl. In embodiments, $R^{6b}$ is unsubstituted ethyl. In embodiments, $R^{6b}$ is unsubstituted propyl.

In embodiments, $R^{6b}$ is hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^{6b}$ is hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 9 membered heteroaryl.

In some embodiments of the compounds provided herein, $R^{6b}$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{26b}$-substituted or unsubstituted alkyl, $R^{26b}$-substituted or unsubstituted heteroalkyl, $R^{26b}$-substituted or unsubstituted cycloalkyl, $R^{26b}$-substituted or unsubstituted heterocycloalkyl, $R^{26b}$-substituted or unsubstituted aryl, or $R^{26b}$-substituted or unsubstituted heteroaryl.

$R^{26b}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{27b}$-substituted or unsubstituted alkyl, $R^{27b}$-substituted or unsubstituted heteroalkyl, $R^{27b}$-substituted or unsubstituted cycloalkyl, $R^{27b}$-substituted or unsubstituted heterocycloalkyl, $R^{27b}$-substituted or unsubstituted aryl, or $R^{27b}$-substituted or unsubstituted heteroaryl.

$R^{27b}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{28b}$-substituted or unsubstituted alkyl, $R^{28b}$-substituted or unsubstituted heteroalkyl, $R^{28b}$-substituted or unsubstituted cycloalkyl, $R^{28b}$-substituted or unsubstituted heterocycloalkyl, $R^{28b}$-substituted or unsubstituted aryl, or $R^{28b}$-substituted or unsubstituted heteroaryl.

In embodiments, each $R^7$, $R^8$, $R^9$, $R^{10}$, $R^{7a}$, $R^{8a}$, $R^{9a}$, $R^{10a}$, $R^{7b}$, $R^{8b}$, $R^{9b}$ and $R^{10b}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, each $R^7$, $R^8$, $R^9$, $R^{10}$, $R^{7a}$, $R^{8a}$, $R^{9a}$, $R^{10a}$, $R^{7b}$, $R^{8b}$, $R^{9b}$, and $R^{10b}$ is independently hydrogen, substituted alkyl, substituted heteroalkyl, substituted cycloalkyl, substituted heterocycloalkyl, substituted aryl, or substituted heteroaryl. In embodiments, each $R^7$, $R^8$, $R^9$, $R^{10}$, $R^{7a}$, $R^{8a}$, $R^{9a}$, $R^{10a}$, $R^{7b}$, $R^{8b}$, $R^{9b}$ and $R^{10b}$ is independently hydrogen, unsubstituted alkyl, unsubstituted heteroalkyl, unsubstituted cycloalkyl, unsubstituted heterocycloalkyl, unsubstituted aryl, or unsubstituted heteroaryl. In embodiments, each $R^7$, $R^8$, $R^9$, $R^{10}$, $R^{7a}$, $R^{8a}$, $R^{9a}$, $R^{10a}$, $R^{7b}$, $R^{8b}$, $R^{9b}$ and $R^{10b}$ is independently hydrogen.

In embodiments, each $R^7$, $R^8$, $R^9$, $R^{10}$, $R^{7a}$, $R^{8a}$, $R^{9a}$, $R^{10a}$, $R^{7b}$, $R^{8b}$, $R^{9b}$ and $R^{10b}$ is independently hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, each $R^7$, $R^8$, $R^9$, $R^{10}$, $R^{7a}$, $R^{8a}$, $R^{9a}$, $R^{10a}$, $R^{7b}$, $R^{8b}$, $R^{9b}$ and $R^{10b}$ is independently hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 9 membered heteroaryl.

In some embodiments, $R^7$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl. In embodiments, $R^7$ and $R^8$ substituents bonded to the same nitrogen atom may be joined to form an $R^{29}$-substituted or unsubstituted heterocycloalkyl or $R^{29}$-substituted or unsubstituted heteroaryl.

$R^{29}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^N$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl.

$R^{30}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl.

In some embodiments, $R^{7a}$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{29a}$-substituted or unsubstituted alkyl, $R^{29a}$-substituted or unsubstituted heteroalkyl, $R^{29a}$-substituted or unsubstituted cycloalkyl, $R^{29a}$-substituted or unsubstituted heterocycloalkyl, $R^{29a}$-substituted or unsubstituted aryl, or $R^{29a}$-substituted or unsubstituted heteroaryl. In embodiments, $R^{7a}$ and $R^{8a}$ substituents bonded to the same nitrogen atom may be joined to form an $R^{29a}$-substituted or unsubstituted heterocycloalkyl or $R^{29a}$-substituted or unsubstituted heteroaryl.

$R^{29a}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{30a}$-substituted or unsubstituted alkyl, $R^{30a}$-substituted or unsubstituted heteroalkyl, $R^{30a}$-substituted or unsubstituted cycloalkyl, $R^{30a}$-substituted or unsubstituted heterocycloalkyl, $R^{30a}$-substituted or unsubstituted aryl, or $R^{30a}$-substituted or unsubstituted heteroaryl.

$R^{30a}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{31a}$-substituted or unsubstituted alkyl, $R^{31a}$-substituted or unsubstituted heteroalkyl, $R^{31a}$-substituted or unsubstituted cycloalkyl, $R^{31a}$-substituted or unsubstituted heterocycloalkyl, $R^{31a}$-substituted or unsubstituted aryl, or $R^{31a}$-substituted or unsubstituted heteroaryl.

In some embodiments, $R^{7b}$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{29b}$-substituted or unsubstituted alkyl, $R^{29b}$-substituted or unsubstituted heteroalkyl, $R^{29b}$-substituted or unsubstituted cycloalkyl, $R^{29b}$-substituted or unsubstituted heterocycloalkyl, $R^{29b}$-substituted or unsubstituted aryl, or $R^{29b}$-substituted or unsubstituted heteroaryl. In embodiments, $R^{7b}$ and $R^{8b}$ substituents bonded to the same nitrogen atom may be joined to form an $R^{29b}$-substituted or unsubstituted heterocycloalkyl or $R^{29b}$-substituted or unsubstituted heteroaryl.

$R^{29b}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{30b}$-substituted or unsubstituted alkyl, $R^{30b}$-substituted or unsubstituted heteroalkyl, $R^{30b}$-substituted or unsubstituted cycloalkyl, $R^{30b}$-substituted or unsubstituted heterocycloalkyl, $R^{30b}$-substituted or unsubstituted aryl, or $R^{30b}$-substituted or unsubstituted heteroaryl.

$R^{30b}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{31b}$-substituted or unsubstituted alkyl, $R^{31b}$-substituted or unsubstituted heteroalkyl, $R^{31b}$-substituted or unsubstituted cycloalkyl, $R^{31b}$-substituted or unsubstituted heterocycloalkyl, $R^{31b}$-substituted or unsubstituted aryl, or $R^{31b}$-substituted or unsubstituted heteroaryl.

In some embodiments, $R^8$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl. In embodiments, $R^7$ and $R^8$ substituents bonded to the same nitrogen atom may be joined to form an $R^{32}$-substituted or unsubstituted heterocycloalkyl or $R^{32}$-substituted or unsubstituted heteroaryl.

$R^{32}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl.

$R^{33}$ is independently oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl.

In some embodiments, $R^{8a}$ is independently hydrogen, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, $R^{32a}$-substituted or unsubstituted alkyl, $R^{32a}$-substituted or unsubstituted heteroalkyl, $R^{32a}$-substituted or unsubstituted cycloalkyl, $R^{32a}$-substituted or unsubstituted heterocycloalkyl, $R^{32a}$-substituted or unsubstituted aryl, or $R^{32a}$-substituted or unsubstituted heteroaryl. In embodiments, $R^{7a}$ and $R^{8a}$ substituents bonded to the same nitrogen atom may be joined to form an $R^{32a}$-substituted or unsubstituted heterocycloalkyl or $R^{32a}$-substituted or unsubstituted heteroaryl.

$R^{32a}$ is independently oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, $R^{33a}$-substituted or unsubstituted alkyl, $R^{33a}$-substituted or unsubstituted heteroalkyl, $R^{33a}$-substituted or unsubstituted cycloalkyl, $R^{33a}$-substituted or unsubstituted heterocycloalkyl, $R^{33a}$-substituted or unsubstituted aryl, or $R^{33a}$-substituted or unsubstituted heteroaryl.

$R^{33a}$ is independently oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, $R^{34a}$-substituted or unsubstituted alkyl, $R^{34a}$-substituted or unsubstituted heteroalkyl, $R^{34a}$-substituted or unsubstituted cycloalkyl, $R^{34a}$-substituted or unsubstituted heterocycloalkyl, $R^{34a}$-substituted or unsubstituted aryl, or $R^{34a}$-substituted or unsubstituted heteroaryl.

In some embodiments, $R^{8b}$ is independently hydrogen, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, $R^{32b}$-substituted or unsubstituted alkyl, $R^{32b}$-substituted or unsubstituted heteroalkyl, $R^{32b}$-substituted or unsubstituted cycloalkyl, $R^{32b}$-substituted or unsubstituted heterocycloalkyl, $R^{32b}$-substituted or unsubstituted aryl, or $R^{32b}$-substituted or unsubstituted heteroaryl. In embodiments, $R^{7b}$ and $R^{8b}$ substituents bonded to the same nitrogen atom may be joined to form an $R^{32b}$-substituted or unsubstituted heterocycloalkyl or $R^{32b}$-substituted or unsubstituted heteroaryl.

$R^{32b}$ is independently oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, $R^{33b}$-substituted or unsubstituted alkyl, $R^{33b}$-substituted or unsubstituted heteroalkyl, $R^{33b}$-substituted or unsubstituted cycloalkyl, $R^{33b}$-substituted or unsubstituted heterocycloalkyl, $R^{33b}$-substituted or unsubstituted aryl, or $R^{33b}$-substituted or unsubstituted heteroaryl.

$R^{33b}$ is independently oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, $R^{34b}$-substituted or unsubstituted alkyl, $R^{34b}$-substituted or unsubstituted heteroalkyl, $R^{34b}$-substituted or unsubstituted cycloalkyl, $R^{34b}$-substituted or unsubstituted heterocycloalkyl, $R^{34b}$-substituted or unsubstituted aryl, or $R^{34b}$-substituted or unsubstituted heteroaryl.

In some embodiments, $R^9$ is independently hydrogen, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, $R^{35}$-substituted or unsubstituted alkyl, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl.

$R^3$, is independently oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, $R^{36}$-substituted or unsubstituted alkyl, $R^{36}$-substituted or unsubstituted heteroalkyl, $R^{36}$-substituted or unsubstituted cycloalkyl, $R^{36}$-substituted or unsubstituted heterocycloalkyl, $R^{36}$-substituted or unsubstituted aryl, or $R^{36}$-substituted or unsubstituted heteroaryl.

$R^{36}$ is independently oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, $R^{37}$-substituted or unsubstituted alkyl, $R^{37}$-substituted or unsubstituted heteroalkyl, $R^{37}$-substituted or unsubstituted cycloalkyl, $R^{37}$-substituted or unsubstituted heterocycloalkyl, $R^{37}$-substituted or unsubstituted aryl, or $R^{37}$-substituted or unsubstituted heteroaryl.

In some embodiments, $R^{9a}$ is independently hydrogen, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, $R^{35a}$-substituted or unsubstituted alkyl, $R^{35a}$-substituted or unsubstituted heteroalkyl, $R^{35a}$-substituted or unsubstituted cycloalkyl, $R^{35a}$-substituted or unsubstituted heterocycloalkyl, $R^{35a}$-substituted or unsubstituted aryl, or $R^{35a}$-substituted or unsubstituted heteroaryl.

$R^{35a}$ is independently oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, $R^{36a}$-substituted or unsubstituted alkyl, $R^{36a}$-substituted or unsubstituted heteroalkyl, $R^{36a}$-substituted or unsubstituted cycloalkyl, $R^{36a}$-substituted or unsubstituted heterocycloalkyl, $R^{36a}$-substituted or unsubstituted aryl, or $R^{36a}$-substituted or unsubstituted heteroaryl.

$R^{36a}$ is independently oxo, halogen, $-CF_3$, $-CN$, $-OH$, $-NH_2$, $-COOH$, $-CONH_2$, $-NO_2$, $-SH$, $-SO_2Cl$, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{37a}$-substituted or unsubstituted alkyl, R$^{37a}$-substituted or unsubstituted heteroalkyl, R$^{37a}$-substituted or unsubstituted cycloalkyl, R$^{37a}$-substituted or unsubstituted heterocycloalkyl, R$^{37a}$-substituted or unsubstituted aryl, or R$^{37a}$-substituted or unsubstituted heteroaryl.

In some embodiments, R$^{9b}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{35b}$-substituted or unsubstituted alkyl, R$^{35b}$-substituted or unsubstituted heteroalkyl, R$^{35b}$-substituted or unsubstituted cycloalkyl, R$^{35b}$-substituted or unsubstituted heterocycloalkyl, R$^{35b}$-substituted or unsubstituted aryl, or R$^{35b}$-substituted or unsubstituted heteroaryl.

R$^{35b}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{36b}$-substituted or unsubstituted alkyl, R$^{36b}$-substituted or unsubstituted heteroalkyl, R$^{36b}$-substituted or unsubstituted cycloalkyl, R$^{36b}$-substituted or unsubstituted heterocycloalkyl, R$^{36b}$-substituted or unsubstituted aryl, or R$^{36b}$-substituted or unsubstituted heteroaryl.

R$^{36b}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{37b}$-substituted or unsubstituted alkyl, R$^{37b}$-substituted or unsubstituted heteroalkyl, R$^{37b}$-substituted or unsubstituted cycloalkyl, R$^{37b}$-substituted or unsubstituted heterocycloalkyl, R$^{37b}$-substituted or unsubstituted aryl, or R$^{37b}$-substituted or unsubstituted heteroaryl.

In some embodiments, R$^{10}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{38}$-substituted or unsubstituted alkyl, R$^{38}$-substituted or unsubstituted heteroalkyl, R$^{38}$-substituted or unsubstituted cycloalkyl, R$^{38}$-substituted or unsubstituted heterocycloalkyl, R$^{38}$-substituted or unsubstituted aryl, or R$^{38}$-substituted or unsubstituted heteroaryl.

R$^{38}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{39}$-substituted or unsubstituted alkyl, R$^{39}$-substituted or unsubstituted heteroalkyl, R$^{39}$-substituted or unsubstituted cycloalkyl, R$^{39}$-substituted or unsubstituted heterocycloalkyl, R$^{39}$-substituted or unsubstituted aryl, or R$^{39}$-substituted or unsubstituted heteroaryl.

R$^{39}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{40}$-substituted or unsubstituted alkyl, R$^{40}$-substituted or unsubstituted heteroalkyl, R$^{40}$-substituted or unsubstituted cycloalkyl, R$^{40}$-substituted or unsubstituted heterocycloalkyl, R$^{40}$-substituted or unsubstituted aryl, or R$^{40}$-substituted or unsubstituted heteroaryl.

In some embodiments, R$^{10a}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{38a}$-substituted or unsubstituted alkyl, R$^{38a}$-substituted or unsubstituted heteroalkyl, R$^{38a}$-substituted or unsubstituted cycloalkyl, R$^{38a}$-substituted or unsubstituted heterocycloalkyl, R$^{38a}$-substituted or unsubstituted aryl, or R$^{38a}$-substituted or unsubstituted heteroaryl.

R$^{38a}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{39a}$-substituted or unsubstituted alkyl, R$^{39a}$-substituted or unsubstituted heteroalkyl, R$^{39a}$-substituted or unsubstituted cycloalkyl, R$^{39a}$-substituted or unsubstituted heterocycloalkyl, R$^{39a}$-substituted or unsubstituted aryl, or R$^{39a}$-substituted or unsubstituted heteroaryl.

R$^{39a}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{40a}$-substituted or unsubstituted alkyl, R$^{40a}$-substituted or unsubstituted heteroalkyl, R$^{40a}$-substituted or unsubstituted cycloalkyl, R$^{40a}$-substituted or unsubstituted heterocycloalkyl, R$^{40a}$-substituted or unsubstituted aryl, or R$^{40a}$-substituted or unsubstituted heteroaryl.

In some embodiments, R$^{10b}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{38b}$-substituted or unsubstituted alkyl, R$^{38b}$-substituted or unsubstituted heteroalkyl, R$^{38b}$-substituted or unsubstituted cycloalkyl, R$^{38b}$-substituted or unsubstituted heterocycloalkyl, R$^{38b}$-substituted or unsubstituted aryl, or R$^{38b}$-substituted or unsubstituted heteroaryl.

R$^{38b}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{39b}$-substituted or unsubstituted alkyl, R$^{39b}$-substituted or unsubstituted heteroalkyl, R$^{39b}$-substituted or unsubstituted cycloalkyl, R$^{39b}$-substituted or unsubstituted heterocycloalkyl, R$^{39b}$-substituted or unsubstituted aryl, or R$^{39b}$-substituted or unsubstituted heteroaryl.

R$^{39b}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, R$^{40b}$-substituted or unsubstituted alkyl, R$^{40b}$-substituted or unsubstituted heteroalkyl, R$^{40b}$-substituted or unsubstituted cycloalkyl, R$^{40b}$-substituted or unsubstituted heterocycloalkyl, R$^{40b}$-substituted or unsubstituted aryl, or R$^{40b}$-substituted or unsubstituted heteroaryl.

In embodiments, v is 1. In embodiments, v is 2. In embodiments, v1 is 1. In embodiments, v1 is 2. In embodiments, v2 is 1. In embodiments, v2 is 2. In embodiments, m is 1. In embodiments, m is 2. In embodiments, m1 is 1. In embodiments, m1 is 2. In embodiments, m2 is 1. In embodiments, m2 is 2. In embodiments, n is independently 0. In embodiments, n is independently 1. In embodiments, n is independently 2. In embodiments, n is independently 3. In embodiments, n is independently 4. In embodiments, n1 is independently 0. In embodiments, n1 is independently 1. In embodiments, n1 is independently 2. In embodiments, n1 is independently 3. In embodiments, n1 is independently 4. In embodiments, n2 is independently 0. In embodiments, n2 is independently 1. In embodiments, n2 is independently 2. In embodiments, n2 is independently 3. In embodiments, n2 is independently 4. In embodiments, X is —Cl. In embodiments, X is —Br. In embodiments, X is —I. In embodiments, X is —F. In embodiments, $X^a$ is —Cl. In embodiments, $X^a$ is —Br. In embodiments, $X^a$ is —I. In embodiments, $X^a$ is —F. In embodiments, $X^b$ is —Cl. In embodiments, $X^b$ is —Br. In embodiments, $X^b$ is —I. In embodiments, $X^b$ is —F. In embodiments, z is 0. In embodiments, z is 1. In embodiments, z is 2. In embodiments, z2 is 1. In embodiments, z2 is 2. In embodiments, z2 is 3. In embodiments, z2 is 4.

In embodiments, the compound has the formula:

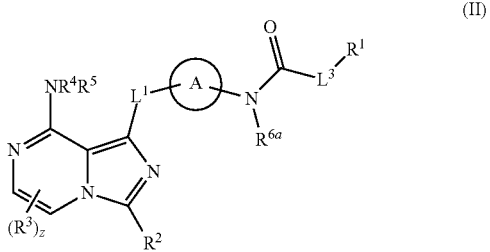

(II)

wherein, $R^1$, $R^2$, $R^3$, $R^4$, $R^5$, $R^{6a}$, $L^1$, ring A and z are as described herein (e.g. compounds of formula I, including embodiments).

$L^3$ is a bond, —O—, —$NR^{6b}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^3$ is a bond. In embodiments, $L^3$ is —$NR^{6b}$—, wherein $R^{6b}$ is as defined herein including embodiments thereof. In embodiments, $L^3$ is —NH—. In embodiments, $L^3$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^3$ is —O—. In embodiments, $L^3$ is $OCH_2$—.

In embodiments, $L^3$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^3$ is substituted alkylene, substituted heteroalkylene, substituted cycloalkylene, substituted heterocycloalkylene, substituted arylene, or substituted heteroarylene. In embodiments, $L^3$ is unsubstituted alkylene, unsubstituted heteroalkylene, unsubstituted cycloalkylene, unsubstituted heterocycloalkylene, unsubstituted arylene, or unsubstituted heteroarylene.

In embodiments, $L^3$ is substituted or unsubstituted $C_1$-$C_8$ alkylene, substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^3$ is substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted $C_6$-$C_{10}$ arylene, or substituted or unsubstituted 5 to 9 membered heteroarylene.

In some embodiments, $L^3$ is independently $R^{47}$-substituted or unsubstituted alkylene, $R^{47}$-substituted or unsubstituted heteroalkylene, $R^{47}$-substituted or unsubstituted cycloalkylene, $R^{47}$-substituted or unsubstituted heterocycloalkylene, $R^{47}$-substituted or unsubstituted arylene, or $R^{47}$-substituted or unsubstituted heteroarylene.

$R^{47}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{48}$-substituted or unsubstituted alkyl, $R^{48}$-substituted or unsubstituted heteroalkyl, $R^{48}$-substituted or unsubstituted cycloalkyl, $R^{48}$-substituted or unsubstituted heterocycloalkyl, $R^{48}$-substituted or unsubstituted aryl, or $R^{48}$-substituted or unsubstituted heteroaryl.

$R^{48}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^{49}$-substituted or unsubstituted alkyl, $R^{49}$-substituted or unsubstituted heteroalkyl, $R^{49}$-substituted or unsubstituted cycloalkyl, $R^{49}$-substituted or unsubstituted heterocycloalkyl, $R^{49}$-substituted or unsubstituted aryl, or $R^{49}$-substituted or unsubstituted heteroaryl.

Each $R^{13}$, $R^{16}$, $R^{19}$, $R^{28a}$, $R^{28b}$, $R^{31}$, $R^{31a}$, $R^{31b}$, $R^{34}$, $R^{34a}$, $R^{34b}$, $R^{37}$, $R^{37a}$, $R^{37b}$, $R^{40}$, $R^{40a}$, $R^{40b}$, $R^{43}$, $R^{46}$, and $R^{49}$ is independently a hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, each $R^{13}$, $R^{16}$, $R^{19}$, $R^{28a}$, $R^{28b}$, $R^{31}$, $R^{31a}$, $R^{31b}$, $R^{34}$, $R^{34a}$, $R^{34b}$, $R^{37}$, $R^{37a}$, $R^{37b}$, $R^{40}$, $R^{40a}$, $R^{40b}$, $R^{43}$, $R^{46}$, and $R^{49}$ is independently hydrogen, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl. In embodiments, each $R^{13}$, $R^{16}$, $R^{19}$, $R^{28a}$, $R^{28b}$, $R^{31}$, $R^{31a}$, $R^{31b}$, $R^{34}$, $R^{34a}$, $R^{34b}$, $R^{37}$, $R^{37a}$, $R^{37b}$, $R^{40}$, $R^{40a}$, $R^{40b}$, $R^{43}$, $R^{46}$, and $R^{49}$ is independently hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted $C_6$-$C_{10}$ aryl, or unsubstituted 5 to 9 membered heteroaryl. In embodiments, each $R^{13}$, $R^{16}$, $R^{19}$, $R^{28a}$, $R^{28b}$, $R^{31}$, $R^{31a}$, $R^{31b}$, $R^{34}$, $R^{34a}$, $R^{34b}$, $R^{37}$, $R^{37a}$, $R^{37b}$, $R^{40}$, $R^{40a}$, $R^{40b}$, $R^{43}$, $R^{46}$, and $R^{49}$ is hydrogen, oxo, halogen, —CF₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —OCF₃, or —OCHF₂.

In embodiments, the compound has the formula:

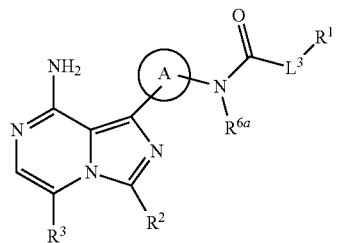

(III)

wherein, $R^1$, $R^2$, $R^3$, $R^{6a}$, $L^3$, and ring A are as described herein (e.g. compounds of formula I or II, including embodiments).

In embodiments, the compound is:

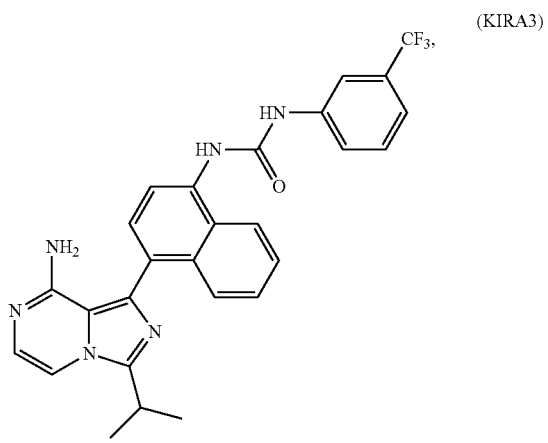

(KIRA3)

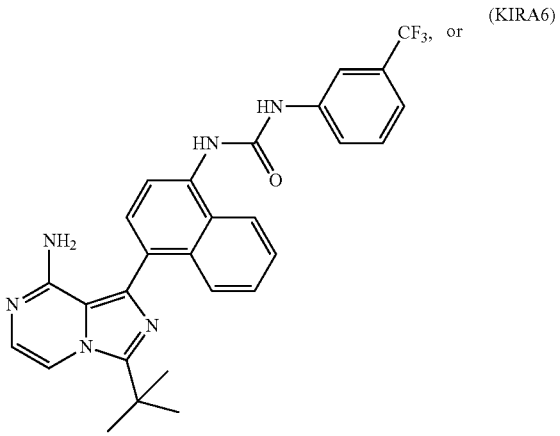

(KIRA6), or

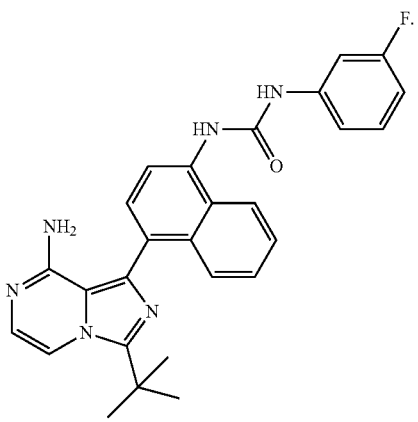

(KIRA7)

In embodiments, the compound is an inhibitor of Ire1. In embodiments, the compound is an inhibitor of Ire1α. In embodiments, the compound is an inhibitor of Ire1α kinase activity. In embodiments, the compound is an inhibitor of Ire1α RNase activity. In embodiments, the compound binds the ATP binding site of Ire1α. In embodiments, the compound binds Ire1α in the DFG-out conformation. In embodiments, the compound induces the DFG-out conformation of Ire1α. In embodiments, the compound is an inhibitor of Ire1α oligomerization. In embodiments, the compound is an inhibitor of Ire1α dimerization. In embodiments, the compound is an inhibitor of Ire1α phosphorylation. In embodiments, the compound is an inhibitor of Ire1α autophosphorylation. In embodiments, the compound is an inhibitor of apoptosis. In embodiments, the compound is an inhibitor of Ire1α induced apoptosis. In embodiments, the compound is an inhibitor of cell death. In embodiments, the compound is an inhibitor of Ire1α induced cell death. In embodiments, the compound is an inhibitor of a pathway induced by Ire1α phosphorylation. In embodiments, the compound is an inhibitor of a pathway induced by Ire1α kinase activity. In embodiments, the compound is an inhibitor of a pathway induced by Ire1α RNase activity. In embodiments, the compound is an inhibitor of neuronal cell death. In embodiments, the compound is a cytotoxic agent. In embodiments, the compound is an anti-cancer agent. In embodiments, the compound is an inhibitor of demyelination. In embodiments, the compound is an inhibitor of diabetes. In embodiments, the compound is an anti-diabetic agent. In embodiments, the compound is a neuroprotective agent. In embodiments, the compound is an inhibitor of fibrosis. In embodiments, the compound decreases apoptosis in cells under ER stress. In embodiments, the compound decreases apoptosis in cells under ER stress but not cells under the same conditions except that they are not under ER stress. In embodiments, the compound decreases apoptosis in cells under ER stress more than in cells under the same conditions except that they are not under ER stress. In embodiments, the compound decreases cleavage of miR-17. In embodiments, the compound decreases Ire1α associated cleavage of miR-17. In embodiments, the compound decreases cleavage of miR-34a. In embodiments, the compound decreases Ire1α associated cleavage of miR-34a. In embodiments, the compound decreases cleavage of miR-96. In embodiments, the compound decreases Ire1α associated cleavage of miR-96. In embodiments, the compound decreases cleavage of miR-125b. In embodiments, the compound decreases Ire1α associated cleavage of miR-125b. In embodiments, the compound decreases XBP1 mRNA splicing. In embodiments, the compound decreases Ire1α associated XBP1 mRNA splicing. In embodiments, the compound decreases the UPR. In embodiments, the compound decreases Ire1α associated UPR. In embodiments, the compound decreases the terminal UPR. In embodiments, the compound decreases Ire1α associated terminal UPR.

Figure 8:
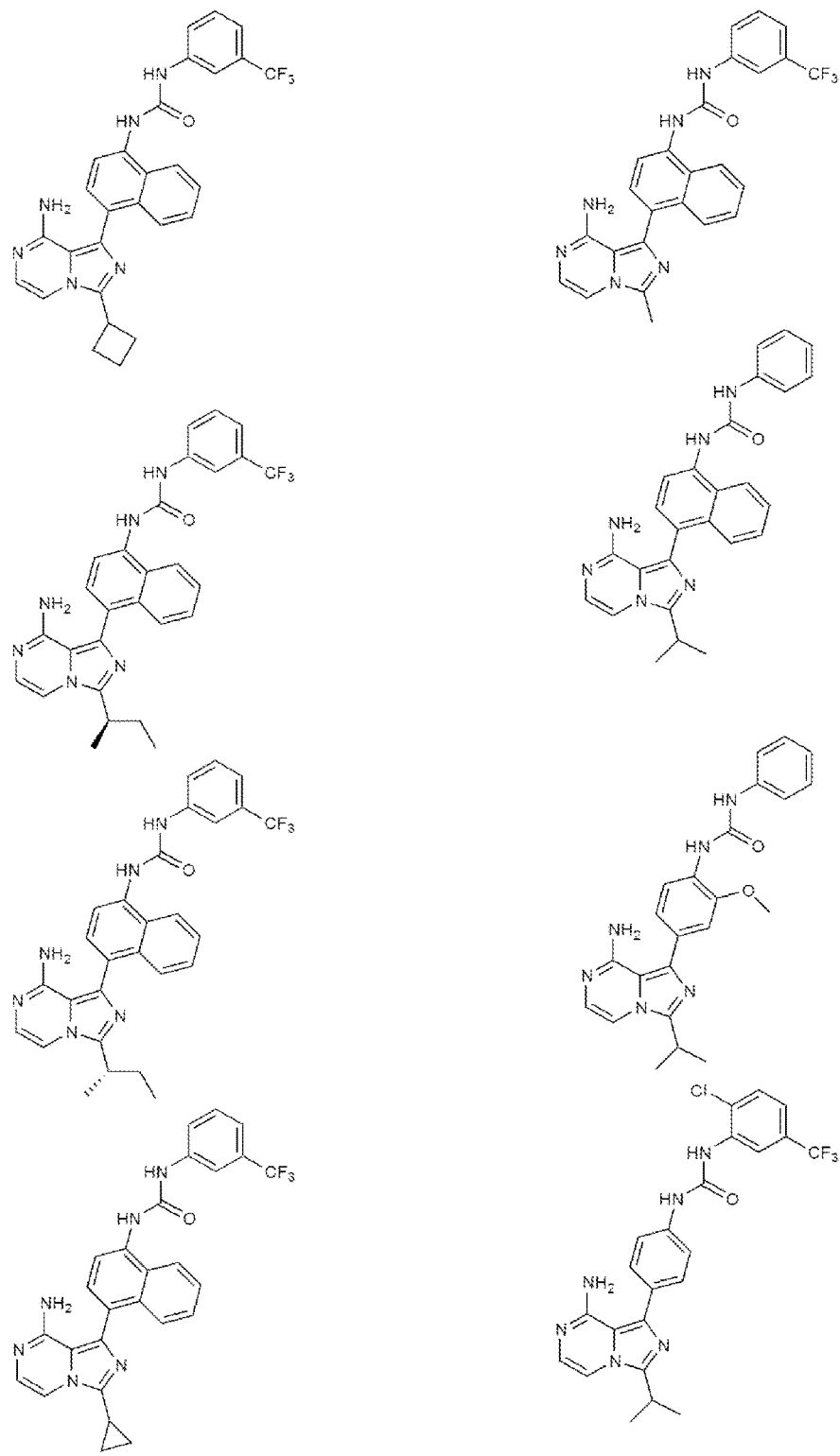
FIG. 8 illustrates analogs of GP146 that demonstrate the ability to modulate and/or inhibit IRE1α RNase activity.
Figure 8:
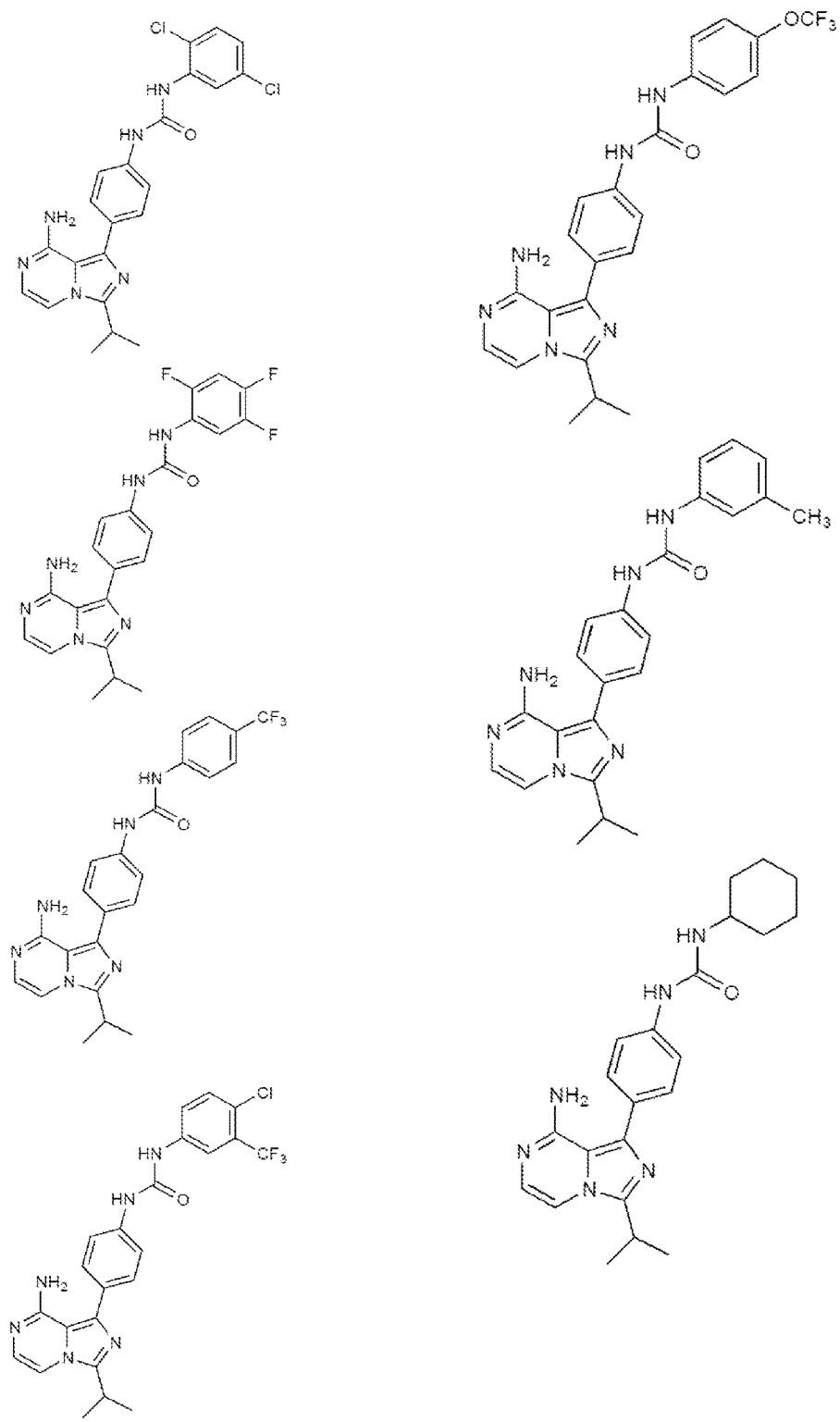
Figure 8:
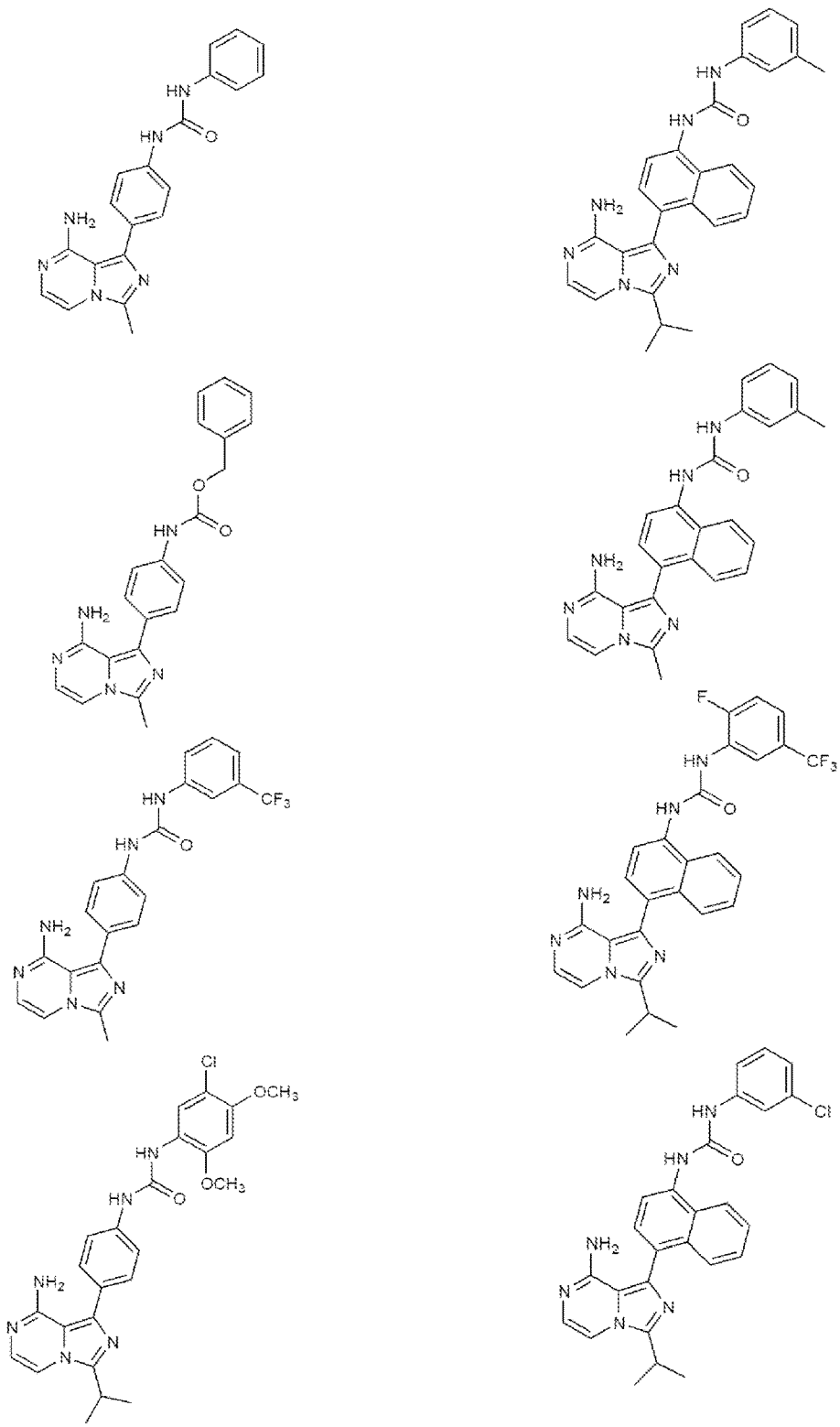
Figure 8:
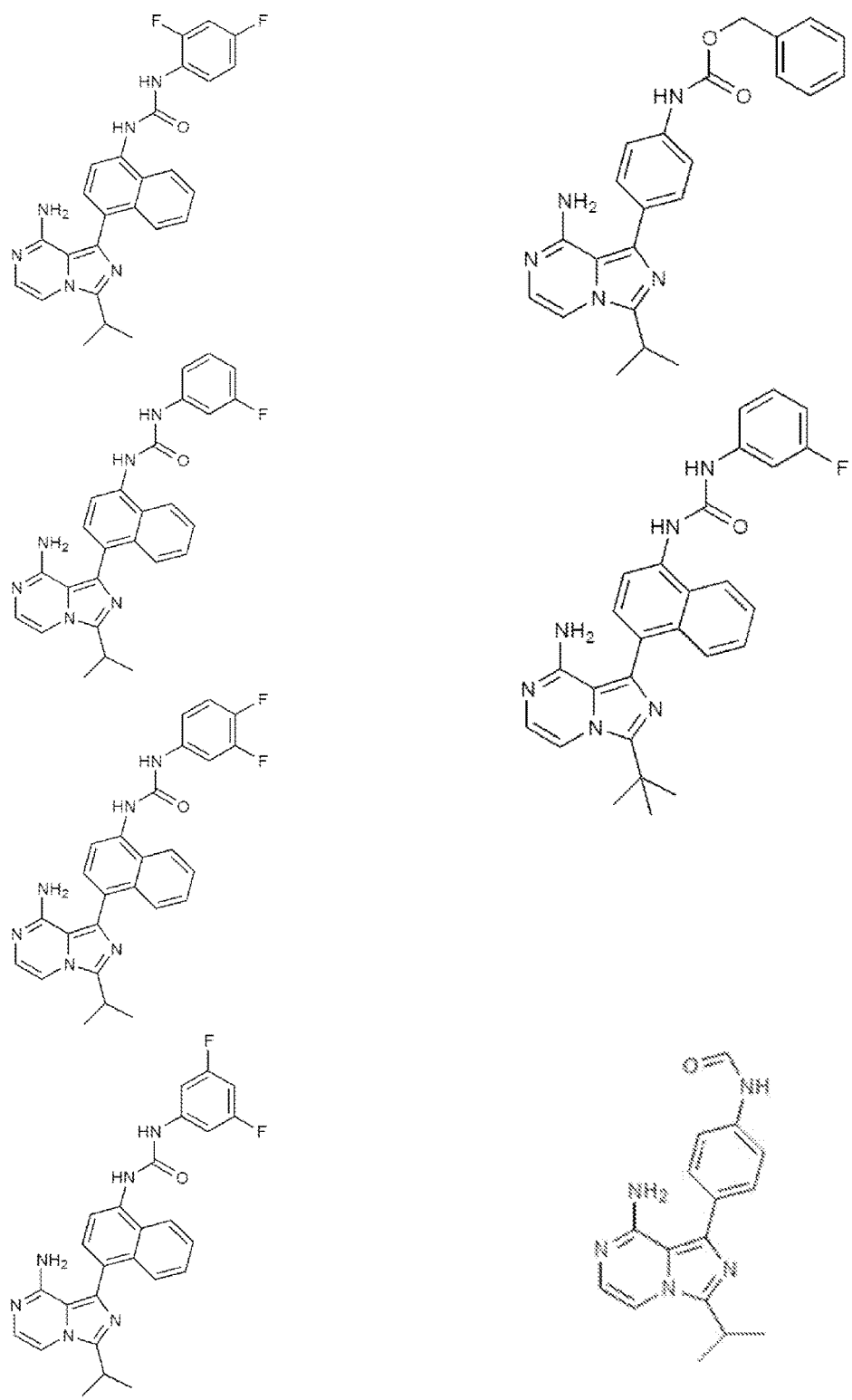
Figure 9:
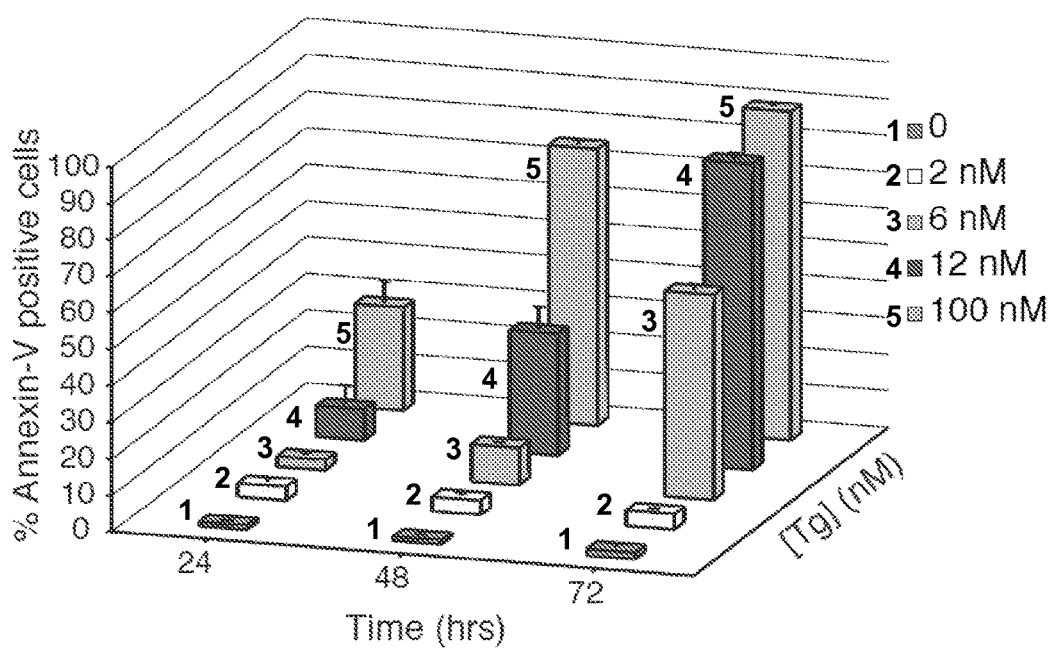
FIG. 9: ER stress-induced apoptosis can be replicated by simply overexpressing IRE1α. (A) Percentage of INS-1 cells staining positive for Annexin V after being treated with increasing concentrations of Thapsigargin (Tg) for 24, 48 and 72 h. (B) Anti-Procaspase-3 and Cleaved Caspase-3 immunoblot of INS-1 cells treated with indicated concentrations of Tg for 12, 24 and 48 h; anti-GAPDH immunoblot serves as loading control. (C) Model of ER stress mediated activation of IRE1α leading to ER-localized mRNA endonucleolytic decay, terminal UPR endpoints, and apoptosis. (D) Anti-Phospho-IRE1α and anti-Myc immunoblot of INS-1 stable line expressing transgenic wild-type IRE1α (WT) under increasing doses of Doxycycline (Dox) for 24 h; anti-GAPDH immunoblot serves as loading control. (E) Ethidium-bromide (EtBr)-stained agarose gel of XBP1 cDNA amplicons after induction by treating INS-1 IRE1α (WT)-expressing stable cells with increasing concentrations of Dox for 24 hours; the cDNA amplicon of unspliced XBP1 mRNA is cleaved by a PstI site within a 26 nucleotide intron to give 2U and 3U; IRE1α-mediated cleavage of the intron and re-ligation in vivo removes the PstI site to give the 1 s (spliced) amplicon; *is a spliced/unspliced XBP1 hybrid amplicon; the ratio of spliced over (spliced+unspliced) amplicons—1S/(1S+2U+3U)—is reported as % XBP1 splicing; three independent biological samples were used. (F) Q-PCR for Insulin1 mRNA (normalized to GAPDH) in INS-1 IRE1 α (WT)-expressing stable cells treated with indicated doses of Dox for 24 h. (G) Percent of INS-1 IRE1 α (WT)-expressing stable cells staining positive for Annexin V after treatment with increasing doses of Dox for 72 h.
Figure 9:
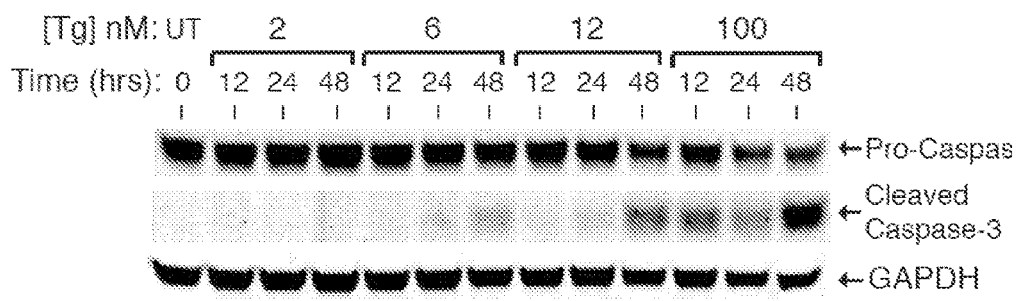
Figure 9:
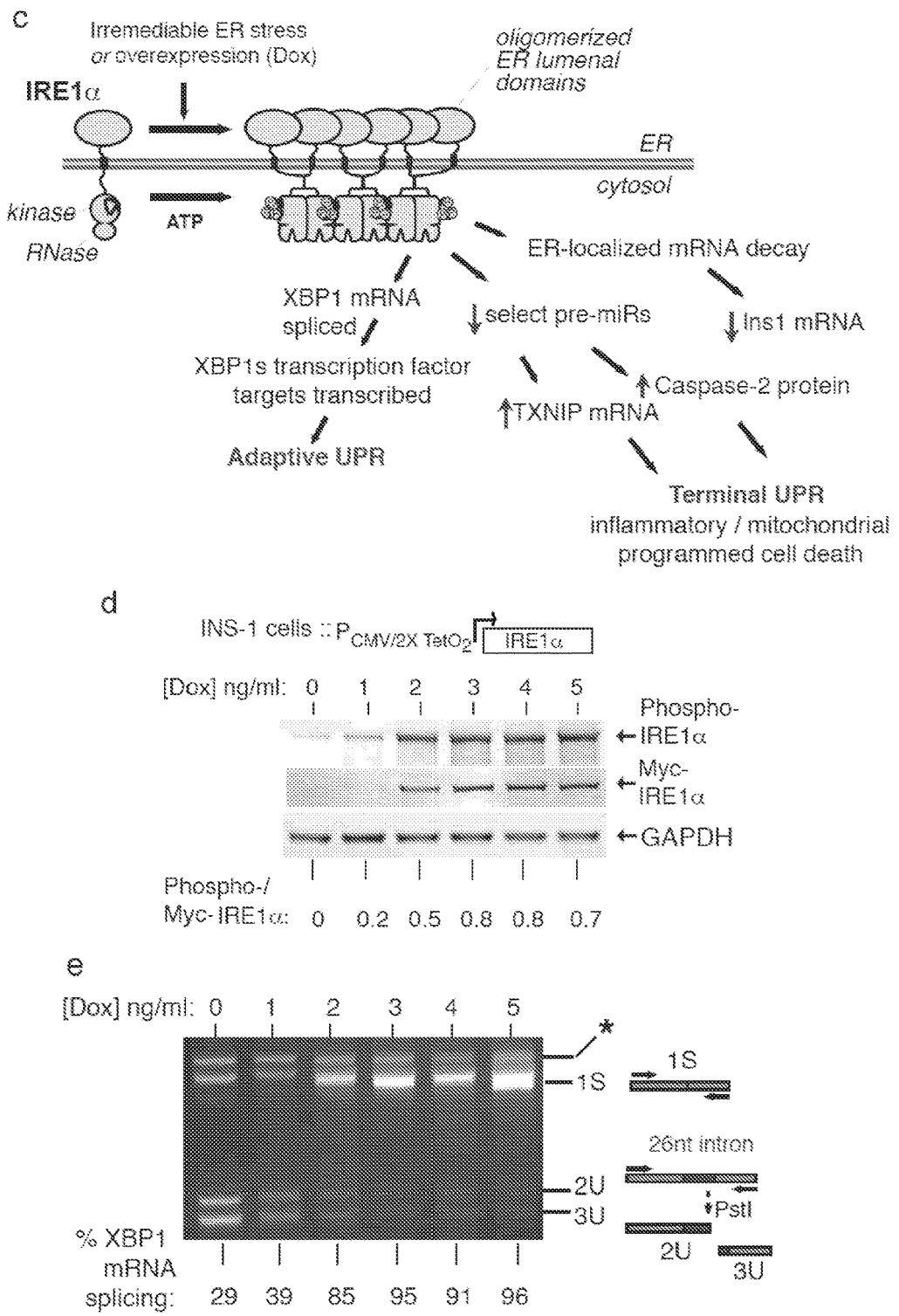
Figure 9:
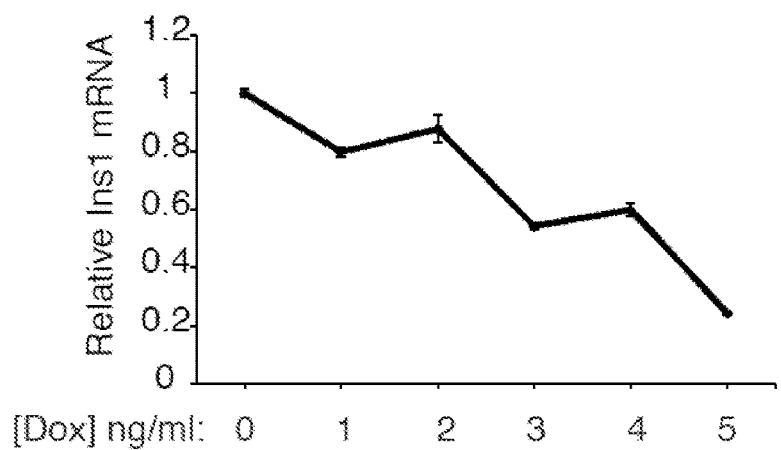
Figure 9:
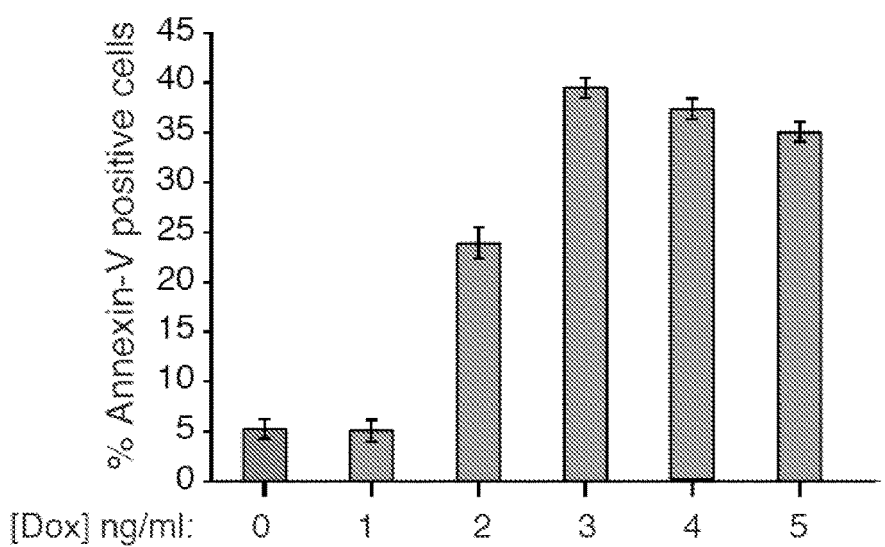
Figure 10:
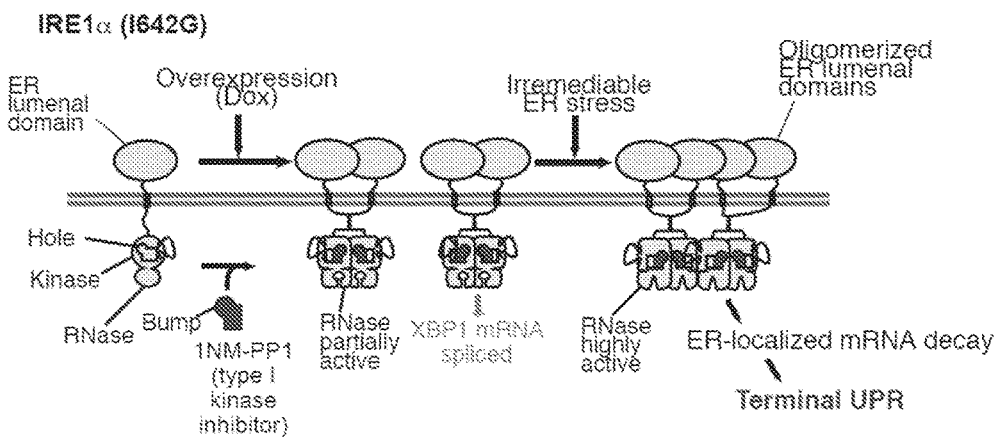
FIG. 10. Chemical-genetic manipulation of IRE1α activity reveals both the necessity and the sufficiency of the IRE1α RNase domain for triggering apoptosis. (A) Model of IRE1α (I642G) "holed"-kinase mutant and its activation by the "bumped" kinase inhibitor, 1NMPP1. (B) Percent XBP1 splicing in INS-1 IRE1(I642G) stable transgenic cells treated for 24 h with 1 µM 1NM-PP1, 1 µg/mL Dox and 6 nM Tg as indicated. (C) Percent of INS-1 IRE1(I642G) cells staining positive for Annexin V after treatment for 72 h with 1 µM 1NM-PP1, 1 µg/mL Dox and 6 nM Tg as indicated. (D) Percent XBP1 splicing in INS-1 IRE1(I642G) and INS-1 IRE1 (I642G/N906A) stable transgenic mutant cells treated for 24 h with 1NM-PP1, Dox and Tg as indicated. (E) Percent of INS-1 IRE1(I642G) and INS-1 IRE1(I642G/N906A) cells staining positive for Annexin V after treatment for 72 h with 1NM-PP1, Dox and Tg as indicated. (F) Anti-Pro and Cleaved Caspase-3 immunoblots of INS-1 IRE1 (I642G) and INS-1 IRE1(I642G/N906A) mutant stable cells treated for 72 h with 1NM-PP1, Dox and Tg as indicated.
Figure 10:
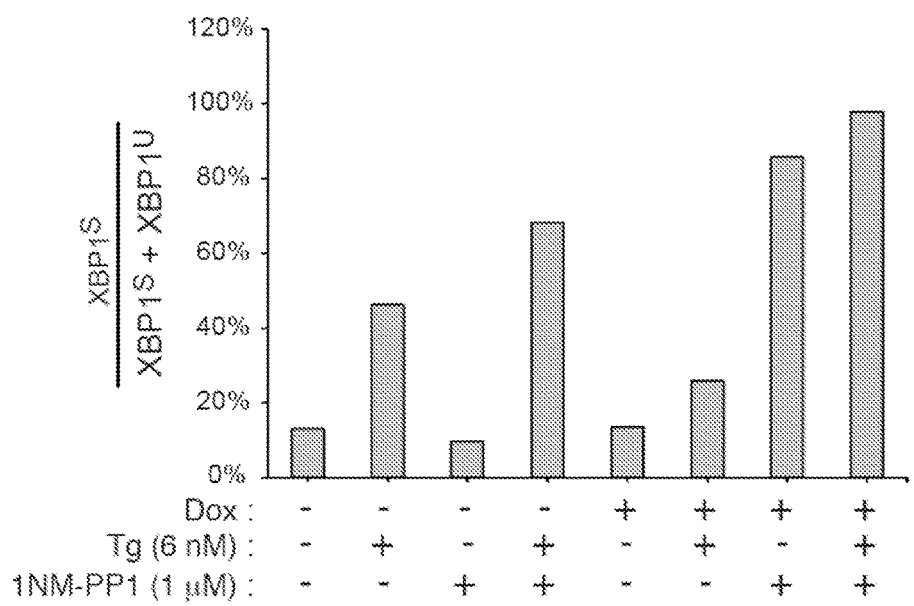
Figure 10:
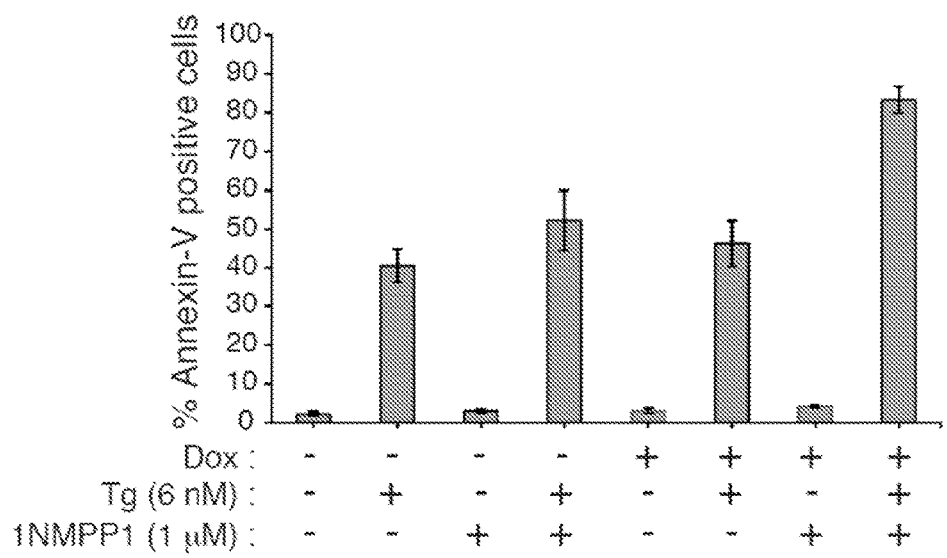
Figure 10:
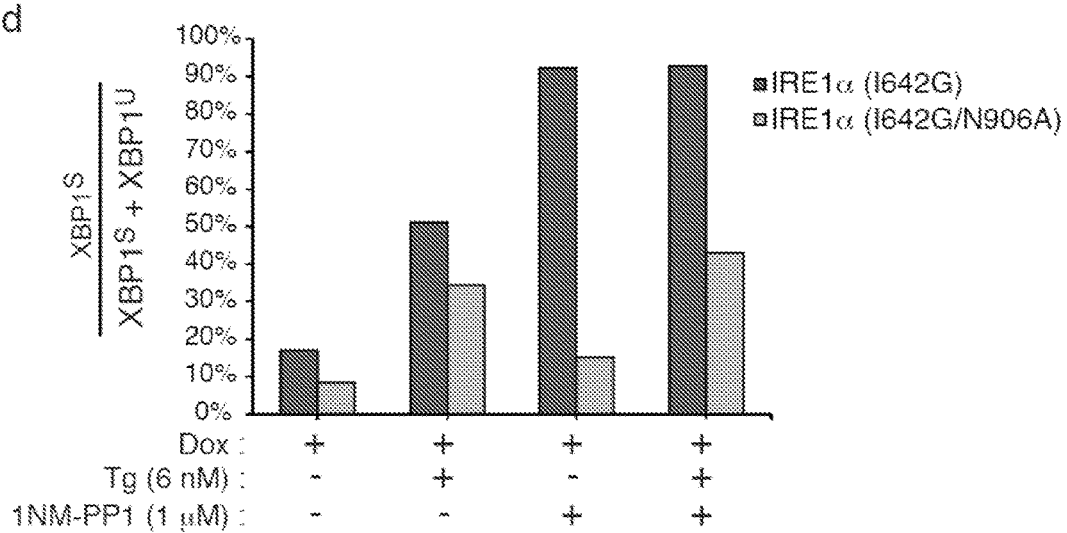
Figure 10:
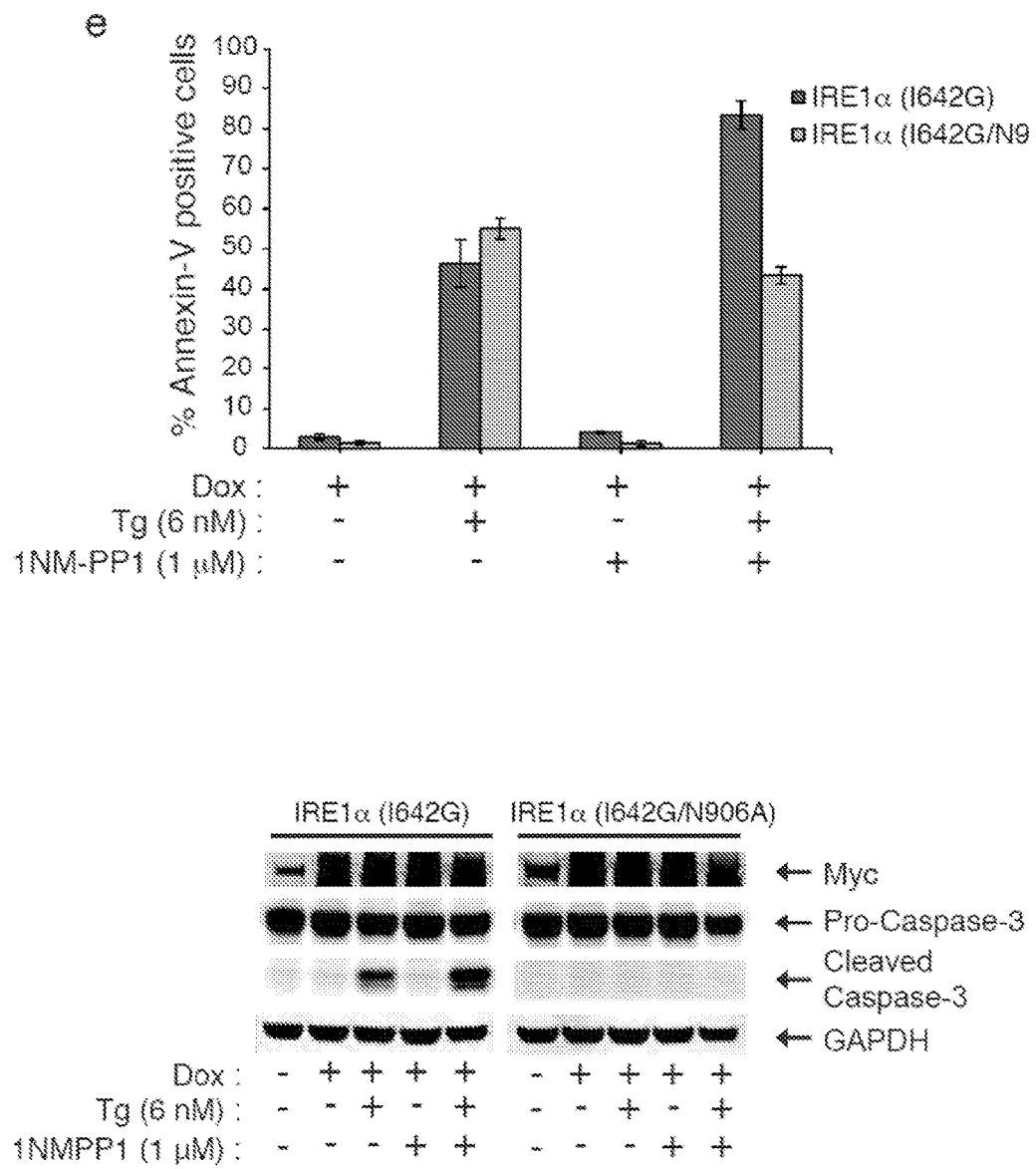
Figure 11:
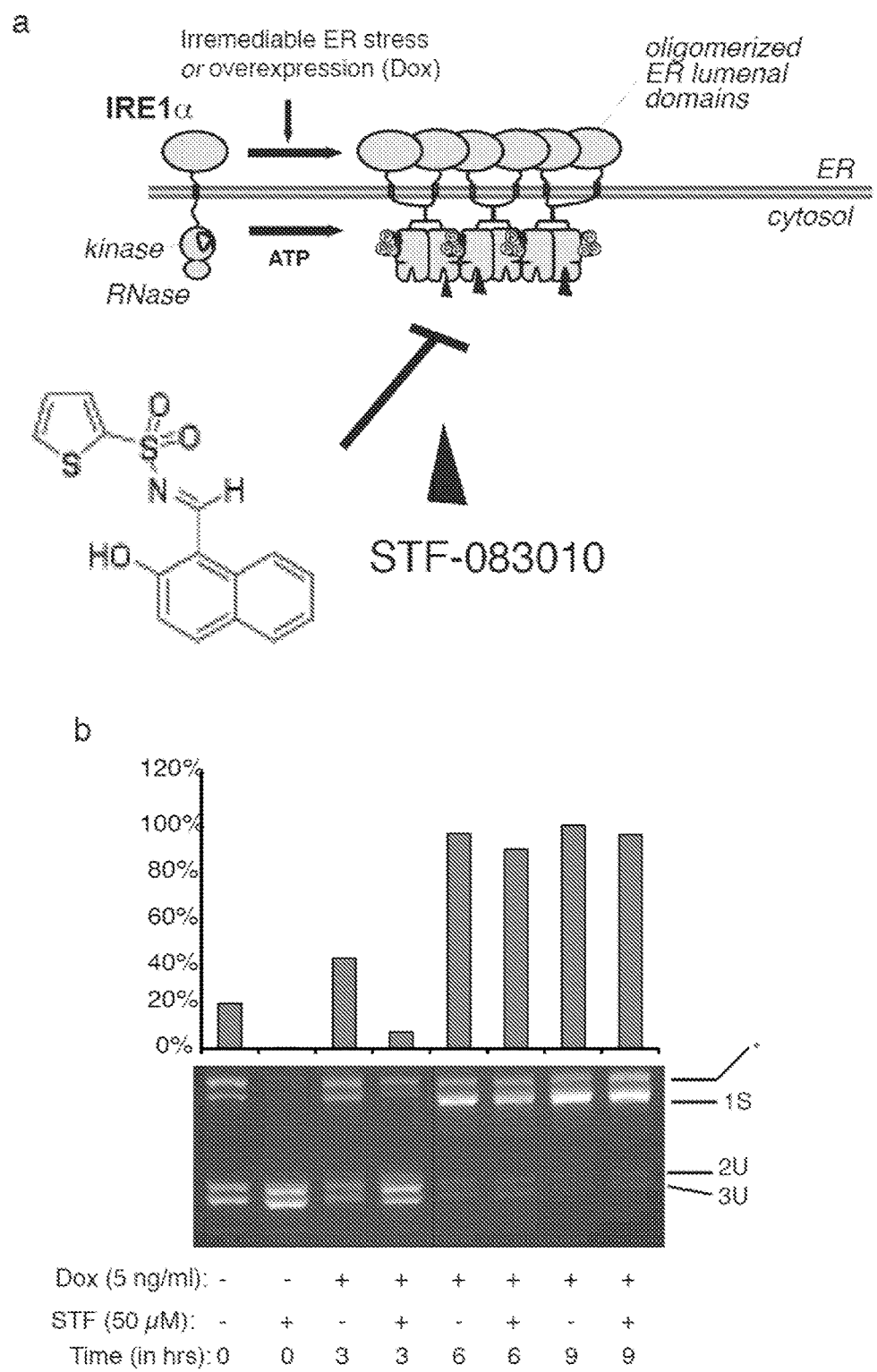
FIG. 11. Direct inhibition of IRE1α RNase prevents IRE1 dependent ER-localized mRNA degradation and ER stress-induced apoptosis. (A) Model of inhibition of IRE1α RNase activity by STF-083010 (STF). (B) Percent XBP1 splicing in INS-1 IRE1 WT stable cells treated with 5 ng/mL Dox and 50 µM STF for indicated times as shown (upper panel). EtBr-stained agarose gel of XBP1 cDNA amplicons is shown for the same samples above (lower panel). (C) Q-PCR for Insulin1 mRNA (normalized to GAPDH) in INS-1 IRE1 WT stable cells treated Dox and STF for 12, 24, 48 and 72 h. (D) Anti-Phospho-IRE1α and Anti-Total IRE1α immunoblots of INS-1 IRE1 WT stable cells treated for 48 h with 5 ng/mL Dox and 50 µM STF. (E) Anti-Phospho and Total JNK immunoblots of same samples. (F) Anti-Pro Caspase and Cleaved Caspase-3 immunoblots of same samples. (G) Percent of INS-1 IRE1 WT stable cells staining positive for Annexin V after treatment for 72 h with Dox and STF as indicated. (H) Percent of INS-1 cells staining positive for Annexin V after treatment for 72 h with increasing doses of Tunicamycin (Tm) and 50 µM STF as indicated. (I) Immunofluorescence staining on islets from 10 week old C57BL6 mice treated with 0.5 µg/mL Tm and 50 µM STF for 16 h as indicated; co-stained for DAPI (left column), insulin (second column from left), and TUNEL (third column from left); merged image is also shown. (J) Quantification of TUNEL positive β-cells normalized to DAPI-positive cells in (I).
Figure 11:
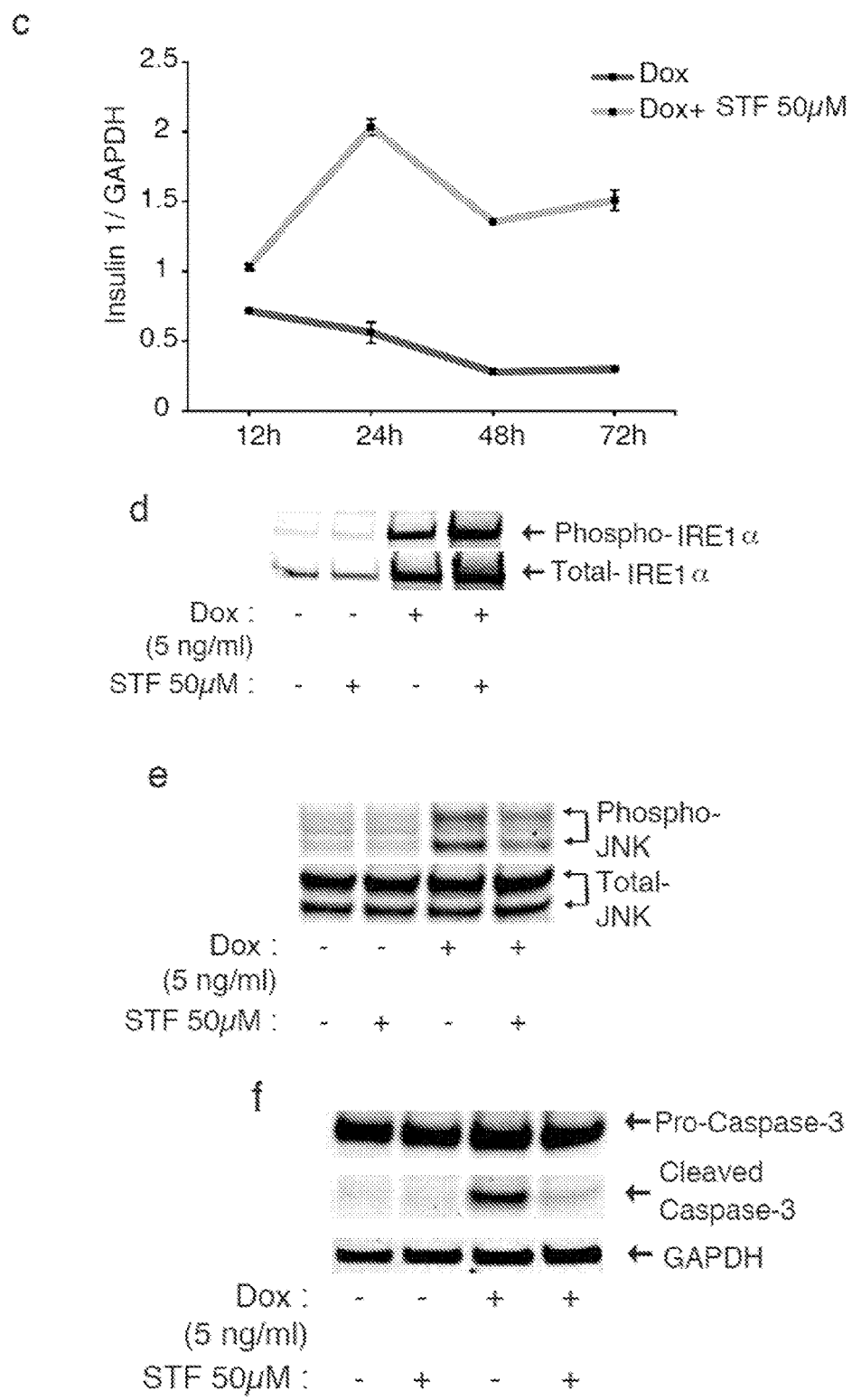
Figure 11:
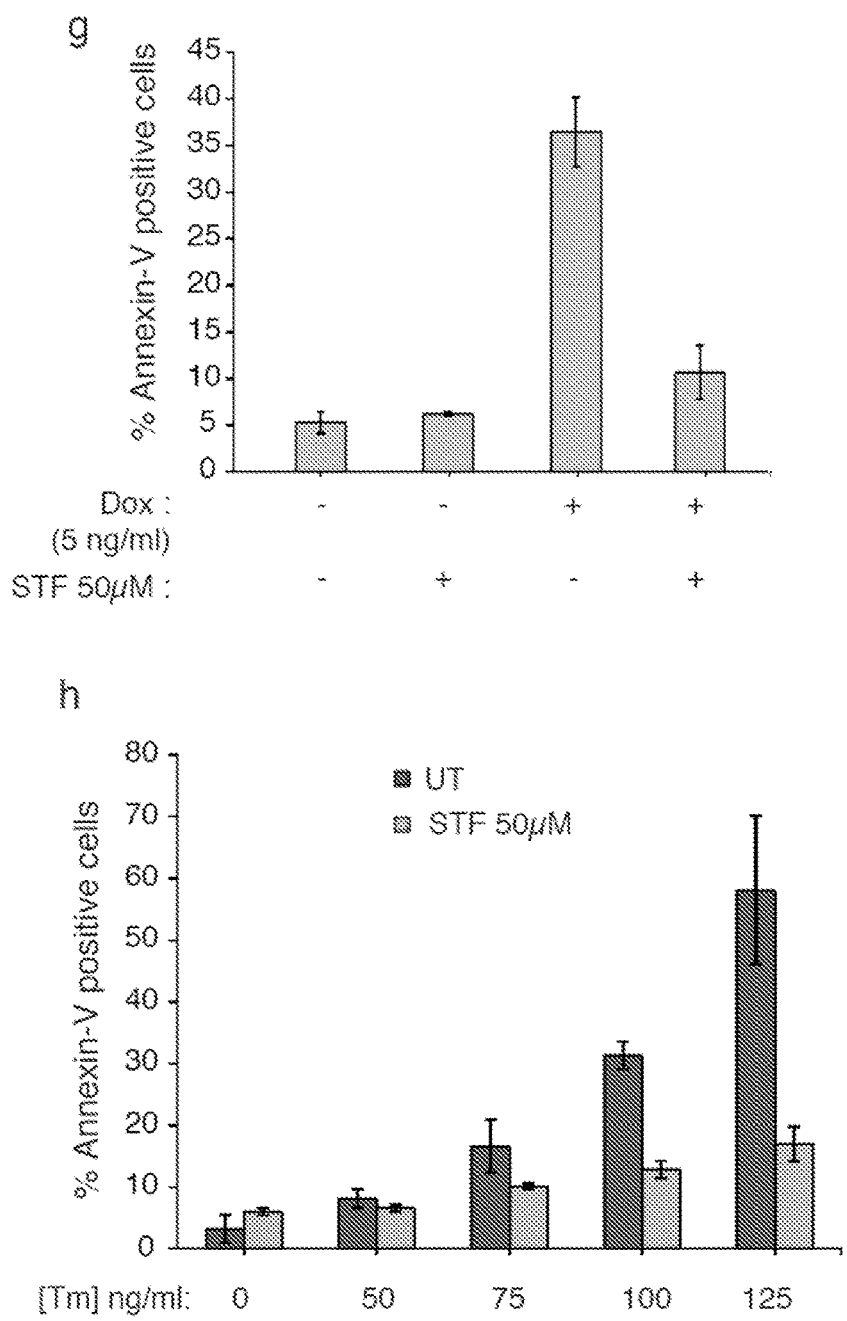
Figure 11:
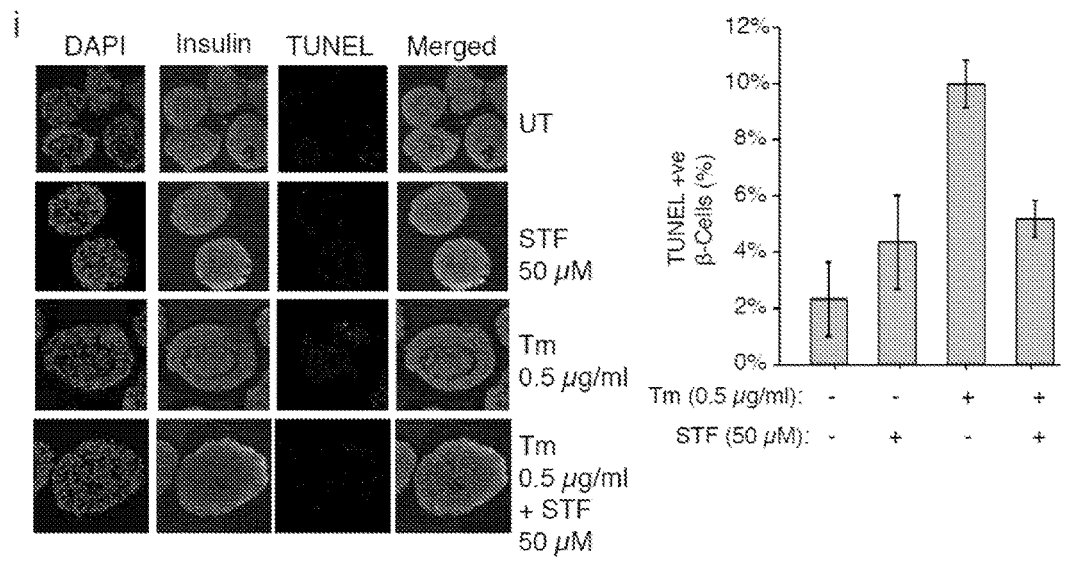
Figure 12:
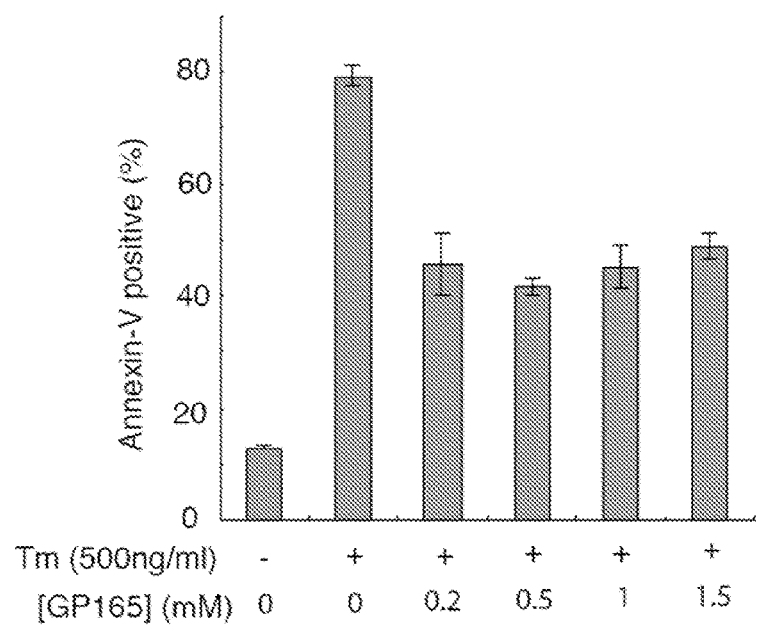
FIG. 12. a) Percent of INS-1 cells staining positive for Annexin-V 72 hrs after treatment of 500 ng/ml Tm+/−GP165. (b) EtBr-stained agarose gel of XBP1 cDNA amplicons from INS-1 cells 8 hrs after treatment of 200 ng/ml Tm+/−GP165. XBP1U, unspliced XBP1; XBP1S, spliced XBP1; the lower panel shows the ratios of spliced XBP1 (XBP1S) over (spliced+unspliced (XBP1U)). (c) Immunoblots for CASP3 cleavage in INS-1 cells 72 hrs after treatment of 500 ng/ml Tm+/−GP165 or 50 µM STF-083010 as positive control. (d) qPCR of insulin mRNA in INS-1 cells 8 hrs after treatment of 500 ng/ml Tm+/−GP165. (e) A schematic model of how GP16, blocks terminal UPR by inhibiting IRE1α activation under ER stress; as a type II kinase inhibitor, GP16, binds to the adenosine binding pocket and inhibits both the kinase and RNase domains of IRE1α and stabilizes the monomeric form; similar results are obtained using GP146. GP16, is KIRA6.
Figure 12:
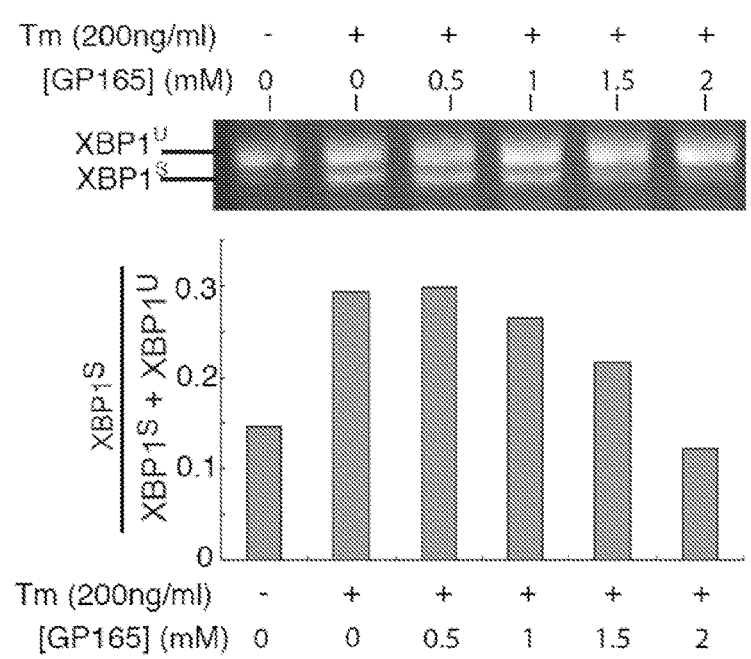
Figure 12:
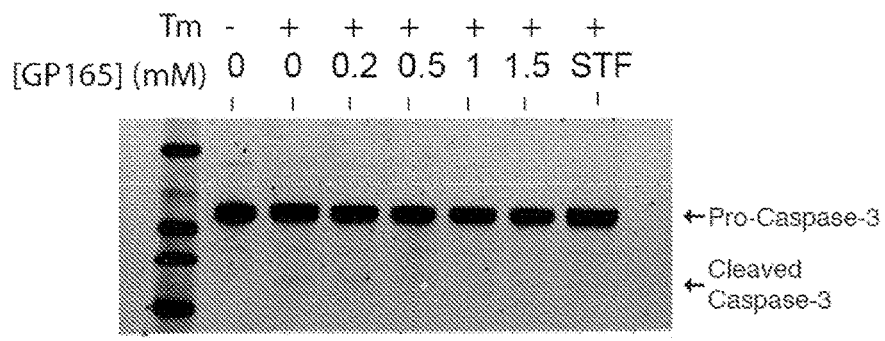
Figure 12:
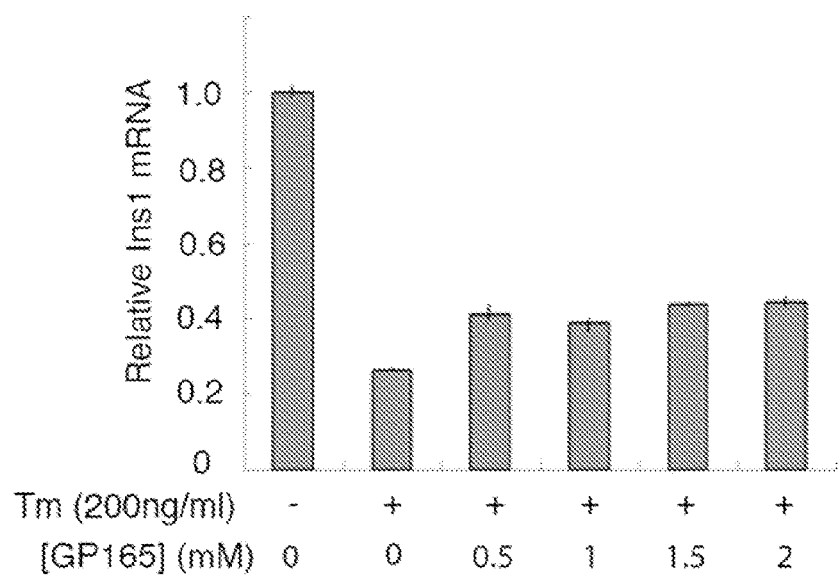
Figure 12:
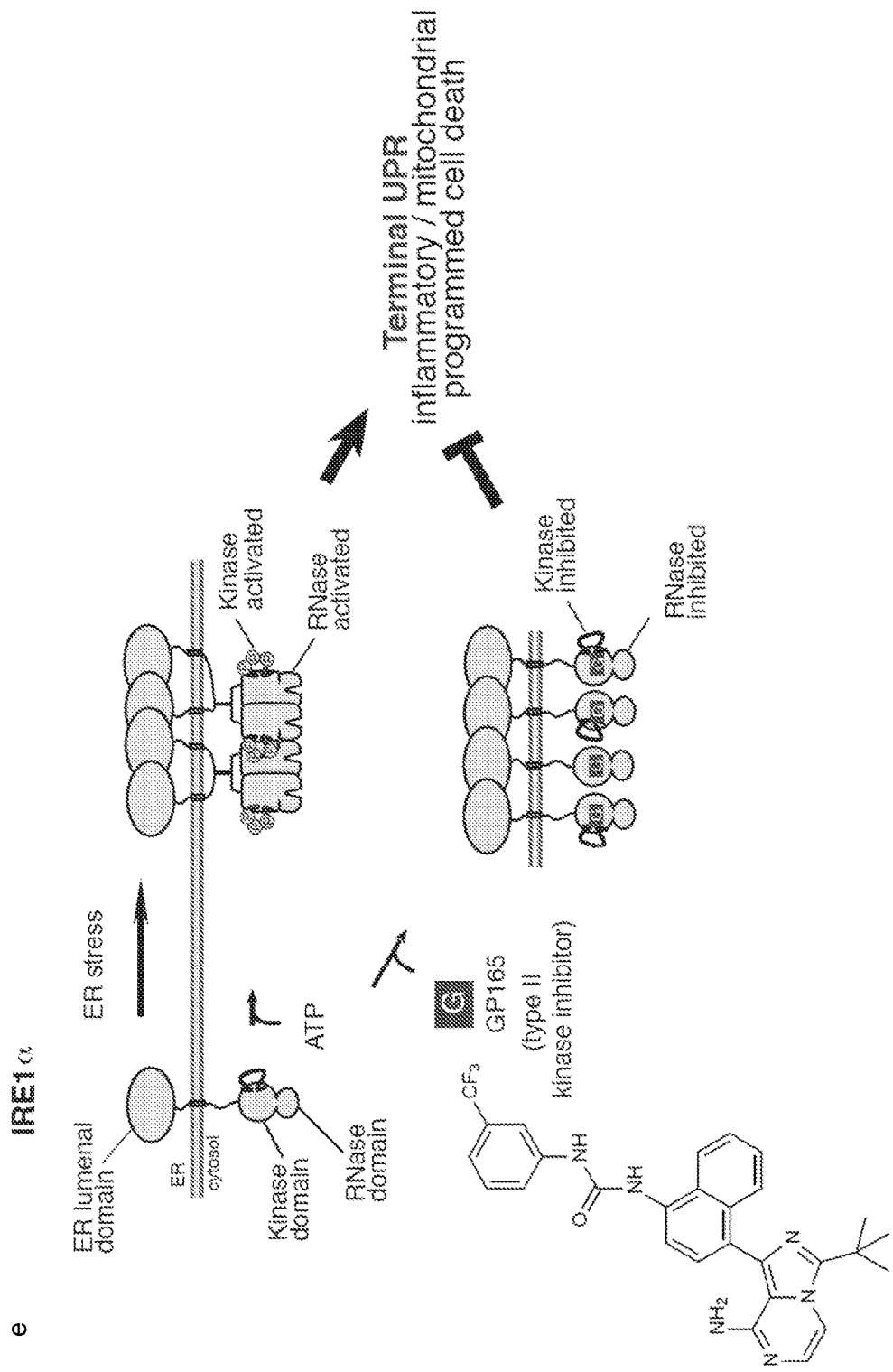
Figure 13:
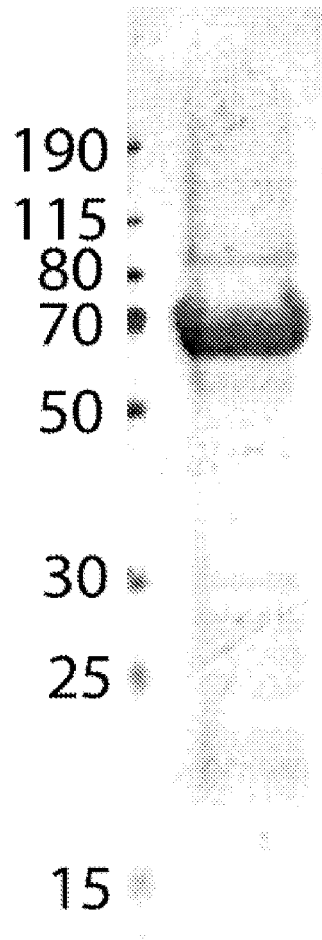
FIG. 13. Coomassie blue-stained PAGE of purified IRE1α*; M, protein marker.
Figure 14:
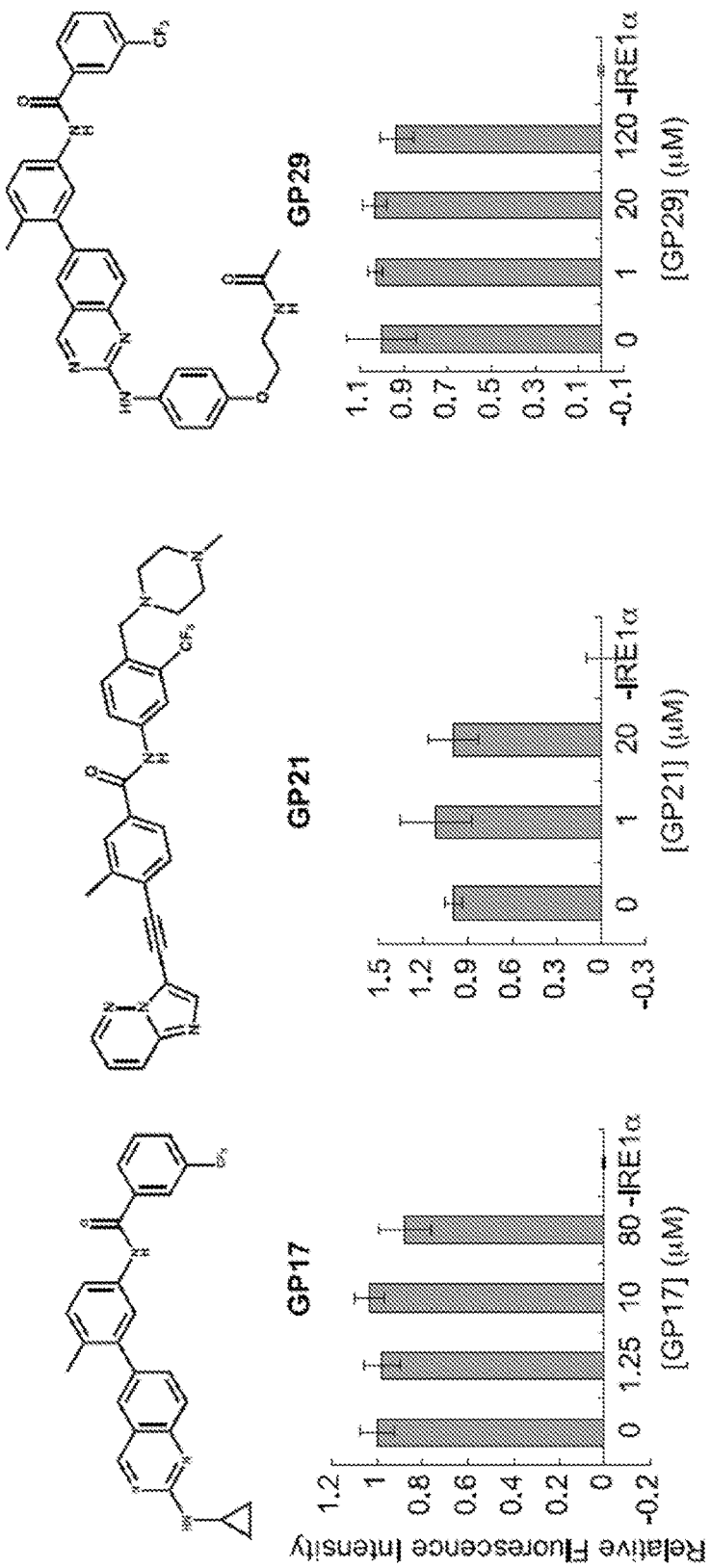
FIG. 14. Structures of several type II kinase inhibitors screened against IRE1α* in the XBP1 RNA minisubstrate assay; the relative endpoint fluorescence intensities for the IRE1α*-catalyzed cleavage reaction of XBP1 minisubstrate in the presence of varying concentrations of inhibitors are shown.
Figure 14:
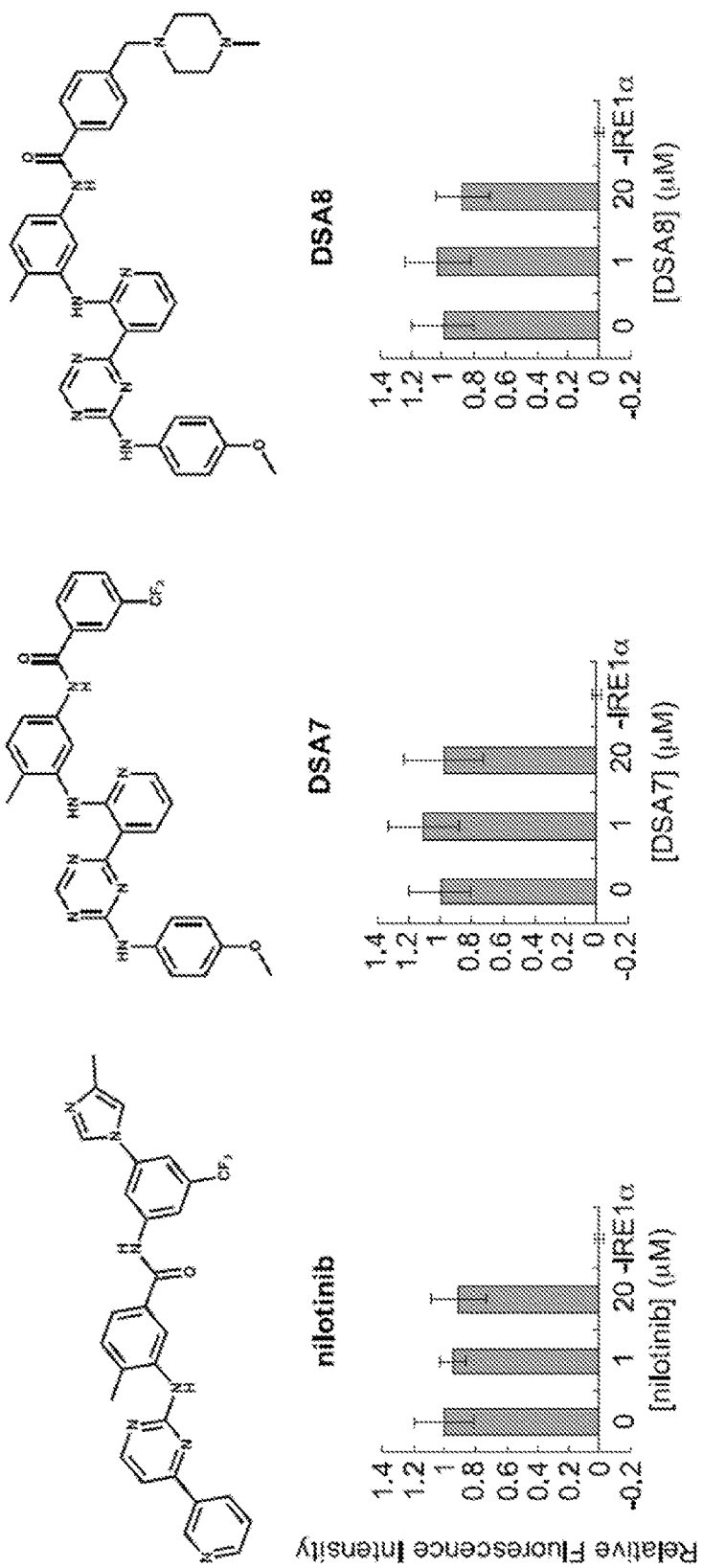
Figure 14:
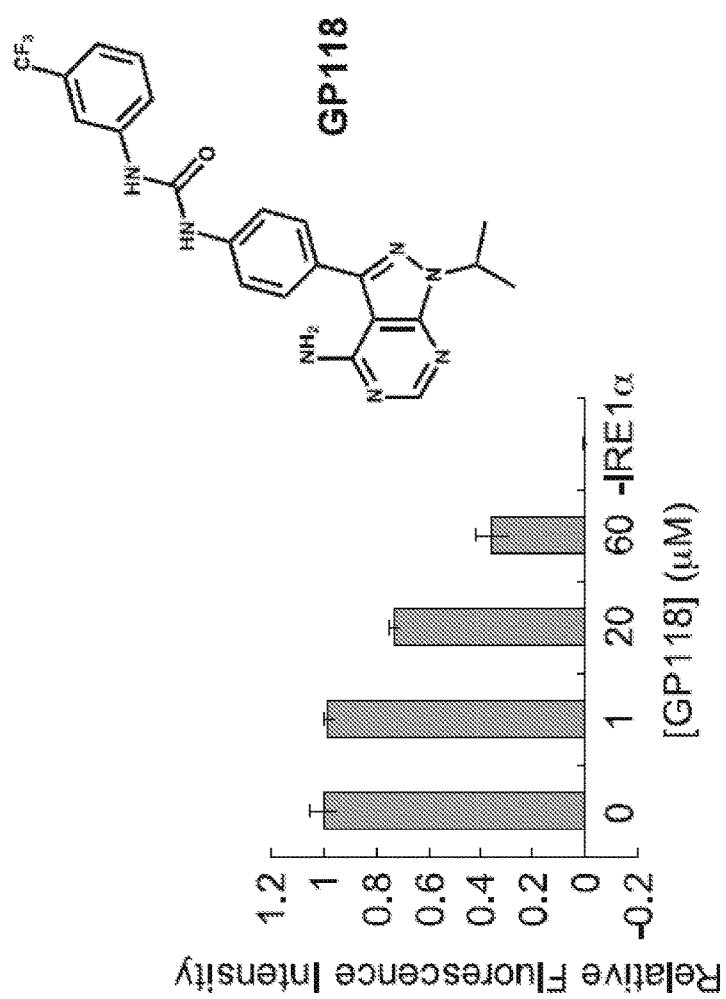
Figure 15:
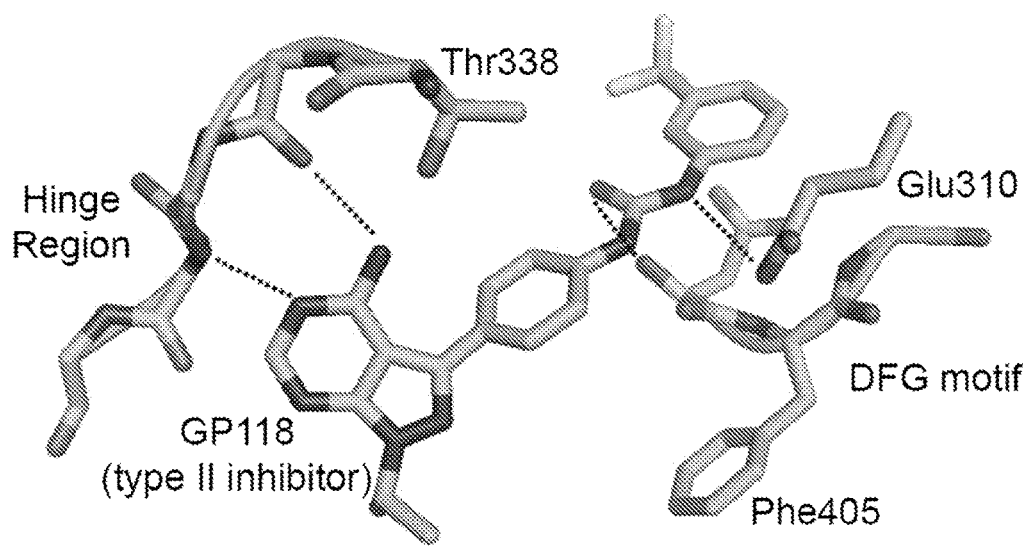
FIG. 15. Crystal structure of Src bound to the type II kinase inhibitor, GP118 (PDB code 3EL8); hydrogen bond interactions between Src and GP118 are denoted as dotted lines; only the backbone atoms are shown for residues in the hinge region except for Thr338 (gatekeeper residue); the proposed model of GP118 bound to IRE1α shown in FIG. 1a is based on the Src-GP118 complex structure.
Figure 16:
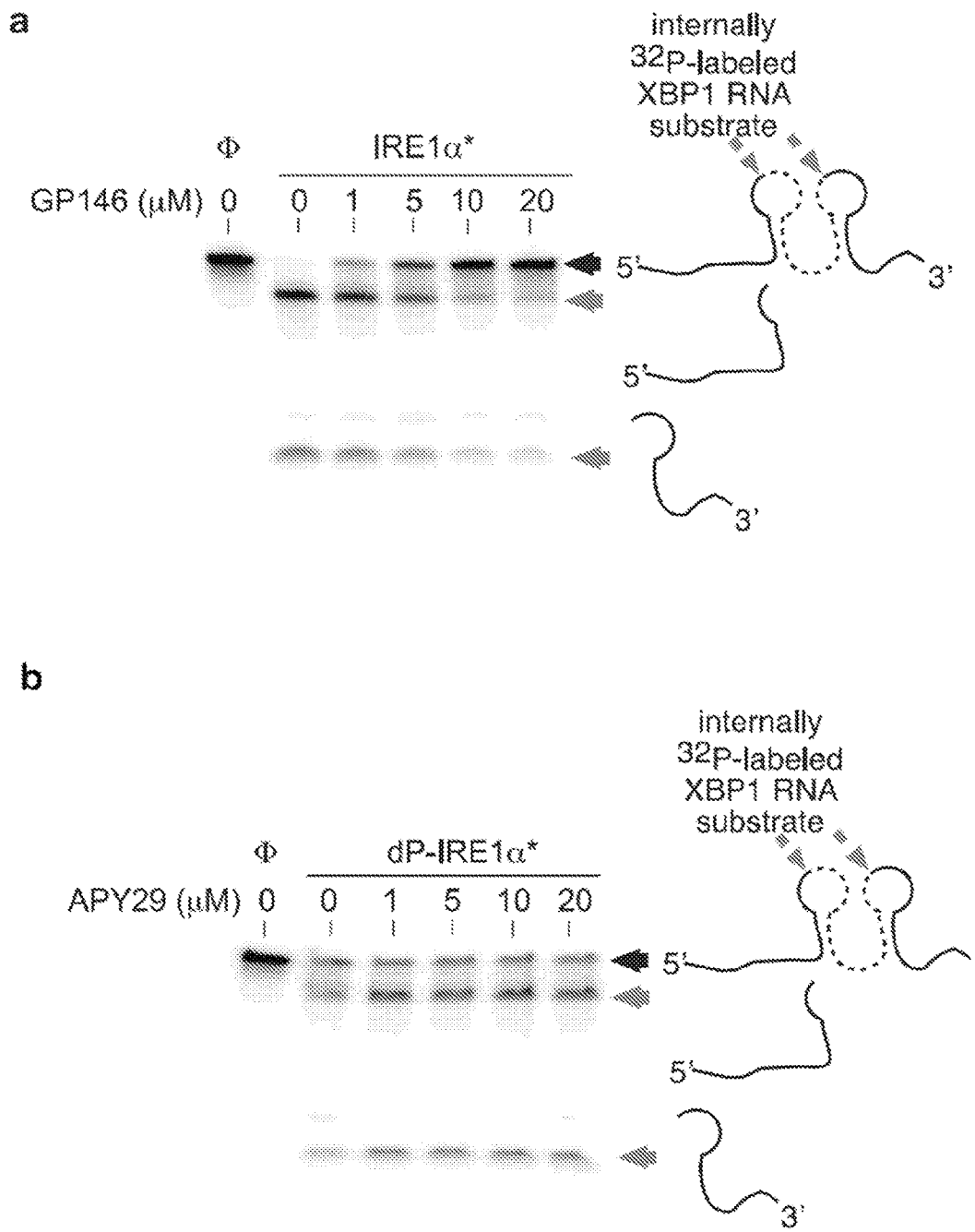
FIG. 16. GP146 and APY29 modulation of IRE1α*-mediated cleavage of an in vitro-transcribed 352 nucleotide, internally a 32P-labeled XBP1 RNA. (a) Urea PAGE analysis of 5 minute cleavage reactions of a 32P-labeled XBP1 RNA by IRE1α* in the presence of varying concentrations of GP146. (b) Urea PAGE analysis of 5 minute cleavage reactions of a 32P-labeled XBP1 RNA by dP-IRE1α* in the presence of varying concentrations of APY29.
Figure 17:
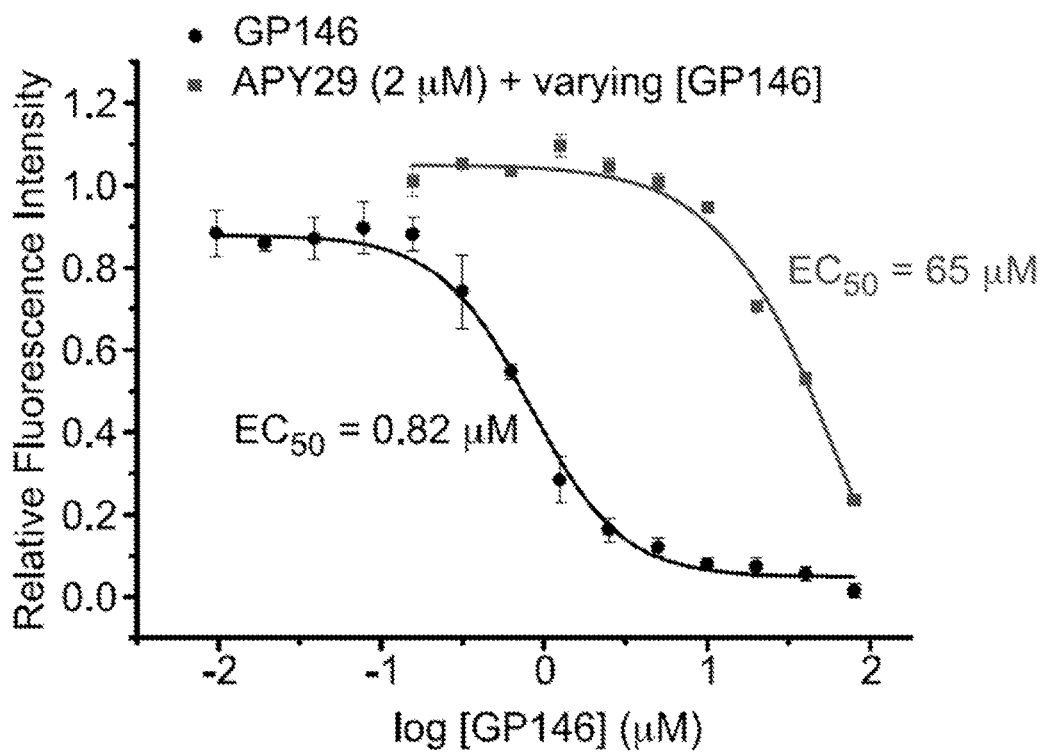
FIG. 17. The EC50 of GP146 for IRE1α* RNase inhibition increases in the presence of a fixed concentration of APY29; the line marked with circles shows IRE1α* RNase inhibition by GP146 in the absence of a competitor (APY29); the line marked with squares shows IRE1α* RNase inhibition by GP146 in the presence of APY29 (2 µM).

In embodiments, the compound is a compound described herein, including in an aspect, embodiment, example, figure, table, or claim. In embodiments, the compound is a compound in FIG. 8.

In embodiments, the compounds set forth herein are provided as pharmaceutical compositions including the compound, or a pharmaceutically acceptable salt thereof, and a pharmaceutically acceptable excipient. In embodiments, the compounds set forth herein are not provided as pharmaceutical compositions. In embodiments, the compound is included in a pharmaceutically acceptable salt. In embodiments, the compound is not included in a pharmaceutically acceptable salt.

Described herein, inter alia, is a new strategy to: (1) inhibit IRE1α's hyperactive RNase by pharmacologically targeting its neighboring kinase domain with small molecules, and (2) test physiological benefits of shutting down IRE1α in cells (e.g. (3-cells) of living mammals (e.g. mice). This work validates IRE1α as a drug target to manipulate ER stress signaling to control cell fate.

In another aspect, provided herein are compounds having the formula (A):

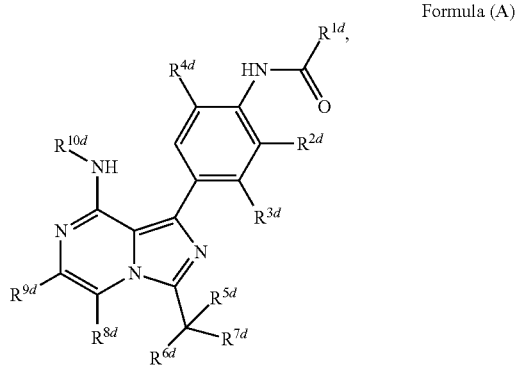

Formula (A)

Figure 7:
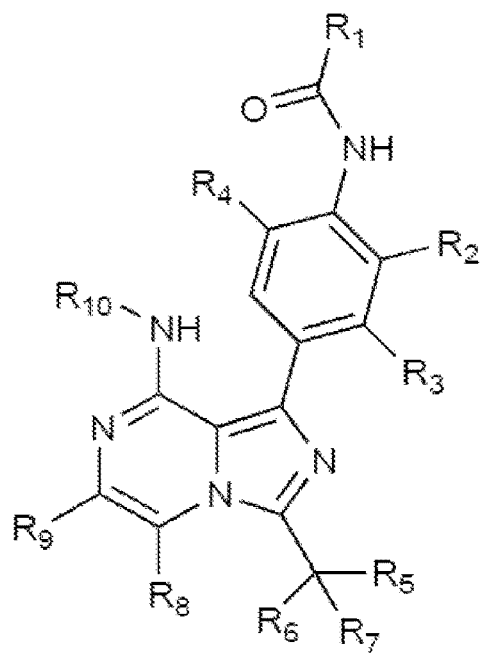
FIG. 7 illustrates the compound Formula (A), wherein the $R^1$, $R^2$, $R^3$, $R^4$, $R^5$, $R^6$, $R^7$, $R^8$, $R^9$, and $R^{10}$ are each defined herein.

(also illustrated in FIG. 7) and pharmaceutically acceptable salts thereof, wherein $R^{1d}$, $R^{2d}$, $R^{3d}$, $R^{4d}$, $R^{5d}$, $R^{6d}$, $R^{7d}$, $R^{8d}$, $R^{9d}$, and $R^{10d}$, are each independently $C_{2-6}$ alkyl, $C_{1-6}$ haloalkyl, $—C_{1-4}$ alkyl-$R^{12d}$, $C_{2-6}$ alkenyl, $C_{2-6}$ alkynyl, $C_{3-8}$ cycloalkyl, monocyclic heterocyclyl, monocyclic heteroaryl, or phenyl, aryl, wherein the cycloalkyl, heterocyclyl, heteroaryl, and phenyl groups are each optionally substituted with one or two $R^{11d}$ groups; each $R^{11d}$ is independently $C_{1-6}$ alkyl, $C_{1-6}$ haloalkyl, $—C(O)R^d$, $—C(O)OR^d$, $—C(O)NR^d_2$, $S(O)_2NR^d_2$, or $S(O)_2R^d$; and $R^{12d}$ is $OR^d$, $—SR^d$, $—NR^d_2$, $—C(O)R^d$, $—C(O)OR^d$, $—C(O)NR^d_2$, $S(O)_2R^d$, $—OC(O)R^d$, $OC(O)OR^d$, $OC(O)NR^d_2$, $—N(R^d)C(O)R^d$, $—N(R^d)C(O)OR^d$, $—N(R^d)C(O)NR^d_2$, phenyl, monocyclic heteroaryl, $C_{3-8}$ cycloalkyl, or monocyclic heterocyclyl, wherein the aryl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, $OR^d$, $—SR^d$, $—NR^d_2$, $—C(O)R^d$, $C(O)OR^d$, $—C(O)NR^d_2$, $S(O)_2R^d$, $—OC(O)R^d$, $—OC(O)OR^d$, $OC(O)NR^d_2$, $N(R^d)C(O)R^d$, $—N(R^d)C(O)OR^d$, or $—N(R^d)C(O)NR^d_2$; and each $R^d$ is independently hydrogen, $C_{1-6}$ alkyl, $C_{2-6}$ alkenyl, $C_{1-6}$ haloalkyl, $C_{3-8}$ cycloalkyl, heterocyclyl, aryl, arylC$_{1-6}$ alkyl, heteroaryl, or heteroarylC$_{1-6}$ alkyl wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, $—OR^{od}$, $SR^{od}$, $NR^{od}2$, $C(O)R^{od}$, $C(O)OR^{od}$, $—C(O)N(R^{od})2$, $S(O)2R^{od}$, $—OC(O)R^{od}$, $—OC(O)OR^{od}$, $OC(O)N(R^{od})2$, $N(R^{od})OC(O)R^{od}$, $—N(R^{od})C(O)OR^{od}$, or $N(R^{od})C(O)N(R^{od})2$, wherein each $R^{od}$ is independently hydrogen or $C_{1-6}$ alkyl, each $R^d$ is independently hydrogen, or $C_{1-6}$ alkyl.

In another aspect, provided herein are compounds having the formula (A):

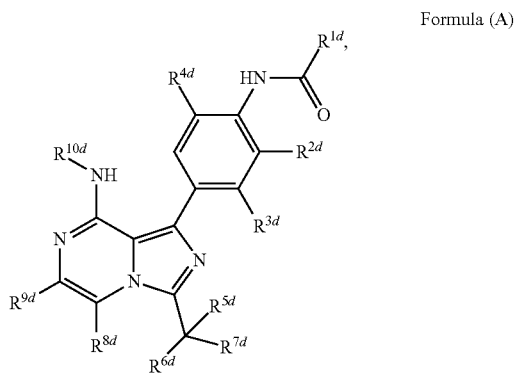

Formula (A)

(also illustrated in FIG. 7) and pharmaceutically acceptable salts thereof, wherein $R^{1d}$, $R^{2d}$, $R^{3d}$, $R^{4d}$, $R^{5d}$, $R^{6d}$, $R^{7d}$, $R^{8d}$, $R^{9d}$, and $R^{10d}$, are each independently $C_{2-6}$ alkyl, $C_{1-6}$ haloalkyl, $—C_{1-4}$ alkyl-$R^{12d}$, $C_{2-6}$ alkenyl, $C_{2-6}$ alkynyl, $C_{3-8}$ cycloalkyl, monocyclic heterocyclyl, monocyclic heteroaryl, or phenyl, aryl, wherein the cycloalkyl, heterocyclyl, heteroaryl, and phenyl groups are each optionally substituted with one or two $R^{11d}$ groups; each $R^{11d}$ is independently $C_{1-6}$ alkyl, $C_{1-6}$ haloalkyl, $—C(O)R^d$, $—C(O)OR^d$, $—C(O)NR^d_2$, $S(O)_2NR^d_2$, or $—S(O)_2R^d$; and $R^{12d}$ is $—OR^d$, $—SR^d$, $—NR^d_2$, $—C(O)R^d$, $—C(O)OR^d$, $—C(O)NR^d_2$, $—S(O)_2R^d$, $—OC(O)R^d$, $OC(O)OR^d$, $OC(O)NR^d_2$, $—N(R^d)C(O)R^d$, $—N(R^d)C(O)OR^d$, $—N(R^d)C(O)NR^d_2$, phenyl, monocyclic heteroaryl, $C_{3-8}$ cycloalkyl, or monocyclic heterocyclyl, wherein the aryl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, $—OR^d$, $—SR^d$, $—NR^d_2$, $—C(O)R^d$, $C(O)OR^d$, $—C(O)NR^d_2$, $S(O)_2R^d$, $—OC(O)R^d$, $—OC(O)OR^d$, $OC(O)NR^d_2$, $N(R^d)C(O)R^d$, $—N(R^d)C(O)OR^d$, or $—N(R^d)C(O)NR^d_2$; and each $R^d$ is independently hydrogen, $C_{1-6}$ alkyl, $C_{2-6}$ alkenyl, $C_{1-6}$ haloalkyl, $C_{3-8}$ cycloalkyl, heterocyclyl, aryl, arylC$_{1-6}$ alkyl, heteroaryl, or heteroarylC$_{1-6}$ alkyl wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, $—OR^{od}$, $SR^{od}$, $NR^{od}2$, $C(O)R^{od}$, $C(O)OR^{od}$, $—C(O)N(R^{od})2$, $S(O)2R^{od}$, $—OC(O)R^{od}$, $—OC(O)OR^{od}$, $OC(O)N(R^{od})2$, $N(R^{od})C(O)R^{od}$, $—N(R^{od})C(O)OR^{od}$, or $N(R^{od})C(O)N(R^{od})2$, wherein each $R^{od}$ is independently hydrogen or $C_{1-6}$ alkyl. In embodiments, each $R^d$ is independently hydrogen or $C_{1-6}$ alkyl.

In another aspect, $R^{2d}$ and $R^{3d}$ are together a phenyl, monocyclic heteroaryl, $C_{3-8}$ cycloalkyl, or monocyclic heterocyclyl, wherein the aryl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, $OR^d$, —$SR^d$, —$NR^d_2$, —$C(O)R^d$, $C(O)OR^d$, —$C(O)NR^d_2$, $S(O)_2R^d$, —$OC(O)R^d$, —$OC(O)OR^d$, $OC(O)NR^d_2$, $N(R^d)C(O)R^d$, —$N(R^d)C(O)OR^d$, or —$N(R^d)C(O)NR^d_2$; wherein each $R^d$ is independently hydrogen, $C_{1-6}$ alkyl, $C_{2-6}$ alkenyl, $C_{1-6}$ haloalkyl, $C_{3-8}$ cycloalkyl, heterocyclyl, aryl, aryl$C_{1-6}$ alkyl, heteroaryl, or heteroaryl$C_{1-6}$ alkyl wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —$OR^{Od}$, $SR^{Od}$, $NR^{Od}2$, $C(O)R^{Od}$, $C(O)OR^{Od}$, $C(O)OR^{Od}$, —$C(O)N(R^{Od})2$, $S(O)2R^{Od}$, —$OC(O)R^{Od}$, —$OC(O)OR^{Od}$, $OC(O)N(R^{Od})2$, $N(R^{Od})C(O)R^{Od}$, —$N(R^{Od})C(O)OR^{Od}$, or $N(R^{Od})C(O)N(R^{Od})2$, wherein each $R^{Od}$ is independently hydrogen or $C_{1-6}$ alkyl, each $R^d$ is independently hydrogen, or $C_{1-6}$ alkyl.

In another aspect, $R^{2d}$ and $R^{3d}$ are together a phenyl, monocyclic heteroaryl, $C_{3-8}$ cycloalkyl, or monocyclic heterocyclyl, wherein the aryl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, $OR^d$, —$SR^d$, —$NR^d_2$, —$C(O)R^d$, $C(O)OR^d$, —$C(O)NR^d_2$, —$S(O)_2R^d$, —$OC(O)R^d$, —$OC(O)OR^d$, $OC(O)NR^d_2$, $N(R^d)C(O)R^d$, —$N(R^d)C(O)OR^d$, or —$N(R^d)C(O)NR^d_2$; wherein each $R^d$ is independently hydrogen, $C_{1-6}$ alkyl, $C_{2-6}$ alkenyl, $C_{1-6}$ haloalkyl, $C_{3-8}$ cycloalkyl, heterocyclyl, aryl, aryl$C_{1-6}$ alkyl, heteroaryl, or heteroaryl$C_{1-6}$ alkyl wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —$OR^{Od}$, $SR^{Od}$, $NR^{Od}2$, $C(O)R^{Od}$, $C(O)OR^{Od}$, —$C(O)N(R^{Od})2$, $S(O)2R^{Od}$, —$OC(O)R^{Od}$, —$OC(O)OR^{Od}$, $OC(O)N(R^{Od})2$, $N(R^{Od})C(O)R^{Od}$, —$N(R^{Od})C(O)OR^{Od}$, or $N(R^{Od})C(O)N(R^{Od})2$, wherein each $R^{Od}$ is independently hydrogen or $C_{1-6}$ alkyl. In embodiments, each $R^d$ is independently hydrogen or $C_{1-6}$ alkyl.

In yet another aspect, $R^{1d}$ is —$OR^d$, —$SR^d$, —$NR^d_2$, —$C(O)R^d$, —$C(O)OR^d$, —$C(O)NR^d_2$, —$N(R^d)C(O)R^d$, —$N(R^d)C(O)OR^d$, —$N(R^d)C(O)NR^d_2$, phenyl, monocyclic heteroaryl, $C_{3-8}$ cycloalkyl, or monocyclic heterocyclyl, wherein the aryl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, $OR^d$, —$SR^d$, —$NR^d_2$, —$C(O)R^d$, $C(O)OR^d$, —$C(O)NR^d_2$, —$S(O)_2R^d$, —$OC(O)R^d$, —$OC(O)OR^d$, $OC(O)NR^d_2$, $N(R^d)C(O)R^d$, —$N(R^d)C(O)OR^d$, or —$N(R^d)C(O)NR^d_2$.

C. PHARMACEUTICAL COMPOSITIONS

In another aspect is provided a pharmaceutical composition including a pharmaceutically acceptable excipient and a compound, or pharmaceutically acceptable salt thereof, as described herein (e.g. formula I, formula II, formula III, aspect, embodiment, example, figure, table, or claim).

In embodiments of the pharmaceutical compositions, the compound, or pharmaceutically acceptable salt thereof, as described herein (e.g. formula I, formula II, formula III, aspect, embodiment, example, figure, table, or claim) is included in a therapeutically effective amount.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments of the pharmaceutical compositions, the second agent is an agent for treating cancer (e.g. multiple myeloma or cancers of secretory cells), neurodegenerative diseases, demyelinating diseases, eye diseases, fibrotic diseases, or diabetes. In embodiments, the second agent is an anti-cancer agent. In embodiments, the second agent is a chemotherapeutic. In embodiments, the second agent is an agent for improving memory. In embodiments, the second agent is an agent for treating a neurodegenerative disease. In embodiments, the second agent is an agent for treating a demyelinating disease. In embodiments, the second agent is an agent for treating an eye disease. In embodiments, the second agent is an agent for treating a fibrotic disease. In embodiments, the second agent is an agent for treating multiple sclerosis. In embodiments, the second agent is an agent for treating Alzheimer's disease. In embodiments, the second agent is an agent for treating Parkinson's disease. In embodiments, the second agent is an agent for treating Huntington's disease. In embodiments, the second agent is an agent for treating a prion disease. In embodiments, the second agent is an agent for treating amyotrophic lateral sclerosis. In embodiments, the second agent is an agent for treating diabetes. In embodiments, the second agent is an agent for treating retinal degeneration. In embodiments, the second agent is an agent for treating retinitis pigmentosa. In embodiments, the second agent is an agent for treating macular degeneration. In embodiments, the second agent is an agent for treating type I diabetes. In embodiments, the second agent is an agent for treating type II diabetes. In embodiments, the second agent is an agent for treating multiple myeloma. In embodiments, the second agent is an agent for treating a cancer of a secretory cell. In embodiments, the second agent is an agent for reducing Ire1 (e.g. Ire1α) kinase activity. In embodiments, the second agent is an agent for reducing Ire1 (e.g. Ire1α) RNase activity. In embodiments, the second agent is an agent for inhibiting a pathway activated by Ire1 (e.g. Ire1α) phosphorylation. In embodiments, the second agent is an agent for inhibiting a pathway activated by Ire1 (e.g. Ire1α) RNase activity. In embodiments, the second agent is an agent for inhibiting Ire1 (e.g. Ire1α) oligomerization. In embodiments, the second agent is an agent for inhibiting apoptosis.

D. METHODS

In an aspect is provided a method of treating a disease in a patient in need of such treatment, the method including administering a therapeutically effective amount of a compound described herein (e.g. formula I, formula II, formula III, aspect, embodiment, example, figure, table, or claim), or a pharmaceutically acceptable salt thereof, to the patient, wherein the disease is a neurodegenerative disease, demyelinating disease, cancer, eye disease, fibrotic disease, or diabetes.

In embodiments, the disease is a neurodegenerative disease, demyelinating disease, cancer, or diabetes. In embodiments, the disease is a neurodegenerative disease. In embodiments, the neurodegenerative disease is retinitis pigmentosa, amyotrophic lateral sclerosis, retinal degeneration, macular degeneration, Parkinson's Disease, Alzheimer Disease, Huntington's Disease, Prion Disease, Creutzfeldt-Jakob Disease, or Kuru. In embodiments, the disease is amyotrophic lateral sclerosis. In embodiments, the disease is retinal degeneration. In embodiments, the disease is retinitis pigmentosa. In embodiments, the disease is a demyelinating disease. In embodiments, the demyelinating disease is Wolfram Syndrome, Pelizaeus-Merzbacher Disease, Transverse Myelitis, Charcot-Marie-Tooth Disease, or Multiple Sclerosis. In embodiments, the disease is Multiple Sclerosis. In embodiments, the disease is cancer. In embodiments, the cancer is multiple myeloma. In embodiments, the disease is diabetes. In embodiments, the diabetes is type I diabetes. In embodiments, the diabetes is type II diabetes. In embodiments, the disease is a neurodegenerative disease, demyelinating disease, cancer, eye disease, fibrotic disease, or diabetes described herein. In embodiments, the disease is an eye disease. In embodiments, the eye disease is retinitis pigmentosa. In embodiments, the eye disease is retinal degeneration. In embodiments, the eye disease is macular degeneration. In embodiments, the eye disease is Wolfram Syndrome. In embodiments, the disease is idiopathic pulmonary fibrosis (IPF). In embodiments, the disease is a fibrotic disease. In embodiments, the fibrotic disease is idiopathic pulmonary fibrosis (IPF), myocardial infarction, cardiac hypertrophy, heart failure, cirrhosis, acetaminophen (Tylenol) liver toxicity, hepatitis C liver disease, hepatosteatosis (fatty liver disease), or hepatic fibrosis. In embodiments, the disease is interstitial lung disease (ILD). In embodiments, the disease is myocardial infarction. In embodiments, the disease is cardiac hypertrophy. In embodiments, the disease is heart failure. In embodiments, the disease is cirrhosis. In embodiments, the disease is acetominophen (Tylenol) liver toxicity. In embodiments, the disease is hepatitis C liver disease. In embodiments, the disease is hepatosteatosis (fatty liver disease). In embodiments, the disease is hepatic fibrosis.

In an aspect is provided a method of modulating the activity of an Ire1 (e.g. Ire1α) protein, the method including contacting the Ire1 (e.g. Ire1α) protein with an effective amount of a compound described herein (e.g. formula I, formula II, formula III, aspect, embodiment, example, figure, table, or claim), or a pharmaceutically acceptable salt thereof.

In embodiments, the modulating is inhibiting. In embodiments, the activity is kinase activity. In embodiments, the kinase activity is autophosphorylation activity. In embodiments, the kinase activity is trans-autophosphorylation activity. In embodiments, the activity is oligomerization activity. In embodiments, the oligomerization activity is dimerization activity. In embodiments, the activity is RNase activity. In embodiments, the activity is miR-17 cleavage. In embodiments, the activity is miR-34a cleavage. In embodiments, the activity is miR-96 cleavage. In embodiments, the activity is miR-125b cleavage. In embodiments, the activity is XBP1 mRNA splicing. In embodiments, the activity is UPR activation. In embodiments, the activity is terminal UPR activation. In embodiments, a cell includes the Ire1 (e.g. Ire1α) protein. In embodiments, the activity of the Ire1 (e.g. Ire1α) protein is increasing apoptosis of the cell. In embodiments, an organ includes the cell. In embodiments, an organism includes the cell. In embodiments, an organism has a disease associated with the Ire1 (e.g. Ire1α) protein activity. In embodiments, the disease is a neurodegenerative disease, a demyelinating disease, cancer, an eye disease, a fibrotic disease, or diabetes. In embodiments, the disease is a neurodegenerative disease. In embodiments, the neurodegenerative disease is retinitis pigmentosa, amyotrophic lateral sclerosis, retinal degeneration, macular degeneration, Parkinson's Disease, Alzheimer Disease, Huntington's Disease, Prion Disease, Creutzfeldt-Jakob Disease, or Kuru. In embodiments, the disease is amyotrophic lateral sclerosis. In embodiments, the disease is retinal degeneration. In embodiments, the disease is retinitis pigmentosa. In embodiments, the disease is a demyelinating disease. In embodiments, the demyelinating disease is Wolfram Syndrome, Pelizaeus-Merzbacher Disease, Transverse Myelitis, Charcot-Marie-Tooth Disease, or Multiple Sclerosis. In embodiments, the disease is Multiple Sclerosis. In embodiments, the disease is cancer. In embodiments, the cancer is multiple myeloma. In embodiments, the disease is diabetes. In embodiments, the diabetes is type I diabetes. In embodiments, the diabetes is type II diabetes. In embodiments, the disease is an eye disease. In embodiments, the eye disease is retinitis pigmentosa. In embodiments, the eye disease is retinal degeneration. In embodiments, the eye disease is macular degeneration. In embodiments, the eye disease is Wolfram Syndrome. In embodiments, the disease is idiopathic pulmonary fibrosis (IPF). In embodiments, the disease is a fibrotic disease. In embodiments, the fibrotic disease is idiopathic pulmonary fibrosis (IPF), myocardial infarction, cardiac hypertrophy, heart failure, cirrhosis, acetominophen (Tylenol) liver toxicity, hepatitis C liver disease, hepatosteatosis (fatty liver disease), or hepatic fibrosis. In embodiments, the disease is interstitial lung disease (ILD). In embodiments, the disease is myocardial infarction. In embodiments, the disease is cardiac hypertrophy. In embodiments, the disease is heart failure. In embodiments, the disease is cirrhosis. In embodiments, the disease is acetominophen (Tylenol) liver toxicity. In embodiments, the disease is hepatitis C liver disease. In embodiments, the disease is hepatosteatosis (fatty liver disease). In embodiments, the disease is hepatic fibrosis. In embodiments, the Ire1 protein is an Ire1α protein. In embodiments, the Ire1 (e.g. Ire1α) protein is a human protein. In embodiments, the Ire1 protein is a human Ire1α protein.

In another aspect, the present disclosure, has identified two classes of kinase inhibitors-called types I and II, which stabilize alternate kinase active site conformations in numerous protein kinase targets (Liu, Y. & Gray, N. S. *Nat. Chem. Biol.* 2, 358-364 (2006)). The present disclosure shows that a type I kinase inhibitor and a novel type II kinase inhibitor both modify IRE1α by shutting down IRE1α trans-autophosphorylation, but have divergent effects on its RNase to activate or inactivate catalytic activity, respectively. The present disclosure further demonstrates that IRE1α RNase activity can be either up or downregulated through selective targeting of its kinase domain to control UPR signaling, and predict that it may be possible to pharmacologically modulate other kinase-coupled enzymes in a similar way.

In an additional aspect, the present disclosure illustrates that IRE1α's kinase-controlled RNase can be regulated in two distinct modes with kinase inhibitors: one class of ligands occupy IRE1α's kinase ATP-binding site to activate RNase-mediated XBP1 mRNA splicing even without upstream ER stress, while a second class can inhibit the RNase through the same ATP-binding site, even under ER stress. Thus, alternative kinase conformations stabilized by distinct classes of ATP-competitive inhibitors can cause allosteric switching of IRE1α's RNase—either on or off. As dysregulation of the UPR has been implicated in a variety of cell degenerative and neoplastic disorders, small molecule control over IRE1α should advance efforts to understand the UPR's role in pathophysiology and to develop drugs for ER stress-related diseases.

E. ADDITIONAL EMBODIMENTS

1. A compound having the formula:

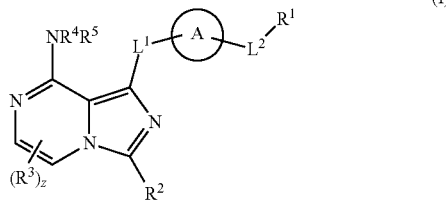

wherein, ring A is substituted or unsubstituted cycloalkylene, substituted or unsubstituted heterocycloalkylene, substituted or unsubstituted arylene, or substituted or unsubstituted heteroarylene; $L^1$ is a bond or unsubstituted $C_1$-$C_5$ alkylene; $L^2$ is a bond, —$NR^{6a}$—, —O—, —S—, —C(O)—, —S(O)—, —S(O)$_2$—, —$NR^{6a}$C(O)—, —C(O)$NR^{6b}$—, —C(O)(CH$_2$)$_{z2}$—, —$NR^{6a}$C(O)O—, —$NR^{6a}$C(O)$NR^{6b}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^1$ is hydrogen, oxo, halogen, —$CX_3$, —CN, —$SO_2Cl$, —$SO_nR^{10}$, —$SO_vNR^7R^8$, —$NHNH_2$, —$ONR^7R^8$, —NHC=(O)NHNH$_2$, —NHC=(O)$NR^7R^8$, N(O)$_m$, —$NR^7R^8$, —C(O)$R^9$, —C(O)—$OR^9$, —C(O)$NR^7R^8$, —$OR^{10}$, —$NR^7SO_nR^{10}$, —$NR^7C$=(O)$R^9$, —$NR^7C(O)OR^9$, —$NR^7OR^9$, —$OCX_3$, —$OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, oxo, halogen, —$CX^a_3$, —CN, —$SO_2Cl$, —$SO_{n1}R^{10a}$, —$SO_{n1}NR^{7a}R^{8a}$, —$NHNH_2$, —$ONR^{7a}R^{8a}$, —NHC=(O)NHNH$_2$, —NHC=(O)$NR^{7a}R^{8a}$, —N(O)$_{m1}$, —$NR^{7a}R^{8a}$, —C(O)$R^{9a}$, —C(O)$OR^{9a}$, —C(O)$NR^{7a}R^{8a}$, —$OR^{10a}$, —$NR^{7a}SO_{n1}R^{10a}$, —$NR^{7a}C$=(O)$R^{9a}$, —$NR^{7a}C(O)OR^{9a}$, —$NR^{7a}OR^{9a}$, —$OCX^a_3$, —$OCHX^a_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is independently hydrogen, oxo, halogen, —$CX^b_3$, —CN, —$SO_2Cl$, —$SO_{n2}R^{10b}$, —$SO_{v2}NR^{7b}R^{8b}$, —$NHNH_2$, —$ONR^{7b}R^{8b}$, —NHC=(O)NHNH$_2$, —NHC=(O)$NR^{7b}R^{8b}$, —N(O)$_{m2}$, —$NR^{7b}R^{8b}$, —C(O)$R^{9b}$, —C(O)—$OR^{9b}$, —C(O)$NR^{7b}R^{8b}$, —$OR^{10b}$, —$NR^{7b}SO_{n2}R^{10b}$, —$NR^{7b}C$=(O)$R^{9b}$, —$NR^{7b}C(O)OR^{9b}$, —$NR^{7b}OR^{9b}$, —$OCX^b_3$, —$OCHX^b_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ and $R^5$ are independently hydrogen or unsubstituted $C_1$-$C_6$ alkyl; $R^7$, $R^8$, $R^9$, $R^{10}$, $R^{6a}$, $R^{7a}$, $R^{8a}$, $R^{9a}$, $R^{10a}$, $R^{6b}$, $R^{7b}$, $R^{8b}$, $R^{9b}$ and $R^{10b}$ are independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)NHNH$_2$, —NHC=(O)$NH_2$, —$NHSO_2H$, —NHC=(O)H, —NHC(O)OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{7a}$ and $R^{8a}$ substituents bonded to the same nitrogen atom may optionally be joined to form a substituted or unsubstituted heterocycloalkyl or substituted or unsubstituted heteroaryl; $R^{7b}$ and $R^{8b}$ substituents bonded to the same nitrogen atom may optionally be joined to form a substituted or unsubstituted heterocycloalkyl or substituted or unsubstituted heteroaryl; each occurrence of the symbols n, n1, and n2 is independently an integer from 0 to 4; each occurrence of the symbols m, m1, m2, v, v1, and v2 is independently an integer from 1 to 2; the symbol z is an integer from 0 to 2; the symbol z2 is an integer from 1 to 4; and each occurrence of the symbols X, $X^a$, and $X^b$ is independently a halogen.

2. The compound of embodiment 1, wherein $R^3$ is independently hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

3. The compound of any one of embodiments 1 to 2, wherein $R^3$ is hydrogen.

4. The compound of any one of embodiments 1 to 3, wherein the symbol z is 1.

5. The compound of any one of embodiments 1 to 4, wherein $R^2$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

6. The compound of any one of embodiments 1 to 5, wherein $R^2$ is substituted or unsubstituted alkyl.

7. The compound of any one of embodiments 1 to 6, wherein $R^2$ is substituted or unsubstituted $C_1$-$C_6$ alkyl.

8. The compound of any one of embodiments 1 to 7, wherein $R^2$ is unsubstituted $C_1$-$C_6$ alkyl.

9. The compound of any one of embodiments 1 to 8, wherein $R^2$ is unsubstituted isopropyl or unsubstituted tert-butyl.

10. The compound of any one of embodiments 1 to 9, wherein $R^4$ and $R^5$ are hydrogen.

11. The compound of any one of embodiments 1 to 10, wherein $L^1$ is a bond.

12. The compound of any one of embodiments 1 to 10, wherein $L^1$ is unsubstituted methylene.

13. The compound of any one of embodiments 1 to 12, wherein $L^2$ is —$NR^{6a}C(O)NR^{6b}$—.

14. The compound of any one of embodiments 1 to 13, wherein $R^ha$ and $R^{6b}$ are hydrogen.

15. The compound of any one of embodiments 1 to 14, wherein $R^1$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

16. The compound of any one of embodiments 1 to 15, wherein $R^1$ is substituted or unsubstituted cycloalkyl, substituted or unsubstituted heterocycloalkyl, substituted or unsubstituted aryl, or substituted or unsubstituted heteroaryl.

17. The compound of any one of embodiments 1 to 16, wherein $R^1$ is substituted or unsubstituted aryl or substituted or unsubstituted heteroaryl.

18. The compound of any one of embodiments 1 to 17, wherein $R^1$ is substituted phenyl.

19. The compound of any one of embodiments 1 to 18, wherein $R^1$ is phenyl substituted with $CF_3$ or halogen.

20. The compound of any one of embodiments 1 to 19, wherein ring A is substituted or unsubstituted arylene or substituted or unsubstituted heteroarylene.

21. The compound of any one of embodiments 1 to 20, wherein ring A is substituted or unsubstituted $C_6$-$C_{10}$ arylene.

22. The compound of any one of embodiments 1 to 21, wherein ring A is unsubstituted naphthalenyl.

23. The compound of any one of embodiments 1 to 22 having the formula:

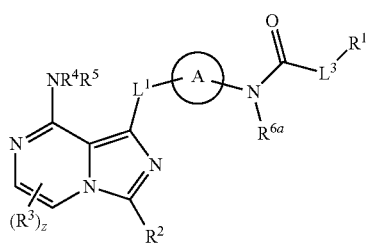

(II)

wherein, $L^3$ is a bond, —$NR^{6b}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

24. The compound of any one of embodiments 1 to 23 having the formula:

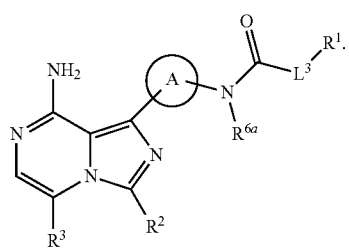

(III)

25. The compound of any one of embodiments 1 to 24 selected from the group consisting of:

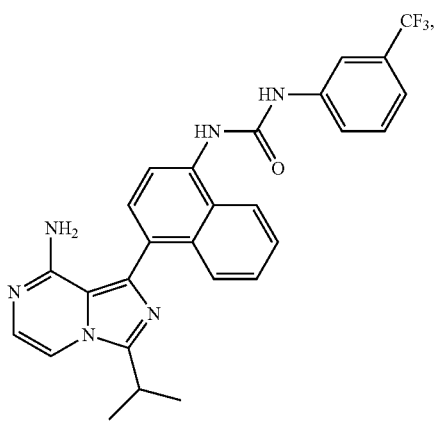

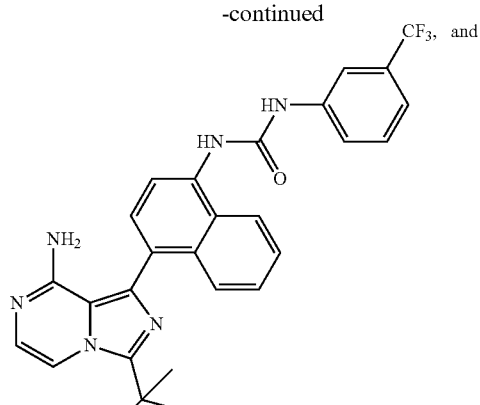

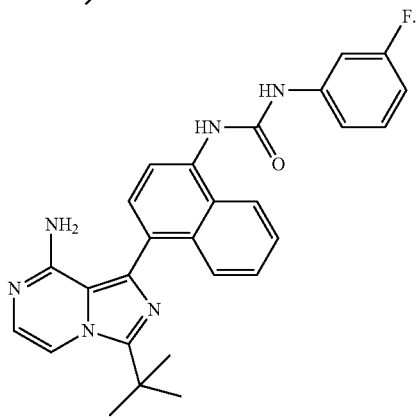

26. A pharmaceutical composition comprising a pharmaceutically acceptable excipient and a compound of any one of embodiments 1 to 25.

27. A method of treating a disease in a patient in need of such treatment, said method comprising administering a therapeutically effective amount of a compound of any one of embodiments 1 to 2, to said patient, wherein the disease is a neurodegenerative disease, demyelinating disease, cancer, eye disease, fibrotic disease, or diabetes.

28. The method of embodiment 27, wherein the disease is a neurodegenerative disease.

29. The method of any one of embodiments 27 and 28, wherein the neurodegenerative disease is retinitis pigmentosa, amyotrophic lateral sclerosis, retinal degeneration, macular degeneration, Parkinson's Disease, Alzheimer Disease, Huntington's Disease, Prion Disease, Creutzfeldt-Jakob Disease, or Kuru.

30. The method of embodiment 27, wherein the disease is a demyelinating disease.

31. The method of any one of embodiments 27 and 30, wherein the demyelinating disease is Wolfram Syndrome, Pelizaeus-Merzbacher Disease, Transverse Myelitis, Charcot-Marie-Tooth Disease, or Multiple Sclerosis.

32. The method of embodiment 27, wherein the disease is cancer.

33. The method of any one of embodiments 27 and 32, wherein the cancer is multiple myeloma.

34. The method of embodiment 27, wherein the disease is diabetes.

35. The method of any one of embodiments 27 and 34, wherein the diabetes is type I diabetes.

36. The method of any one of embodiments 27 and 34, wherein the diabetes is type II diabetes.

37. The method of embodiment 27, wherein the disease is an eye disease.

38. The method of any one of embodiments 27 and 37, wherein the eye disease is retinitis pigmentosa, retinal degeneration, macular degeneration, or Wolfram Syndrome.

39. The method of embodiment 27, wherein the disease is a fibrotic disease.

40. The method of any one of embodiments 27 and 39, wherein the fibrotic disease is idiopathic pulmonary fibrosis (IPF), myocardial infarction, cardiac hypertrophy, heart failure, cirrhosis, acetominophen (Tylenol) liver toxicity, hepatitis C liver disease, hepatosteatosis (fatty liver disease), or hepatic fibrosis.

41. A method of modulating the activity of an Ire1 protein, said method comprising contacting said Ire1 protein with an effective amount of a compound of any one of embodiments 1 to 25.

42. The method of embodiment 41, wherein said modulating is inhibiting.

43. The method of any one of embodiments 41 to 42, wherein said activity is kinase activity.

44. The method of embodiment 43, wherein said kinase activity is autophosphorylation activity.

45. The method of any one of embodiments 41 to 42, wherein said activity is oligomerization activity.

46. The method of embodiment 45, wherein said oligomerization activity is dimerization activity.

47. The method of any one of embodiments 41 to 42, wherein said activity is RNase activity.

48. The method of any one of embodiments 41 to 42, wherein a cell comprises said Ire1 protein.

49. The method of embodiment 48, wherein said activity of the Ire1 protein is increasing apoptosis of said cell.

50. The method of any one of embodiments 48 to 49, wherein an organ comprises said cell.

51. The method of any one of embodiments 48 to 50, wherein an organism comprises said cell.

52. The method of embodiment 51, wherein said organism has a disease associated with said Ire1 protein activity.

53. The method of embodiment 52, wherein said disease is a neurodegenerative disease, demyelinating disease, cancer, eye disease, fibrotic disease, or diabetes.

54. The method of embodiment 53, wherein the disease is a neurodegenerative disease.

55. The method of any one of embodiments 53 and 54, wherein the neurodegenerative disease is retinitis pigmentosa, amyotrophic lateral sclerosis, retinal degeneration, macular degeneration, Parkinson's Disease, Alzheimer Disease, Huntington's Disease, Prion Disease, Creutzfeldt-Jakob Disease, or Kuru.

56. The method of embodiment 53, wherein the disease is cancer.

57. The method of any one of embodiments 53 and 56, wherein the cancer is multiple myeloma.

58. The method of embodiment 53, wherein the disease is diabetes.

59. The method of any one of embodiments 53 and 58, wherein the diabetes is type I diabetes.

60. The method of any one of embodiments 53 and 58, wherein the diabetes is type II diabetes.

61. The method of embodiment 53, wherein the disease is a demyelinating disease.

62. The method of any one of embodiments 53 and 61, wherein the demyelinating disease is Wolfram Syndrome, Pelizaeus-Merzbacher Disease, Transverse Myelitis, Charcot-Marie-Tooth Disease, or Multiple Sclerosis.

63. The method of any one of embodiments 53, 61, and 62, wherein the demyelinating disease is Multiple Sclerosis.

64. The method of embodiment 53, wherein the disease is an eye disease.

65. The method of any one of embodiments 53 and 64, wherein the eye disease is retinitis pigmentosa, retinal degeneration, macular degeneration, or Wolfram Syndrome.

66. The method of embodiment 53, wherein the disease is a fibrotic disease.

67. The method of any one of embodiments 53 and 66, wherein the fibrotic disease is idiopathic pulmonary fibrosis (IPF), myocardial infarction, cardiac hypertrophy, heart failure, cirrhosis, acetominophen (Tylenol) liver toxicity, hepatitis C liver disease, hepatosteatosis (fatty liver disease), or hepatic fibrosis.

68. A compound of the formula

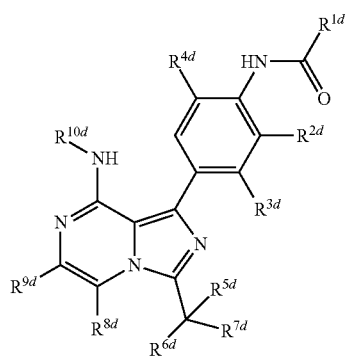

or a pharmaceutically acceptable salt thereof, wherein $R^{1d}$, $R^{2d}$, $R^{3d}$, $R^{4d}$, $R^{5d}$, $R^{6d}$, $R^{7d}$, $R^{8d}$, $R^{9d}$, and $R^{10d}$, are each independently $C_{2-6}$ alkyl, $C_{1-6}$ haloalkyl, —$C_{1-4}$ alkyl-$R^{12d}$, $C_{2-6}$ alkenyl, $C_{2-6}$ alkynyl, $C_{3-8}$ cycloalkyl, monocyclic heterocyclyl, monocyclic heteroaryl, or phenyl, aryl, wherein the cycloalkyl, heterocyclyl, heteroaryl, and phenyl groups are each optionally substituted with one or two $R^{11d}$ groups; each $R^{11d}$ is independently $C_{1-6}$ alkyl, $C_{1-6}$ haloalkyl, —C(O)$R^d$, —C(O)O$R^d$, —C(O)N$R^d_2$, S(O)$_2$N$R^d_2$, or S(O)$_2$ $R^d$; and $R^{12d}$ is O$R^d$, —S$R^d$, —N$R^d_2$, —C(O)$R^d$, —C(O) O$R^d$, —C(O)N$R^d_2$, S(O)$_2$$R^d$, —OC(O)$R^d$, OC(O)O$R^d$, OC(O)N$R^d_2$, —N($R^d$)C(O)$R^d$, —N($R^d$)C(O)O$R^d$, —N($R^d$) C(O)N$R^d_2$, phenyl, monocyclic heteroaryl, $C_{3-8}$ cycloalkyl, or monocyclic heterocyclyl, wherein the aryl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, O$R^d$, —S$R^d$, —N$R^d_2$, —C(O)$R^d$, C(O)O$R^d$, —C(O)N$R^d_2$, S(O)$_2$$R^d$, —OC(O) $R^d$, —OC(O)O$R^1$, OC(O) N$R^d_2$, N($R^d$)C(O)$R^d$, —N($R^d$)C(O)O$R^d$, or —N($R^d$)C(O) N$R^d_2$; and each $R^d$ is independently hydrogen, $C_{1-6}$ alkyl, $C_{2-6}$ alkenyl, $C_{1-6}$ haloalkyl, $C_{3-8}$ cycloalkyl, heterocyclyl, aryl, aryl$C_{1-6}$ alkyl, heteroaryl, or heteroaryl$C_{1-6}$ alkyl wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —OR$^{Od}$, SR$^{Od}$, NR$^{Od}_2$, C(O)R$^{Od}$, C(O)OR$^{Od}$, —C(O)N(R$^{Od}$)2, S(O)2R$^{Od}$, —OC(O)R$^{Od}$, —OC (O)OR$^{Od}$, OC(O)N(R$^{Od}$)2, N(R$^{Od}$)C(O)R$^{Od}$, —N(R$^{Od}$)C(O) OR$^{Od}$, or N(R$^{Od}$)C(O)N(R$^{Od}$)2, wherein each R$^{Od}$ is independently hydrogen or $C_{1-6}$ alkyl, each $R^d$ is independently hydrogen, or $C_{1-6}$ alkyl.

69. A compound of the formula

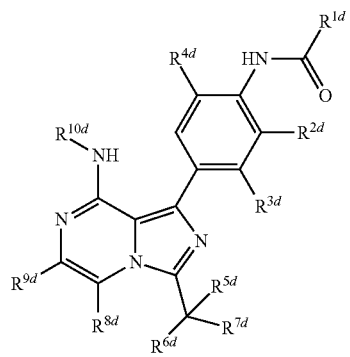

or a pharmaceutically acceptable salt thereof, wherein $R^{1d}$ is —$OR^d$, —$SR^d$, —$NR^d_2$, —$C(O)R^d$, —$C(O)OR^d$, —$C(O)NR^d_2$, —$N(R^d)C(O)R^d$, —$N(R^d)C(O)OR^d$, —$N(R^d)C(O)NR^d_2$, phenyl, monocyclic heteroaryl, $C_{3-8}$ cycloalkyl, or monocyclic heterocyclyl, wherein the aryl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, $OR^d$, —$SR^d$, —$NR^d_2$, —$C(O)R^d$, $C(O)OR^d$, —$C(O)NR^d_2$, $S(O)_2R^d$, —$OC(O)R^d$, —$OC(O)OR^d$, $OC(O)NR^d_2$, —$N(R^d)C(O)R^d$, —$N(R^d)C(O)OR^d$, or —$N(R^d)C(O)NR^d_2$; and $R^{2d}$ and $R^{3d}$ are together a phenyl, monocyclic heteroaryl, $C_{3-8}$ cycloalkyl, or monocyclic heterocyclyl, wherein the aryl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, —$OR^d$, —$SR^d$, —$NR^d_2$, —$C(O)R^d$, $C(O)OR^d$, —$C(O)NR^d_2$, $S(O)_2R^d$, —$OC(O)R^d$, —$OC(O)OR^d$, $OC(O)NR^d_2$, $N(R^d)C(O)R^d$, —$N(R^d)C(O)OR^d$, or —$N(R^d)C(O)NR^d_2$; wherein each $R^d$ is independently hydrogen, $C_{1-6}$ alkyl, $C_{2-6}$ alkenyl, $C_{1-6}$ haloalkyl, $C_{3-8}$ cycloalkyl, heterocyclyl, aryl, aryl$C_{1-6}$ alkyl, heteroaryl, or heteroaryl$C_{1-6}$ alkyl wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —$OR^{od}$, $SR^{od}$, $NR^{od}2$, $C(O)R^{od}$, $C(O)OR^{od}$, —$C(O)N(R^{od})2$, $S(O)2R^{od}$, —$OC(O)R^{od}$, —$OC(O)OR^{od}$, $OC(O)N(R^{od})2$, $N(R^{od})C(O)R^{od}$, —$N(R^{od})C(O)OR^{od}$, or $N(R^{od})C(O)N(R^{od})2$, wherein each $R^{od}$ is independently hydrogen or $C_{1-6}$ alkyl, each $R^d$ is independently hydrogen, or $C_{1-6}$ alkyl.

70. A composition comprising any of the formulas of embodiments 68 and 69 or a pharmaceutically acceptable salt thereof.

71. A pharmaceutical composition for inhibiting IRE1α RNase activity, the composition comprising: Formula (A), Formula (B), any derivatives of Formula (A) and Formula (B) disclosed herein, GP17, GP21, GP29, DSA7, DSA5, GP117, GP118, GP146, GP146 (NMe), GP146(Am), compounds shown FIGS. 7 and 8, any of the formulas from embodiments 68 and 69, and combinations thereof.

72. A pharmaceutical composition for activating IRE1α RNase activity, the composition comprising murine IRE1α.

73. A method for inhibiting IRE1α RNase activity, the method comprising providing a subject in need of such inhibition an effective amount of either: a. a compound of embodiment 68, Formula (A), Formula (B), GP17, GP21, GP29, DSA7, DSA8, GP117, GP118, GP146, GP146 (NMe), GP146(Am), a compound shown FIG. 7 or 8, any of the formulas of embodiments 68 and 69, and any combinations thereof, or b. a pharmaceutical composition comprising a compound from 73(a) and a pharmaceutically acceptable excipient, carrier, or diluent.

74. A method for activating IRE1α RNase activity, the method comprising providing a subject in need of such inhibition an effective amount of either: a. murine IRE1α; or b. a pharmaceutical composition comprising murine IRE1α and a pharmaceutically acceptable excipient, carrier, or diluent.

75. The method of any one of embodiments 41 to 67, wherein said Ire1 is Ire1α.

76. The method of any one of embodiments 41 to 67 and 75, wherein said Ire1 is a human Ire1.

F. EXAMPLES

1. Screening and Optimization of IRE1α Modulators

The particulars shown herein are by way of example and for purposes of illustrative discussion of embodiments of the present invention only and are presented in the cause of providing what is believed to be a readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Inhibition of IRE1α's RNase activity through the ATP-binding site of its kinase domain using kinase inhibitors. Generation of more potent and selective analogs of IRE1α kinase inhibitors Discovery of ATP-Competitive Kinase Inhibitors that are Able to Inhibit the RNase Domain of IRE1α from a Distance.

Previous studies have demonstrated that the RNase activity of IRE1α is dependent on kinase domain autophosphorylation. Shown herein is an unexpected relationship between the kinase and RNase domains, where ligands that interact with the ATP-binding site of the kinase domain are able to bypass the autophosphorylation requirement and activate the RNase domain (Papa, F. R. et al. *Science* 302, 1533-1537 (2003)). For instance, the orthogonal ATP-competitive inhibitor 1NM-PP1 is able to rescue the RNase activity of IRE1α mutants that lack kinase activity (Han, D. et al. *Biochemical and biophysical research communications* 365, 777-783, (2008)). Other ligands that interact with the ATP-binding site of wild-type IRE1α, including the endogenous co-factors ADP and ATP, are also able to activate RNase activity directly (Lee, K. P. et al. *Cell* 132, 89-100, (2008); Ali, M. M. et al. *The EMBO journal* 30, 894-905, (2011)). Also, the ATP-competitive inhibitors APY29 and sunitinib directly activate the RNase of yeast and murine IRE1α (Han, D. et al. *Cell* 138, 562-575, (2009); Korennykh, A. V. et al. *Nature* 457, 687-693, (2009)). A crystal structure of APY29 bound to yeast IRE1 shows that the kinase catalytic domain is in an active conformation (Korennykh, A. V. et al. *Nature* 457, 687-693, (2009)), which is a conformation adopted by protein kinases capable of catalyzing phosphate transfer. By stabilizing an active conformation of IRE1α's ATP-binding site, certain co-factors and ATP-competitive inhibitors act as ligands that allosterically activate its adjacent RNase domain. Given the ability to allosterically activate IRE1α's RNase through its kinase domain, it should be possible to also inhibit the RNase through the same kinase domain with a different class of kinase inhibitors that stabilize an inactive ATP-binding site conformation. Two classes of ATP-competitive kinase inhibitors—called types I and II—have been identified (FIG. 1A), which stabilize alternate kinase active site conformations in numerous protein kinase targets [51,52]. Type I inhibitors—like APY29 and sunitinib—stabilize an active ATP-binding site conformation. In contrast, type II inhibitors—like the clinically-approved drugs imatinib and sorafenib—selectively stabilize an inactive ATP-binding site conformation[53-55]. The inactive ATP-binding site conformation stabilized by type II inhibitors is characterized by outward movement of the catalytically-important Asp-Phe-Gly (DFG) motif, and is therefore called the DFG-out conformation (FIG. 1A)[51,52]. Described herein is the generation of a diverse panel of type II inhibitors and characterization of their interactions with a number of protein kinases (Krishnamurty, R. et al. *Nature chemical biology* 9, 43-50, (2013); Han, D. et al. *Biochemical and biophysical research communications* 365, 777-783, (2008); Brigham, J. L. et al. *ACS Chem. Biol.* (2013); Hill, Z. B. et al. *ACS Chem. Biol.* 7, 487-49, (2012)). These pharmacological tools served as a starting point towards the goal of identifying ATP-competitive inhibitors able to allosterically inactivate the IRE1α RNase.

Figure 1:
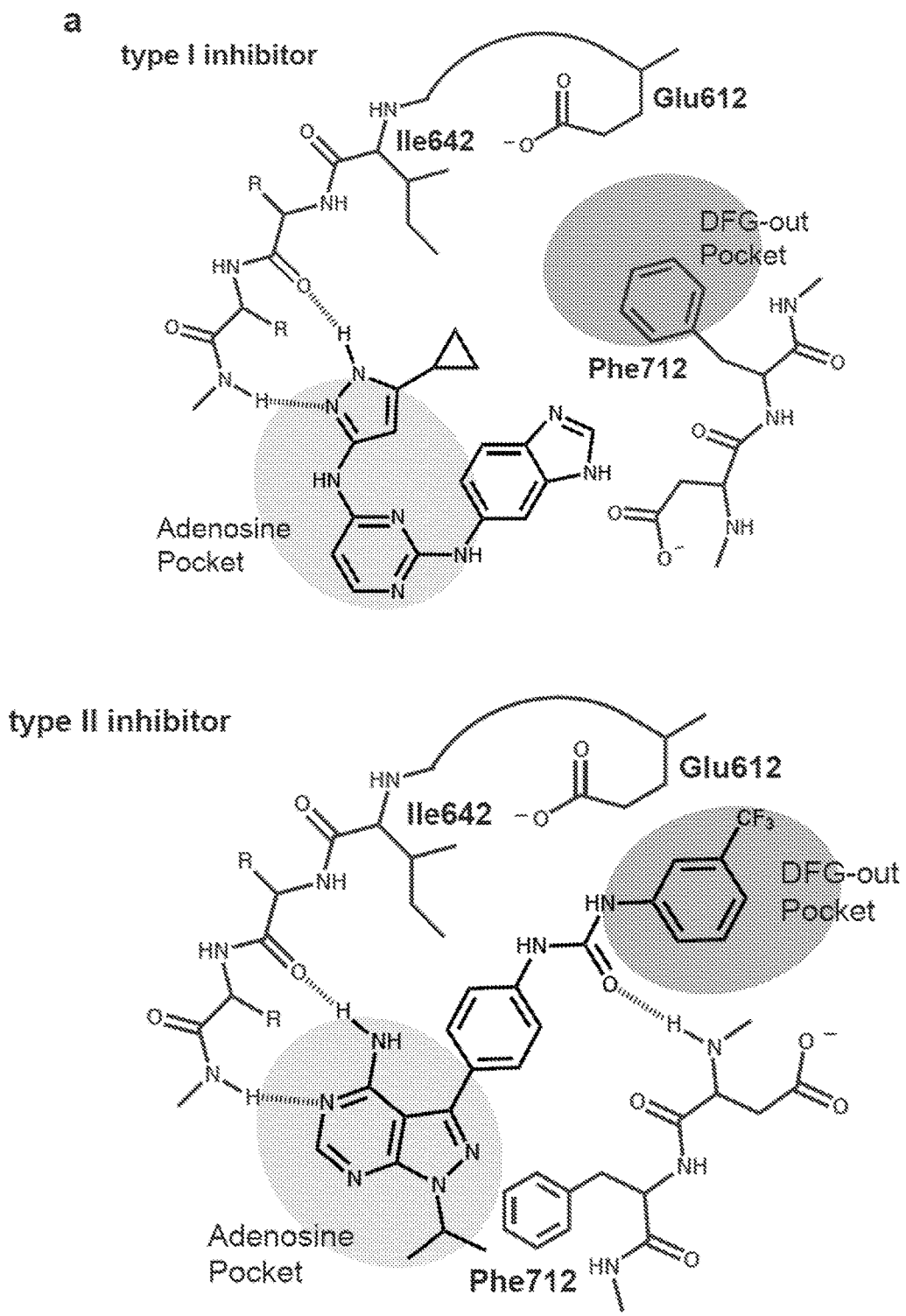
FIG. 1. Interaction of ATP-competitive inhibitors with the bifunctional kinase/RNase, IRE1α. (a) Proposed binding modes of type I and type II kinase inhibitors with the ATP-binding pocket of IRE1 α. Left panel shows the contacts a type I inhibitor, APY29, forms with yeast IRE1α (PDB code 3SDJ)[18] (SEQ ID NO:3). The right panel shows the proposed contacts a type II inhibitor, GP118, forms with IRE1α based on the co-crystal structure of the same inhibitor bound to Src (PDB code 3EL8) (SEQ ID NO:4) (also see FIG. 15). (b) XBP1 RNA minisubstrate assay used for screening IRE1α modulators; the recombinant human IRE1α—IRE1α*—in the assay spans residues 469-977, which includes the cytosolic kinase and RNase domains; cleavage of the 5'FAM-3'BHQ-labeled XBP1 minisubstrate by IRE1α* results in FRET-dequenching. (c) Endpoint fluorescence of IRE1α* catalyzed cleavage reaction of XBP1 minisubstrate in the presence of varying concentrations of inhibitors, or DMSO; STF-083010 is an imine-based compound that covalently inhibits the RNase domain; relative fluorescence intensity is scaled to the signal observed with IRE1α* (1.0), or without IRE1α* (0). (mean±SD, n=3). (d) Structures of type II kinase inhibitors that inhibit the RNase activity of IRE1α* (GP118/KIRA1, GP117/KIRA2, GP146/KIRA3). Numbering of amino acid residues from Ire1α in figures uses amino acid numbering of human Ire1α (e.g. including numbering used for human IRE1α (469-977) sequence in SEQ ID NO:2 as numbered in the Examples section herein).
Figure 1:
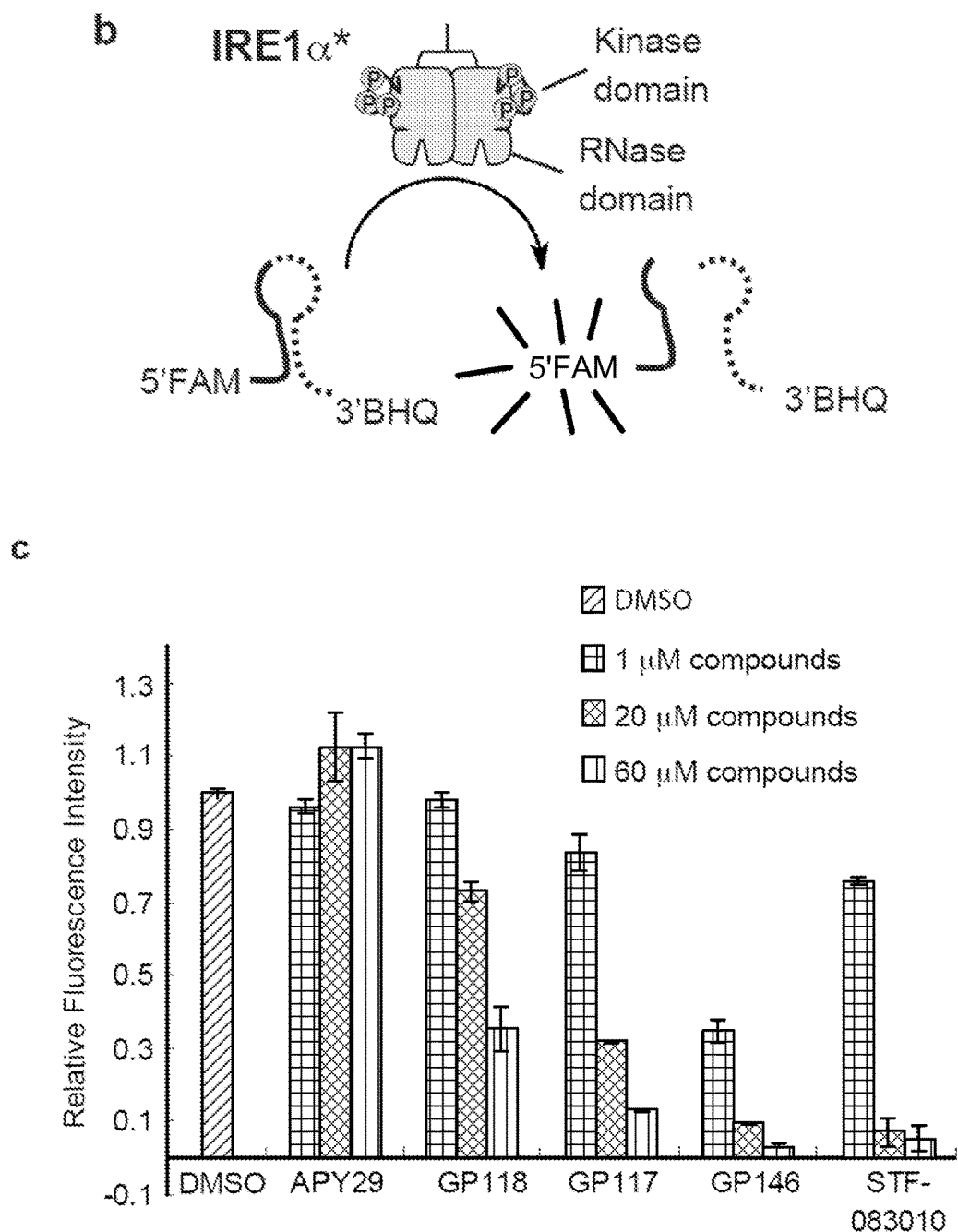
Figure 1:
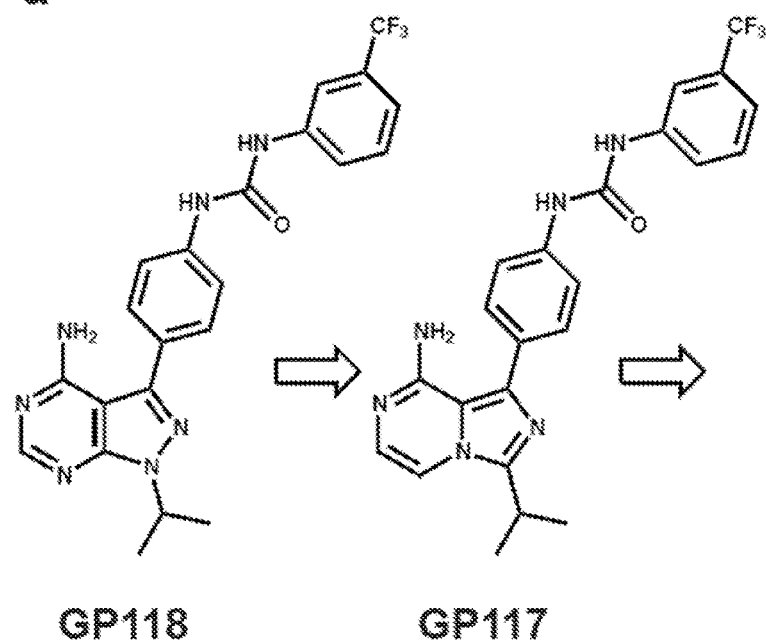
Figure 1:
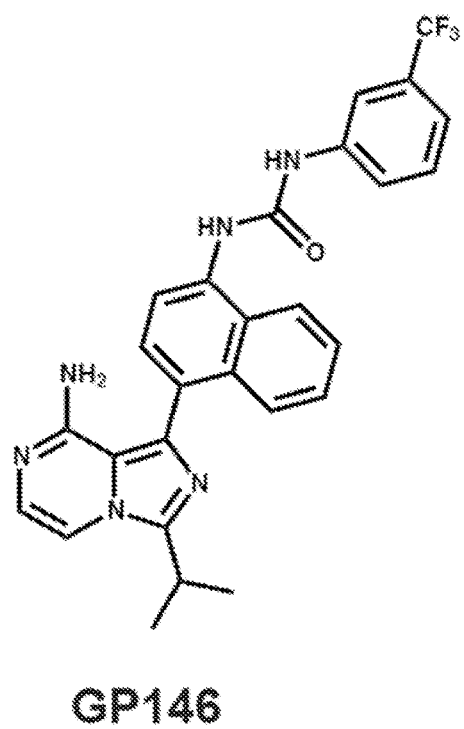

The diverse panel of type II inhibitors were screened for their ability to block the RNase activity of a recombinant soluble human IRE1α mini-protein construct (expressed in baculovirus) containing the kinase/RNase domains—called IRE1α* (Zhang, J. et al. *Nature reviews. Cancer* 9, 28-39, (2009)). Since IRE1α* is basally autophosphorylated, its RNase is active, and can be assayed using a FRET-quenched XBP1 RNA mini-substrate. While all the type II inhibitors tested with this assay contain the core binding elements predicted to stabilize the DFG-out conformation, only one ligand, demonstrated measurable inhibition of IRE1α*'s RNase activity at a concentration of 60 µM (FIGS. 1C and 1D). Because these type II kinase inhibitors also attenuate the RNase activity of IRE1α*, they were designated KIRAs—for kinase-inhibiting RNase attenuators. KIRA1 is a pyrazolopyrimidine-based inhibitor that has been shown to stabilize the DFG-out conformation of the non-receptor tyrosine kinases Src and Abl (Dar, A. C. et al. *Chemistry & Biology* 15, 1015-1022 (2008)). Based on the co-crystal structure of KIRA1 bound to Src (PDB: 3EL8) and molecular modeling, proposed contacts with IRE1α are shown in FIG. 1A.

Despite its modest potency, KIRA1 served as a suitable starting point for developing higher affinity allosteric RNase inhibitors. A number of similar analogs were generated and tested for RNase inhibition. While most modifications of KIRA1 were deleterious, replacing the pyrazolopyrimidine scaffold with an imidazopyrazine core provided a significant increase in overall potency (KIRA2, FIGS. 1C and 1D). Furthermore, substituting the 4-anilino group at the C-3 position of KIRA2 with a naphthylamine moiety provided KIRA3. Notably, KIRA3 inhibits XBP1 RNA cleavage to a similar degree as STF-083010, an imine-based small molecule that directly inhibits the IRE1α RNase through covalent modification.

Figure 2:
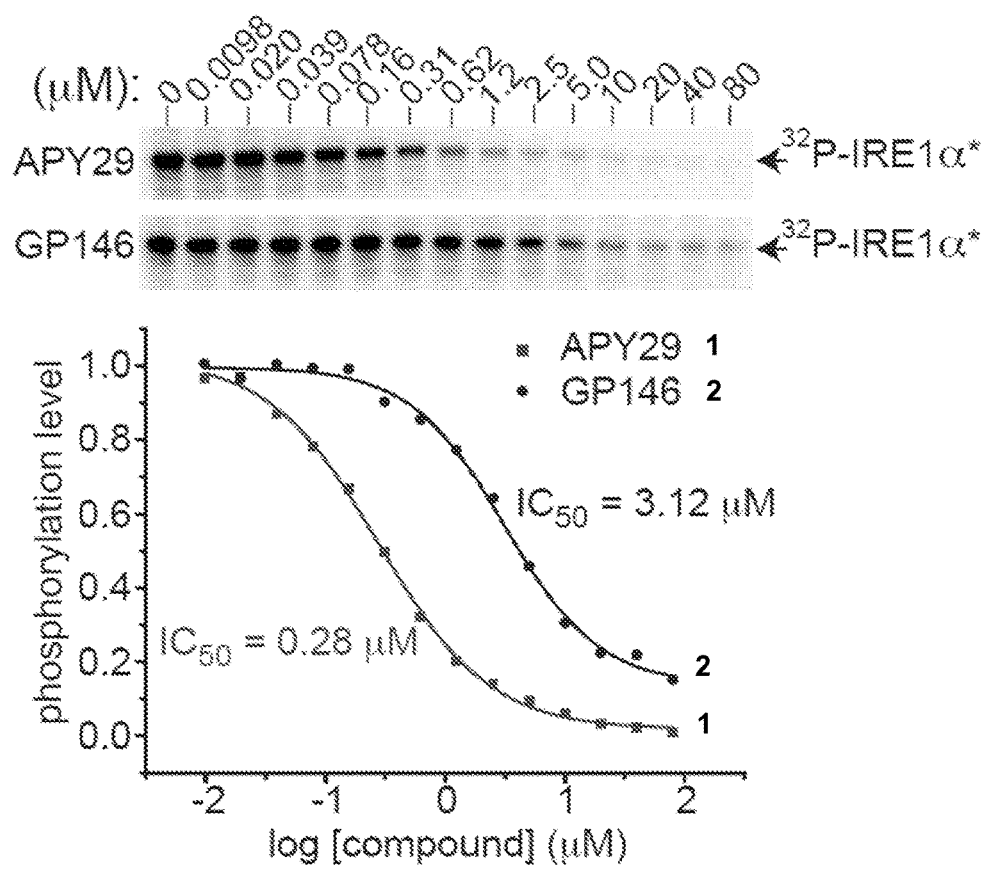
FIG. 2. APY29 and GP146 (KIRA3) divergently modulate the RNase activity and oligomerization state of IRE1α*. (a) Inhibition of IRE1α* autophosphorylation in vitro by APY29 and GP146; top panels show autoradiograms of autophosphorylation levels under serial two-fold dilutions of the respective inhibitors (from 80 µM to 0.0098 µM); the lower panel shows normalized autophosphorylation levels and $IC_{50}$ values for both compounds. (b) λ-PPase treatment of IRE1α* produces dephosphorylated IRE1α* (dP-IRE1α*); immunoblots using anti-IRE1α and anti-phospho IRE1α antibodies are shown. (c) RNase activities of IRE1α* and dP-IRE1α* under varying [APY29] or [GP146] (KIRA3) per the assay of FIG. 1b; $EC_{50}$ values were determined by fitting normalized fluorescence intensities (mean±SD, n=3). (d) Urea PAGE of XBP1 mini-substrate cleavage by IRE1α* and dP-IRE1α* with and without GP146 (KIRA3) or APY29. (e) RNase competition assays between APY29 and GP146 (KIRA3); the line marked with circles shows IRE1α* RNAse activity under fixed GP146 (KIRA3) and varying [APY29]; the line marked with squares shows IRE1α* RNAse activity under fixed APY29 and varying [GP146] (KIRA3); the line marked with triangles shows IRE1α* RNAse activity under fixed STF-083010 and varying [APY29] (mean±SD, n=3).
Figure 2:
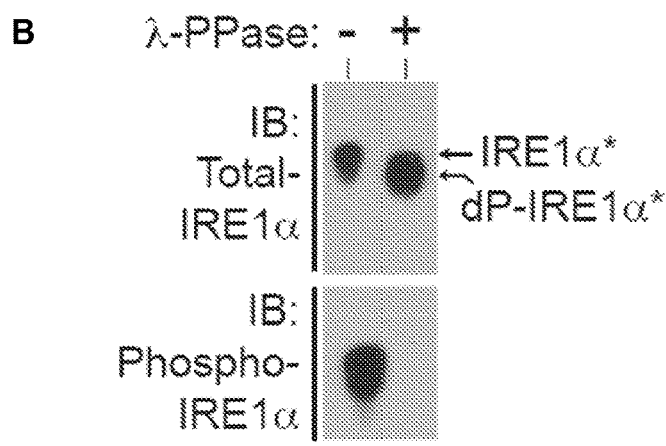
Figure 2:
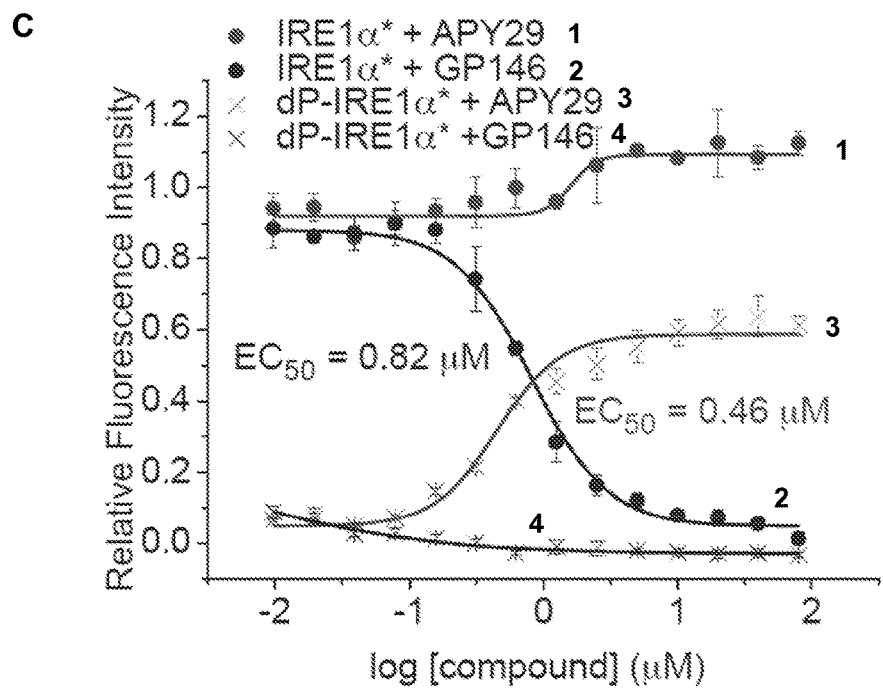
Figure 2:
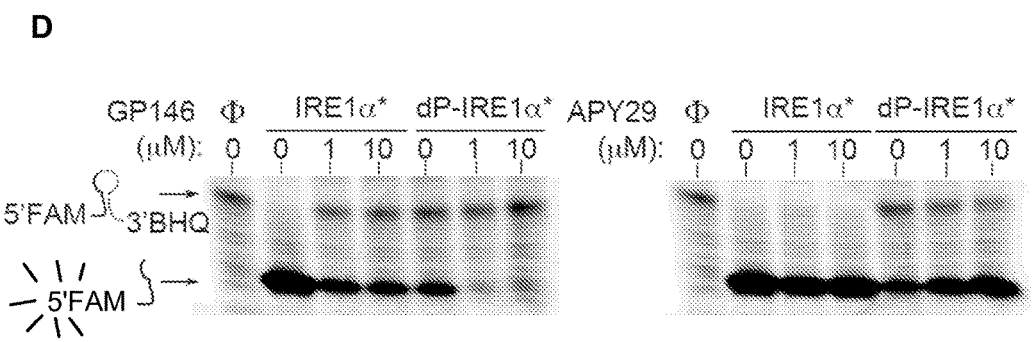
Figure 2:
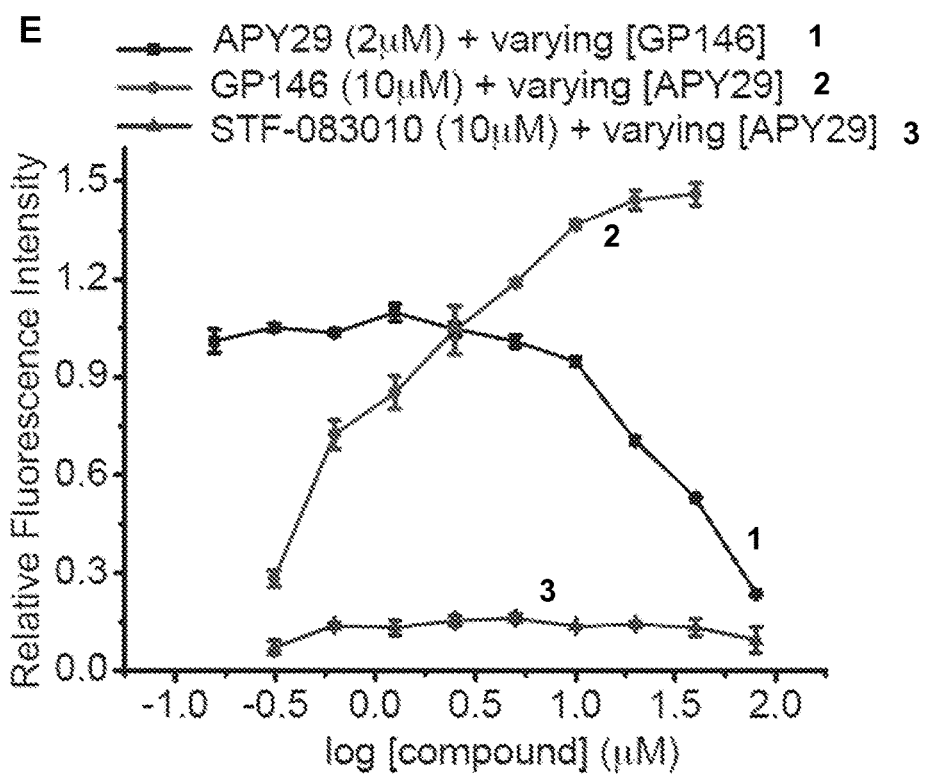

Similar to the type I inhibitor APY29 (IC$_{50}$ (autophosphorylation)=0.28 µM), KIRA3 (IC$_{50}$ (autophosphorylation) =3.1 µM) demonstrates dose-dependent reduction of IRE1α*kinase autophosphorylation in vitro. Thus, although KIRA3 and APY29 are both IRE1α* kinase inhibitors, they demonstrate opposing effects on its RNase activity, with APY29 acting as an activator. To further characterize differences between the two kinase inhibitors, a version of IRE1α* was generated with low basal RNase activity by using λ-phosphatase to remove activating phosphates. As expected, the dephosphorylated variant of IRE1α* (dP-IRE1α*) has significantly lower basal RNase activity than IRE1α*; incubating dP-IRE1α* with increasing APY29 progressively restores its ability to cleave the XBP1 minisubstrate, plateauing at 60% of the levels of IRE1α* (FIG. 2C). In contrast, KIRA3 suppresses residual RNase activity of dP-IRE1α*. Competition experiments were performed to further explore the opposing effects of APY29 and KIRA3. Increasing concentrations of APY29 progressively reverse IRE1α* RNase inhibition caused by a fixed concentration of KIRA3 (FIG. 2E). Furthermore, the type I inhibitor sunitinib also opposes the RNase inhibitory effect of KIRA3. On the other hand, increasing concentrations of KIRA3 restore RNase inhibition under a fixed concentration of APY29, with an expected increase in the IC$_{50}$. As predicted, APY29 cannot rescue direct inhibition caused by the covalent RNase modifier STF-083010. Taken together, these results strongly suggest that APY29 and KIRA3 are exerting their opposing effects on RNase activity through the same binding site.

Figure 18:
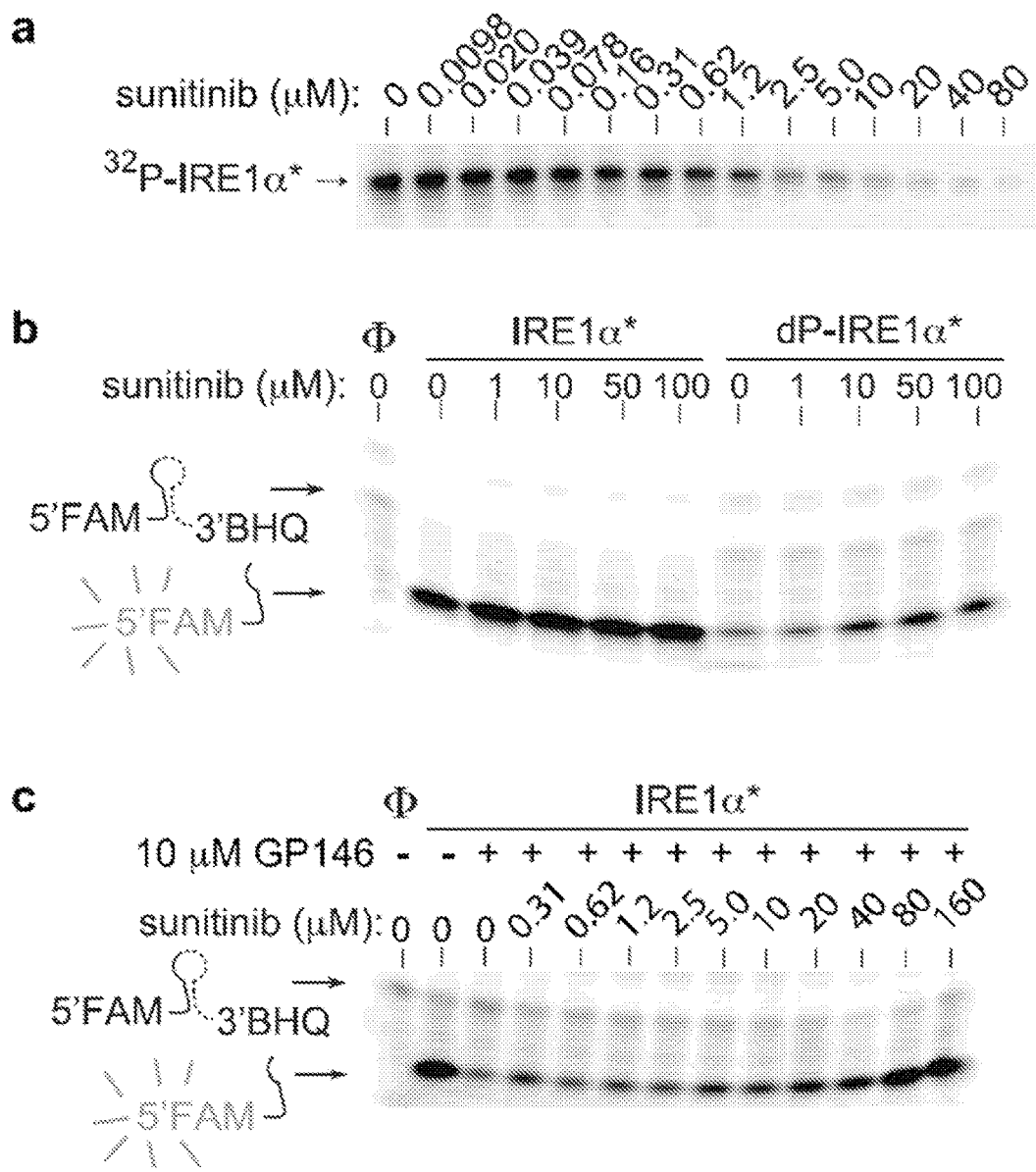
FIG. 18. Sunitinib inhibits IRE1α* autophosphorylation but activates the RNase domain. (a) Autoradiograms of IRE1α* autophosphorylation levels under serial two-fold dilutions of sunitinib (from 80 µM to 0.0098 µM). (b) Urea PAGE analysis of XBP1 minisubstrate cleavage by IRE1α* and dP-IRE1α* with and without sunitinib. (c) Urea PAGE analysis of XBP1 minisubstrate cleavage by IRE1α* with fixed GP146 (10 µM) and varying sunitinib concentrations.

The drug sunitinib is a promiscuous type I inhibitor that has been shown to inhibit the kinase activity of yeast and human IRE1α 16,19. To investigate the differences between GP146 (KIRA3) and other ATP-competitive inhibitors of IRE1α, the interaction of sunitinib with the IRE1α* and dP-IRE1α* constructs was further characterized. As expected, sunitinib is a dose-dependent inhibitor of the autophosphorylation activity of IRE1α* (FIG. 18a). In addition, sunitinib activates the RNase activity of dP-IRE1α*, which is consistent with its type I pharmacophore (FIG. 18b). Therefore, both APY29 and sunitinib stabilize an ATP-binding site conformation that activates the RNase domain of IRE1α. Like APY29, increasing amounts of sunitinib are able to rescue the RNase activity of IRE1α* in the presence of a fixed concentration of GP146 (FIG. 18c). Together, these results show that GP146 opposes the stereotypic RNase activation demonstrated by various type I ATP-competitive inhibitors of IRE1α.

KIRA3 Prevents Dimerization and Oligomerization of IRE1α.

Figure 24:
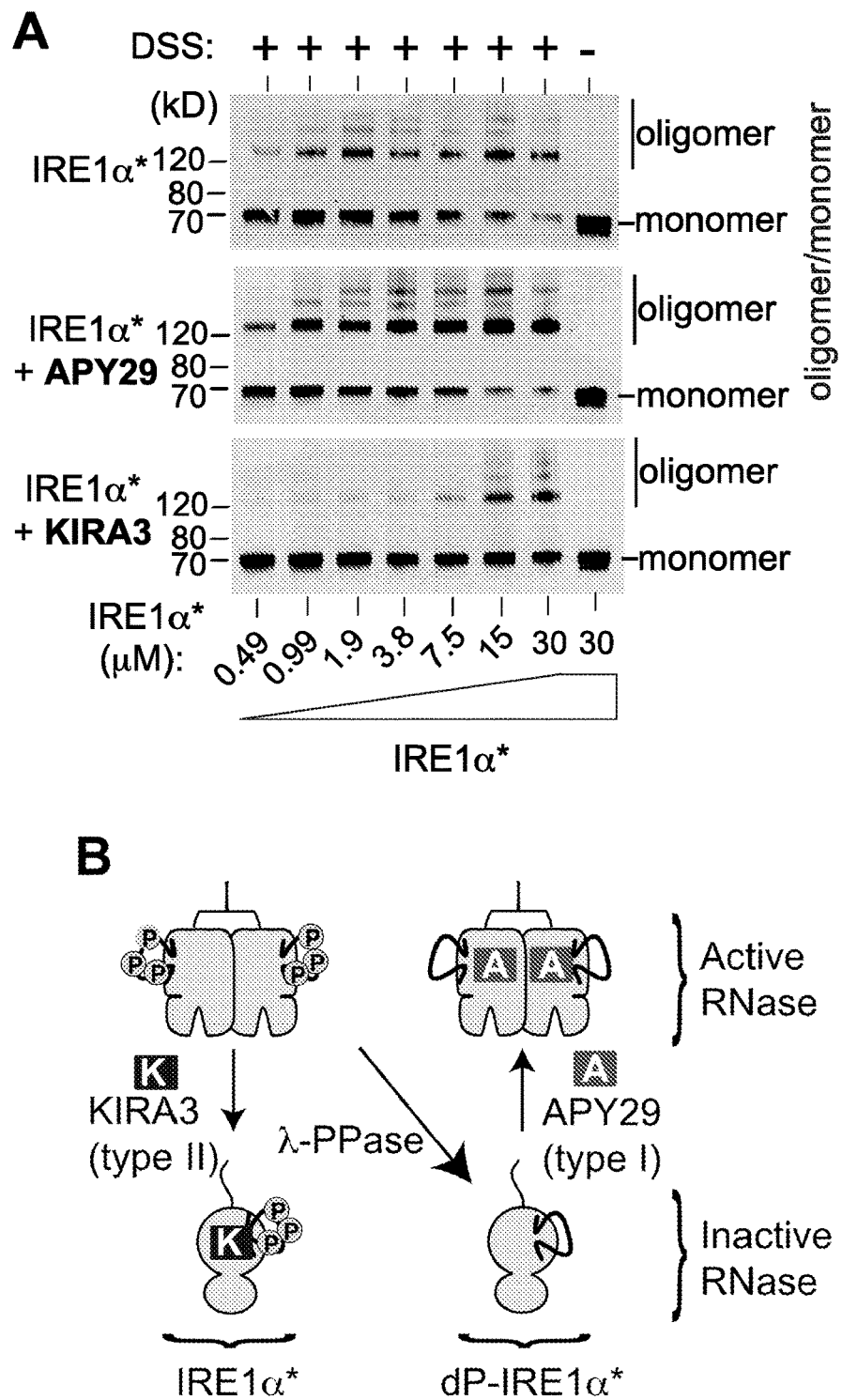
FIG. 24. (A) Immunoblots of IRE1α* after treatment with the crosslinker DSS; increasing concentrations of IRE1α* were incubated with DMSO, APY29, or KIRA3. (B) Model of how type kinase inhibitors can affect the RNase activities and oligomeric states of IRE1α* and dP-IRE1α*.

Self-association of kinase/RNase monomers has been reported to increase RNase activity as dimers and/or higher-order oligomers form in yeast and mammalian IRE1 proteins. furthermore, the degree of order may correlate directly with activity. Thus, APY29 and KIRA3 were used to test the prediction that they would divergently affect the oligomerization state of human IRE1α as a basis for their opposing effects on its RNase activity. Specifically, RNase activators should drive monomers into higher-order species from baseline. To test this, increasing concentrations of IRE1α* were incubated with either DMSO, or saturating concentrations of APY29 or KIRA3 and the ratio of oligomeric defined as all species greater than monomers—to monomeric IRE1α was determined (FIG. 24). In the absence of ligands, IRE1α* shows a concentration-dependent increase in the oligomer/monomer ratio. APY29 further enhances—whereas KIRA3 decreases—this concentration-dependent increase in the IRE1α* oligomer/monomer ratio. Taken together, the in vitro data support a model in which these two classes of kinase inhibitors divergently modulate IRE1α* RNase activity by exerting opposing effects on the oligomerization state of the enzyme.

2. Synthesis and Characterization of Compositions

Unless otherwise noted, all reagents were obtained from commercial suppliers and used without purification. TLC was performed on EMD Millipore silica gel 60 F254 plates. 1H-NMR spectra were obtained on a Bruker AV-300 or AV301 instrument at room temperature and 13C-NMR spectra were obtained on a Bruker AV-500 instrument at room temperature. Chemical shifts are reported in ppm, and coupling constants are reported in Hz. 1H and 13C resonances are referenced to residual MeOH. Mass spectrometry was performed on a Bruker Esquire Ion Trap MS instrument. The purity of all final compounds was determined by analytical HPLC with two different solvent systems. Analytical conditions A: [C18 (150×2.1 mm), CH3CN/H2O—0.1% CF3CO2H=1:99 to 100:0 over 33 min; 1 mL/min; 220 and 254 nm detection for 33 min]. Analytical conditions B: [C18 (150×2.1 mm), CH3OH/H2O—0.1% CF3CO2H=1:99 to 100:0 over 33 min; 1 mL/min; 220 and 254 nm detection for 33 min].

STF-083010, Sunitinib, nilotinib, and GP21 were obtained from commercial suppliers. All compounds were verified to be >95% pure by analytical HPLC. APY29 and GP118 was prepared according to a previously reported procedures.

1-iodo-3-isopropylimidazo[1,5-a]pyrazin-8-amine (compound 1). Compound 1 was synthesized according to a previously described procedure. 1-(4-(4,4,5,5-tetramethyl-1,3,2-dioxaborolan-2-yl)phenyl)-3-(3-(trifluoromethyl)phenyl)urea (compound 2). A mixture of 4-Aminophenylboronic acid pinacol ester (50.0 mg, 0.23 mmol) and 3-(Trifluoromethyl)phenyl isocyanate (46.0 uL, 0.31 mmol) in THF (1.9 mL) was stirred overnight at room temperature. The mixture was concentrated, diluted with dichloromethane and washed with water. The organic layer was dried over Na2SO4, concentrated in vacuo and the resultant crude product was purified by flash chromatography (20% ethyl acetate in hexanes) to afford 92.5 mg of compound 2 (98% yield). TLC (hexanes:EtOAc, 80:20 v/v): Rf=0.4; 1H NMR (300 MHz, MeOD): δ 7.90 (s, 1H), 7.71-7.68 (m, 2H), 7.60 (d, J=6.0 Hz, 1H), 7.48-7.42 (m, 3H), 7.29 (d, J=9.0 Hz, 1H), 1.34 (s, 12H); ESI-MS (m/z): [M]+ calcd. for C20H22BF3N2O3, 406.17; [M+1]+ found, 407.5. 1-(4-(4,4,5,5-tetramethyl-1,3,2-dioxaborolan-2-yl)naphthalen-1-yl)-3-(3-(trifluoromethyl)phenyl)urea (compound 3). A mixture of 4-Aminonaphthalene-1-boronic acid pinacol ester (31.2 mg, 0.11 mmol) and 3-(Trifluoromethyl)phenyl isocyanate (21.0 μL, 0.31 mmol) in THF (0.9 mL) was stirred over night at room temperature. The mixture was concentrated, diluted with dichloromethane and washed with water. The organic layer was dried over Na2SO4, concentrated in vacuo and the resultant crude product was purified by flash chromatography (20% ethyl acetate in hexanes) to afford 43.6 mg of compound 3 (86% yield). TLC (hexanes:EtOAc, 80:20 v/v): Rf=0.4; 1H NMR (300 MHz, MeOD): δ 8.87-8.82 (m, 1H), 8.11-7.91 (m, 4H), 7.67 (d, J=9.0 Hz, 1H), 7.60-7.47 (m, 3H), 7.36-7.31 (m, 1H), 1.44 (s, 12H); ESI-MS (m/z): [M]+ calcd. for C24H24BF3N2O3, 456.18; [M+1]+ found, 457.3. N-(4-(4,4,5,5-tetramethyl-1,3,2-dioxaborolan-2-yl)naphthalen-1-yl)-3-(trifluoromethyl)benzamide (compound 4). 4-Aminonaphthalene-1-boronic acid pinacol ester (75.0 mg, 0.267 mmol), 3-(Trifluoromethyl)benzoic acid (67.5 mg, 0.348 mmol), HOBt (55.1 mg, 0.348 mmol), EDCI (68.0 mg, 0.348 mmol) and DIPEA (141 μl, 0.803 mmol) were dissolved in DMF (790 μL) and stirred overnight at room temperature. The crude mixture was diluted in ethyl acetate and washed with NH4Cl and Na2CO3. The organic layer was dried over Na2SO4 and concentrated in vacuo. The crude organic product was purified by column chromatography (20% ethyl acetate in hexanes) to afford 16.6 mg of compound 4 (14% yield). TLC (hexanes:EtOAc, 80:20 v/v): Rf=0.4; 1H NMR (300 MHz, MeOD) δ 8.87-8.84 (m, 1H), 8.41-8.36 (m, 2H), 8.13-8.04 (m, 2H), 8.01-7.96 (m, 1H), 7.85-7.78 (m, 1H), 7.68 (d, J=6.0 Hz, 1H), 7.58-7.5, (m, 2H), 1.47 (s, 12H); ESI-MS (m/z): [M]+ calcd. for C24H23BF3NO3, 441.17; [M+1]+ found, 442.2. 8-chloro-1-iodo-3-isopropylimidazo[1,5-a]pyrazine (compound 5). Compound 5 was synthesized according to previously published procedure. 1-iodo-3-isopropyl-N-methylimidazo[1,5-a]pyrazin-8-amine (compound 6). Compound 5 (21.8 mg, 0.068 mmol) was dissolved in a solution of 40% MeNH2 in MeOH (91 μL) and was stirred at 80° C. for 2 h in a microwave. The reaction mixture was concentrated in vacuo to obtain 20.3 mg of compound 6 (94% yield). TLC (hexanes:EtOAc, 50:50 v/v): Rf=0.2; 1H NMR 1H NMR (300 MHz, MeOD) δ 7.51 (d, J=6.0 Hz, 1H), 7.04 (d, J=6.0 Hz, 1H), 3.42-3.34 (m, 1H), 3.07 (s, 3H), 1.37 (d, J=6.0 Hz, 6H); ESI-MS (m/z): [M]+ calcd. for C10H13IN4, 316.02; [M+1]+ found, 317.1.

1-(4-(8-amino-3-isopropylimidazo[1,5-a]pyrazin-1-yl)phenyl)-3-(3-(trifluoromethyl)phenyl)urea (KIRA2). A mixture of compound 1 (22.1 mg, 0.073 mmol), compound 2 (35.5 mg, 0.087 mmol), tetrakis(triphenylphosphine)palladium (2.6 mg, 2.1 mmol) and sodium carbonate (17.0 mg, 0.161 mmol) was dissolved in a 3:1 mixture of DME/water (280 uL). The mixture was heated overnight at 85° C. The crude mixture was then allowed to cooled to room temperature, diluted in a mixture of acetonitrile/water and purified by reverse phase chromatography (HPLC) to obtain 11.5 mg of KIRA2 (35% yield). TLC (CH2Cl2:MeOH, 95:5 v/v): Rf=0.5; 1H NMR (300 MHz, MeOD): δ 7.9, (s, 1H), 7.68-7.64 (m, 1H), 7.65-7.63 (m, 2H), 7.60-7.56 (m, 2H), 7.55-7.48 (m, 2H), 7.34-7.31 (m, 1H), 7.02-7.00 (dd, J=6.0 Hz, J=3.0 Hz, 1H), 3.49-3.43 (m, 1H), 1.44 (d, J=6.0 Hz, 6H); ESI-MS (m/z): [M]+ calcd. for C23H21F3N6O, 454.17; [M+1]+ found, 455.5. HPLC Purification Conditions: C18 column (250×21 mm), CH3CN/H2O—0.1% CF3CO2H=1:99 to 100:0 over 78 min; 8 mL/min; 220 nm and 254 nm detection for 78 min. The purity of GP117 was determined to be >98% by analytical HPLC in two different solvent systems.

1-(4-(8-amino-3-isopropylimidazo[1,5-a]pyrazin-1-yl)naphthalen-1-yl)-3-(3-(trifluoromethyl)phenyl)urea (KIRA3). A mixture of compound 1 (12.0 mg, 0.040 mmol), compound 3 (21.9 mg, 0.048 mmol), tetrakis(triphenylphosphine)palladium (1.4 mg, 1.2 mmol) and sodium carbonate (9.3 mg, 0.088 mmol) was dissolved in a 3:1 mixture of DME/water (160 uL). The mixture was heated overnight at 85° C. The crude mixture was cooled to room temperature, diluted in a mixture of acetonitrile/water and purified by reverse phase chromatography (HPLC) to obtain 12.3 mg of GP146 (61% yield). TLC (CH2Cl2:MeOH, 95:5 v/v): Rf=0.4; 1H NMR (300 MHz, MeOD): δ 8.27-8.22 (m, 1H), 8.02-7.96 (m, 2H), 7.90-7.86 (m, 1H), 7.83-7.79 (m, 1H), 7.72-7.49 (m, 5H), 7.37-7.32 (m, 1H), 7.04-6.99 (m, 1H), 3.66-3.5, (m, 1H), 1.54-1.48 (m, 6H); 13C NMR (500 MHz, MeOD): δ 154.9, 151.6, 149.8, 140.2, 135.9, 132.9, 129.4, 128.7, 128.7, 127.1, 126.6, 126.6, 125.8, 125.7, 121.9, 121.9, 121.8, 120.2, 118.7, 118.7, 115.1, 114.6, 112.9, 108.4, 25.8, 19.6; [M+1]+ found, 505.4. HPLC Purification Conditions: C18 column (250×21 mm), CH3CN/H2O—0.1% CF3CO2H=1:99 to 100:0 over 78 min; 8 mL/min; 220 nm and 254 nm detection for 78 min. The purity of GP146 was determined to be >98% by analytical HPLC in two different solvent systems.

1-(4-(3-isopropyl-8-(methylamino)imidazo[1,5-a]pyrazin-1-yl)naphthalen-1-yl)-3-(3-(trifluoromethyl)phenyl)urea (GP146(NMe)). A mixture of compound 6 (11.1 mg, 0.03, mmol), compound 3 (19.3 mg, 0.042 mmol), Tetrakis(triphenylphosphine)palladium (1.3 mg, 1.0 umol) and sodium carbonate (8.2 mg, 0.08 mmol) was dissolved in a 3:1 mixture of DME/water (130 uL). The mixture was heated overnight at 85° C. The crude mixture was cooled to room temperature, diluted in a mixture of acetonitrile/water and purified by reverse phase chromatography (HPLC) to obtain 5.0 mg of the GP146(NMe) (27% yield). TLC (CH2Cl2:MeOH, 95:5 v/v): Rf=0.6; 1H NMR (300 MHz, MeOD) δ 8.26 (d, J=9.0 Hz, 1H), 8.03 (s, 1H), 7.96 (d, J=9.0, 1H), 7.90 (d, J=6.0 Hz, 1H), 7.84 (d, J=9.0 Hz, 1H), 7.72-7.66 (m, 3H), 7.62-7.51 (m, 2H), 7.37-7.34 (m, 1H), 7.04 (d, J=6.0 Hz, 1H), 3.66-3.57 (m, 1H), 2.99 (s, 3H), 1.50 (dd, J=15.0, 6.0 Hz, 6H); 13C NMR (500 MHz, MeOD): δ 154.99, 151.22, 148.86, 140.19, 135.97, 133.04, 131.68, 129.36, 128.96, 128.80, 128.64, 128.54, 126.97, 126.63, 125.86, 125.80, 121.97, 121.84, 120.45, 118.68, 114.99, 114.55, 113.05, 108.47, 28.25, 25.75, 19.60; ESI-MS (m/z): [M]+ calcd. for C28H25F3N6O, 518.2; [M+1]+ found, 519.5. The purity of GP146(NMe) was determined to be >98% by analytical HPLC.

N-(4-(8-amino-3-isopropylimidazo[1,5-a]pyrazin-1-yl)naphthalen-1-yl)-3-(trifluoromethyl)benzamide (GP146(Am)). A mixture of compound 1 (9.5 mg, 0.031 mmol), compound 4 (16.6 mg, 0.038 mmol), Tetrakis(triphenylphosphine)palladium (1.1 mg, 0.94 mmol) and sodium carbonate (7.3 mg, 0.069 mmol) was dissolved in a 3:1 mixture of DME/water (120 µL). The mixture was heated overnight at 85° C. The crude mixture was cooled to room temperature, diluted in a mixture of acetonitrile/water and purified by reverse phase chromatography (HPLC) to obtain 5.3 mg of GP146(Am) (34% yield). TLC (CH2Cl2:MeOH, 95:5 v/v): Rf=0.5; 1H NMR (300 MHz, MeOD) δ 8.46 (s, 1H), 8.42 (d, J=6.0 Hz, 2H), 8.16-8.13 (m, 1H), 8.01-7.98 (m, 1H), 7.86-7.84 (m, 1H), 7.81-7.77 (m, 2H), 7.72-7.69 (m, 1H), 7.68-7.62 (m, 2H), 7.60-7.54 (m, 1H), 7.06 (d, J=6.0 Hz, 1H), 3.61-3.52 (m, 1H), 1.53-1.46 (m, 6H); ESI-MS (m/z): [M]+ calcd. for C27H22F3N5O, 489.18; [M+1]+ found, 490.4 The purity of GP146(Am) was determined to be >98% by analytical HPLC.

1-(4-(8-amino-3-tert-butylimidazo[1,5-a]pyrazin-1-yl)naphthalen-1-yl)-3-(3-(trifluoromethyl)phenyl)urea (KIRA6). A mixture of 1-iodo-3-tertbutylimidazo[1,5-a]pyrazin-8-amine (60.0 mg, 0.120 mmol), 3 (66 mg, 0.1, mmol), tetrakis(triphenylphosphine)palladium (5 mg, 4 µmol) and sodium carbonate (928 mg, 0.27 mmol) was dissolved in a 3:1 mixture of DME/water (0.5 mL). The mixture was heated overnight at 85° C. The crude mixture was cooled to room temperature, diluted in a mixture of acetonitrile/water and purified by reverse phase chromatography (HPLC) to obtain 53 mg of KIRA6. TLC (CH2Cl2:MeOH, 95:5 v/v): Rf=0.4; 1H NMR (300 MHz, MeOD): δ 8.26 (m, 1H), 8.08-7.99 (m, 2H), 7.90-7.86 (m, 1H), 7.83-7.79 (m, 1H), 7.69-7.52 (m, 5H), 7.3, (d, J=7.4 Hz, 1H), 6.98 (m, 1H), 1.6, (s, 9H); 13C NMR (126 MHz, MeOD): δ 154.8, 140.2, 135.7, 133.0, 132.4, 131.7, 131.6, 131.0, 130.7, 129.4, 128.8, 128.6, 128.5, 127.0, 126.6, 125.9, 125.4, 123.2, 121.9, 120.1, 118.7, 115.0, 114.4, 110.1, 33.6, 27.3; ESI-MS (m/z): [M]+ calcd. for C28H25F3N6O (M+H+): 519.2; found 519.4.

Generate Potent and Selective Reversible Type II Inhibitors of IRE1α.

As described above, a type II ATP-competitive inhibitor (KIRA3) that can inactivate IRE1α RNase and kinase activities has been identified, in vitro and in vivo (Zhang, J. et al. Nature reviews. Cancer 9, 28-39, (2009)). Described herein are efforts to increase the potency and selectivity of these type II inhibitors. Using structure-based drug design, KIRA3 was further optimized. Initially, a homology model of the IRE1α ATP-binding site in the DFG-out conformation, will be used to guide analog synthesis, including use of structures of KIRAs bound to on-targets (IRE1α) and off-targets (Src) to refine the inhibitor docking protocol. Described herein is the development of irreversible inhibitors that target a non-conserved cysteine in IRE1α's activation loop. Described herein is the development of KIRA3 analogs that contain an electrophile that targets a cysteine predicted to be accessible when IRE1α is in the DFG-out conformation. Details are described below.

Figure 25:
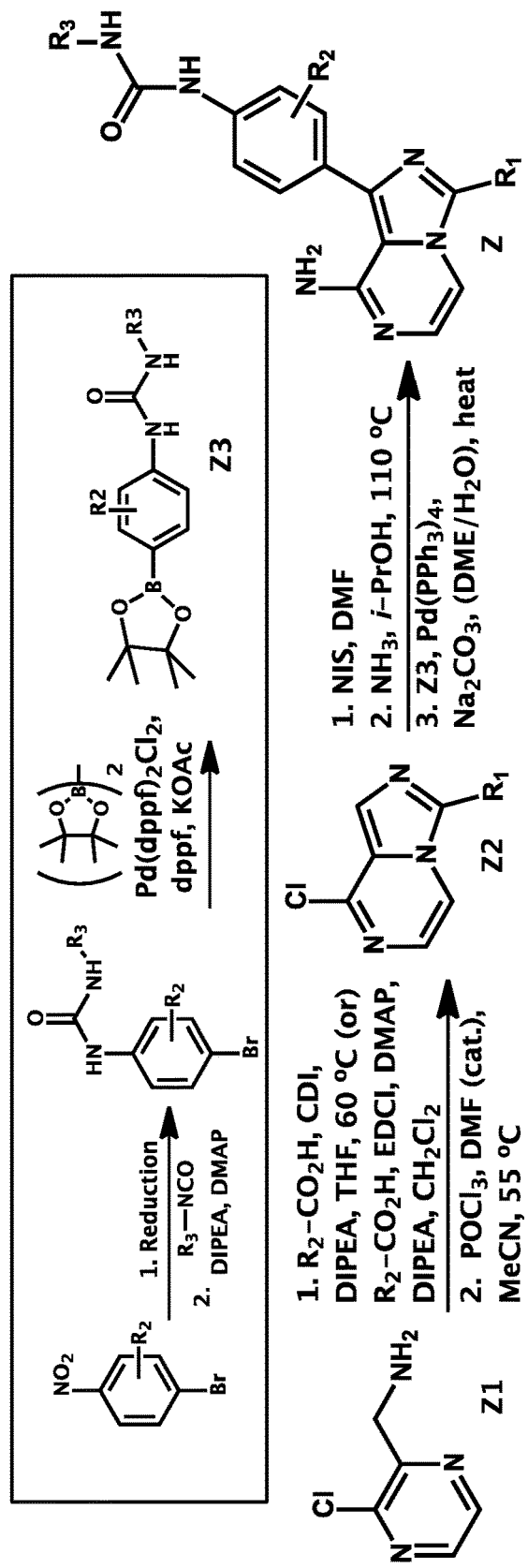
FIG. 25. Synthetic strategy for generating KIRAs.
Figure 26:
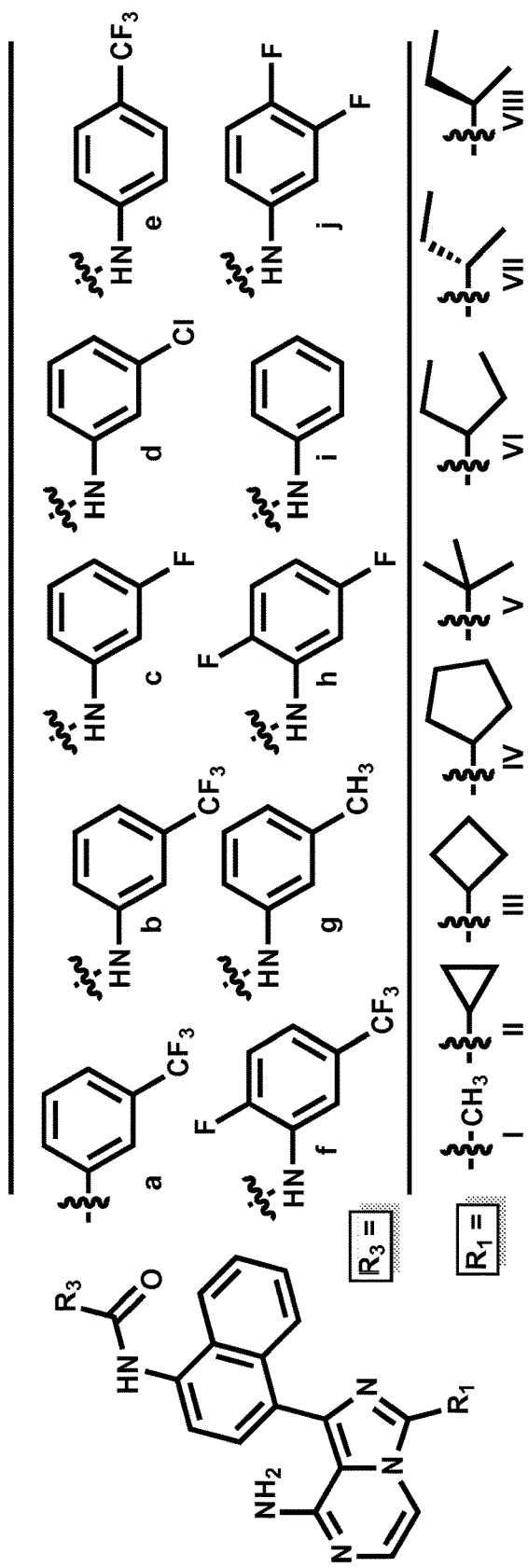
FIG. 26. Representative KIRAs synthesized and tested.

KIRA Analog Synthesis:

The synthetic strategy for generating inhibitors of general structure Z is shown FIG. 25. Acylation of commercially available amine Z1 with carboxylic acids ($R_1$—$CO_2H$) that have been activated with 1,1'-carbonyldiimidazole (CDI) (or activated with EDCI, DMAP), followed by cyclization with $POCl_3$ generates imidazopyrimidines (Z2) that are substituted at the 1-position ($R_1$) (Mulvihill, M. J. et al. Bioorg. Med. Chem. 16, 1359-137, (2008); Mulvihill, M. J. et al. Bioorganic & Medicinal Chemistry Letters 17, 1091-1097 (2007)). Urea substituents are introduced at the C-3 position by iodinating the scaffold with NIS, nucleophilic substitution with ammonia in isoproponal (in a sealed reaction vessel) and palladium-mediated Suzuki couplings to urea-containing boronic esters (prepared as shown in the box) (Jin, M. et al. Bioorganic & Medicinal Chemistry Letters 21, 1176-1180 (2011); Wang, J.-X. et al. Org. Lett. 10, 2923-2926 (2008); Board, J. et al. Org. Lett. 11, 5118-5121 (2009)). An alternate synthetic route that introduces substituents at the C-3 position ($R_2$ substituents) without using a metal-mediated cross-coupling can also be used (Mulvihill, M. J. et al. Bioorganic & Medicinal Chemistry Letters 17, 1091-1097 (2007)). Over 40 analogs have been generated using this synthetic methodology. Representative inhibitors are shown in FIG. 26. KIRA6 ($R_1$=V; $R_3$=B), a more potent ($IC_{50}$(RNase)=210 nM; $IC_{50}$(kinase)=620 nM) analog of KIRA3, is extensively profiled in Aim 2. KIRA7 ($R_1$=V; $R_3$=C) is one of the most potent KIRA ($IC_{50}$(RNase)= <30 nM; $IC_{50}$(kinase)=35 nM) generated to date.

Figure 27:
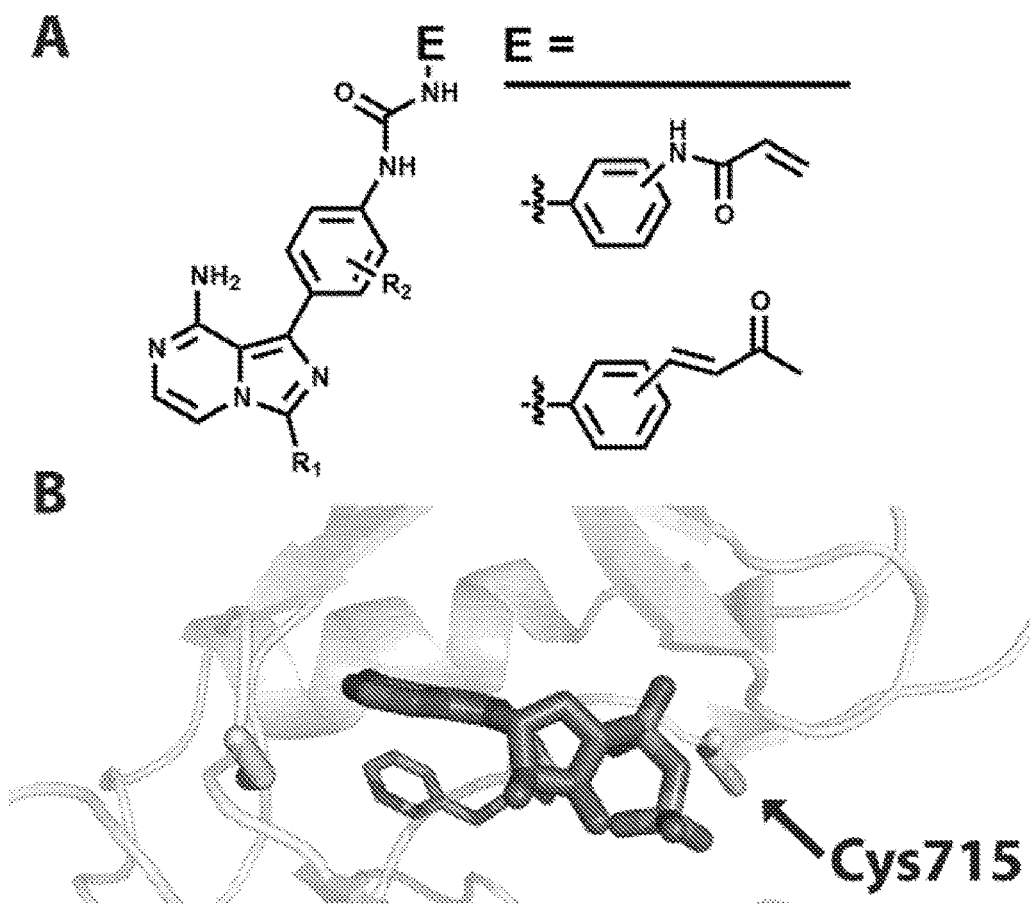
FIG. 27. (A) General structure of irreversible KIRAs that target a cysteine residue located in the activation loop of IRE1; representative electrophiles are shown. (B) A close-up of the ATP-binding site of IRE1α.

Irreversible KIRAs that target Cys71, in the activation loop. The IRE1α kinase domain possesses a cysteine residue (Cys715) two residues C-terminal to the DFG motif (FIG. 27). Cys715 is rapidly alkylated with haloacetamide-containing ICAT reagents, and the rate is increased under KIRA3 (Zhang, J. et al. Nature reviews. Cancer 9, 28-39, (2009)). Modeling suggests that Cys715 is in close proximity to the $R_3$ substituent of the KIRA scaffold when the DFG motif is in the "out" conformation (the conformation the IRE1α ATP-binding site adopts when bound to KIRAs). Of the 518 kinases in the human kinome, 42 have a cysteine residue at an equivalent or adjacent position (Leproult, E. et al. J. Med. Chem. 54, 1347-135, (2011)). However, chemical proteomic profiling studies with type II inhibitors suggest that none of these 42 kinases, except IRE1α, are able to adopt the DFG-out inactive conformation (Krishnamurty, R. et al. Nature chemical biology 9, 43-50, (2013); Brigham, J. L. et al. ACS Chem. Biol. 130123155823009). Therefore, it should be possible to selectively target Cys71, with a properly oriented electrophile displayed from the KIRA scaffold. Representative irreversible KIRAs that are being generated are shown in FIG. 27 (electrophiles will be introduced in the last synthetic step to avoid instability issues during the palladium-mediated cross coupling). A number of highly selective irreversible kinase inhibitors have been developed by targeting non-conserved cysteine residues (Kwarcinski, F. E. et al. *ACS Chem. Biol.* 7, 1910-1917 (2012); Barouch-Bentov, R. et al. *Molecular Cell* 33, 43-52 (2009); Zhang, T. et al. *Chemistry & Biology* 19, 140-154 (2012); Zhou, W. et al. *Bioorganic & Medicinal Chemistry Letters* 21, 638-643 (2011); Zhou, W. et al. *Chemistry & Biology* 17, 285-29, (2010); Zhou, W. et al. *Nature* 462, 1070-1074 (2009); Serafimova, I. M. et al. *Nature Chemical Biology* 8, 471-476 (2012); Henise, J. C. & Taunton, J. *J. Med. Chem.* 54, 4133-4146 (2011); Cohen, M. S. f et al. *Science* 308, 1318-1321 (2005)).

3. Analysis of the GP146-IRE1α and APY29-IRE1α Interactions.

Figure 3:
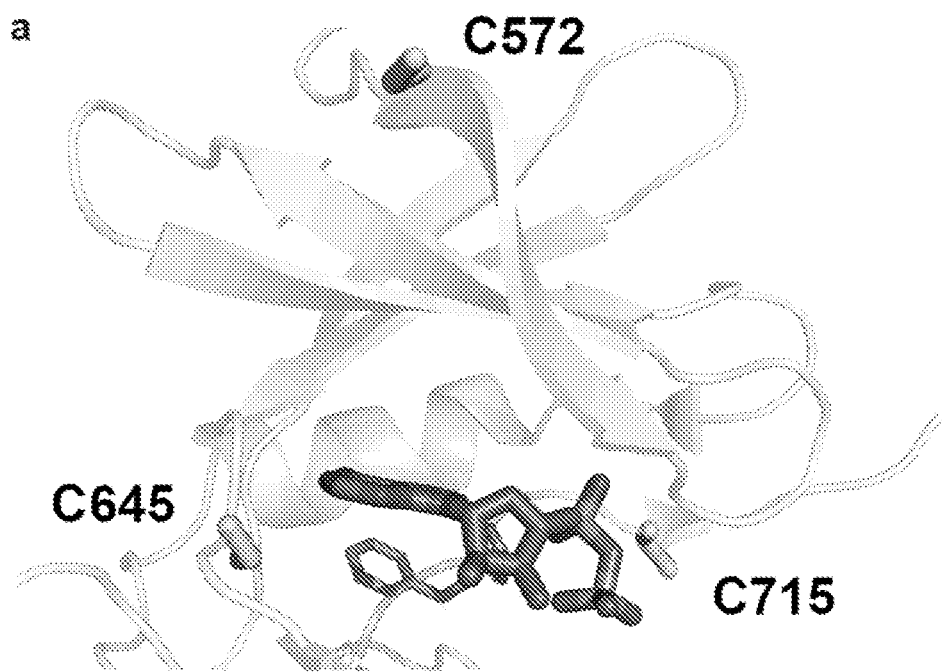
FIG. 3. Characterization of GP146's interaction with the ATP-binding site of IRE1α. (a) A crystal structure of the kinase domain of human IRE1α bound to ADP; the native cysteine residues that were monitored using the ICAT footprinting method are labeled and shown as thick rods and the DFG-motif is shown as thin bars; cys71, is part of the hinge region of IRE1α and its side chain partially occupies the ATP-binding site; cys64, is in the activation loop, two residues away from the DFG-motif; cys572 is located on the top of the N-terminal lobe of the catalytic domain and is distant from the ATP-binding site. (b) Results of the ICAT footprinting experiments with IRE1α*; alkylation rates were measured in the presence of DMSO (circle), APY29 (square) (20 µM), or GP146 (triangle) (20 µM) (mean±SD, n=3). (c) A molecular model of GP146's interaction with the ATP-binding site of IRE1α; IRE1α is in the DFG-out inactive conformation; the imidazopyrazine ring of GP146 occupies the adenine pocket and the 3-trifluoromethylurea occupies the DFG-out pocket; no favorable poses for GP146 bound to the DFG-in conformation of IRE1α could be determined. (d) Control compounds that were generated to test the docked structure of GP146 bound to the DFG-out conformation of IRE1α; GP146(NMe) contains a methyl group that is predicted to disrupt a critical hydrogen bond to the hinge region of IRE1α GP146(Am) contains an amide rather than a urea group linker between the naphthyl ring and the trifluormethylpheny group; the amide linker is predicted to lead to a less favorable interaction with the DFG-out pocket; the $IC_{50}$s for each compound against IRE1α* is listed below their structure.
Figure 3:
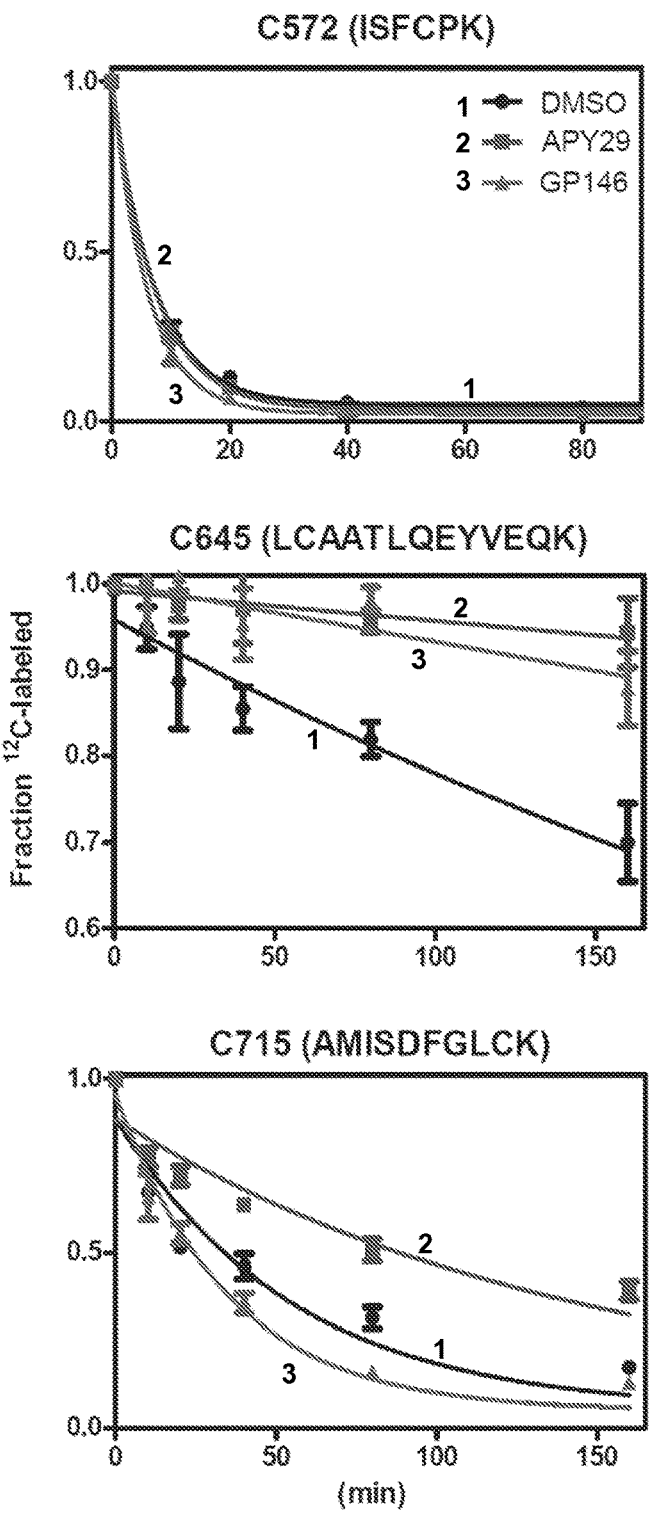
Figure 3:
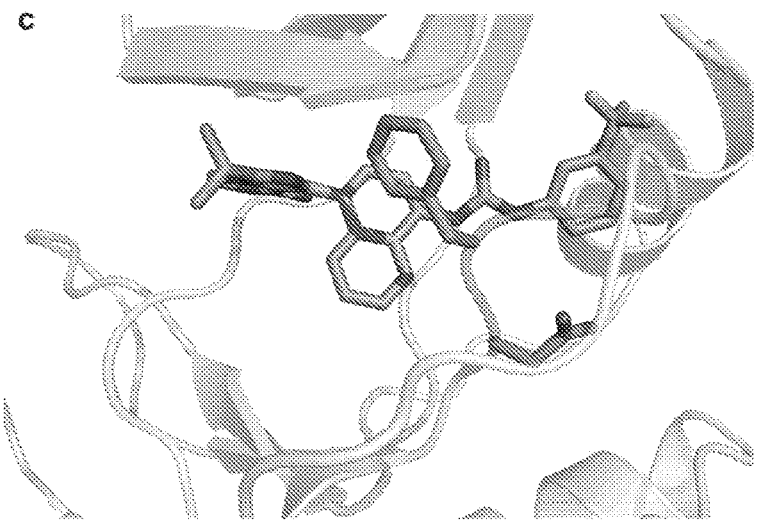
Figure 3:
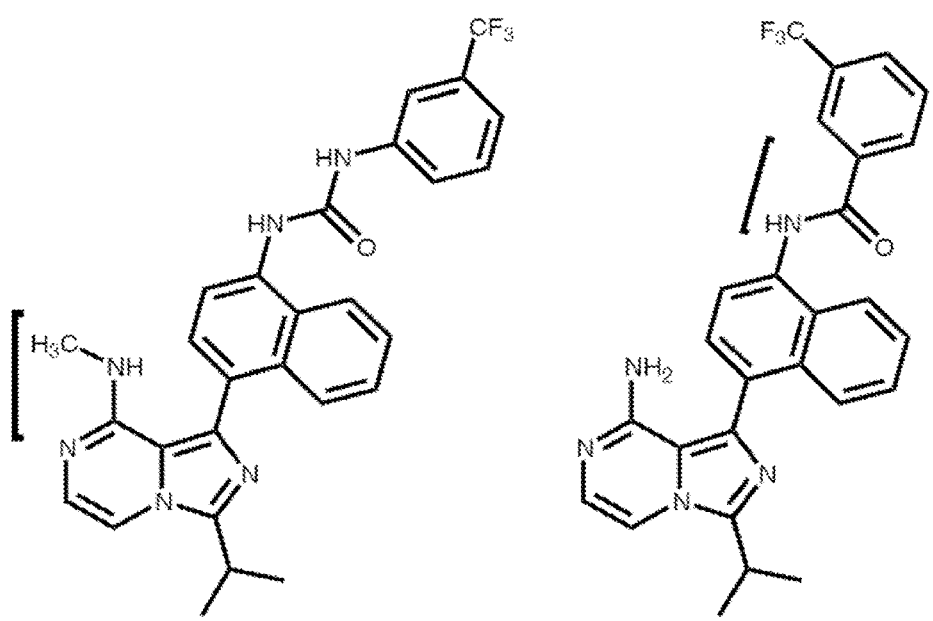

To further confirm that AYP29 and GP146 are exerting their opposing effects through the same ATP-binding site, a series of biochemical footprinting experiments were conducted (Tu, B. P. & Wang, J. C. *Proc. Natl. Acad. Sci. USA* 96, 4862-4867 (1999); Underbakke, E. S. et al. *Angew. Chem. Int. Ed.* 47, 9677-9680 (2008)). Specifically, the accessibility of three native cysteine residues within human IRE1α (Cys572, Cys645, and Cys715) to alkylating agents in the presence or absence of APY29 and GP146 was determined (FIG. 3a). For these studies, electrophilic isotope-coded affinity tag (ICAT) reagents were used to allow a ratiometric and, therefore, quantitative comparison of alkylation rates (Underbakke, E. S. et al. *Angew. Chem. Int. Ed.* 47, 9677-9680 (2008)). As Cys64, and Cys71, are located within the ATP-binding cleft of IRE1α, the accessibility of these residues would be expected to be affected by ligands that occupy this site, while Cys572 is a solvent-exposed residue located on the top of the N-terminal lobe of the kinase. Consistent with both APY29 and GP146 occupying the ATP-binding site of IRE1α, Cys645, which is located in the kinase hinge region, is highly shielded from alkylating agents in the presence of either inhibitor (FIG. 3b). In contrast, these inhibitors exert opposing effects on the accessibility of Cys715, with APY29 slowing the rate of alkylation and GP146 increasing it. Cys71, is located in the activation loop of IRE1α (two residues C-terminal to the DFG-motif) and the divergent influence of APY29 and GP146 on this residue is concordant with these ligands stabilizing different conformations of the activation loop (FIG. 3b). As expected, no detectable difference in the accessibility of Cys572, which is distal to the kinase active site of IRE1α, is observed in the presence of either inhibitor.

Figure 19:
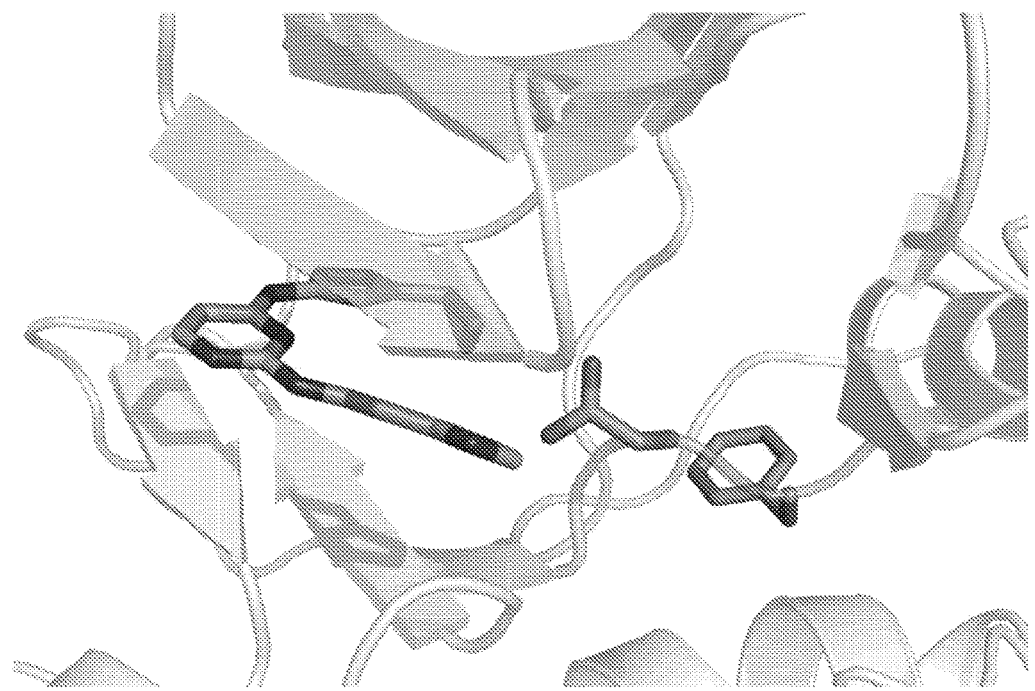
FIG. 19. A molecular model of APY29's interaction with the DFG-in conformation of human IRE1α. IRE1α is in the DFG-in active conformation; the pyrimidine ring of APY29 occupies the adenine pocket and the 3-aminopyraozole makes several hydrogen bonds with the kinase hinge; no favorable poses for APY29 bound to the DFG-out conformation of IRE1α could be determined.

Next, molecular docking experiments were performed to obtain a better understanding of how GP146 and APY29 interact with the ATP-binding site of human IRE1α. A model of the DFG-in ATP-binding site conformation was generated from a co-crystal structure of human IRE1α bound to ADP (PDB code 3P23, chain A) (Ali, M. M. et al. *EMBO J.* 30, 894-90, (2011)). As a structure of IRE1α in the DFG-out conformation has not yet been described, a homology model of this form was generated by using the activation loop of another kinase, the tyrosine kinase Ab12, as a template. Both the DFG-in and DFG-out models were optimized using multi-step all-atom minimization and explicit water molecular dynamics (MD) simulations (Bowers, K. J. et al. in *Proceedings of the ACM/IEEE Conference on Supercomputing* (SC06) (Tampa, Fla., USA, 2006)). Predictably, the docked structure of APY29 bound to the DFG-in conformation of human IRE1α is similar to that of this ligand bound to the yeast IRE1 enzyme (FIG. 19) (Korennykh, A. V. et al. *Nature* 457, 687-693 (2009)). The pyrazole ring of APY29 forms hydrogen bonds with the kinase hinge region and the pyrimidine moiety occupies the adenine pocket. Attempts to obtain a favorable pose of APY29 bound to the DFG-out conformation of IRE1α were unsuccessful, which is consistent with the ability of this ligand to exclusively stabilize the active conformation of the ATP-binding site.

The most favorable docking pose for GP146 bound to the DFG-out conformation of IRE1α is shown in FIG. 3c. In this pose, the pyrazolopyrimidine ring of this ligand forms two hydrogen bonds with the hinge region and occupies the adenine pocket. The bulky naphthyl ring of GP146 adopts an almost orthogonal conformation relative to the core scaffold and stacks against the Ile gatekeeper residue. Like other type II inhibitors, the trifluoromethylphenyl moiety of GP146 occupies the hydrophobic pocket created by movement of the Phe sidechain in the DFG-motif. While GP146 is well accommodated in the DFG-out conformation of human IRE1α, no favorable poses were observed for this inhibitor bound to the DFG-in conformation. Indeed, the docking studies predict that the only way that GP146 can bind to IRE1α without movement of the DFG motif in the activation loop is if the inhibitor disrupts canonical interactions with the hinge region of the kinase.

To further experimentally test the docking model, analogs of GP146 that contain structural elements predicted to lower inhibitor potency were generated (FIG. 3d). GP146(NMe) contains an N-methyl group that would be predicted to disrupt its interaction with the hinge region of IRE1α, and the amide linkage of GP146(Am) should not allow the trifluoromethylphenyl moiety to form as favorable interactions with the hydrophobic pocket created by movement of the DFG-motif. Consistent with the model, both GP146 (NMe) and GP(146Am) show a markedly diminished ability to inhibit the RNase activity of IRE1α compared to GP146 (FIG. 3d).

4. GP146 and APY29 Divergently Affect the Oligomerization State of IRE1α

Figure 4:
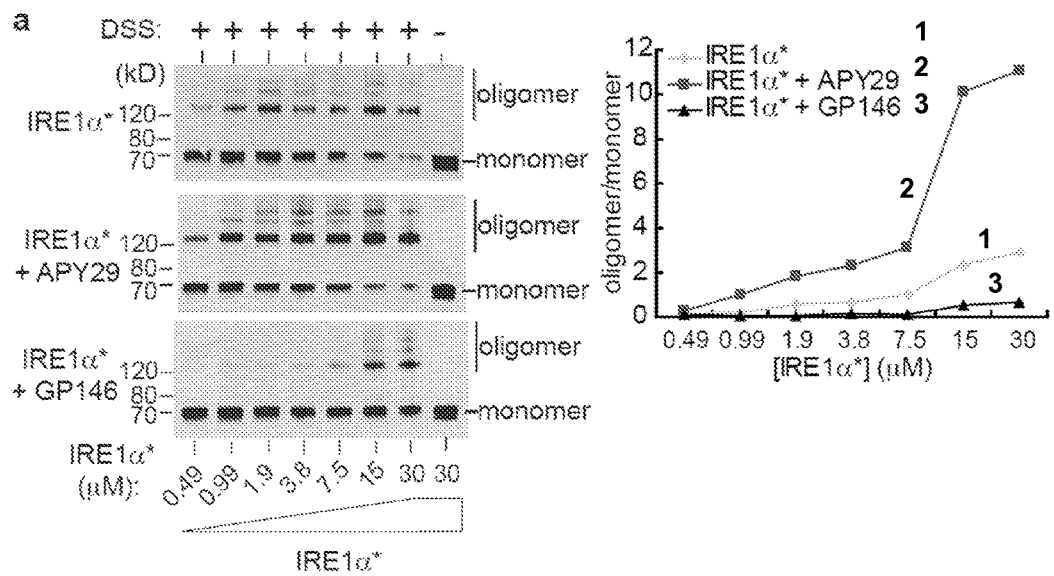
FIG. 4. APY29 and GP146 differentially affect oligomerization state of IRE1α*. (a) Left panels shows immunoblots of IRE1α* after treatment with the crosslinker DSS (250 µM); increasing concentrations of IRE1α* were incubated with DMSO, APY29 (200 µM), or GP146 (200 µM); the right panel shows quantitation of the ratios of oligomeric to monomeric IRE1α* (b) Model of how type I and type II kinase inhibitors affect the RNase activities and oligomeric states of IRE1α * and dP-IRE1α*.
Figure 4:
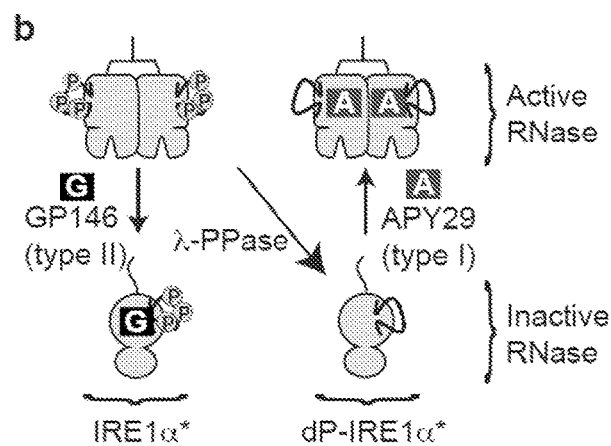

Increasing concentrations of IRE1α* were incubated with either DMSO, or saturating concentrations of APY29 or GP146 and the ratio of oligomeric—defined as all species greater than monomers (mostly dimers) to monomeric IRE1α was determined (FIG. 4a). In the absence of ligands, IRE1α* shows a concentration-dependent increase in the oligomer/monomer ratio. The presence of APY29 further enhances—whereas GP146 decreases—this concentration-dependent increase in the IRE1α* oligomer/monomer ratio. Taken together, the in vitro data support a model in which these two classes of kinase inhibitors divergently modulate IRE1α* RNase activity by exerting opposing effects on the oligomerization state of the enzyme (FIG. 4b).

5. IRE1α Mutants with an Enlarged ATP-Binding Pocket Show Increased Sensitivity to GP146

Figure 20:
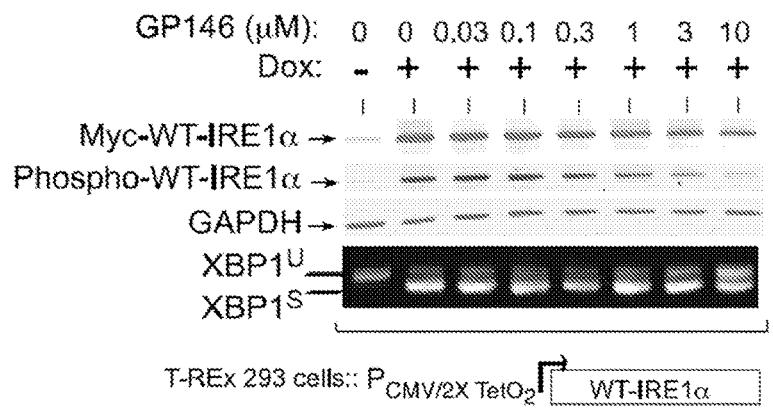
FIG. 20. GP146 inhibits autophosphorylation and XBP1 mRNA splicing by WT IRE1α in T-REx 293 cells. (a) Anti-total and anti-phospho IRE1α immunoblots, and EtBr-stained agarose gel of XBP1 cDNA amplicons from T-REx 293 cells expressing WT IRE1α under Doxycycline (Dox) control; cells were pre-treated for 1 hr with GP146 at indicated concentrations, then induced with Dox (1 µM) for 8 hrs. (b) The plot shows normalized phosphorylation levels under varying [GP146] (mean±SD, n>=3). (c) GP146(NMe) does not inhibit XBP1 splicing in T-REx 293 cells expressing WT IRE1α EtBr-stained agarose gel of XBP1 cDNA amplicons from T-REx 293 cells expressing WT IRE1α are shown; cells were pre-treated for 1 hr with GP146(NMe) at indicated concentrations, then induced with Dox (1 µM) for 8 hrs.
Figure 20:
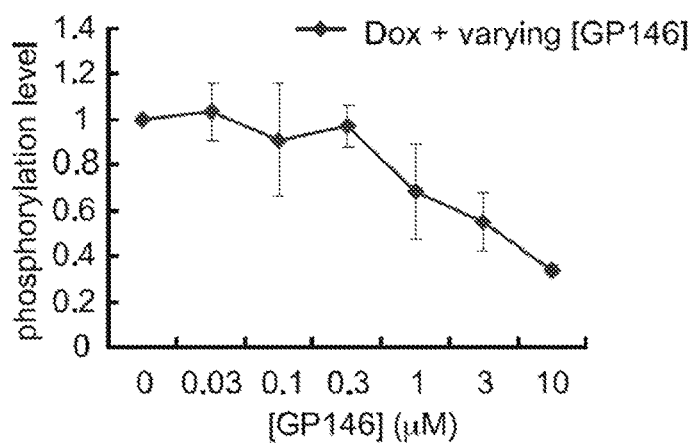
Figure 20:
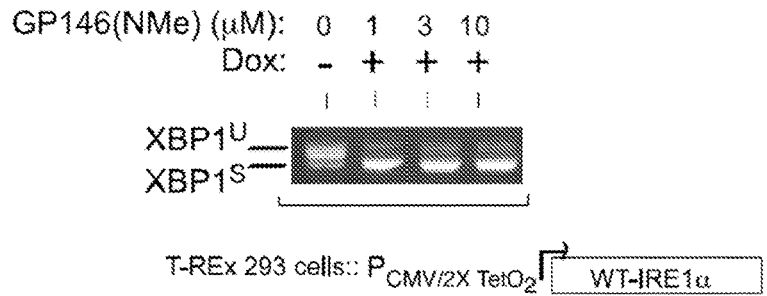
Figure 21:
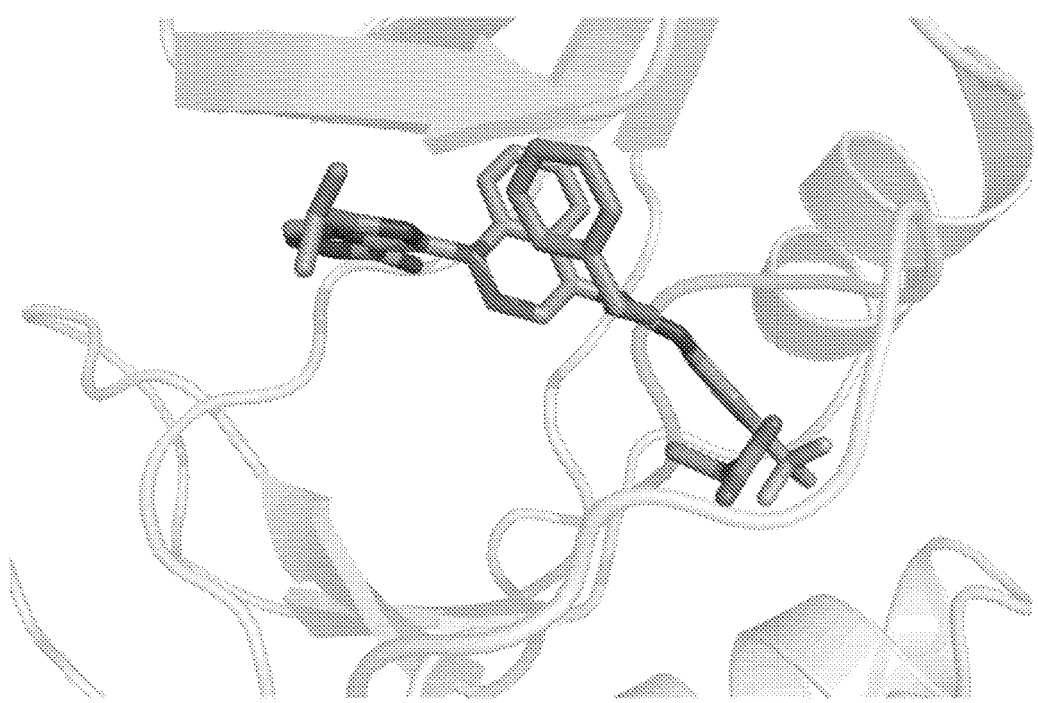
FIG. 21. Molecular model of GP146 bound to the ATP-binding site of human IRE1α$^{1642A}$; IRE1α is in the DFG-out inactive conformation; the imidazopyrazine ring of GP146 occupies the adenine pocket and the 3-trifluoromethylurea occupies the DFG-out pocket; the naphthyl ring of GP146 rotates 180 degrees and is able to access the enlarged hydrophobic pocket next to the gatekeeper residue; no favorable poses for GP146 bound to the DFG-in conformation of IRE1α$^{1642A}$ could be determined.
Figure 22:
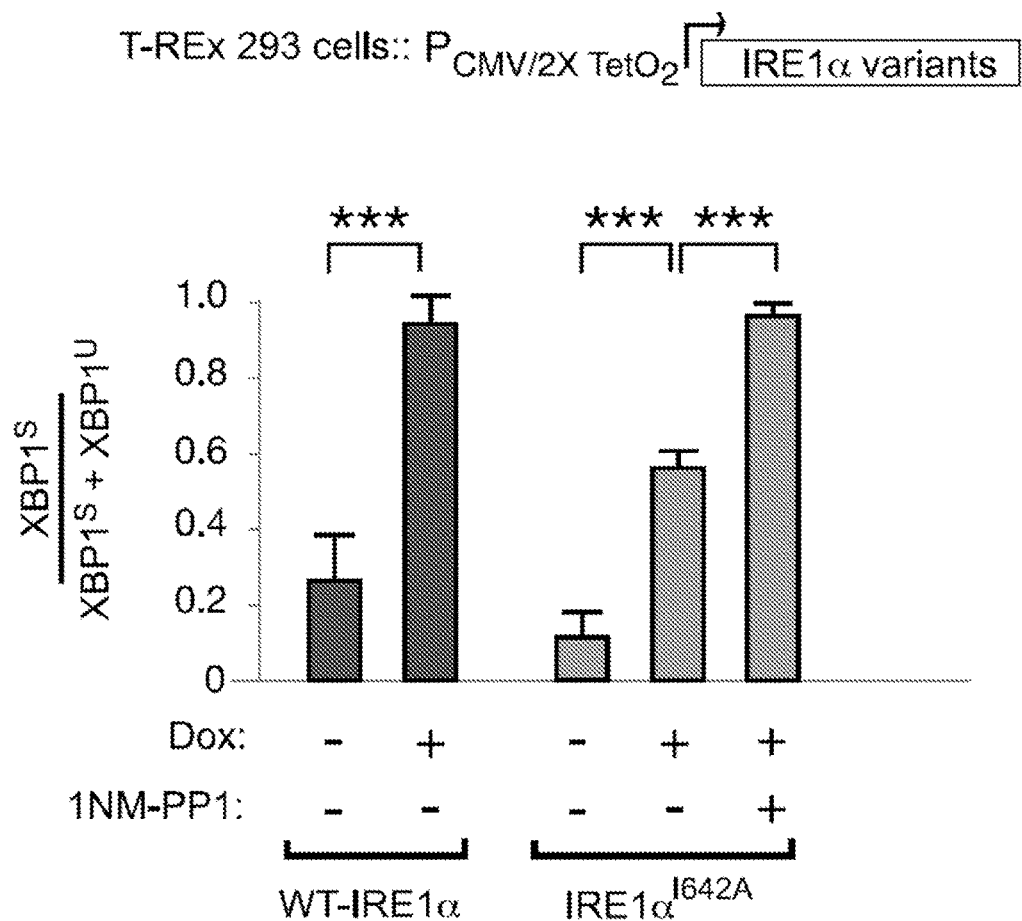
FIG. 22. Forced XBP1 mRNA splicing through conditional overproduction of IRE1α isogenic T-REx 293 stable cell lines; quantitation of EtBr-stained agarose gels of XBP1 cDNA amplicons from T-REx 293 cells stably expressing either WT-IRE1α or the "holed" IRE1α (1642A) mutant under Doxycycline (Dox) control; cells were induced with Dox (1 µM) for 8 hrs, followed by provision of 1NM-PP1 (5 µM)—or DMSO—for 4 more hours; the ratio of spliced XBP1 (XBP1 S) over (XBP1S+unspliced amplicons (XBP1U)) at the endpoint is plotted in the histograms (mean±SD, n>=3).
Figure 23:
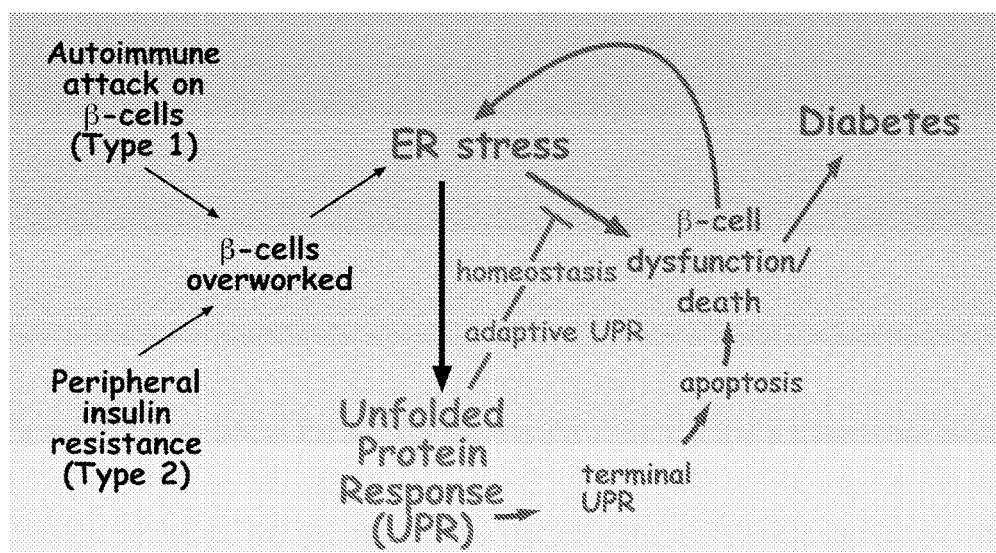
FIG. 23. Death of pancreatic islet β-cells due to unchecked ER stress and terminal UPR signaling is central to development of types 1 and 2 diabetes. Compounds, pharmaceutical compositions, and methods described herein may modulate the UPR and treat diseases associated with ER stress and the UPR.

Having used a truncated form of IRE1α for in vitro studies, cell-based experiments were used to test whether it would be possible to replicate divergent modulation of the full-length IRE1α transmembrane protein with the two classes of kinase inhibitors. The on-target effects of GP146 were tested and confirmed using IRE1α chemical-genetic systems previously developed (Han, D. et al. *Cell* 138, 562-575, (2009)). Specifically, tetracycline-inducible isogenic T-REx 293 stable cell lines expressing either WT or a "holed" IRE1α gatekeeper mutant$^{I642A}$ were used to determine whether GP146 is able to block the RNase activity of IRE1α in vivo. Induced with doxycycline (Dox), the transgenic WT-IRE1α or IRE1α$^{I642A}$ spontaneously cluster in the ER, trans-autophosphorylate and splice XBP1 mRNA, without requiring upstream ER stress (FIG. 5a and FIG. 20). As expected, GP146 inhibits autophosphorylation and XBP1 mRNA splicing in the WT cell lines (FIGS. 20a and 20b). Consistent with these inhibitory effects occurring through a direct interaction with IRE1α, control compound GP146 (NMe) does not affect either of these parameters, even at the highest concentration tested (FIG. 20c). Furthermore, it was hypothesized that the enlarged ATP-binding pocket of IRE1α$^{I642A}$ would better accommodate the bulky C-3 substituent of GP146, leading to enhanced sensitivity. Indeed, the docking studies suggest that the naphthyl ring of GP146 is able to occupy a hydrophobic pocket that is accessible in IRE1α$^{I642A}$ and not the wild type protein (FIG. 21). Confirming this notion, low nanomolar concentrations of GP146 are sufficient to completely block autophosphorylation and XBP1 splicing through this mutant (FIGS. 5a and 5b). Furthermore, increasing concentrations of the type I "bumped" inhibitor 1NM-PP1, which is selective for mutant kinases that contain Ala or Gly gatekeeper residues, is able to rescue the RNase activity of IRE1α$^{I642A}$ in the presence of GP146 (FIG. 5c).

Figure 5:
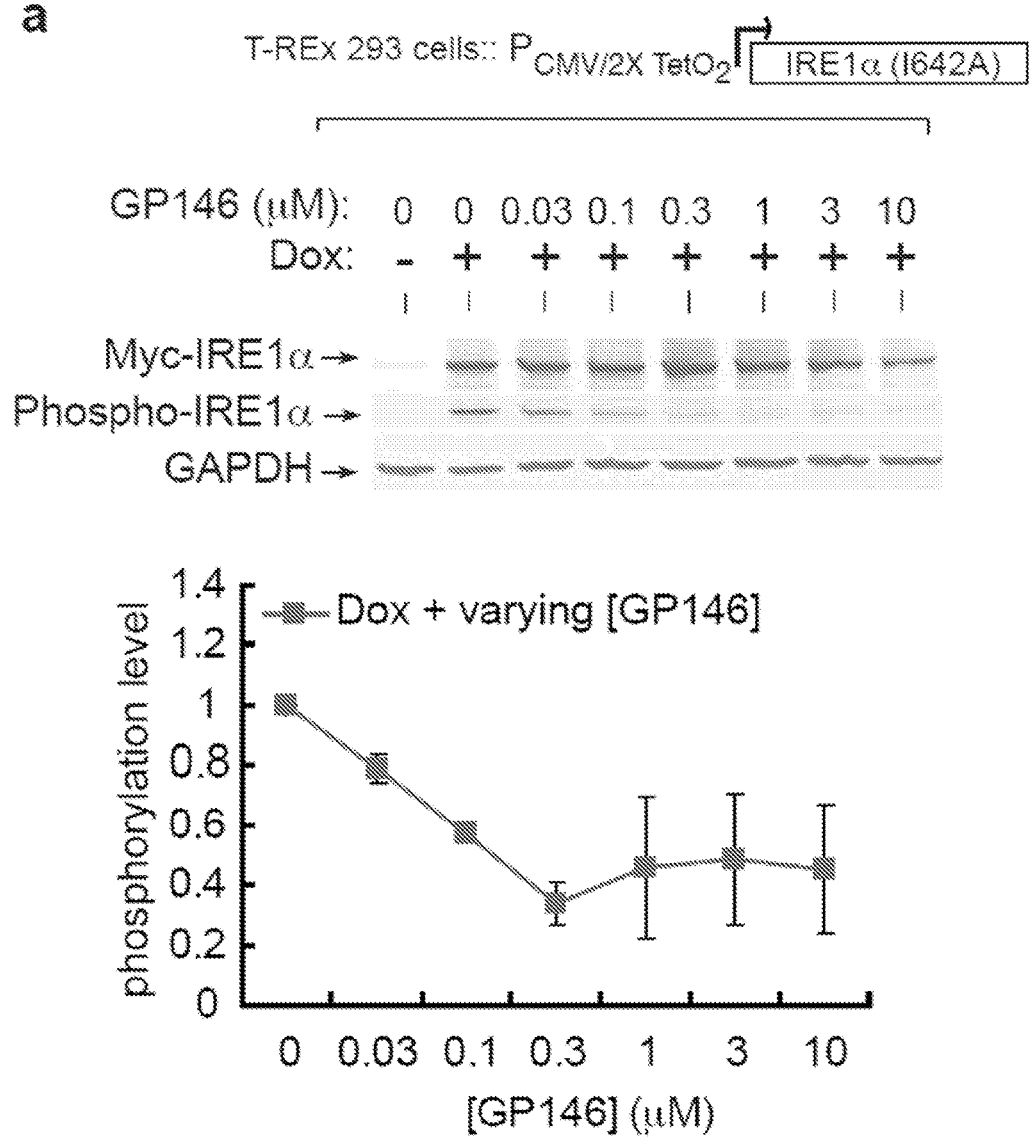
FIG. 5. Chemical-genetic modulation of IRE1α kinase and RNase activity in vivo. (a) Anti-total and anti-phospho IRE1α immunoblots of T-Rex 293 cells expressing "holed" IRE1α I642A under Doxycycline (Dox) control; cells were pre-treated for 1 hr with GP146 at indicated concentrations, then induced with Dox (1 µM) for 8 hrs; plots show normalized phosphorylation levels and ratios of spliced XBP1 mRNA under varying [GP146] (mean±SD, n>=3). (b) EtBr-stained agarose gel of XBP1 cDNA amplicons from the cells described in (a). (c) Competition between the "bumped" kinase inhibitor 1NM-PP1 and GP146 against IRE1α I642A; T-Rex 293 cells expressing IRE1α I642A were pre-treated for 1 hr with GP146 (1 µM)±varying [1NM-PP1] before Dox induction (1 µM) for 8 hrs; histograms show ratios of spliced XBP1 mRNA as a function of [GP146] and [1NM-PP1]. (d) Model of divergent allosteric modulation of IRE1α RNase by type I and II kinase inhibitors; when overproduced, IRE1α I642A oligomerizes and trans-autophosphorylates, activating XBP1 mRNA splicing by the RNase; type I inhibitor 1NM-PP1 increases—whereas type II inhibitor GP146 decreases—RNase activity; cartoons are not meant to differentiate between the relative orientations of monomer subunits in IRE1α.
Figure 5:
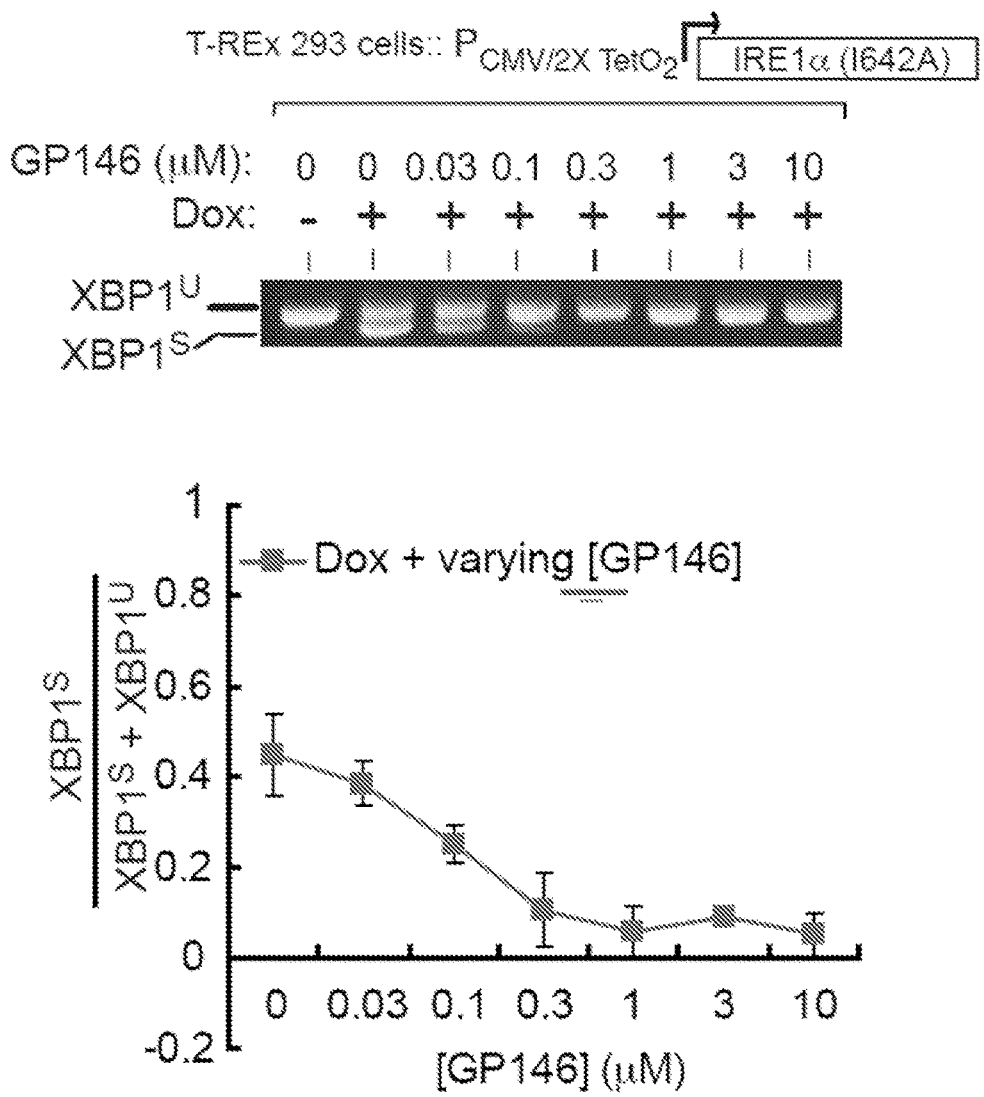
Figure 5:
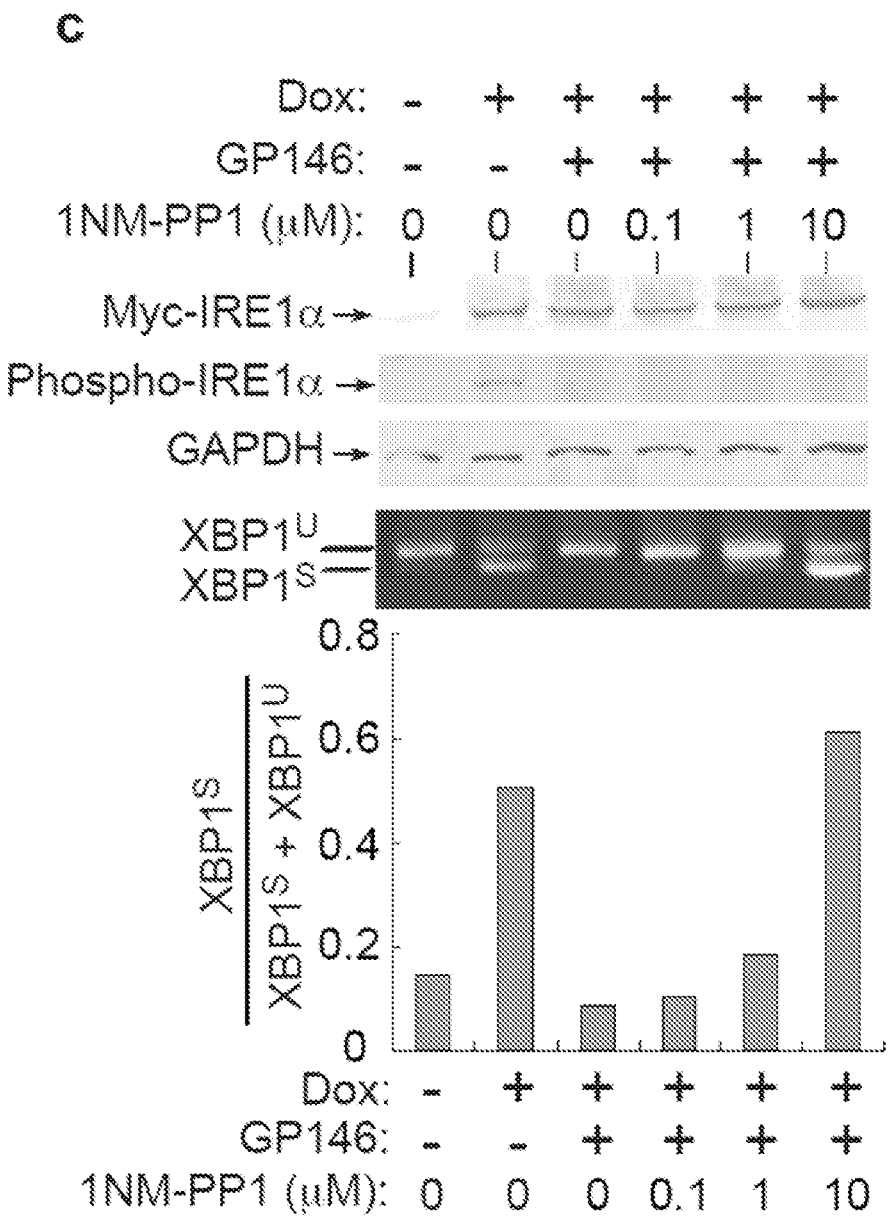
Figure 5:
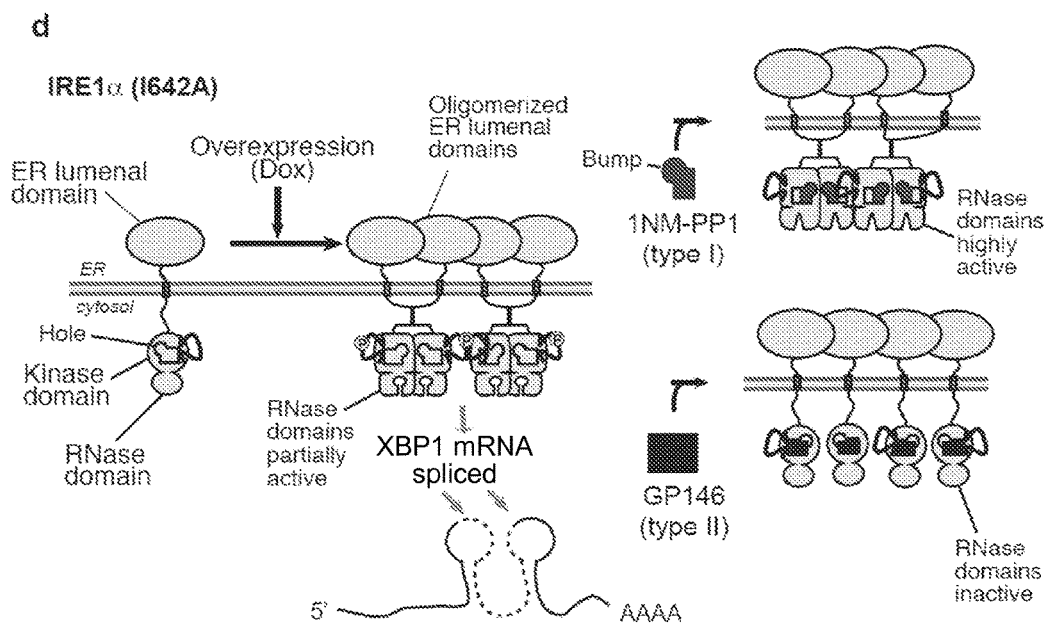

The data illustrates a model for IRE1α$^{I642A}$, which can be activated merely through overexpression to basally splice 50% of cellular XBP1 mRNA, that 1NM-PP1 further increases while GP146 reduces—the activity of the RNase (FIG. 5d). These divergent effects proceed from the stabilization of the kinase active site in two distinct modes by these inhibitors, with 1NM-PP1 acting on the "holed" IRE1α$^{I642A}$ kinase in a similar fashion as APY29 does for WT IRE1α. In summary, the type II pharmacophore GP146 likely enforces an inactive kinase conformation in IRE1α and as it does with WT IRE1α.

Figure 6:
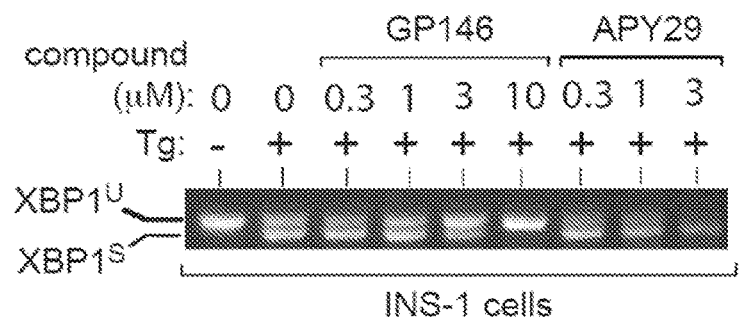
FIG. 6. Divergent modulation of endogenous IRE1α RNase activity under ER stress with types I and II kinase inhibitors. (a) EtBr-stained agarose gel of XBP1 complementary DNA (cDNA) amplicons from INS-1 cells pre-treated for 1 hr with GP146 or APY29 at indicated concentrations, followed by thapsigargin (Tg) (6 nM) for 4 hrs; ratios of spliced XBP1 (XBP1S) over (spliced+unspliced (XBP1U)) are plotted (mean±SD, n=3). (b) Anti-total and anti-phospho IRE1α immunoblots using extracts from INS-1 cells pre-treated for 1 hr with GP146, sunitinib, or STF-083010 at indicated concentrations, followed by Tg (6 nM) for 2 hrs. (c) EtBr-stained agarose gel of XBP1 complementary DNA (cDNA) amplicons from the INS-1 cells described in (b). (d) EtBr-stained agarose gel of XBP1 complementary DNA (cDNA) amplicons from INS-1 cells pre-treated for 1 hr with GP146(NMe) at indicated concentrations, followed by thapsigargin (Tg) (6 nM) for 4 hrs. (e) Model of how type I kinase inhibitors (APY29), type II kinase inhibitors (GP146), and RNase inhibtors (STF-083010) modulate the enzymatic activities of WT IRE1α. APY29 inhibits IRE1α trans-autophosphorylation but promotes oligomerization and activates the RNase domain; STF-083010 inhibits the RNase activity of IRE1α but does not affect kinase activity or the overall oligomerization state. GP146 inhibits both the kinase and RNase domains of IRE1α and stabilizes the monomeric form; cartoons are not meant to differentiate between the relative orientations of monomer subunits in IRE1α.
Figure 6:
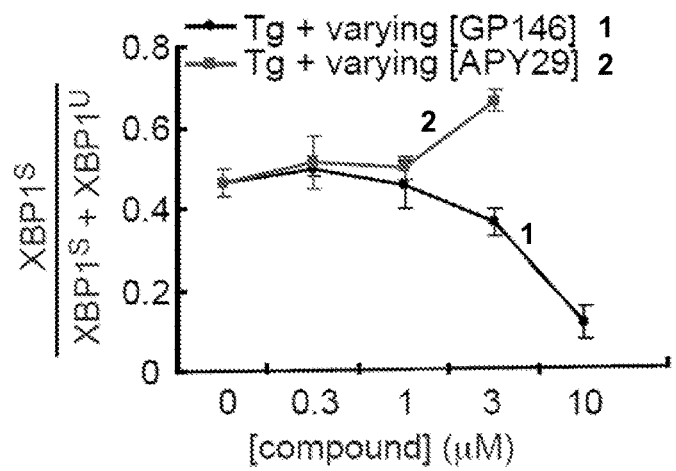
Figure 6:
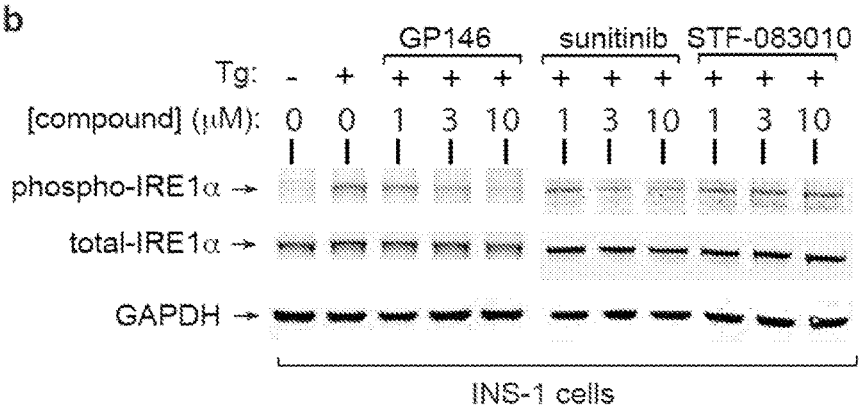
Figure 6:
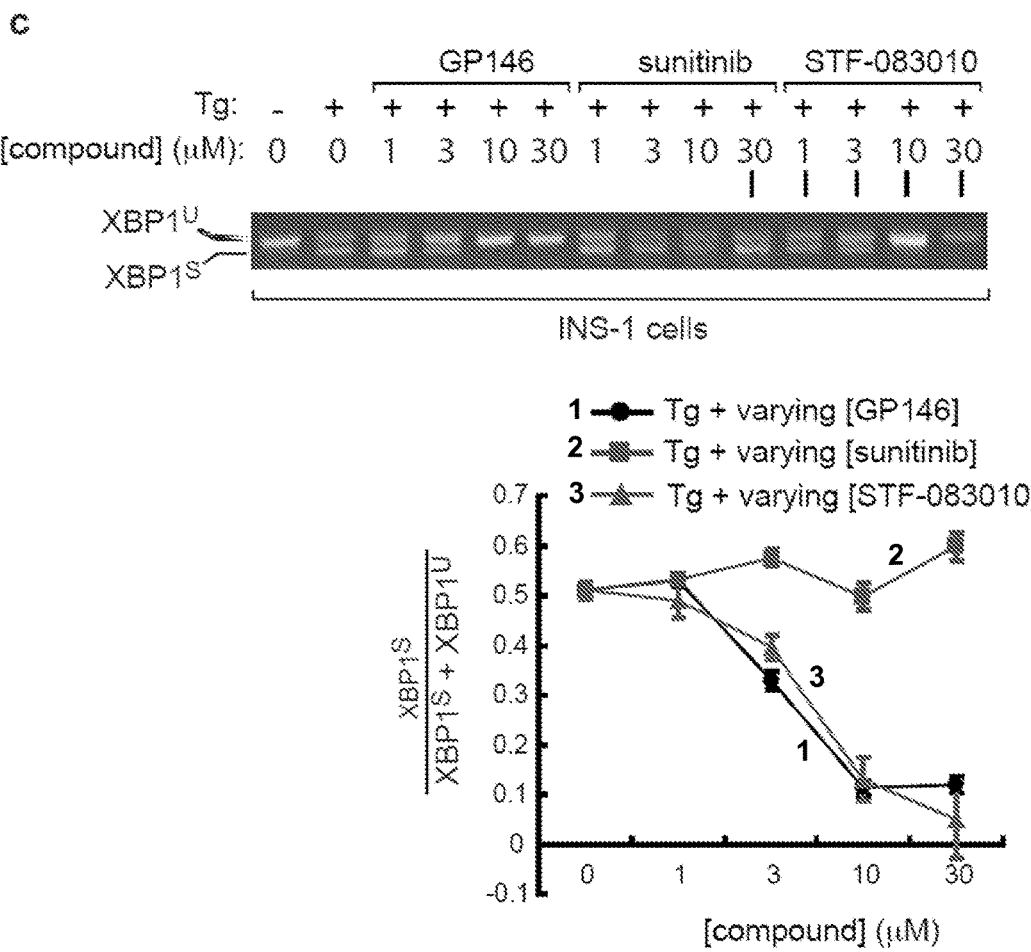
Figure 6:
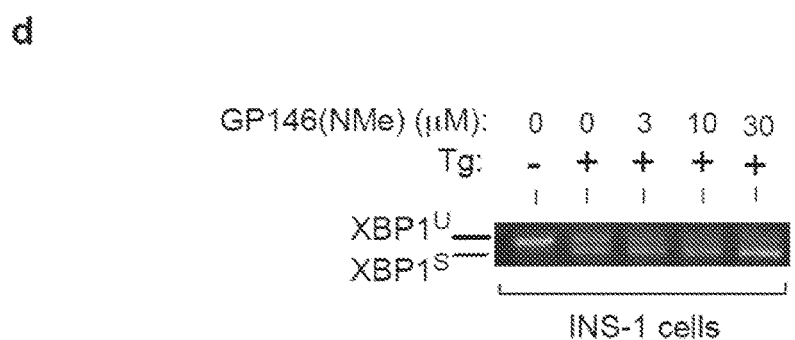
Figure 6:
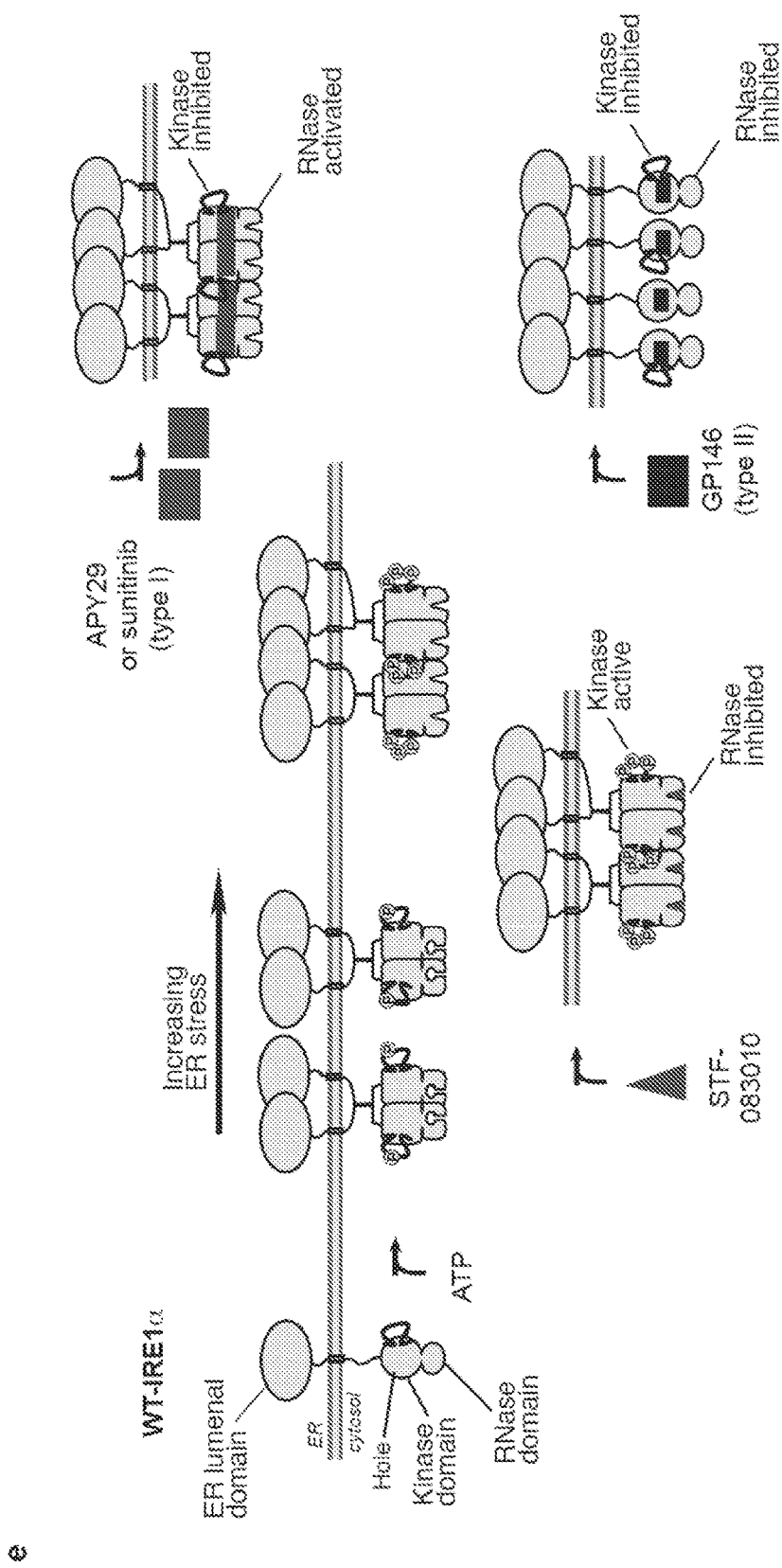

6. GP146 Blocks Both the Autophosphorylation and RNase Activities of Endogenous IRE1α In Vivo To further explore how IRE1α modulators affect the kinase and RNase activities of endogenous IRE1α under ER stress, in vivo studies using INS-1 rat insulinoma cell lines, which are derived from insulin-producing pancreatic β-cell tumors and contain large well-developed ERs, were conducted. These cells were treated with the ER SERCA ATPase pump inhibitor, thapsigargin (Tg), to induce ER stress and IRE1α activation at levels causing 50% splicing of cellular XBP1 mRNA (FIG. 6a). Recapitulating the in vitro results, GP146 and APY29 demonstrate opposing dose-dependent effects on ER stress-induced activation of the RNase of endogenous IRE1α (FIG. 6a). Furthermore, GP146 abrogates IRE1α autophosphorylation at a similar concentration as it blocks RNase activity (FIGS. 6b and 6c). Control compound GP146(NMe) does not block the splicing of XBP1 mRNA (FIG. 6d). Consistent with its in vitro activity, the type I inhibitor sunitinib is able to partially inhibit the kinase activity of IRE1α, but has no effect on the RNase activity of this enzyme (FIGS. 6b and 6c) at the concentrations tested. The RNase inhibitor STF-083010 was also tested in INS-1 cells that had been treated with Tg. As expected, this compound inhibits XBP1 splicing in a dose-dependent manner, but does not prevent IRE1α auto-phosphorylation (FIGS. 6b and 6c). Therefore, GP146 is the only compound identified to date that has the ability to block both enzymatic activities of IRE1α, both in vitro and in vivo (FIG. 6e).

7. Expression and Purification of IRE1α* and dP-IRE1α*.

A construct containing the cytosolic kinase and RNase domains of human IRE1α (residues 469-977, IRE1α*) was expressed in SF9 insect cells by using Bac-to-Bac baculovirus expression system (Invitrogen) with a 6-His-tag at the N-terminus, and purified with a Ni-NTA (Qiagen) column. To generate dP-IRE1α*, basal phosphorylation sites were removed by incubating IRE1α* with λ-PPase (NEB) at a molar ratio of 5:1 (IREα*: λ-PPase) in 50 mM HEPES pH 7.5, 100 mM NaCl, 1 mM MnCl2, 2 mM DTT, 0.01% Brij 35 for 40 min at RT. Dephosphorylation was verified by immunoblotting with an anti-phosphoIRE1α antibody.

8. In Vitro Characterization of Compounds (IRE1α*)

KIRAs are tested for ability to inhibit IRE1α* kinase and RNase activities in vitro. The XBP1 minisubstrate assay shown in FIG. 1B-1D, is amenable to 96- or 384-well format, and is used to determine RNase IC$_{50}$s. In parallel, kinase IC$_{50}$s for all KIRAs are determined in a 96-well dot blot assay with 32γ-ATP and STK peptide substrate 2 as substrates. Time-dependence of inhibition is determined for all electrophile-containing KIRAs. RNase and kinase assays have been used to profile the KIRAs in FIG. 26, showing a strong correlation between kinase and RNase IC$_{50}$s. The most potent KIRAs are tested in an IRE1α* autophosphorylation assay. Compounds that exhibit an IC$_{50}$(RNase)<200 nM are counter-screened against a panel of kinases that are likely off-targets (Src, Abl, p38α), affect cell fate (mTor, IKKβ), down-regulate protein translation (PKR, PERK, GCN2, HRI), are down-stream targets of IRE1 signaling (Jnk1/2, MKK4, MKK7), and are representative of the entire kinome (AurA, Erk2, Cdk2, EGFR, FAK, MAP3K5, PKA). The profiling data obtained from these screens are used to design more selective KIRAs. KIRA3 and KIRA6 have been tested against 12 kinases in this panel and the only off-target inhibition observed is for the tyrosine kinases Src and Abl. Thus, the structure-based design strategy uses these two kinases as counter targets (described below).

9. Kinase Assays.

Inhibitors (initial concentration=80 μM, 2-fold serial dilutions) were incubated with IRE1α* in cleavage buffer (20 mM Hepes at pH 7.5, 0.05% Triton X100, 50 mM KOAC, 1 mM Mg(OAC)$_2$, 1 mM DTT) for 20 min, followed by incubation with 10 μCi [γ-$^{32}$P]ATP (3000 Ci/mmol, Perkin Elmer) at RT for 30 min. Samples were then separated by SDS-PAGE, and autoradiographed. The auto-phosphorylation level were quantified by setting the band intensity of IRE1α* without compound treatment as 1 and the background as 0.

10. In Vitro RNase Assay.

5'FAM-3'BHQ-labeled XBP1 single stem-loop minisubstrate (5'FAM-CUGAGUCCGCAGCACUCAG-3'BHQ) was purchased from Dharmacon. 0.2 μM IRE1α* or dP-IRE1α* were incubated with inhibitors or DMSO for 20 min in cleavage buffer, followed by incubation with 3 μM RNA substrate for 5 min. The reaction was quenched by adding urea to a final concentration of 4 M, and the fluorescence was detected on a SpectraMax M5 microplate reader (Molecular Devices) with excitation and emission wavelengths of 494 nm and 52, nm, respectively. The fluorescence intensities were normalized by setting the signal for the reaction with IRE1α* and DMSO to 1 and the reaction without IRE1α* to 0. The cleavage products were also resolved by urea PAGE after phenol/chloroform extraction and ethanol precipitation. Internally $^{32}$P-labelled mouse XBP1 RNA was also used as a substrate, as described (Han, D. et al. *Cell* 138, 562-575, (2009)).

11. ICAT Footprinting.

Heavy and light iodonated ICAT reagents were made as previously described (Underbakke, E. S. et al. *Angew. Chem. Int. Ed.* 47, 9677-9680 (2008)). Purified human Ire1α was exchanged into 50 mM Tris (pH 8.0), 50 mM KCl, 5 mM MgCl2, and 0.5 mM TCEP. One 3 μM stock solution was divided into three solutions, and each was mixed with either DMSO, APY29, or GP146 to yield solutions containing 1%

DMSO and 20 µM of inhibitor. Heavy labeling reagent was added to the protein solutions, and 25 µL aliquots were taken at specified times and quenched with excess DTT. Samples were precipitated with 0.2% sodium deoxycholate and 10% trichloroacetic acid on ice for 10 min. The mixtures were centrifuged at 4° C. for 15 min, and pellets were washed with cold acetone. The pellets were then resuspended in 30 µL of 200 mM Tris (pH 8.0), 7 M urea, and 2.4 mM light labeling reagent, and incubated in the dark for 30 min. The solutions were diluted with 210 µL 200 mM Tris (pH 8.0), 5.7 mM $CaCl_2$, 0.5 µg porcine trypsin (TPCK treated, Sigma), and 12, ng GluC (Roche), and incubated at room temperature overnight. Samples (0.3 pmol) were injected onto a Thermo Scientific Dionex Acclaim Pepmap100 NanoLC capillary column ($C_{18}$, 150 mm length, I.D. 75 µm, 3 µm particle size) connected inline to a Finnigan LCQ mass spectrometer. Peptides of interest were identified by MS/MS data (Sequest), and corresponding XIC peaks were integrated. Alkylation curves were fit using GraphPad Prism software (Binding Kinetics, Dissociation—One-phase exponential decay).

12. Molecular Modeling.

Molecular modeling of KIRA interactions with the ATP-binding site of IRE1α: To gain insight into how KIRA3 and KIRA6 interact with the IRE1α ATP-binding site, molecular modeling experiments were used. A model of the DFG-in ATP-binding site conformation was generated from a co-crystal structure of human IRE1α bound to ADP. As a structure of IRE1α in the DFG-out conformation has not yet been described, a homology model of this form was generated by using the activation loop of another kinase, the tyrosine kinase Ab12, as a template. Both the DFG-in and DFG-out models were optimized using multi-step all-atom minimization and explicit water molecular dynamics (MD) simulations. Consistent with the observed SAR and type II pharmacophores of KIRA3 and KIRA6, these ligands are only accommodated in the ATP-binding site of IRE1α when the DFG-motif is in the "out" conformation (DFG-out). Furthermore, the most favorable docking poses for both KIRA3 and KIRA6 involve both of these ligands making all of the canonical contacts of type II inhibitors. Using this model, the predicted docking scores for the KIRAs shown in FIG. 3c are very consistent with in vitro kinase and RNase inhibition results. For example, KIRA7 ($R_1$=V; $R_3$=C: $IC_{50}$ (RNase)=<30 nM; $IC_{50}$(kinase)=35 nM) and KIRA6 ($R_1$=V; $R_3$=B: $IC_{50}$(RNase)=210 nM; $IC_{50}$(kinase)=620 nM) have significantly and slightly more favorable Glide_SP and MMGBSA scores than KIRA3, respectively. Furthermore, this model has been used to design inactive KIRA3 analogs for controls in cellular assays. Currently, the model for the IRE1α"DFG-out" inactive conformation is used to filter potential analog syntheses based upon their docking scores.

The DFG-in structure of IRE1α was generated from a co-crystal structure of human IRE1α bound to ADP (PDB code 3P23, chain A) (Ali, M. M. et al. *EMBO J.* 30, 894-90, (2011)). The structure was prepared using the protein preparation workflow in Maestro (Schrodinger) to assign hydrogens, optimize hydrogen bonds, and to perform constraint minimization (impref). The homology model of IRE1α in the DFG-out conformation was built using the activation loop of a DFG-out template kinase (Ab12; PDB code 3GVU) (SEQ ID NO:6) (Salah, E. et al. *J. Med. Chem.* 54, 2359-2367 (2011)) in Prime (Schrodinger). The initial DFG-out model was optimized using the protein preparation workflow described above. Both DFG-in and DFG-out models were then optimized using a multi-step all-atom minimization and molecular dynamics (MD) simulation implemented in the software package Desmond (DE Shaw Research) (Bowers, K. J. et al. in *Proceedings of the ACM/IEEE Conference on Supercomputing* (SC06) (Tampa, Fla., USA, 2006)). Optimizations were run using the OPLS-AA force field, the TIP4P explicit solvent model in an orthorhombic simulation box 10 Å distance in all directions and adding counter ions. Simulations were performed at 300 K and 1.0132, bar using the NPT ensemble class. All other settings were default. The production simulation time was 12 ns. Simulations were run on an IBM E-server 1350 cluster (36 nodes of 8 Xeon 2.3 GHZ cores and 12 GB of memory). Several later simulation frames were extracted from the DFG-in and DFG-out simulations based on conformational diversity and low (stable) RMSD. These frames were then used to generate the DFG-in and DFG-out models of IRE1α$^{I642A}$. To avoid side chain clashes, constraint (impref) minimization (in Maestro, Schrodinger) was performed for the WT and I642A structures of IRE1α. These structures were then used for further modeling.

Using the optimized DFG-in and DFG-out structures of WT and IRE1α$^{I642A}$ described above, initial binding poses for APY29 and GP146 were generated as follows. Ligands were prepared using ligprep (Schrodinger Inc.) to generate ionization states (pH=7) and stereoisomers resulting in two representations for GP146 and four for APY29. Ligands were initially docked into the DFG-in and DFG-out models of IRE1α using the Induced Fit Docking (IFD) (Schrodinger Inc.) protocol with default settings. The IFD protocol includes a constraint receptor minimization step followed by initial flexible Glide docking of the ligand using a softened potential to generate an ensemble of poses. For each pose, the nearby receptor structure was then refined using Prime. Each ligand was then re-docked (using Glide) into its corresponding optimized low-energy receptor structure and ranked by Glide score. The best pose with highest IFD score obtained for each ligand was again subjected to MD simulation (8-10 ns production runs) for further optimization of the protein ligand complex. The MD protocol includes a multi-step procedure for minimizations and short MD runs followed by the production MD simulation. Ligand poses were observed to be stable during the production MD runs. The final frames of these simulations were then used for ligand docking after constraint (impref) minimization (Maestro, Schrodinger Inc.). The best pose for each ligand was selected based on the Glide score, known interactions and visual inspection. The 3D plots of ligand poses were produced using PyMol.

13. IRE1α* Cross-Linking to Determine Oligomer to Monomer Ratio.

Structural analysis of IRE1-KIRA and off-target kinase-KIRA complexes: For KIRAs that show sufficient potency and selectivity, further biochemical and biophysical characterization are performed. It is determined if new KIRA analogs are able to prevent the dimerization/oligomerization of IRE1α using the crosslinking strategy shown in FIGS. 4 and 30. KIRA6, like KIRA3, stabilizes the monomeric state of IRE1α. Analytical ultra-centrifugation (AUC) is used to further confirm that KIRAs stabilize the monomeric form of IRE1α[49]. Crystal structures of the most promising KIRAs bound to IRE1α and the off-target kinase Src are being obtained. These structures are used to refine the docking protocols for IRE1α, which aid computational design of inhibitors with increased potency. Structures of KIRA-Src complexes are used to identify interactions that are unique to IRE1α and inform the design of KIRAs that possess increased selectivity. On-target/off-target structural strategy has been used to develop highly potent and selective inhibitors of *Toxoplasma gondii* and *Cryptosporidium parvum* CDPK1 (Murphy, R. C. et al. *ACS Med. Chem. Lett.* 1, 331-33, (2010); Larson, E. T. et al. *J. Med. Chem.* 55, 2803-2810 (2012); Johnson, S. M. et al. *J. Med. Chem.* 55, 2416-2426 (2012); Ojo, K. K. et al. *J. Clin. Invest.* 122, 2301-230, (2012)). Diffraction-quality crystals of Src bound to KIRA3 have been obtained. A structure of human IRE1α bound to ADP has been reported[48]. Using the same IRE1α expression construct, and purification protocol multi-milligram quantities of homogenous unphosphorylated IRE1α have been obtained. This protein is currently being used by to screen for diffraction quality crystals of IRE1α-KIRA3 and IRE1α-KIRA6 complexes, and initial screening results are very promising.

Increasing concentrations of IRE1α* (0.49-30 μM) were incubated with DMSO, GP146 (200 μM), or APY29 (200 μM) for 20 min, then cross-linked by adding 250 μM disuccinimidyl suberate (DSS) (Pierce) for 1 hr at RT in cleavage buffer. The reaction was quenched by addition of 50 mM Tris-HCl (pH 7.5). The samples were then boiled, resolved on SDS-PAGE, and immunoblotted for IRE1α with an anti-IRE1α antibody, (visualization and quantification with a LI-COR Odyssey scanner).

Cell culture and XBP1 mRNA splicing. INS-1 cells were grown in RPMI, 10% fetal calf serum, 1 mM sodium pyruvate, 10 mM HEPES, Pen/strep, 2 mM glutamine and 50 mM β-mercaptoethanol. T-REx 293 IRE1α or IRE1α$^{I642A}$ were grown in DME H-21 with 10% fetal calf serum and Pen/strep. After 1 hr incubation with compounds, INS-1 cells were treated with 6 nM thapsigargin for 4 hrs, and T-Rex 293 IRE1α-expressing cells were treated with 1 μM Dox for 8 hrs. The RNA was then extracted using RNeasy Mini Kit (Qiagen), and reverse transcribed using the QuantiTect Reverse Transcription Kit (Qiagen). XBP1 splicing was performed as previously described'. Primers used: sense primer rXBP 1.3S (5'-AAACAGAGTAGCAGCACA-GACTGC-3") (SEQ ID NO:7) and antisense primer rXBP 1.2AS (5'-GGATCTCTAAGACTAGAGGCTTGGTG-3') (SEQ ID NO:8) for INS-1 cell line, while sense primer mXBP1.3S (5'-AAACAGAGTAGCAGCGCAGACTGC-3') (SEQ ID NO:9) and antisense primer mXBP1.2AS (5'-GGATCTCTAAAACTAGAGGCTTGGTG-3') (SEQ ID NO:10) for T-Rex 293 cell line. PCR products were resolved on 2.5% agarose gels, stained with EtBr, and quantified by ImageJ.

Immunoblot analysis. INS-1 cells were incubated with compounds or DMSO for 1 hr, followed by 1 μM Tg for 2 hrs. T-Rex 293 IRE1α-expressing cells were incubated with compounds or DMSO for 1 hr and then treated with 1 μM Dox for 8 hrs. Cells were lysed in RIPA buffer (20 mM Tris-HCl, pH 7.5, 0.1% SDS, 1% Triton X-100, 1% sodium deoxycholate, 150 mM NaCl, 1 mM EDTA, 1% NP-40, complete EDTA-free protease inhibitor (Roche) and phosphatase inhibitor cocktail (Sigma)), and cleared lysates were subjected to SDS-PAGE and transferred to nitrocellulose. Blocking, antibody incubation, and washing were done in PBS or TBS with 0.05% Tween-20 (v/v) and 5% (w/v) non-fat dry milk or BSA, or blocking buffer (Odyssey). Primary antibodies were diluted: IRE1α (1:1000) (Santa Cruz Biotechnology), phospho-IRE1α (1:1000) (Novus Biologicals), GAPDH (1:3000) (Santa Cruz Biotechnology), Myc (1:4000) (Santa Cruz Biotechnology). The antibody binding was detected by using near-infrared-dye-conjugated secondary antibodies and visualized on the LI-COR Odyssey scanner.

As described herein, IRE1α* means a recombinant human (rh) IRE1α. rh IRE1α has the human IRE1α (469-977) sequence: SEQ ID NO:1 (w/ his tag); and SEQ ID NO:2 (w/o his tag).

14. Determine Whether Blocking the Terminal UPR with IRE1α Kinase Inhibitors Prevents ER Stress-Induced β-Cell Degeneration. On-Target Effects of KIRAs, Underlying Mechanisms, and Amelioration of Beta Cell Death and Preservation of Function Under ER Stress by KIRA6

Inhibiting IRE1α's RNase activity using KIRAs shuts down endonucleolytic decay of mRNAs localizing to the ER membrane. ER-localized mRNA decay has been directly linked to the terminal UPR. One model holds that depletion of key mRNAs encoding factors needed to maintain ER structural and functional integrity (e.g. ER chaperones) may underlie apoptotic effects. IRE1α RNase targets select microRNA (miR) precursors to terminate their biogenesis. These mature miRs normally exert inhibitory effects on gene expression of key pro-apoptotic targets; e.g., depletion of four select miRs leads to: (i) translational derepression of the apoptosis initiator caspase 2, and (ii) stabilization of the mRNA encoding pro-oxidant thioredoxin-interacting protein (TXNIP). Using engineered chemical-genetic systems is elucidating these mechanistic signature events of IRE1α RNase-induced cell death, and helping to understand the physiological consequences of inhibiting IRE1α RNase activity by KIRAs.

15. Duration and Magnitude of ER Stress Determine Entry into the Terminal UPR Through High-Order Oligomerization and Hyperactivation of IRE1α Kinase/RNase Catalytic Domains.

Figure 28:
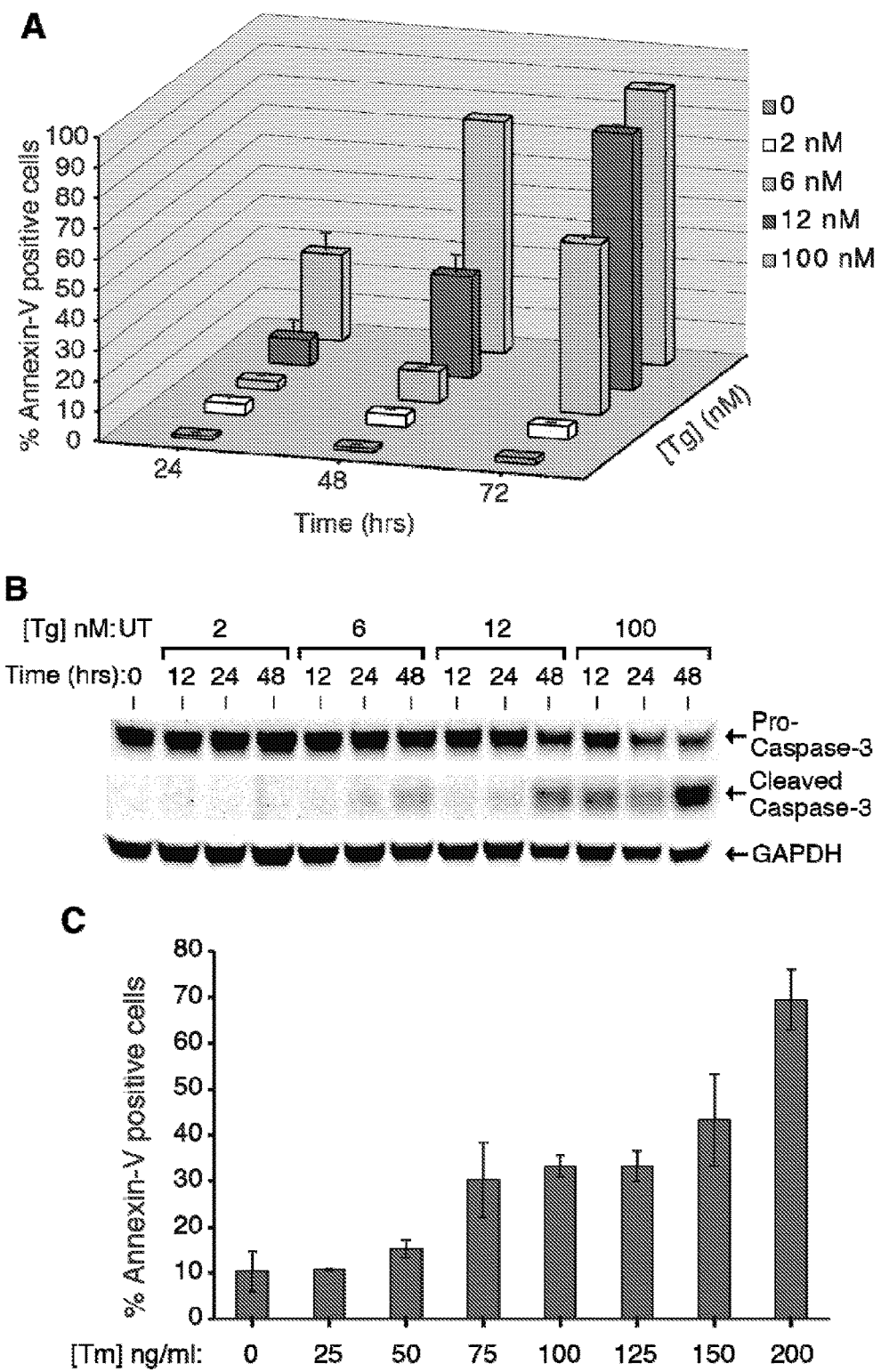
FIG. 28. Increasing magnitude and duration of exposure of cells to myriad ER stressors causes increasing activation of IRE1α (autophosphorylation, XBP1 mRNA splicing, ER localized decay of Ins1 mRNA), and switch-like entry of the stressed into dysfunctional states culminating in apoptosis (see text for details); (A) Percent Annexin-V staining INS-1 cells treated in a time course of increasing concentrations of Tg. (B) Pro- and cleaved Caspase-3 immunoblot of Tg-treated INS-1 cells. (C) Time of exposure to the agent are directly linked to the percentage of cells entering apoptosis, as can be defined for other ER stress inducers such as the glycosylation inhibitor, tunicamycin (Tm) (D) Increasing ER stress causes progressive increases in endogenous IRE1α phosphorylation. (E) Increasing ER stress causes progressive increases in endogenous XBP1 mRNA splicing. (F) Increasing ER stress causes progressive depletion through endonucleolytic decay of the ER-localized mRNA, Ins1, which encodes proinsulin. (G) Increasing ER stress causes progressive induction of the pro-apoptotic transcription factor, CHOP. (H) Diagram of effects due to increasing exposure to ER stress inducers and increasing severity of ER stress.
Figure 28:
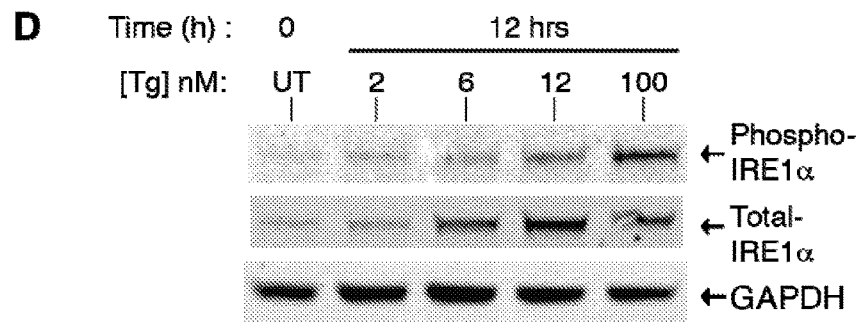
Figure 28:
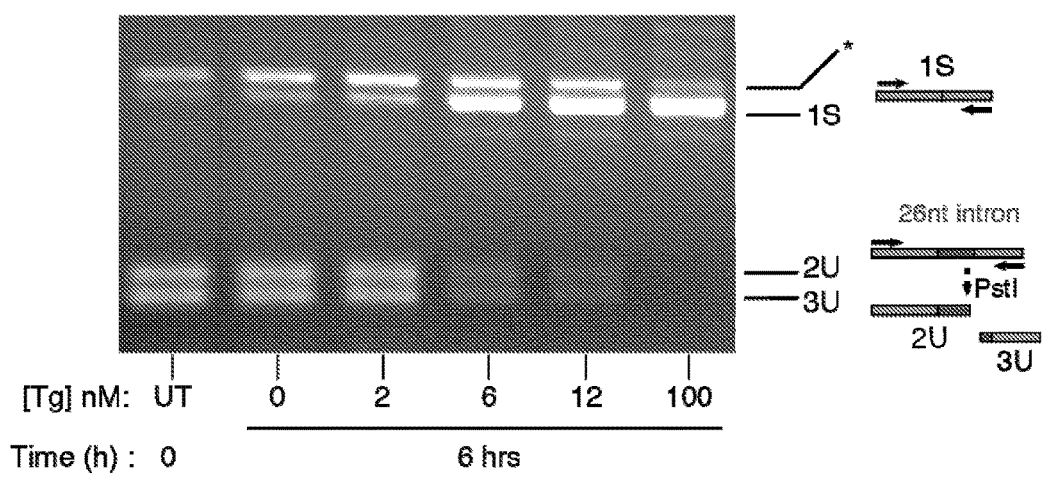
Figure 28:
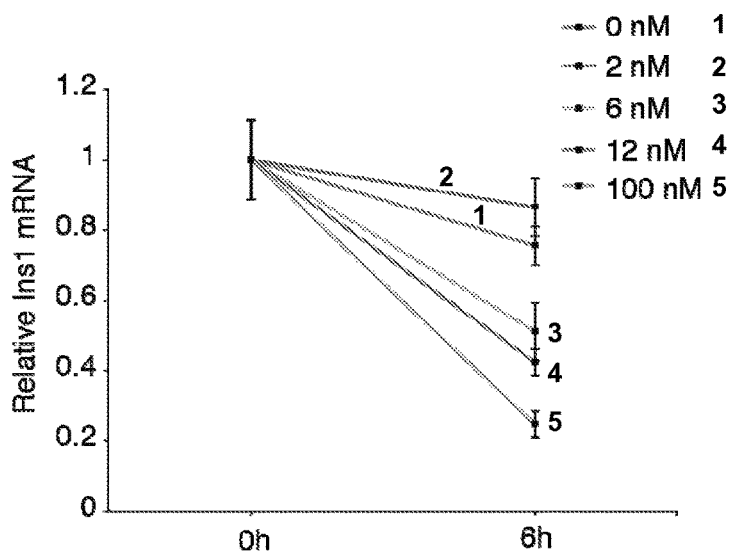
Figure 28:
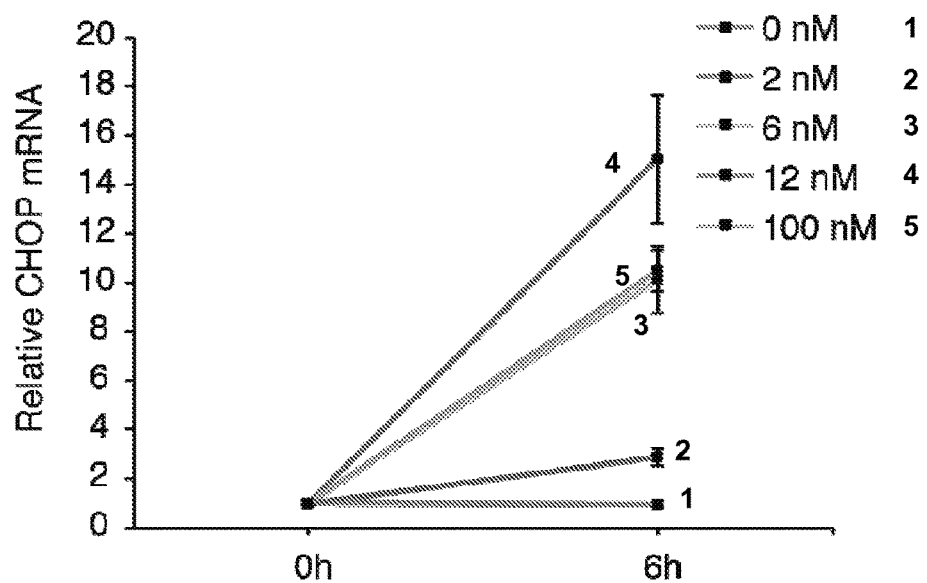
Figure 28:
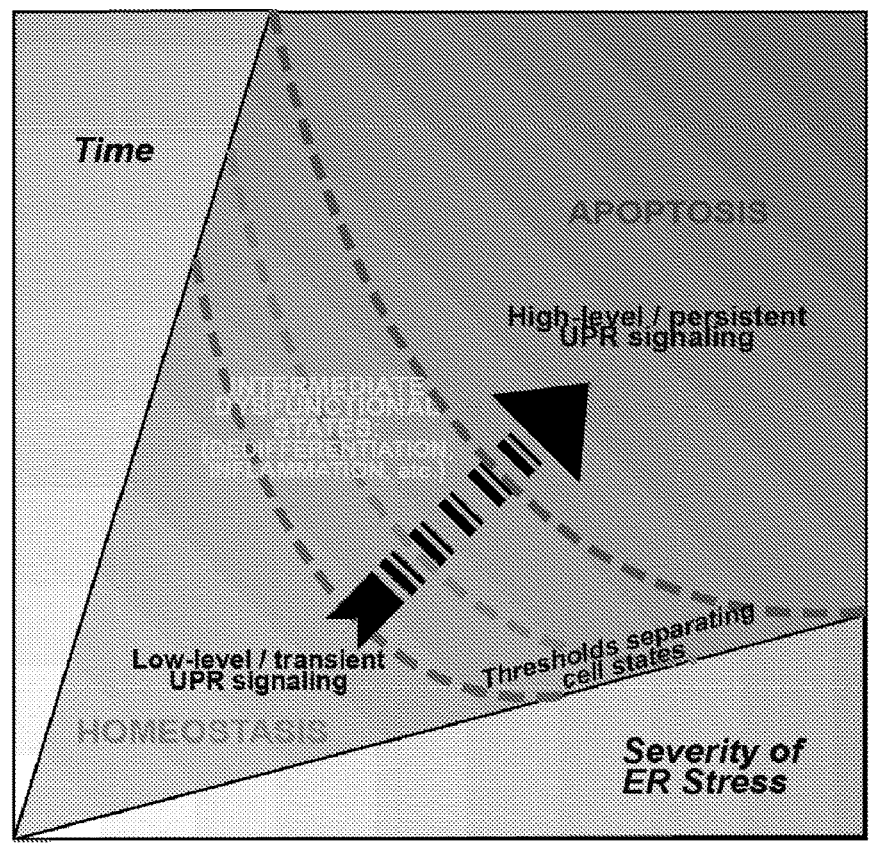

To rigorously test for cytoprotective effects, thresholds of ER stress were dilenated that when crossed push cells into apoptosis. Using rat insulinoma (INS-1) cells that have a well-developed ER and secrete insulin, the duration and magnitude of ER stress that triggers apoptosis were quantified. Two variables—concentration of ER stress inducer (e.g. Thapsigargin—Tg) and time of exposure to the agent—are directly linked to the percentage of cells entering apoptosis (FIGS. 28, A and B). Such regimes can be defined for other ER stress inducers such as the glycosylation inhibitor, tunicamycin (Tm) (FIG. 28,C). Increasing ER stress causes progressive increases in endogenous IRE1α phosphorylation, increases in XBP1 mRNA splicing (FIG. 28, E), depletion through endonucleolytic decay of the ER-localized mRNA, Ins1, which encodes proinsulin (FIG. 28, F), and induction of the pro-apoptotic transcription factor, CHOP (FIG. 28, G).

Figure 29:
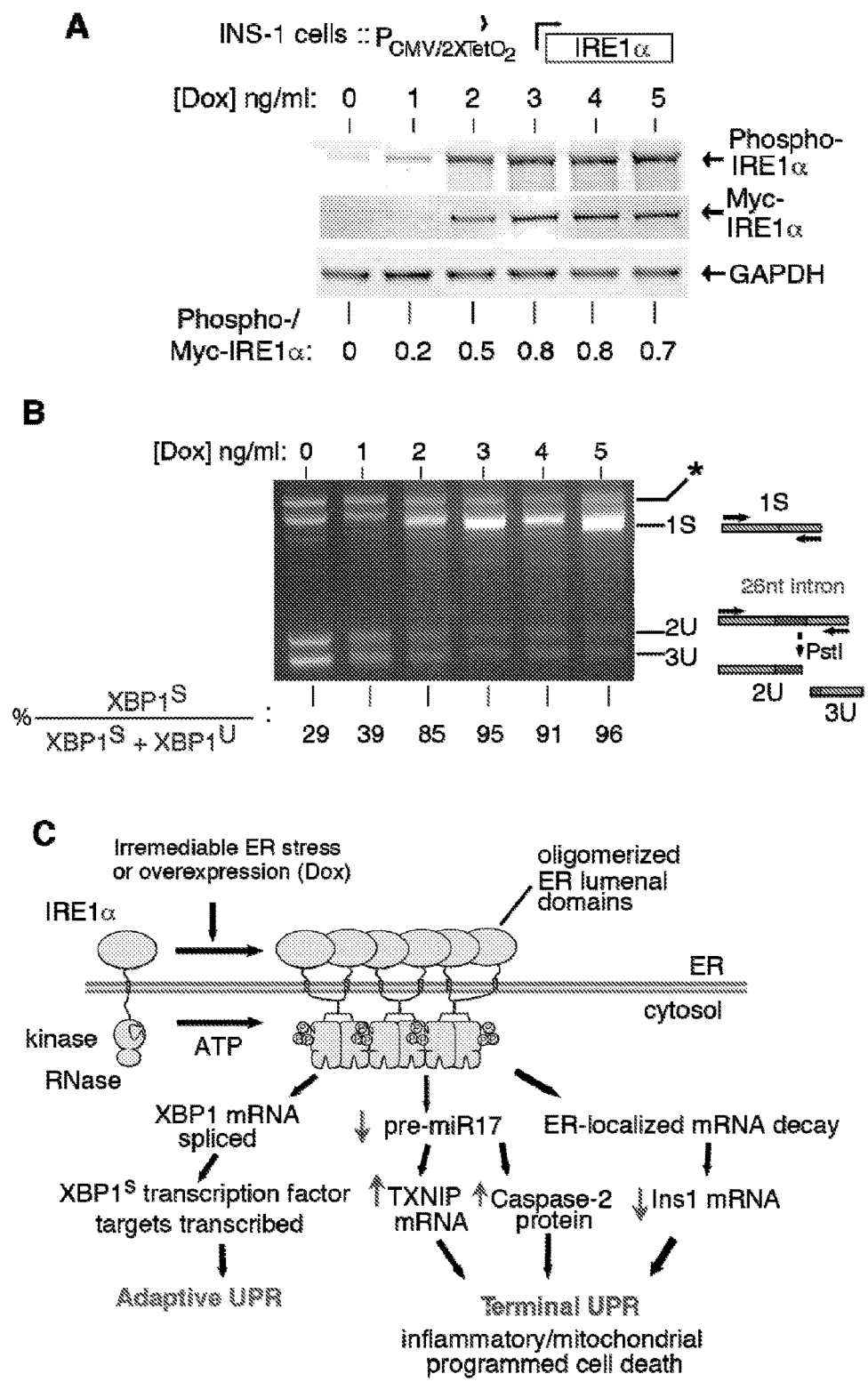
FIG. 29. Conditional overexpression (using Dox) of IRE1α in stable INS-1 cells mimics a Terminal UPR by forcing IRE1α autophosphorylation, XBP1 mRNA splicing, ER localized decay of Ins1 mRNA, decay of miR-17, induction of CHOP, accumulation and cleavage of upstream (Caspase 2) and downstream (Caspase 3) caspases of the mitochondrial apoptotic pathway, as well as inflammatory (Caspase 1) caspase mediating pyroptosis, and switch-like entry of cells into programmed cell death. (A) Anti-Phospho-IRE1α and anti-Myc-IRE1α immunoblot of INS-1 IRE1α (WT) cells treated with increasing concentrations of Dox for 24 h. (B) Agarose gel of PstI-digested XBP1 cDNA amplicons from INS-1 IRE1α (WT) cells treated with increasing [Dox] for 24 h. % XBP1 splicing represents the ratio of spliced over (spliced+unspliced) amplicons—1S/(1S+2U+3U). (C) Model of how severe ER stress causes IRE1α to switched from homeostatic to apoptotic outputs. (D) Q-PCR for miR-17 in INS-1 IRE1α (WT) cells treated with increasing [Dox] for 72 h. (E) Q-PCR for Insulin1 (Ins1) and CHOP mRNA in INS-1 IRE1α (WT) cells treated with increasing [Dox] for 24 h; anti-Proinsulin immunoblot of INS-1 IRE1α (WT) cells treated with increasing [Dox] for 72 h. (F) Immunoblot of Pro- and cleaved Caspase-1, Pro- and cleaved Caspase-2 from INS-1 IRE1α (WT) cells treated with increasing [Dox] for 72 h and immunoblot of Pro-Caspase-3 and cleaved Caspase-3 from INS-1 IRE1α (WT) cells treated with increasing [Dox] for 72 h. (G) Percent Annexin-V staining of INS-1 IRE1α (WT) cells treated with increasing [Dox] for 72 h; three independent biological samples were used for XBP1 splicing, Q-PCR and Annexin V staining experiments; each data point represents the mean value±SD; P-values: *<0.0, and ** <0.01, ns=not significant.
Figure 29:
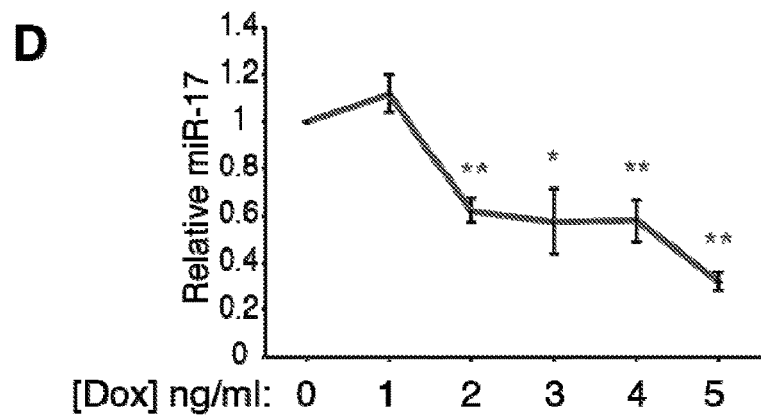
Figure 29:
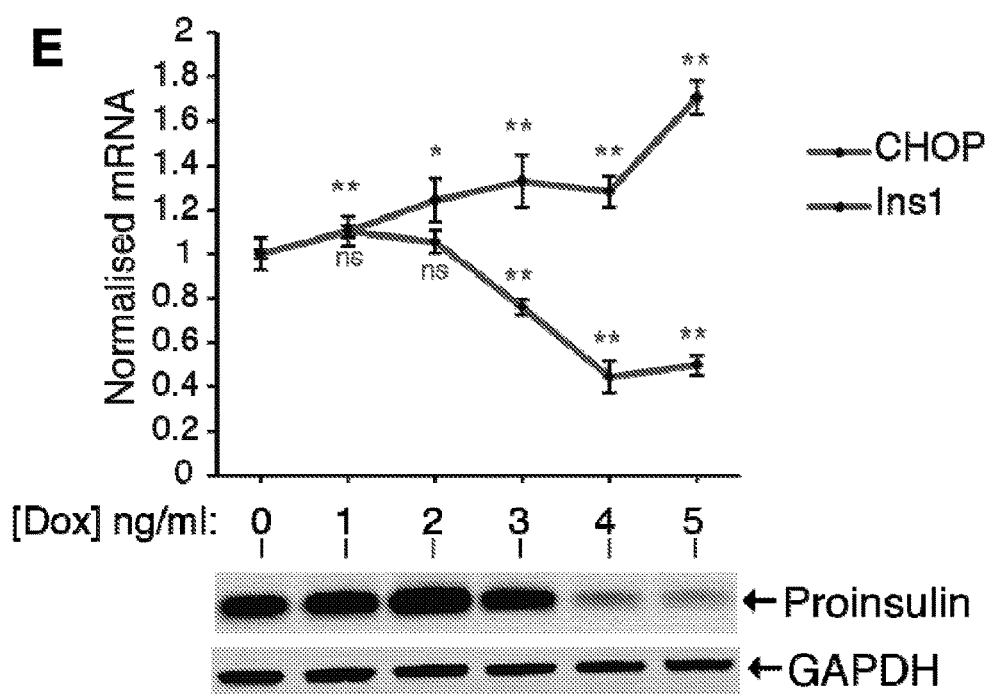
Figure 29:
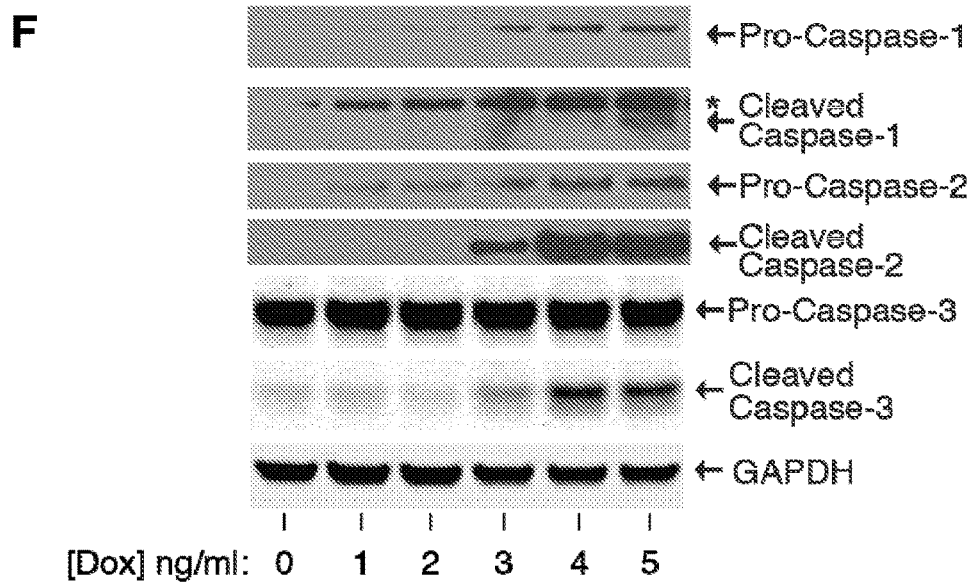
Figure 29:
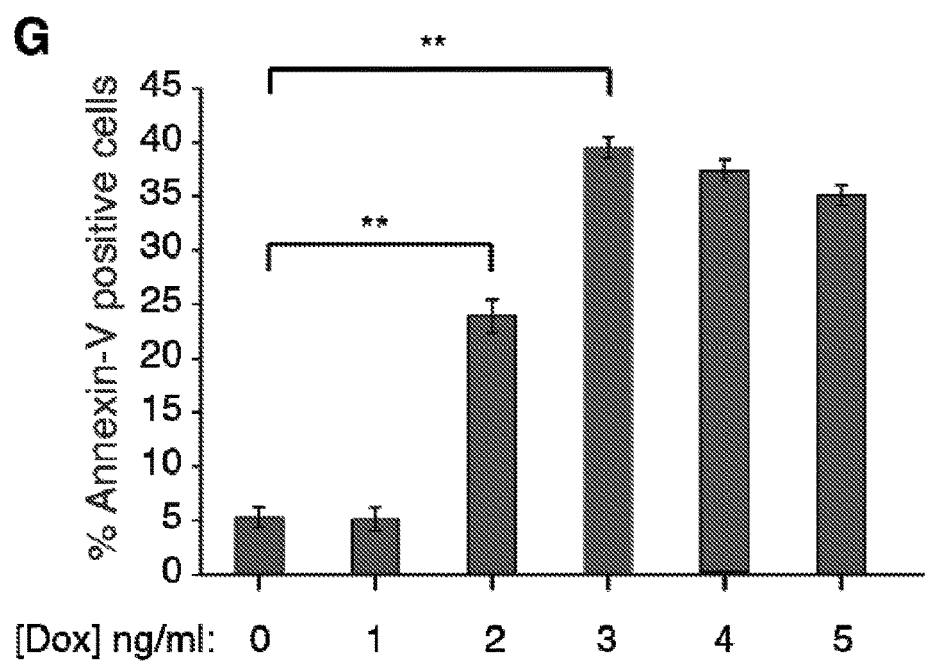

These aforementioned terminal UPR signaling events can be completely mimicked simply by controlled over-expression of IRE1α, in the complete absence of upstream ER stress. Tetracycline-inducible isogenic INS-1 stable cell lines expressing WT IRE1α were generated. Induced with doxycycline (dox) the transgenic IRE1α proteins oligomerize, spontaneously trans-autophosphorylate and trigger XBP1 mRNA splicing (FIGS. 29, A and B). The transgenic systems are finely tuneable, with increasing [Dox] causing progressively greater IRE1α induction (the transgenic IRE1α protein is Myc-tagged). Phospho/Myc IRE1α ratios are finely controllable (and measureable) with increasing [Dox], as is XBP1 mRNA splicing. Mimicking dose-dependency by ER stress agents into a terminal UPR, increasing [Dox] spontaneously triggers entry into a terminal UPR by causing IRE1α kinase hyper-phosphorylation and RNase hyperactivation past a critical threshold and induction of key signature events of the terminal UPR (FIG. 29, C). These include reduction of miR-17 (FIG. 29, D) and Ins1 mRNA, induction of CHOP mRNA (FIG. 29, E), induction and proteolytic cleavage of caspases 1,2, and 3 (FIG. 29, F), and apoptosis as measured by Annexin-V staining (FIG. 29, G).

KIRAs break high-order oligomerization of IRE1α kinase domains, attenuate RNAse activity, and reduce entry of cells into the Terminal UPR. In exciting preliminary data, all these terminal UPR endpoints are curtailed by pre-treating cells with KIRA6, before exposing them to ER stress inducers. in vitro, KIRA6 inhibits IRE1α* RNase and kinase activities with similar $IC_{50}$s (FIGS. 30, B and C). in vivo, KIRA6 inhibits endogenous IRE1α auto-phosphorylation in a dose-dependent manner (FIG. 30, D); in contrast the aldehyde-based IRE1α RNase-inhibitor, STF, does not inhibit IRE1α auto-phosphorylation, nor does a control compound KIRA6(in).

Figure 30:
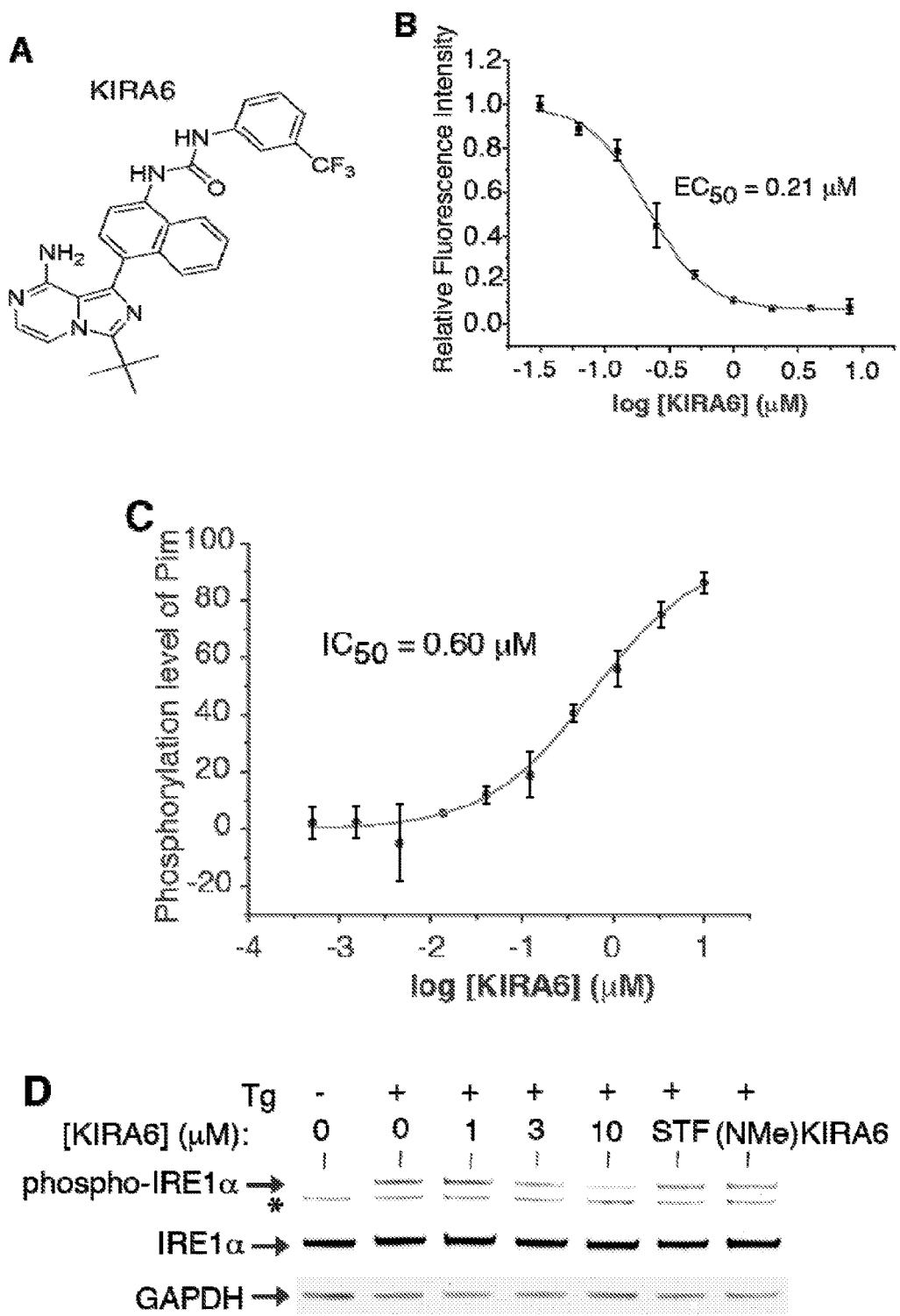
FIG. 30. KIRA6 inhibits IRE1α autophosphorylation, breaks oligomers, reduces RNase activity, and protects cells from entry into apoptosis. (A) Structure of KIRA6. (B) RNase activities of IRE1α* under varying [KIRA6]; half-maximum effective concentration ($EC_{50}$) values were determined by fitting normalized fluorescence intensities (mean±s.d., n=3). (C) Inhibition of IRE1α* kinase activity in vitro by KIRA6; $IC_{50}$ values were determined by fitting percent phosphorylation. (D) In vivo, KIRA6 inhibits endogenous IRE1α auto-phosphorylation in a dose-dependent manner; in contrast the aldehyde-based IRE1α RNase-inhibitor, STF, does not inhibit IRE1α auto-phosphorylation, nor does a control compound KIRA6(in). (E) Immunoblots of IRE1α* (WT) incubated with DMSO or KIRA6 (200 μM) followed by treatment with the crosslinker DSS (250 μM); quantification is on the right. (F) Agarose gel of XBP1 cDNA amplicons from INS-1 cells pre-treated with indicated concentrations of KIRA6 for 1 h, followed by 0.5 μg/ml Tm for 8 h. (G) KIRA6 inhibits ER-localized endonucleolytic decay of Ins1 mRNA at lower doses of the drug than needed to inhibit XBP1 mRNA splicing. (H) KIRAs reduce entry of INS1-1 cells into apoptosis. (I) Immunofluorescence of islets from 10 wk old C57BL/6 mice treated with 0.5 μg/mL Tm plus/minus 0.5 μM KIRA6 for 16 hr. Co-stained for DAPI, insulin, and TUNEL; Quantification of TUNEL positive β-cells (white arrows) normalized to DAPI-positive cells is shown. (J) KIRA6 cytoprotective effects are dependent on IRE1α because they are absent in Ire1α$^{-/-}$ mouse embryonic fibroblasts (MEFs), but still demonstrable in WT and Xbp1$^{-/-}$ MEFs. (K) Model of how KIRA6 prevents the terminal UPR by inhibiting IRE1α.
Figure 30:
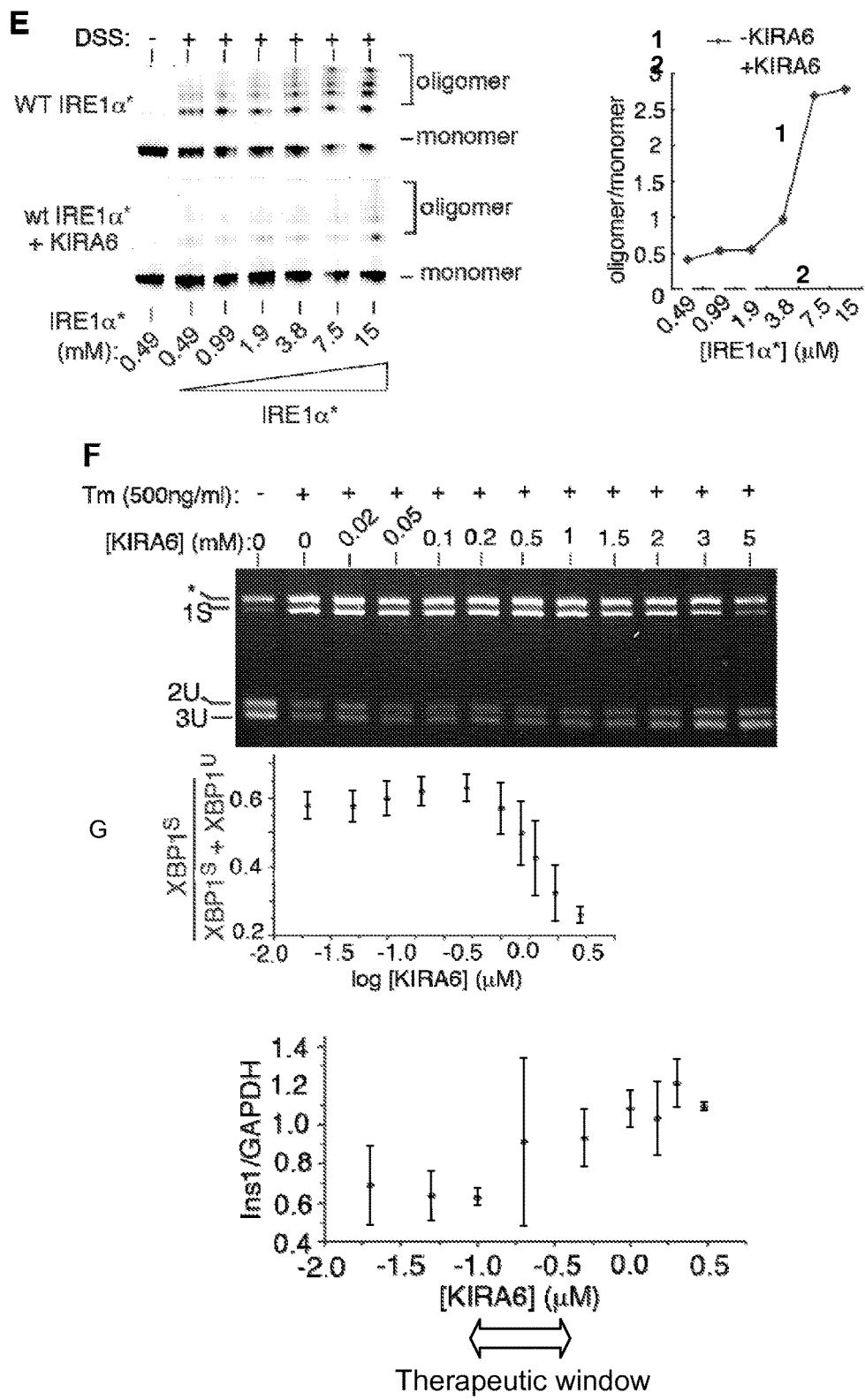
Figure 30:
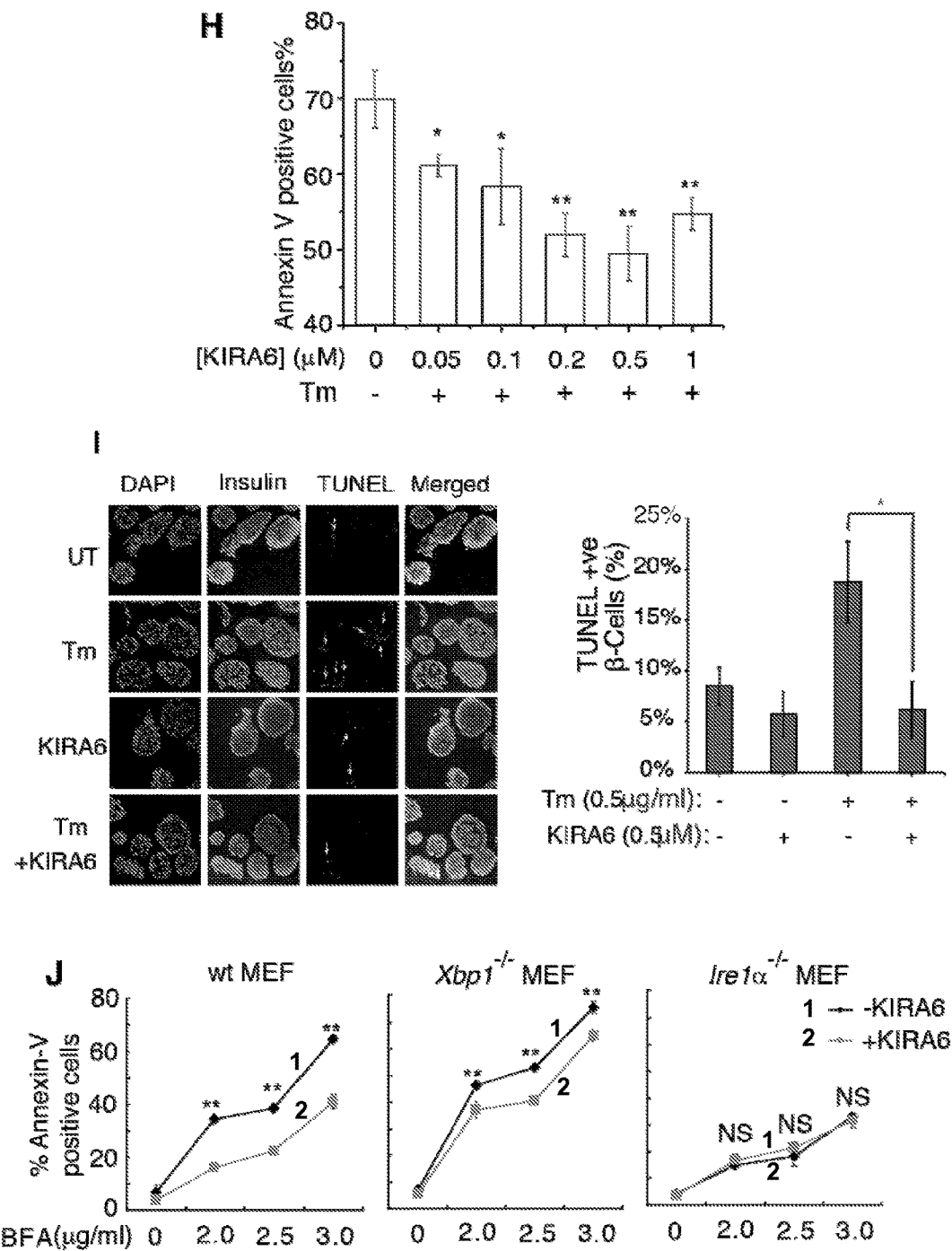
Figure 30:
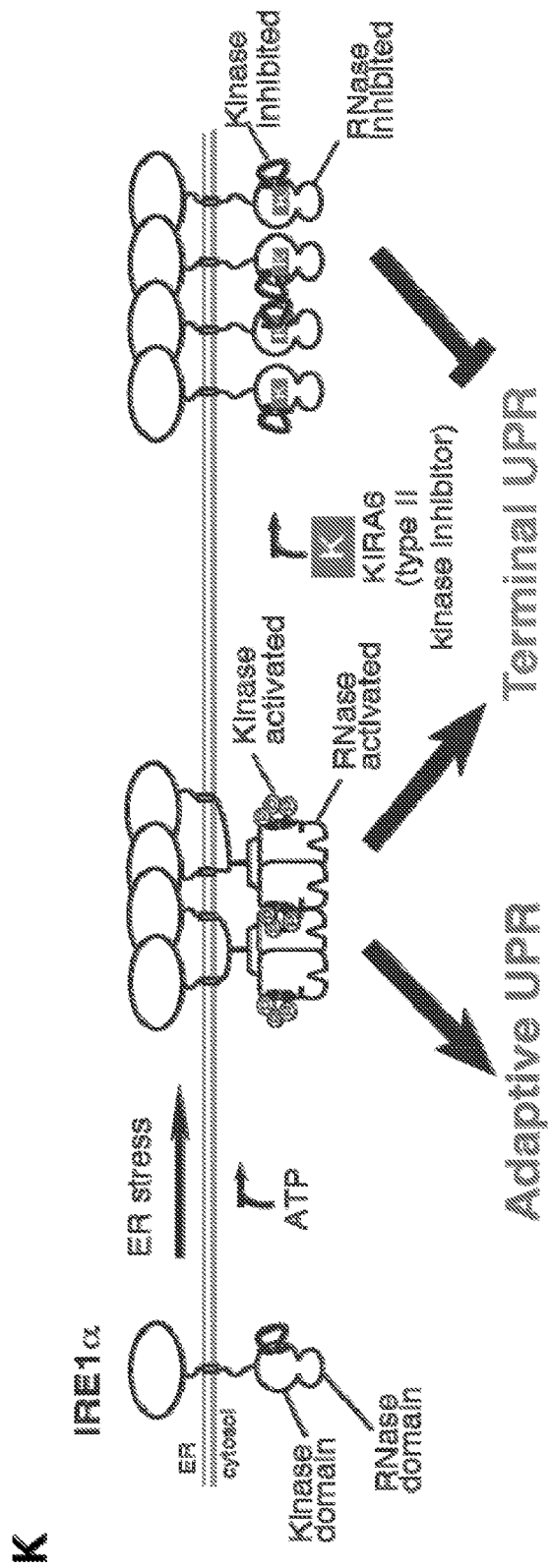

Furthermore, in vitro, KIRA6 reduces concentration-dependent oligomerization of IRE1α* (FIG. 30, E). in vivo, KIRA6 inhibits endogenous IRE1α mediated XBP1 mRNA splicing provoked by Tm (FIG. 30, F). Intriguingly, KIRA6 inhibits ER-localized endonucleolytic decay of Ins1 mRNA at lower doses of the drug than needed to inhibit XBP1 mRNA splicing (FIG. 30, G); this discriminatory effect may occur because higher-order oligomers are needed to catalyze Ins1 mRNA decay, whereas dimers suffice for XBP1 mRNA splicing. Because ER-localized endonucleolytic mRNA decay promotes apoptosis—in contrast to XBP1 mRNA splicing, which promotes adaptation—this differential effect of KIRAs reveals the existence of a natural "therapeutic window" which reduces entry of INS1-1 cells into apoptosis (FIG. 30, H). These cytoprotective effects of KIRA6 extend to myriad cell types, including freshly harvested pancreatic islets from C57/BL6 mice treated with Tm (FIG. 30, I). KIRA6 cytoprotective effects are dependent on IRE1α because they are absent in Ire1α$^{-/-}$ mouse embryonic fibroblasts (MEFs), but still demonstrable in WT and Xbp1$^{-/-}$ MEFs (FIG. 30, J). A model of KIRA6-mediated cytoprotection is shown (FIG. 30, J); it posits that the type II kinase inhibitor, KIRA6, reduces kinase/RNAse homo-oligomerization on the cytosolic face of IRE1α, which consequently reduces RNase hyperactivity under ER stress, preventing pro-apoptotic ER-localized mRNA decay and granting cells extended reprieve from programmed cell death.

16. UPR and Diabetes

β-cells from mouse and human islets exposed to irremediably high ER stress will show activation of many of the terminal UPR endpoints described herein. Besides the ER-localized mRNAs and select micro RNAs so far identified as IRE1α substrates, other miRs and small non-coding RNAs remain to be discovered and related changes will constitute a Terminal UPR signature that can be followed as therapeutic endpoints for amelioration by KIRAs.

Figure 31:
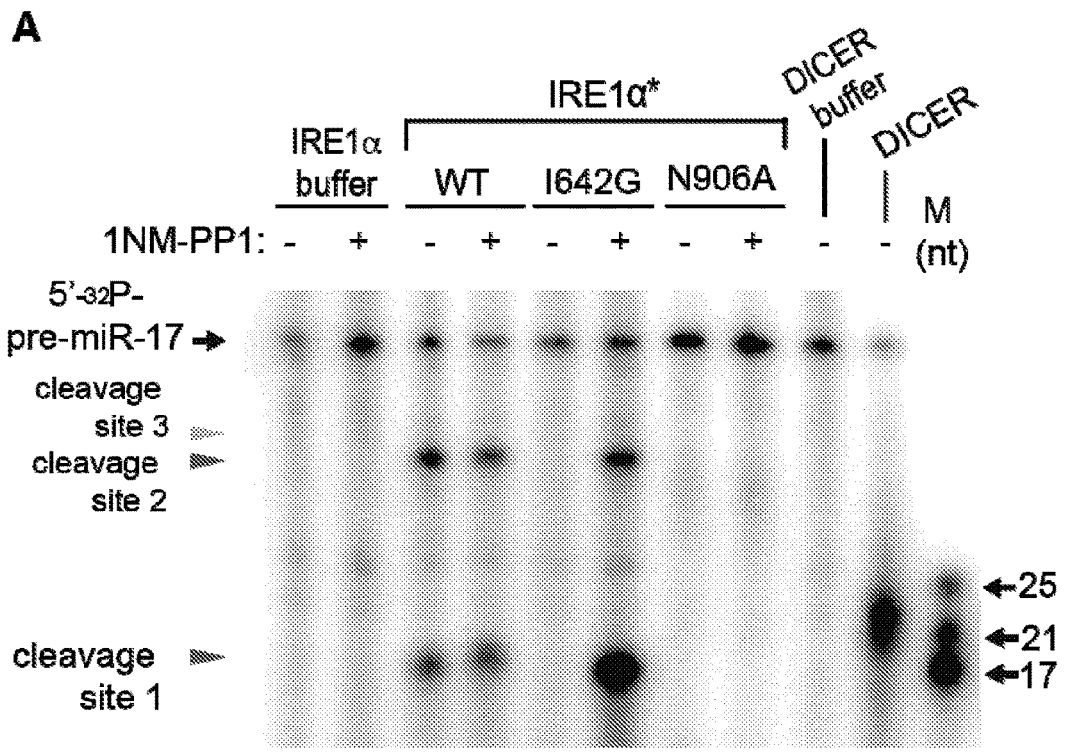
FIG. 31. KIRA6 inhibits IRE1α* RNAse endonucleolytically cleaves pre-miR-17 at sites distinct from those cleaved by DICER but related to XBP1 scission sites (A), KIRA6 prevents cleavage of pre-miR-17 by IRE1α* in vitro (B) cleavage sites (C) pre-miR-17 (D), rescues mature miR-17 levels in vivo (E), reduces caspase 2 accumulation and cleavage (F), and prevents TXNIP protein accumulation in C57BL/6 islets exposed to ER stress inducers (G). Sequence legend (FIG. 31B): SEQ ID NOs:11-15 (in order top to bottom)
Figure 31:
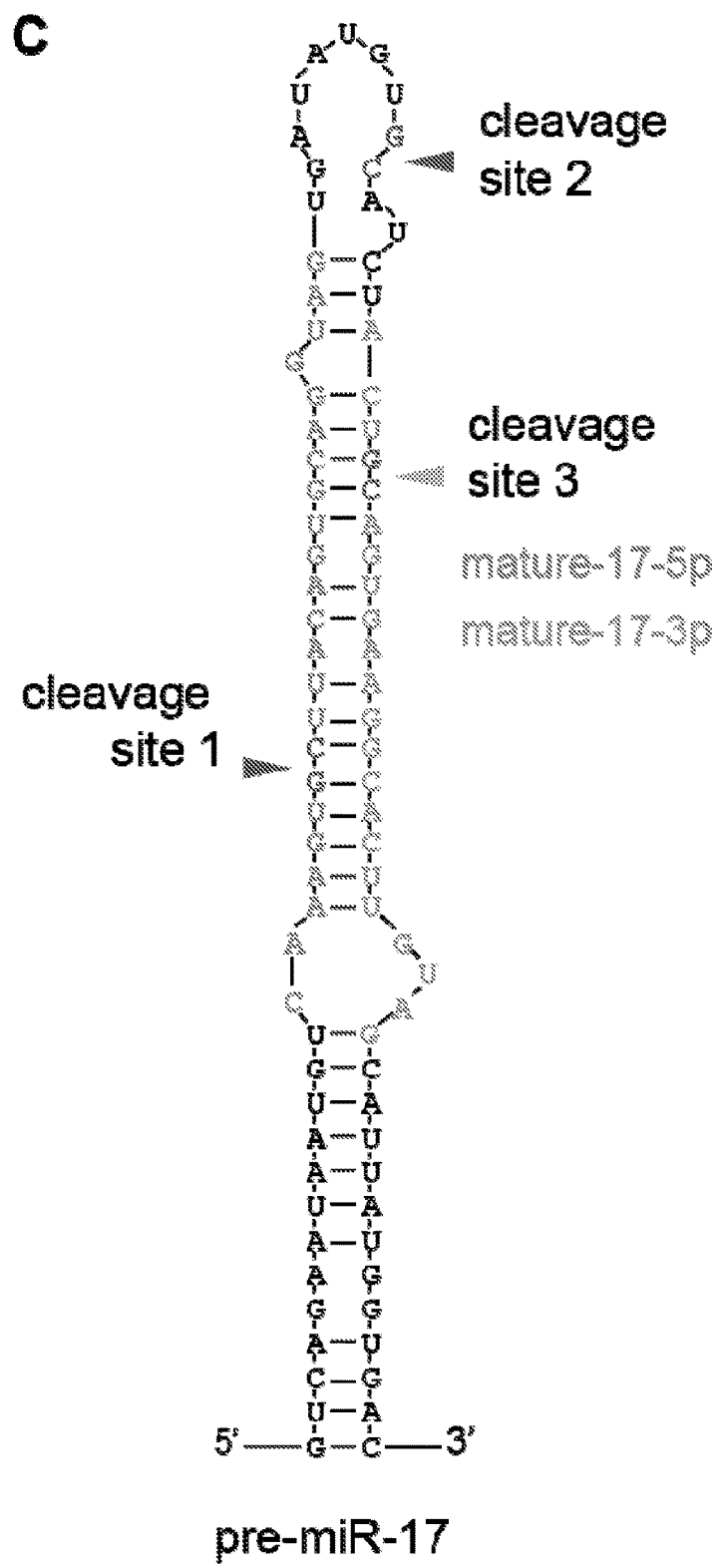
Figure 31:
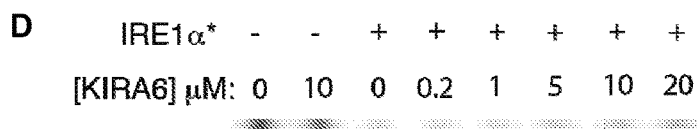
Figure 31:
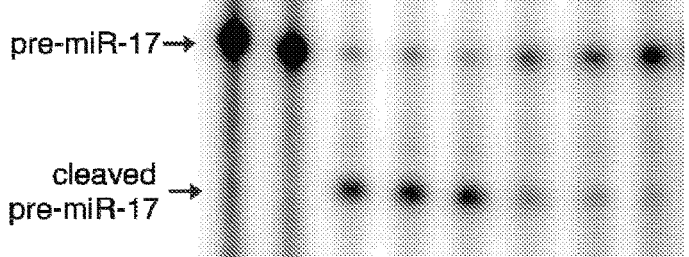
Figure 31:
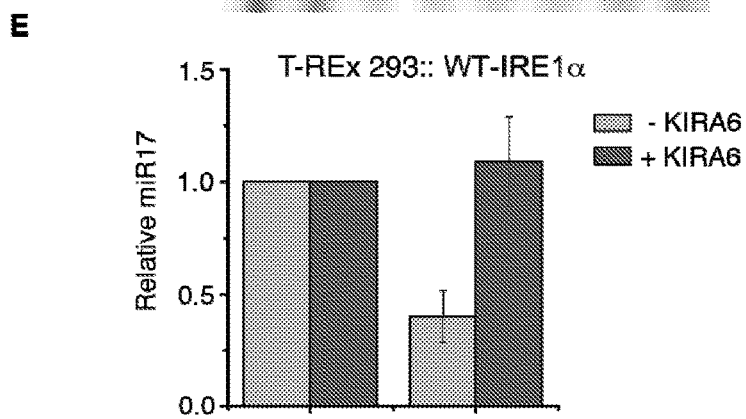
Figure 31:
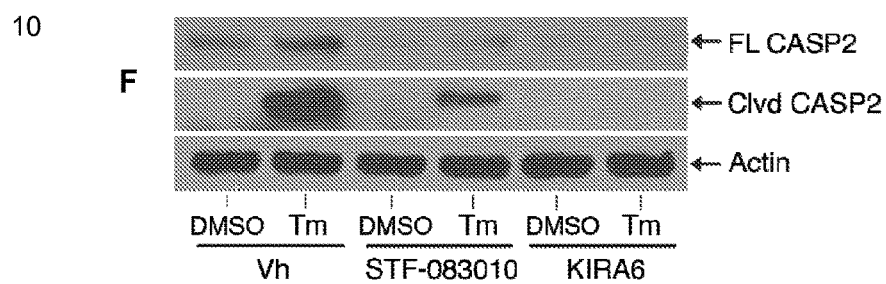
Figure 31:
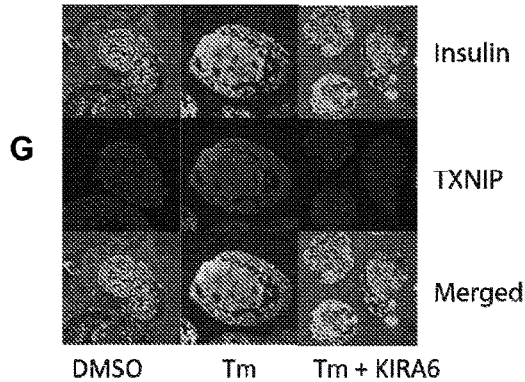

Described herein is the characterization of four select miRs that decay in vivo upon IRE1α hyperactivation. These are miR-17, miR-34a, miR-96, and miR-125b. WT-IRE1α* directly cleaved pre-miR-17 in vitro at sites distinct from those cleaved by DICER, as mapped by primer extension. The scission sites of pre-miR-17 are identical to those of XBP1 mRNA—(G/C)—and diverge at the flanking regions. Thus, by reducing levels of pre-miRs, IRE1α antagonizes DICER action to reduce cellular levels of the corresponding mature miRs. Intriguingly, IRE1α* (I642G), which can be activated by 1NM-PP1 to cleave XBP1 mRNA in vitro, can also cleave pre-miR-17 under 1NM-PP1. An RNAse mutant, IRE1α* (N906A), is compromised for cleavage of pre-miR-17 (FIG. 31, A-C). This provokes the hypothesis that IRE1α is capable of exhibiting extra-XBP1 mRNA endonucleolytic activity in a graded fashion. As IRE1α homo-oligomerizes in the ER membrane in proportion to the concentration of unfolded proteins in the ER lumen, it progressively trans-autophosphorylates. Furthermore, salt bridges between phospho-amino acid groups and other residues reinforce higher-order homo-oligomerization of kinase/RNAse domains, as was shown using yeast IRE1. Thus, as IRE1α protein clusters into higher-order oligomers, it acquires increasing activity towards its RNA substrates. The most efficient substrate is XBP1 mRNA, followed by select pre-miRs (e.g. 17, 34a, 96, and 125b), then followed by the ER-localized mRNA substrate, Ins1.

By breaking higher-order IRE1α oligomers with KIRAs, many miR targets will be preserved at levels found in unstressed cells. As the four miRs found to exert inhibitory effects on post-transcriptional gene regulation of caspase 2 and the NLRP3 inflammasome activator, TXNIP, KIRA6 will reduce levels of these amplifiers of ER stress, even though unfolded proteins still persist in the ER lumen. Preliminary data are consistent with these predictions. It is an interesting possibility that it is not unfolded proteins in the ER per se that compromise cell function and lead to programmed cell death, but instead active terminal UPR signaling through IRE1α RNase hyperactivation. Thus, IRE1α KIRAs should reduce oligomerization by reinforcing the DFG-out, inactive ATP-binding site conformation, and consequently reduce RNase activity to decrease ER stress-induced cell death. As a corollary, type I kinase inhibitors, such as 1NM-PP1, should increase oligomerization by reinforcing the DFG-in, active ATP-binding site conformation, and consequently increase RNase activity to increase ER stress-induced cell death.

Figure 32:
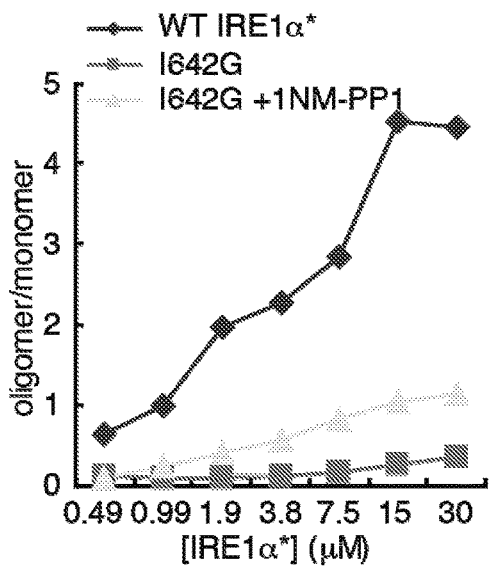
FIG. 32. Bumped type I kinase inhibitor, 1NM-PP1, increases oligomeric state of holed IRE1α* (I642G) mutant to promote RNAse activity and cell death under ER stress. (A) Quantitation of the ratios of oligomeric to monomeric IRE1α*from immunoblots of increasing concentrations of recombinant IRE1α*(WT), IRE1α*(I642G) or IRE1α* (I642G) incubated with 1NM-PP1, before treatment with the crosslinker disuccinimidyl suberate (DSS) (250 Mm) and quantitation of time course of cleavage reactions of $\alpha^{32}P$-labeled XBP1 RNA or Insulin2 (Ins2) RNA by recombinant IRE1α*(WT), IRE1α*(I642G), and IRE1α*(I642G) incubated with 1NM-PP1 (10 μM) from urea PAGE. (B) Percent XBP1 splicing (24 hr), relative Insulin1 (Ins1) mRNA levels by Q-PCR (24 hr) and percent Annexin V staining (72 hr) in 1 μg/mL Dox treated INS-1 IRE1α (I642G) cells plus/minus 1 μM 1 NM-PP1 and plus/minus 6 nM Tg; three independent biological samples were used for each experiment and plotted as mean value±SD; P-values: ** <0.01. (C) Model for how IRE1α (I642G) is partially activated by 1NMPP1 to splice XBP1 mRNA in the absence of ER stress; when driven into an oligomeric state by irremediable ER stress, 1NM-PP1-bound IRE1α (I642G) induces ER-localized mRNA decay and Terminal UPR.
Figure 32:
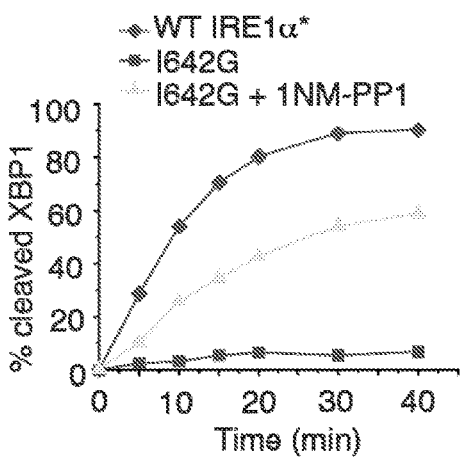
Figure 32:
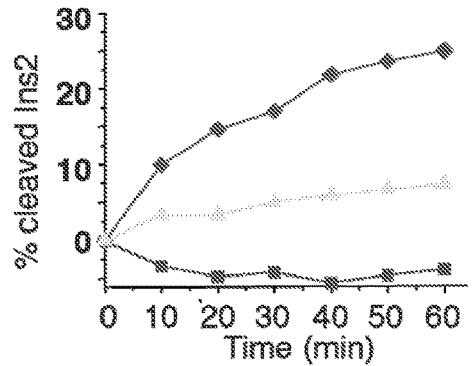
Figure 32:
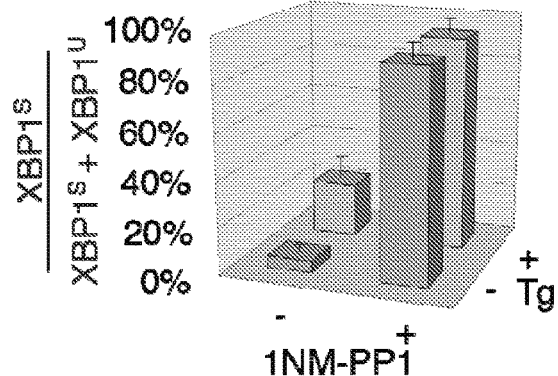
Figure 32:
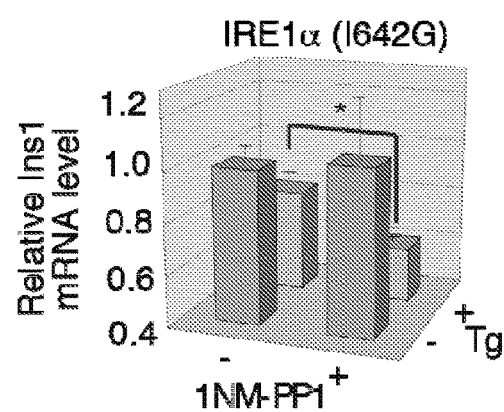
Figure 32:
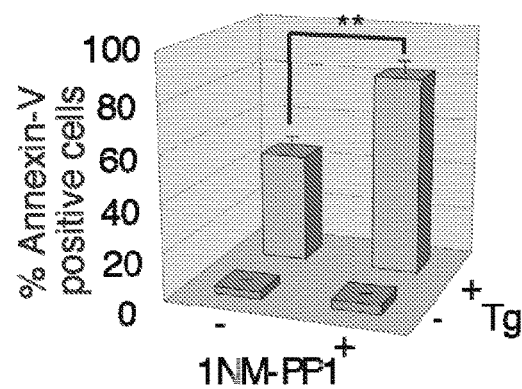
Figure 32:
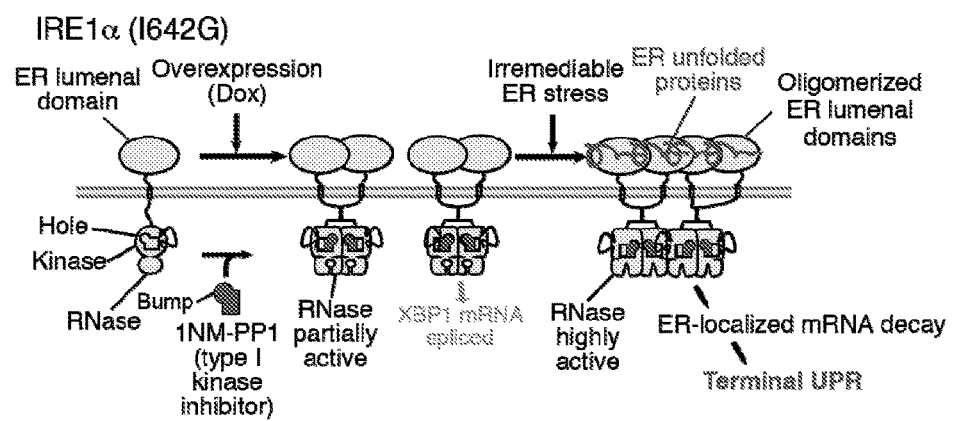
Figure 33:
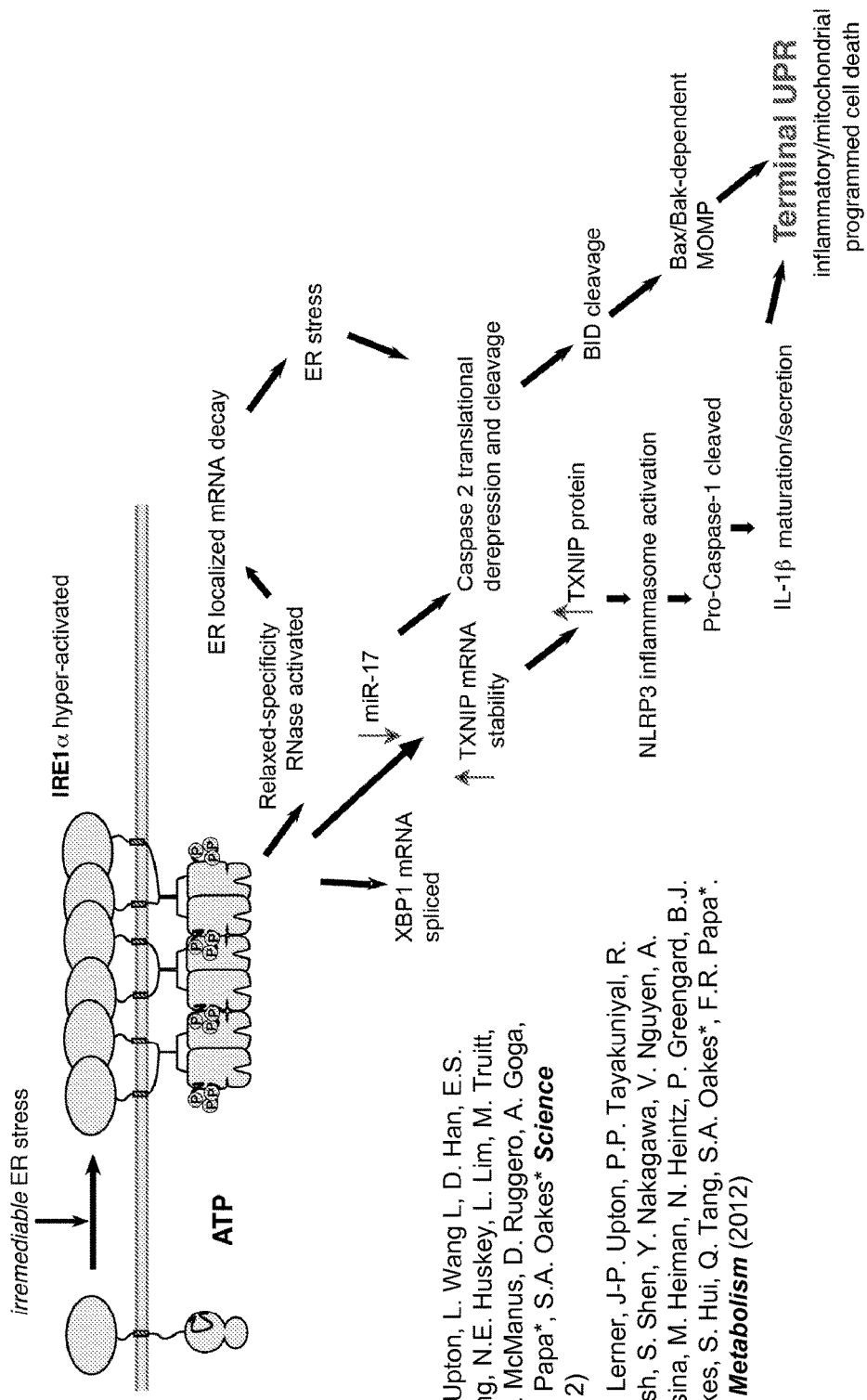
FIG. 33. IRE1α RNAse hyperactivation pushes cells into the Terminal UPR. Compounds, pharmaceutical compositions, and methods described herein may modulate the terminal UPR.
Figure 34:
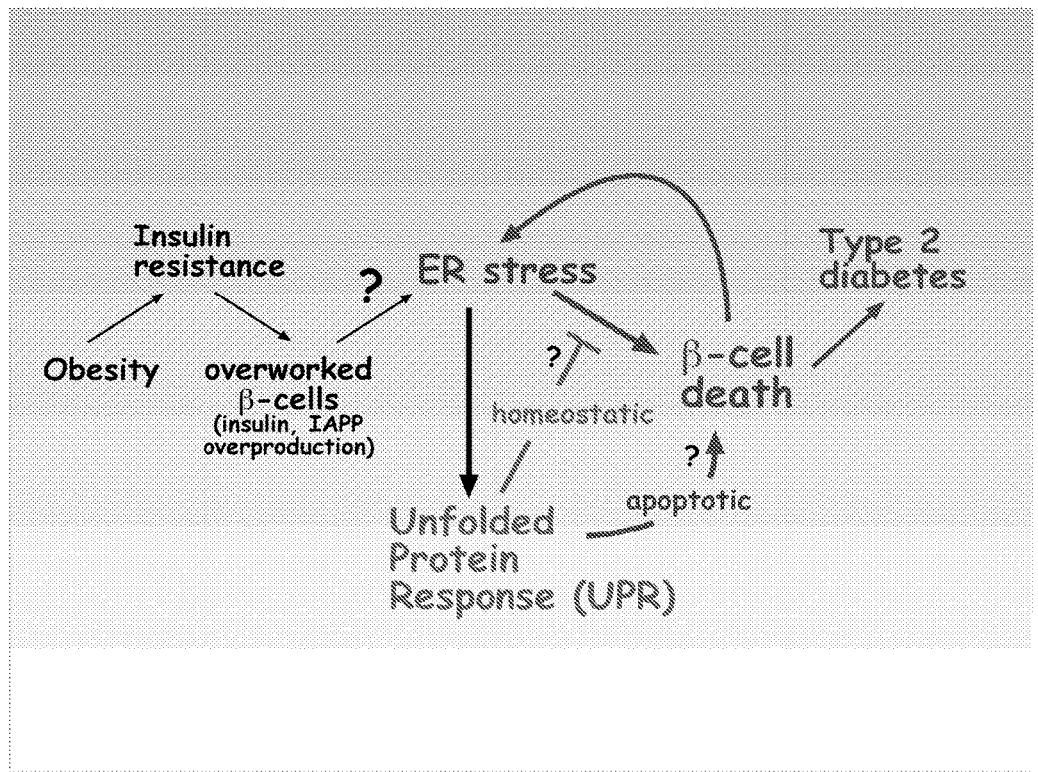
FIG. 34. Death of pancreatic islet β-cells due to unchecked ER stress and terminal UPR signaling is central to development of types 1 and 2 diabetes. Compounds, pharmaceutical compositions, and methods described herein may modulate the UPR and treat diseases associated with ER stress and the UPR.
Figure 35:
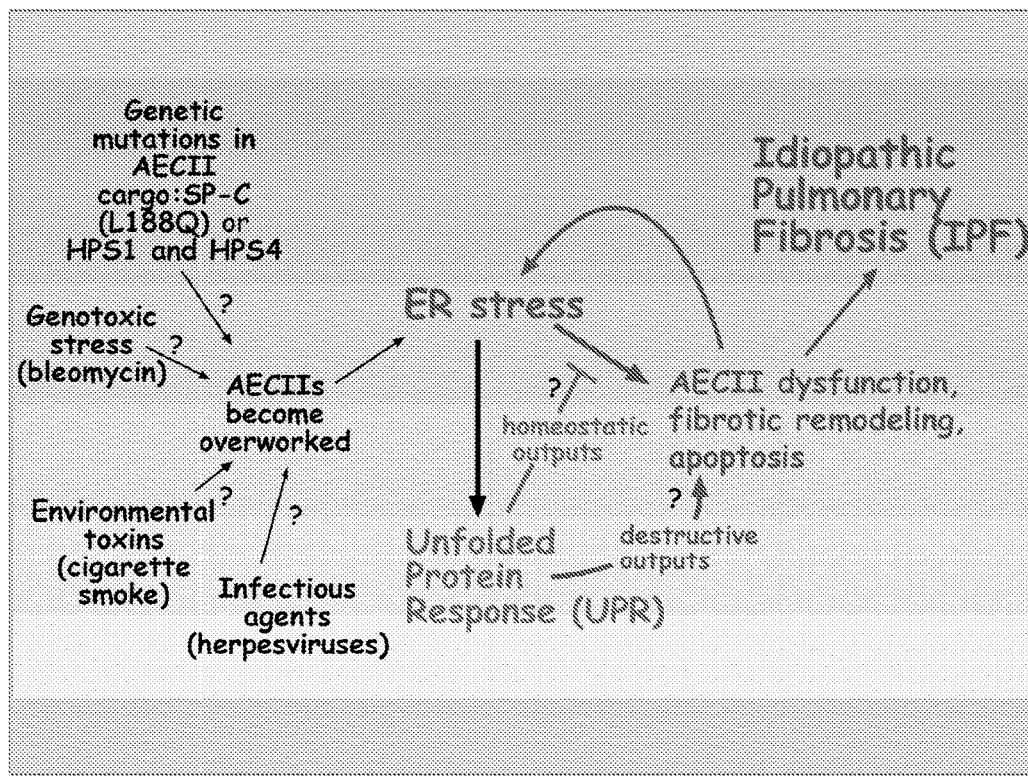
FIG. 35. Fibrotic remodeling due to unchecked ER stress is central to development of fibrotic disease such as idiopathic pulmonary fibrosis (IPF). Compounds, pharmaceutical compositions, and methods described herein may modulate the UPR and treat diseases associated with ER stress and the UPR.

Type I kinase inhibitors antagonize the effects of type II kinase inhibitors (KIRAs) to promote cell death under ER stress. FIG. 32 shows data consistent with this notion. KIRAs should ameliorate terminal UPR endpoints promoted by 1NM-PP1 in the context of the IRE1α (I642G) cellular chemical genetic systems under ER stress: Ins1 and 2 mRNA decay, miR-17, 34a, 96, and 125b decay, Caspase 1, 2, and 3 cleavage, TXNIP mRNA stabilization and translation, and consequent IL-1β maturation and secretion. Measurement of cell death endpoints (Annexin-V staining) are being made in the engineered cell systems as a function of the competing effects of 1NM-PP1 and KIRAs. As a prelude to testing in in vivo mouse models, is testing of all terminal UPR endpoints, with and without KIRA6, in freshly-harvested murine (C57BL/6) islets subjected to exogenous ER stress agents, as well as islets from two spontaneous models of diabetes: the Ins2(C96Y)—"Akita"—diabetic mouse and overexpression of IRE1α in islets.

17. Characterization of KIRAs

Potent and selective IRE1α inhibitors are being tested for their general toxicity against human cultured cell lines. For compounds that lack toxicity, the ADME, pharmacokinetic and toxicological properties are being determined. Compounds with favorable PK/ADMET properties are tested for efficacy in two mouse diabetic models—the proinsulin folding mutant, Akita, and overexpression of IRE1α in murine islets.

Cytotoxicity Testing:

Any KIRAs that show sub-micromolar potency in the cellular models described above are subjected to cytotoxicity assays against seven mammalian cell lines. These assays are helpful in predicting any general or tissue specific toxicity that may occur when KIRAs are administered to animals. KIRAs are tested against the following seven cell lines: L1210 (mouse lymphoblasts), W1-L2 (human lymphoblasts), HT-1080 (human fibrosarcoma), SF-539 (human glioblastoma), NCI-H460 (human large cell lung carcinoma), HCC-2998 (human colon carcinoma), and HL-60 (human promyelocytes). This panel provides sufficient diversity to predict cellular toxicity in a wide variety of tissues. The fold difference between efficacy in models and mammalian cell cytotoxicity provides a rough therapeutic index (TI). In some embodiments, there is >50-fold TI for KIRAs that are tested in vivo.

In Vivo PK/ADMET Studies:

KIRAs that are sufficiently potent in the cellular assays are subjected to pharmacokinetic and toxicity studies in mice. First, compounds are tested in a dose escalation study for any observed toxicity. Mice are sequentially injected with single IV doses of 1 mg/kg, 10 mg/kg, and 100 mg/kg of compound. During these single dose studies, the mice are observed for signs of acute toxicity, such as respiratory or neurological abnormalities. Compounds that are not toxic at 10 mg/kg are subjected to PK/ADME testing. This involves administration of a single dose (10 mg/kg by IV) followed by blood sampling at intervals of 30, 60, 120, 180, 240, and 300 minutes. These experiments are performed with groups of 3 mice per KIRA. Plasma is separated and extracted with acetonitrile for compound concentration measurements by combined liquid chromatography/electrospray-ionization mass spectrometry (LCMS). The results provide the maximum concentration ($C_{max}$), time of maximum concentration ($T_{max}$), area under the curve (AUC), and an estimation of half-life ($T_{1/2}$). Compounds that demonstrate sufficient exposure are candidates for the in vivo efficacy studies described herein.

18. Inhibitors of IRE1α Kinase/Endoribonuclease to Treat Retinitis Pigmentosa

KIRAs inhibit IRE1α in cultured cells at concentrations of less than 100 nM and strikingly protect cell viability and function under conditions of ER stress. Moreover, the leading compound in this class has shown efficacy in a rodent model of RP caused by mutation in rhodopsin. Described herein is the optimization of potency and efficacy in the KIRA class of compounds against retinal degeneration to develop a clinical candidate for treatment of RP.

19. Allosteric Modulation of the IRE1α RNase with Novel Kinase Inhibitor.

KIRA6, a more potent version of earlier KIRAs, whose structure is shown in FIG. 30A has been developed. This compound dose-dependently reduces kinase autophosphorylation and XBP1 splicing activity of IRE1α* (WT) (FIG. 30B-C). In addition, KIRA6 dose-dependently inhibits IRE1α* (WT) cleavage of pre-miR-17 (FIG. 31D).

20. Intravitreal Injections of Small Molecules

Based on known rat vitreous volumes, 2 µl was injected intravitreally into each eye. Tm (20 µg/µL final concentration) plus/minus KIRA6 (10 µM final concentration) was injected into SD rats at P21 with an equivalent amount of DMSO as a vehicle control. Retinas were collected at 48 and 72 hrs after injections in Trizol (Invitrogen) for qPCR analysis. Eyes were examined by optical coherence tomography (OCT) 7 days post injection and subsequently collected for morphological analysis. P23H rats were injected with KIRA6 (10 µM final concentration) or DMSO vehicle control at P9 and P15, and eyes were examined at P40 by OCT, and morphological analysis.

21. Image Guided Optical Coherence Tomography (OCT)

Mice were anaesthetized with 1.5-3% isoflurane, eyes were dilated with 2.5% phenylephrine hydrochloride and 1% tropicamide, and corneas were kept moist with regular application of 2.5% methylcellulose. Eyes were examined using a Micron III retinal imaging system (Phoenix Research Labs). Spectral domain OCT images were acquired with a Micron Image Guided OCT System (Phoenix Research Labs) by averaging 10 to 50 scans.

22. Morphological Analysis of Retinas

Outer nuclear layers (ONL) were quantified as previously described (Lewin, A. S. et al., Nature medicine 4, 967-971 (1998)). Briefly, rats were euthanized by $CO_2$ inhalation and their eyes were immediately enucleated and immersed in 2% paraformaldehyde and 2.5% glutaraldehyde in phosphate buffered saline. Subsequently, eyes were bisected on the vertical meridian through the optic nerve head and embedded in Epon-Araldite resin; 1 µm sections were cut and stained with toluidine blue. ONL thickness was measured at 54 locations around the retina using Bioquant image analysis (Bioquant; R&M Biometrics).

```
                                                          SEQ ID NO: 1
                       MSYYHHHHHHDYDIPTTENLYFQGAMDPE hq qqqlqhqqfq    480 kelekiqllq qqqqqlpfhp pgdtaqdgel ldtsgpyses sgtsspstsp rasnhslcsg   540 ssaskagssp sleqddgdee tsvvivgkis fcpkdvlghg aegtivyrgm fdnrdvavkr   600 ilpecfsfad revqllresd ehpnviryfc tekdrqfqyi aielcaatlq eyveqkdfah   660 lglepitllq qttsglahlh slnivhrdlk phnilismpn ahgkikamis dfglckklav   720 grhsfsrrsg vpgtegwiap emlsedcken ptytvdifsa gcvfyyvise gshpfgkslq   780 rqanillgac sldclhpekh edviarelie kmiamdpqkr psakhvlkhp ffwslekqlq   840 ffqdvsdrie kesldgpivk qlerggravv kmdwrenitv plqtdlrkfr tykggsvrdl   900 lramrnkkhh yrelpaevre tlgslpddfv cyftsrfphl lahtyramel csherlfqpy   960 yfheppepqp pvtpdal

SEQ ID NO: 2
                                                    hq qqqlqhqqfq    480 kelekiqllq qqqqqlpfhp pgdtaqdgel ldtsgpyses sgtsspstsp rasnhslcsg   540 ssaskagssp sleqddgdee tsvvivgkis fcpkdvlghg aegtivyrgm fdnrdvavkr   600 ilpecfsfad revqllresd ehpnviryfc tekdrqfqyi aielcaatlq eyveqkdfah   660
```

-continued

```
lglepitllq qttsglahlh slnivhrdlk phnilismpn ahgkikamis dfglckklav    720 grhsfsrrsg vpgtegwiap emlsedcken ptytvdifsa gcvfyyvise gshpfgkslq    780 rcianillgacsldclhpekh edviarelie kmiamdpqkr psakhvlkhp ffwslekqlq    840 ffqdvsdrie kesldgpivk glerggravy kmdwrenitv plqtdlrkfr tykggsvrdl    900 lramrnkkhh yrelpaevre tlgslpddfv cyftsrfphl lahtyramel csherlfqpy    960 yfheppepqp pvtpdal
```

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

```
                        SEQUENCE LISTING

<160> NUMBER OF SEQ ID NOS: 16

<210> SEQ ID NO 1
    <211> LENGTH: 538
    <212> TYPE: PRT
    <213> ORGANISM: Artificial Sequence
    <220> FEATURE:
    <223> OTHER INFORMATION: Synthetic polypeptide

<400> SEQUENCE: 1

Met Ser Tyr Tyr His His His His His His Asp Tyr Asp Ile Pro Thr
    1               5                   10                  15

Thr Glu Asn Leu Tyr Phe Gln Gly Ala Met Asp Pro Glu His Gln Gln
                    20                  25                  30

Gln Gln Leu Gln His Gln Gln Phe Gln Lys Glu Leu Glu Lys Ile Gln
                35                  40                  45

Leu Leu Gln Gln Gln Gln Gln Leu Pro Phe His Pro Pro Gly Asp
            50                  55                  60

Thr Ala Gln Asp Gly Glu Leu Leu Asp Thr Ser Gly Pro Tyr Ser Glu
    65                  70                  75                  80

Ser Ser Gly Thr Ser Ser Pro Ser Thr Ser Pro Arg Ala Ser Asn His
                    85                  90                  95

Ser Leu Cys Ser Gly Ser Ser Ala Ser Lys Ala Gly Ser Ser Pro Ser
                100                 105                 110

Leu Glu Gln Asp Asp Gly Asp Glu Glu Thr Ser Val Val Ile Val Gly
                115                 120                 125

Lys Ile Ser Phe Cys Pro Lys Asp Val Leu Gly His Gly Ala Glu Gly
            130                 135                 140

Thr Ile Val Tyr Arg Gly Met Phe Asp Asn Arg Asp Val Ala Val Lys
    145                 150                 155                 160

Arg Ile Leu Pro Glu Cys Phe Ser Phe Ala Asp Arg Glu Val Gln Leu
                    165                 170                 175

Leu Arg Glu Ser Asp Glu His Pro Asn Val Ile Arg Tyr Phe Cys Thr
                180                 185                 190

Glu Lys Asp Arg Gln Phe Gln Tyr Ile Ala Ile Glu Leu Cys Ala Ala
                195                 200                 205

Thr Leu Gln Glu Tyr Val Glu Gln Lys Asp Phe Ala His Leu Gly Leu
            210                 215                 220

Glu Pro Ile Thr Leu Leu Gln Gln Thr Thr Ser Gly Leu Ala His Leu
    225                 230                 235                 240

His Ser Leu Asn Ile Val His Arg Asp Leu Lys Pro His Asn Ile Leu
```

```
                        245                 250                 255
    Ile Ser Met Pro Asn Ala His Gly Lys Ile Lys Ala Met Ile Ser Asp
                    260                 265                 270

Phe Gly Leu Cys Lys Lys Leu Ala Val Gly Arg His Ser Phe Ser Arg
                275                 280                 285

Arg Ser Gly Val Pro Gly Thr Glu Gly Trp Ile Ala Pro Glu Met Leu
            290                 295                 300

Ser Glu Asp Cys Lys Glu Asn Pro Thr Tyr Thr Val Asp Ile Phe Ser
    305                 310                 315                 320

Ala Gly Cys Val Phe Tyr Tyr Val Ile Ser Glu Gly Ser His Pro Phe
                    325                 330                 335

Gly Lys Ser Leu Gln Arg Gln Ala Asn Ile Leu Leu Gly Ala Cys Ser
                340                 345                 350

Leu Asp Cys Leu His Pro Glu Lys His Glu Asp Val Ile Ala Arg Glu
            355                 360                 365

Leu Ile Glu Lys Met Ile Ala Met Asp Pro Gln Lys Arg Pro Ser Ala
    370                 375                 380

Lys His Val Leu Lys His Pro Phe Phe Trp Ser Leu Glu Lys Gln Leu
    385                 390                 395                 400

Gln Phe Phe Gln Asp Val Ser Asp Arg Ile Glu Lys Glu Ser Leu Asp
                    405                 410                 415

Gly Pro Ile Val Lys Gln Leu Glu Arg Gly Gly Arg Ala Val Val Lys
                420                 425                 430

Met Asp Trp Arg Glu Asn Ile Thr Val Pro Leu Gln Thr Asp Leu Arg
            435                 440                 445

Lys Phe Arg Thr Tyr Lys Gly Gly Ser Val Arg Asp Leu Leu Arg Ala
    450                 455                 460

Met Arg Asn Lys Lys His His Tyr Arg Glu Leu Pro Ala Glu Val Arg
    465                 470                 475                 480

Glu Thr Leu Gly Ser Leu Pro Asp Asp Phe Val Cys Tyr Phe Thr Ser
                    485                 490                 495

Arg Phe Pro His Leu Leu Ala His Thr Tyr Arg Ala Met Glu Leu Cys
                500                 505                 510

Ser His Glu Arg Leu Phe Gln Pro Tyr Tyr Phe His Glu Pro Pro Glu
            515                 520                 525

Pro Gln Pro Pro Val Thr Pro Asp Ala Leu
                530                 535

<210> SEQ ID NO 2
<211> LENGTH: 509
<212> TYPE: PRT
<213> ORGANISM: Homo sapiens

<400> SEQUENCE: 2

His Gln Gln Gln Leu Gln His Gln Gln Phe Gln Lys Glu Leu Glu
    1               5                   10                  15

Lys Ile Gln Leu Leu Gln Gln Gln Gln Gln Leu Pro Phe His Pro
                    20                  25                  30

Pro Gly Asp Thr Ala Gln Asp Gly Glu Leu Leu Asp Thr Ser Gly Pro
                35                  40                  45

Tyr Ser Glu Ser Ser Gly Thr Ser Ser Pro Ser Thr Ser Pro Arg Ala
        50                  55                  60

Ser Asn His Ser Leu Cys Ser Gly Ser Ser Ala Ser Lys Ala Gly Ser
    65                  70                  75                  80
```

```
Ser Pro Ser Leu Glu Gln Asp Asp Gly Asp Glu Thr Ser Val Val
                85                  90                  95

Ile Val Gly Lys Ile Ser Phe Cys Pro Lys Asp Val Leu Gly His Gly
            100                 105                 110

Ala Glu Gly Thr Ile Val Tyr Arg Gly Met Phe Asp Asn Arg Asp Val
            115                 120                 125

Ala Val Lys Arg Ile Leu Pro Glu Cys Phe Ser Phe Ala Asp Arg Glu
130                 135                 140

Val Gln Leu Leu Arg Glu Ser Asp Glu His Pro Asn Val Ile Arg Tyr
145                 150                 155                 160

Phe Cys Thr Glu Lys Asp Arg Gln Phe Gln Tyr Ile Ala Ile Glu Leu
                165                 170                 175

Cys Ala Ala Thr Leu Gln Glu Tyr Val Glu Gln Lys Asp Phe Ala His
            180                 185                 190

Leu Gly Leu Glu Pro Ile Thr Leu Leu Gln Gln Thr Thr Ser Gly Leu
            195                 200                 205

Ala His Leu His Ser Leu Asn Ile Val His Arg Asp Leu Lys Pro His
            210                 215                 220

Asn Ile Leu Ile Ser Met Pro Asn Ala His Gly Lys Ile Lys Ala Met
225                 230                 235                 240

Ile Ser Asp Phe Gly Leu Cys Lys Lys Leu Ala Val Gly Arg His Ser
                245                 250                 255

Phe Ser Arg Arg Ser Gly Val Pro Gly Thr Glu Gly Trp Ile Ala Pro
            260                 265                 270

Glu Met Leu Ser Glu Asp Cys Lys Glu Asn Pro Thr Tyr Thr Val Asp
            275                 280                 285

Ile Phe Ser Ala Gly Cys Val Phe Tyr Tyr Val Ile Ser Glu Gly Ser
290                 295                 300

His Pro Phe Gly Lys Ser Leu Gln Arg Gln Ala Asn Ile Leu Leu Gly
305                 310                 315                 320

Ala Cys Ser Leu Asp Cys Leu His Pro Glu Lys His Glu Asp Val Ile
                325                 330                 335

Ala Arg Glu Leu Ile Glu Lys Met Ile Ala Met Asp Pro Gln Lys Arg
            340                 345                 350

Pro Ser Ala Lys His Val Leu Lys His Pro Phe Phe Trp Ser Leu Glu
            355                 360                 365

Lys Gln Leu Gln Phe Phe Gln Asp Val Ser Asp Arg Ile Glu Lys Glu
370                 375                 380

Ser Leu Asp Gly Pro Ile Val Lys Gln Leu Glu Arg Gly Gly Arg Ala
385                 390                 395                 400

Val Val Lys Met Asp Trp Arg Glu Asn Ile Thr Val Pro Leu Gln Thr
                405                 410                 415

Asp Leu Arg Lys Phe Arg Thr Tyr Lys Gly Gly Ser Val Arg Asp Leu
            420                 425                 430

Leu Arg Ala Met Arg Asn Lys Lys His His Tyr Arg Glu Leu Pro Ala
            435                 440                 445

Glu Val Arg Glu Thr Leu Gly Ser Leu Pro Asp Asp Phe Val Cys Tyr
450                 455                 460

Phe Thr Ser Arg Phe Pro His Leu Leu Ala His Thr Tyr Arg Ala Met
465                 470                 475                 480

Glu Leu Cys Ser His Glu Arg Leu Phe Gln Pro Tyr Tyr Phe His Glu
                485                 490                 495

Pro Pro Glu Pro Gln Pro Pro Val Thr Pro Asp Ala Leu
```

-continued

```
            500             505

<210> SEQ ID NO 3
<211> LENGTH: 448
<212> TYPE: PRT
<213> ORGANISM: Saccharomyces cerevisiae

<400> SEQUENCE: 3

Pro Glu Lys Lys Arg Lys Arg Gly Ser Arg Gly Lys Gly
1               5                   10              15

Arg Lys Ser Arg Ile Ala Asn Ile Pro Asn Phe Glu Gln Ser Leu Lys
                20                  25                  30

Asn Leu Val Val Ser Glu Lys Ile Leu Gly Tyr Gly Ser Ser Gly Thr
            35                  40                  45

Val Val Phe Gln Gly Ser Phe Gln Gly Arg Pro Val Ala Val Lys Arg
    50                  55                  60

Met Leu Ile Asp Phe Cys Asp Ile Ala Leu Met Glu Ile Lys Leu Leu
65                  70                  75                  80

Thr Glu Ser Asp Asp His Pro Asn Val Ile Arg Tyr Tyr Cys Ser Glu
                85                  90                  95

Thr Thr Asp Arg Phe Leu Tyr Ile Ala Leu Glu Leu Cys Asn Leu Asn
                100                 105                 110

Leu Gln Asp Leu Val Glu Ser Lys Asn Val Ser Asp Glu Asn Leu Lys
            115                 120                 125

Leu Gln Lys Glu Tyr Asn Pro Ile Ser Leu Leu Arg Gln Ile Ala Ser
        130                 135                 140

Gly Val Ala His Leu His Ser Leu Lys Ile Ile His Arg Asp Leu Lys
145                 150                 155                 160

Pro Gln Asn Ile Leu Val Ser Thr Ser Arg Phe Thr Ala Asp Gln
                165                 170                 175

Gln Thr Gly Ala Glu Asn Leu Arg Ile Leu Ile Ser Asp Phe Gly Leu
            180                 185                 190

Cys Lys Lys Leu Asp Ser Gly Gln Ser Ser Phe Arg Thr Asn Leu Asn
        195                 200                 205

Asn Pro Ser Gly Thr Ser Gly Trp Arg Ala Pro Glu Leu Leu Glu Glu
    210                 215                 220

Ser Thr Lys Arg Arg Leu Thr Arg Ser Ile Asp Ile Phe Ser Met Gly
225                 230                 235                 240

Cys Val Phe Tyr Tyr Ile Leu Ser Lys Gly Lys His Pro Phe Gly Asp
                245                 250                 255

Lys Tyr Ser Arg Glu Ser Asn Ile Ile Arg Gly Ile Phe Ser Leu Asp
            260                 265                 270

Glu Met Lys Cys Leu His Asp Arg Ser Leu Ile Ala Glu Ala Thr Asp
        275                 280                 285

Leu Ile Ser Gln Met Ile Asp His Asp Pro Leu Lys Arg Pro Thr Ala
    290                 295                 300

Met Lys Val Leu Arg His Pro Leu Phe Trp Pro Lys Ser Lys Lys Leu
305                 310                 315                 320

Glu Phe Leu Leu Lys Val Ser Asp Arg Leu Glu Ile Glu Asn Arg Asp
                325                 330                 335

Pro Pro Ser Ala Leu Leu Met Lys Phe Asp Ala Gly Ser Asp Phe Val
            340                 345                 350

Ile Pro Ser Gly Asp Trp Thr Val Lys Phe Asp Lys Thr Phe Met Asp
        355                 360                 365
```

```
Asn Leu Glu Arg Tyr Arg Lys Tyr His Ser Ser Lys Leu Met Asp Leu
    370                 375                 380
Leu Arg Ala Leu Arg Asn Lys Tyr His Asn Phe Met Asp Leu Pro Glu
385                 390                 395                 400
Asp Ile Ala Glu Leu Met Gly Pro Val Pro Asp Gly Phe Tyr Asp Tyr
                405                 410                 415
Phe Thr Lys Arg Phe Pro Asn Leu Leu Ile Gly Val Tyr Met Ile Val
                420                 425                 430
Lys Glu Asn Leu Ser Asp Asp Gln Ile Leu Arg Glu Phe Leu Tyr Ser
                435                 440                 445

<210> SEQ ID NO 4
<211> LENGTH: 286
<212> TYPE: PRT
<213> ORGANISM: Gallus gallus

<400> SEQUENCE: 4

Gly His Met Gln Thr Gln Gly Leu Ala Lys Asp Ala Trp Glu Ile Pro
1               5                   10                  15
Arg Glu Ser Leu Arg Leu Glu Val Lys Leu Gly Gln Gly Cys Phe Gly
                20                  25                  30
Glu Val Trp Met Gly Thr Trp Asn Gly Thr Thr Arg Val Ala Ile Lys
                35                  40                  45
Thr Leu Lys Pro Gly Thr Met Ser Pro Glu Ala Phe Leu Gln Glu Ala
    50                  55                  60
Gln Val Met Lys Lys Leu Arg His Glu Lys Leu Val Gln Leu Tyr Ala
65                  70                  75                  80
Val Val Ser Glu Glu Pro Ile Tyr Ile Val Thr Glu Tyr Met Ser Lys
                85                  90                  95
Gly Ser Leu Leu Asp Phe Leu Lys Gly Glu Met Gly Lys Tyr Leu Arg
                100                 105                 110
Leu Pro Gln Leu Val Asp Met Ala Ala Gln Ile Ala Ser Gly Met Ala
            115                 120                 125
Tyr Val Glu Arg Met Asn Tyr Val His Arg Asp Leu Arg Ala Ala Asn
    130                 135                 140
Ile Leu Val Gly Glu Asn Leu Val Cys Lys Val Ala Asp Phe Gly Leu
145                 150                 155                 160
Ala Arg Leu Ile Glu Asp Asn Glu Tyr Thr Ala Arg Gln Gly Ala Lys
                165                 170                 175
Phe Pro Ile Lys Trp Thr Ala Pro Glu Ala Ala Leu Tyr Gly Arg Phe
            180                 185                 190
Thr Ile Lys Ser Asp Val Trp Ser Phe Gly Ile Leu Leu Thr Glu Leu
    195                 200                 205
Thr Thr Lys Gly Arg Val Pro Tyr Pro Gly Met Val Asn Arg Glu Val
210                 215                 220
Leu Asp Gln Val Glu Arg Gly Tyr Arg Met Pro Cys Pro Pro Glu Cys
225                 230                 235                 240
Pro Glu Ser Leu His Asp Leu Met Cys Gln Cys Trp Arg Lys Asp Pro
                245                 250                 255
Glu Glu Arg Pro Thr Phe Glu Tyr Leu Gln Ala Phe Leu Glu Asp Tyr
            260                 265                 270
Phe Thr Ser Thr Glu Pro Gln Tyr Gln Pro Gly Glu Asn Leu
    275                 280                 285

<210> SEQ ID NO 5
```

```
<211> LENGTH: 432
<212> TYPE: PRT
<213> ORGANISM: Homo sapiens

<400> SEQUENCE: 5

Met Gly Ser Ser Pro Ser Leu Glu Gln Asp Asp Gly Asp Glu Glu Thr
1               5                   10                  15

Ser Val Val Ile Val Gly Lys Ile Ser Phe Cys Pro Lys Asp Val Leu
            20                  25                  30

Gly His Gly Ala Glu Gly Thr Ile Val Tyr Arg Gly Met Phe Asp Asn
        35                  40                  45

Arg Asp Val Ala Val Lys Arg Ile Leu Pro Glu Cys Phe Ser Phe Ala
    50                  55                  60

Asp Arg Glu Val Gln Leu Leu Arg Glu Ser Asp Glu His Pro Asn Val
65                  70                  75                  80

Ile Arg Tyr Phe Cys Thr Glu Lys Asp Arg Gln Phe Gln Tyr Ile Ala
                85                  90                  95

Ile Glu Leu Cys Ala Ala Thr Leu Gln Glu Tyr Val Glu Gln Lys Asp
            100                 105                 110

Phe Ala His Leu Gly Leu Glu Pro Ile Thr Leu Leu Gln Gln Thr Thr
        115                 120                 125

Ser Gly Leu Ala His Leu His Ser Leu Asn Ile Val His Arg Asp Leu
    130                 135                 140

Lys Pro His Asn Ile Leu Ile Ser Met Pro Asn Ala His Gly Lys Ile
145                 150                 155                 160

Lys Ala Met Ile Ser Asp Phe Gly Leu Cys Lys Lys Leu Ala Val Gly
                165                 170                 175

Arg His Ser Phe Ser Arg Arg Ser Gly Val Pro Gly Thr Glu Gly Trp
            180                 185                 190

Ile Ala Pro Glu Met Leu Ser Glu Asp Cys Lys Glu Asn Pro Thr Tyr
        195                 200                 205

Thr Val Asp Ile Phe Ser Ala Gly Cys Val Phe Tyr Tyr Val Ile Ser
    210                 215                 220

Glu Gly Ser His Pro Phe Gly Lys Ser Leu Gln Arg Gln Ala Asn Ile
225                 230                 235                 240

Leu Leu Gly Ala Cys Ser Leu Asp Cys Leu His Pro Glu Lys His Glu
                245                 250                 255

Asp Val Ile Ala Arg Glu Leu Ile Glu Lys Met Ile Ala Met Asp Pro
            260                 265                 270

Gln Lys Arg Pro Ser Ala Lys His Val Leu Lys His Pro Phe Phe Trp
        275                 280                 285

Ser Leu Glu Lys Gln Leu Gln Phe Phe Gln Asp Val Ser Asp Arg Ile
    290                 295                 300

Glu Lys Glu Ser Leu Asp Gly Pro Ile Val Lys Gln Leu Glu Arg Gly
305                 310                 315                 320

Gly Arg Ala Val Val Lys Met Asp Trp Arg Glu Asn Ile Thr Val Pro
                325                 330                 335

Leu Gln Thr Asp Leu Arg Lys Phe Arg Thr Tyr Lys Gly Gly Ser Val
            340                 345                 350

Arg Asp Leu Leu Arg Ala Met Arg Asn Lys Lys His His Tyr Arg Glu
        355                 360                 365

Leu Pro Ala Glu Val Arg Glu Thr Leu Gly Thr Leu Pro Asp Asp Phe
    370                 375                 380

Val Cys Tyr Phe Thr Ser Arg Phe Pro His Leu Leu Ala His Thr Tyr
```

```
                385                 390                 395                 400
Arg Ala Met Glu Leu Cys Ser His Glu Arg Leu Phe Gln Pro Tyr Tyr
                    405                 410                 415

Phe His Glu Pro Pro Glu Pro Gln Pro Pro Val Thr Pro Asp Ala Leu
                420                 425                 430

<210> SEQ ID NO 6
<211> LENGTH: 292
<212> TYPE: PRT
<213> ORGANISM: Homo sapiens

<400> SEQUENCE: 6

Met Gly His His His His His His Ser Ser Gly Val Asp Leu Gly Thr
 1               5                  10                  15

Glu Asn Leu Tyr Phe Gln Ser Met Asp Lys Trp Glu Met Glu Arg Thr
                20                  25                  30

Asp Ile Thr Met Lys His Lys Leu Gly Gly Gly Gln Tyr Gly Glu Val
                35                  40                  45

Tyr Val Gly Val Trp Lys Lys Tyr Ser Leu Thr Val Ala Val Lys Thr
        50                  55                  60

Leu Lys Glu Asp Thr Met Glu Val Glu Glu Phe Leu Lys Glu Ala Ala
65                  70                  75                  80

Val Met Lys Glu Ile Lys His Pro Asn Leu Val Gln Leu Leu Gly Val
                85                  90                  95

Cys Thr Leu Glu Pro Pro Phe Tyr Ile Val Thr Glu Tyr Met Pro Tyr
                100                 105                 110

Gly Asn Leu Leu Asp Tyr Leu Arg Glu Cys Asn Arg Glu Glu Val Thr
                115                 120                 125

Ala Val Val Leu Leu Tyr Met Ala Thr Gln Ile Ser Ser Ala Met Glu
        130                 135                 140

Tyr Leu Glu Lys Lys Asn Phe Ile His Arg Asp Leu Ala Ala Arg Asn
145                 150                 155                 160

Cys Leu Val Gly Glu Asn His Val Val Lys Val Ala Asp Phe Gly Leu
                165                 170                 175

Ser Arg Leu Met Thr Gly Asp Thr Tyr Thr Ala His Ala Gly Ala Lys
                180                 185                 190

Phe Pro Ile Lys Trp Thr Ala Pro Glu Ser Leu Ala Tyr Asn Thr Phe
                195                 200                 205

Ser Ile Lys Ser Asp Val Trp Ala Phe Gly Val Leu Leu Trp Glu Ile
        210                 215                 220

Ala Thr Tyr Gly Met Ser Pro Tyr Pro Gly Ile Asp Leu Ser Gln Val
225                 230                 235                 240

Tyr Asp Leu Leu Glu Lys Gly Tyr Arg Met Glu Gln Pro Glu Gly Cys
                245                 250                 255

Pro Pro Lys Val Tyr Glu Leu Met Arg Ala Cys Trp Lys Trp Ser Pro
                260                 265                 270

Ala Asp Arg Pro Ser Phe Ala Glu Thr His Gln Ala Phe Glu Thr Met
                275                 280                 285

Phe His Asp Ser
    290

<210> SEQ ID NO 7
<211> LENGTH: 24
<212> TYPE: DNA
<213> ORGANISM: Artificial Sequence
<220> FEATURE:
```

<223> OTHER INFORMATION: Synthetic oligonucleotide

<400> SEQUENCE: 7
aaacagagta gcagcacaga ctgc                                          24

<210> SEQ ID NO 8
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 8
ggatctctaa gactagaggc ttggtg                                        26

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 9
aaacagagta gcagcgcaga ctgc                                          24

<210> SEQ ID NO 10
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 10
ggatctctaa aactagaggc ttggtg                                        26

<210> SEQ ID NO 11
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 11
tgagtccgca gcactca                                                  17

<210> SEQ ID NO 12
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 12
gacctctgca gcaggtc                                                  17

<210> SEQ ID NO 13
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 13
tcaaagtgct tacagtg                                                  17

```
<210> SEQ ID NO 14
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 14
gatatgtgca tctactg                                                  17

<210> SEQ ID NO 15
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 15
atctactgca gtgaagg                                                  17

<210> SEQ ID NO 16
<211> LENGTH: 84
<212> TYPE: RNA
<213> ORGANISM: Homo sapiens

<400> SEQUENCE: 16
gucagaauaa ugucaaagug cuuacagugc agguagugau augugcaucu acugcaguga   60
aggcacuugu agcauuaugg ugac                                          84
```

20. A compound selected from the group consisting of:
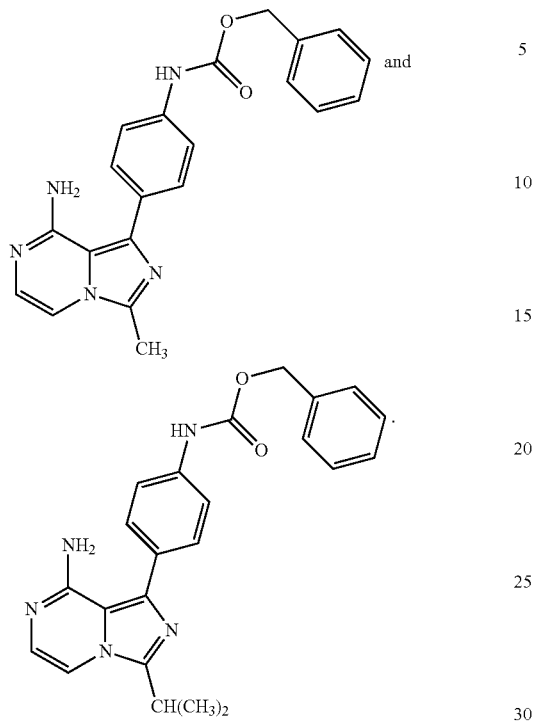

What is claimed is:

1. A compound having the Formula (I):

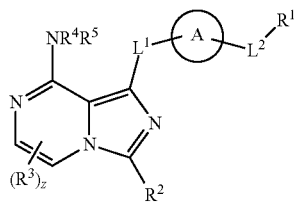

(I)

or a pharmaceutically acceptable salt thereof,
wherein:
ring A is $R^{41}$-substituted or unsubstituted cycloalkylene, $R^{41}$-substituted or unsubstituted heterocycloalkylene, $R^{41}$-substituted or unsubstituted arylene or $R^{41}$-substituted or unsubstituted heteroarylene;
$L^1$ is a bond or unsubstituted $C_1$-$C_5$ alkylene;
$L^2$ is —$NR^{6a}C(O)NR^{6b}$— or —NHC(O)OCH$_2$—;
$R^1$ is hydrogen, oxo, halogen, —CX$_3$, —CN, —S(O)$_2$Cl, —S(O)$_n$R$^{10}$, —S(O)$_v$NR$^7$R$^8$, —NHNH$_2$, —ONR$^7$R$^8$, —NHC(O)NHNH$_2$, —NHC(O)NR$^7$R$^8$, —N(O)$_m$, —NR$^7$R$^8$, —C(O)R$^9$, —C(O)OR$^9$, —C(O)NR$^7$R$^8$, —OR$^{10}$, —NR$^7$S(O)$_n$R$^{10}$, —NR$^7$C(O)R$^9$, —NR$^7$C(O)OR$^9$, —NR$^7$OR$^9$, —OCX$_3$, —OCHX$_2$, $R^{11}$-substituted or unsubstituted alkyl, $R^{11}$-substituted or unsubstituted heteroalkyl, $R^{11}$-substituted or unsubstituted cycloalkyl, $R^{11}$-substituted or unsubstituted heterocycloalkyl, $R^{11}$-substituted or unsubstituted aryl or $R^{11}$-substituted or unsubstituted heteroaryl;
$R^2$ is hydrogen, $R^{14}$-substituted or unsubstituted alkyl or $R^{14}$-substituted or unsubstituted cycloalkyl;
each $R^3$ is independently hydrogen, halogen, —CX$^b_3$, —CN, —S(O)$_2$Cl, —S(O)$_{n2}$R$^{10b}$, —S(O)$_{v2}$NR$^{7b}$R$^{8b}$, —NHNH$_2$, —ONR$^{7b}$R$^{8b}$, —NHC(O)NHNH$_2$, —NHC(O)NR$^{7b}$R$^{8b}$, —N(O)$_{m2}$, —NR$^{7b}$R$^{8b}$, —C(O)R$^{9b}$, —C(O)OR$^{9b}$, —C(O)NR$^{7b}$R$^{8b}$, —OR$^{10b}$, —NR$^{7b}$S(O)$_{n2}$R$^{10b}$, —NR$^{7b}$C(O)R$^{9b}$, —NR$^{7b}$C(O)OR$^{9b}$, —NR$^{7b}$OR$^{9b}$, —OCX$^b_3$, —OCHX$^b_2$, $R^{17}$-substituted or unsubstituted alkyl, $R^{17}$-substituted or unsubstituted heteroalkyl, $R^{17}$-substituted or unsubstituted cycloalkyl, $R^{17}$-substituted or unsubstituted heterocycloalkyl, $R^{17}$-substituted or unsubstituted aryl or $R^{17}$-substituted or unsubstituted heteroaryl;
$R^4$ is hydrogen or unsubstituted $C_1$-$C_6$ alkyl;
$R^5$ is hydrogen or unsubstituted $C_1$-$C_6$ alkyl;
$R^7$, $R^8$, $R^9$, $R^{10}$, $R^{6a}$, $R^{6b}$, $R^{7b}$, $R^{8b}$, $R^{9b}$ and $R^{10b}$ are each independently hydrogen, oxo, halogen, —CF$_3$, —CN, —OH, —NH$_2$, —C(O)OH, —C(O)NH$_2$, —NO$_2$, —SH, —S(O)$_2$Cl, —S(O)$_3$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl or unsubstituted heteroaryl; or
$R^7$ and $R^8$, together with the nitrogen to which they are bonded, may optionally form a unsubstituted heterocycloalkyl or unsubstituted heteroaryl; or
$R^{7b}$ and $R^{8b}$, together with the nitrogen to which they are bonded, may optionally form a unsubstituted heterocycloalkyl or unsubstituted heteroaryl;
each $R^{11}$ is independently oxo, halogen, —CF$_3$, —CN, —OH, —NH$_2$, —C(O)OH, —C(O)NH$_2$, —NO$_2$, —SH, —S(O)$_2$Cl, —S(O)$_3$H, —S(O)$_2$NH$_2$, —NHNH$_2$, —ONH$_2$, —NHC(O)NHNH$_2$, —NHC (O)NH$_2$, —NHS(O)$_2$H, —NHC(O)H, —NHC(O)OH, —NHOH, —OCF$_3$, —OCHF$_2$, R$^{12}$-substituted or unsubstituted alkyl, R$^{12}$-substituted or unsubstituted heteroalkyl, R$^{12}$-substituted or unsubstituted cycloalkyl, R$^{12}$-substituted or unsubstituted heterocycloalkyl, R$^{12}$-substituted or unsubstituted aryl or R$^{12}$-substituted or unsubstituted heteroaryl;

each R$^{12}$ is independently oxo, halogen, —CF$_3$, —CN, —OH, —NH$_2$, —C(O)OH, —C(O)NH$_2$, —NO$_2$, —SH, —S(O)$_2$Cl, —S(O)$_3$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)OH, —NHOH, —OCF$_3$, —OCHF$_2$, R$^{13}$-substituted or unsubstituted alkyl, R$^{13}$-substituted or unsubstituted heteroalkyl, R$^{13}$-substituted or unsubstituted cycloalkyl, R$^{13}$-substituted or unsubstituted heterocycloalkyl, R$^{13}$-substituted or unsubstituted aryl or R$^{13}$-substituted or unsubstituted heteroaryl;

each R$^{13}$ is independently oxo, halogen, —CF$_3$, —CN, —OH, —NH$_2$, —C(O)OH, —C(O)NH$_2$, —NO$_2$, —SH, —S(O)$_2$Cl, —S(O)$_3$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)OH, —NHOH, —OCF$_3$, —OCHF$_2$, unsubstituted alkyl, unsubstituted heteroalkyl, cycloalkyl, unsubstituted heterocycloalkyl, unsubstituted aryl or unsubstituted heteroaryl;

each R$^{14}$ is independently oxo, halogen, —CF$_3$, —CN, —OH, —NH$_2$, —C(O)OH, —C(O)NH$_2$, —NO$_2$, —SH, —S(O)$_2$Cl, —S(O)$_3$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)OH, —NHOH, —OCF$_3$, —OCHF$_2$, R$^{15}$-substituted or unsubstituted alkyl, R$^{15}$-substituted or unsubstituted heteroalkyl, R$^{15}$-substituted or unsubstituted cycloalkyl, R$^{15}$-substituted or unsubstituted heterocycloalkyl, R$^{15}$-substituted or unsubstituted aryl or R$^{15}$-substituted or unsubstituted heteroaryl;

each R$^{15}$ is independently oxo, halogen, —CF$_3$, —CN, —OH, —NH$_2$, —C(O)OH, —C(O)NH$_2$, —NO$_2$, —SH, —S(O)$_2$Cl, —S(O)$_3$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)OH, —NHOH, —OCF$_3$, —OCHF$_2$, R$^{16}$-substituted or unsubstituted alkyl, R$^{16}$-substituted or unsubstituted heteroalkyl, R$^{16}$-substituted or unsubstituted cycloalkyl, R$^{16}$-substituted or unsubstituted heterocycloalkyl, R$^{16}$-substituted or unsubstituted aryl or R$^{16}$-substituted or unsubstituted heteroaryl;

each R$^{16}$ is independently oxo, halogen, —CF$_3$, —CN, —OH, —NH$_2$, —C(O)OH, —C(O)NH$_2$, —NO$_2$, —SH, —S(O)$_2$Cl, —S(O)$_3$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl or unsubstituted heteroaryl;

each R$^{17}$ is independently oxo, halogen, —CF$_3$, —CN, —OH, —NH$_2$, —C(O)OH, —C(O)NH$_2$, —NO$_2$, —SH, —S(O)$_2$Cl, —S(O)$_3$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)OH, —NHOH, —OCF$_3$, —OCHF$_2$, R$^{18}$-substituted or unsubstituted alkyl, R$^{18}$-substituted or unsubstituted heteroalkyl, R$^{18}$-substituted or unsubstituted cycloalkyl, R$^{18}$-substituted or unsubstituted heterocycloalkyl, R$^{18}$-substituted or unsubstituted aryl or R$^{18}$-substituted or unsubstituted heteroaryl;

each R$^{18}$ is independently oxo, halogen, —CF$_3$, —CN, —OH, —NH$_2$, —C(O)OH, —C(O)NH$_2$, —NO$_2$, —SH, —S(O)$_2$Cl, —S(O)$_3$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)OH, —NHOH, —OCF$_3$, —OCHF$_2$, R$^{19}$-substituted or unsubstituted alkyl, R$^{19}$-substituted or unsubstituted heteroalkyl, R$^{19}$-substituted or unsubstituted cycloalkyl, R$^{19}$-substituted or unsubstituted heterocycloalkyl, R$^{19}$-substituted or unsubstituted aryl or R$^{19}$-substituted or unsubstituted heteroaryl;

each R$^{19}$ is independently oxo, halogen, —CF$_3$, —CN, —OH, —NH$_2$, —C(O)OH, —C(O)NH$_2$, —NO$_2$, —SH, —S(O)$_2$Cl, —S(O)$_3$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl or unsubstituted heteroaryl;

each R$^{41}$ is independently oxo, halogen, —CF$_3$, —CN, —OH, —NH$_2$, —C(O)OH, —C(O)NH$_2$, —NO$_2$, —SH, —S(O)$_2$Cl, —S(O)$_3$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)OH, —NHOH, —OCF$_3$, —OCHF$_2$, R$^{42}$-substituted or unsubstituted alkyl, R$^{42}$-substituted or unsubstituted heteroalkyl, R$^{42}$-substituted or unsubstituted cycloalkyl, R$^{42}$-substituted or unsubstituted heterocycloalkyl, R$^{42}$-substituted or unsubstituted aryl or R$^{42}$-substituted or unsubstituted heteroaryl;

each R$^{42}$ is independently oxo, halogen, —CF$_3$, —CN, —OH, —NH$_2$, —C(O)OH, —C(O)NH$_2$, —NO$_2$, —SH, —S(O)$_2$Cl, —S(O)$_3$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)OH, —NHOH, —OCF$_3$, —OCHF$_2$, R$^{43}$-substituted or unsubstituted alkyl, R$^{43}$-substituted or unsubstituted heteroalkyl, R$^{43}$-substituted or unsubstituted cycloalkyl, R$^{43}$-substituted or unsubstituted heterocycloalkyl, R$^{43}$-substituted or unsubstituted aryl or R$^{43}$-substituted or unsubstituted heteroaryl;

each R$^{43}$ is independently oxo, halogen, —CF$_3$, —CN, —OH, —NH$_2$, —C(O)OH, —C(O)NH$_2$, —NO$_2$, —SH, —S(O)$_2$Cl, —S(O)$_3$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl or unsubstituted heteroaryl;

each occurrence of X and X$^b$ is independently a halogen;

each occurrence of m and m2 is independently 1 or 2;

each occurrence of n and n2 is independently 0, 1, 2, 3 or 4;

each occurrence of v and v2 is independently 1 or 2; and z is 0, 1 or 2.

2. The compound of claim 1, or a pharmaceutically acceptable salt thereof, wherein ring A is R$^{41}$ substituted or unsubstituted arylene or R$^{41}$-substituted or unsubstituted heteroarylene.

3. The compound of claim 1, or a pharmaceutically acceptable salt thereof, wherein ring A is unsubstituted naphthalenyl.

4. The compound of claim 1, or a pharmaceutically acceptable salt thereof, wherein $L^1$ is a bond.

5. The compound of claim 1, or a pharmaceutically acceptable salt thereof, wherein $L^2$ is —$NR^{6a}C(O)NR^{6b}$—.

6. The compound of claim 5, or a pharmaceutically acceptable salt thereof, wherein $R^{6a}$ and $R^{6b}$ are each independently hydrogen.

7. The compound of claim 1, or a pharmaceutically acceptable salt thereof, wherein $R^1$ is $R^{11}$-substituted or unsubstituted cycloalkyl, $R^{11}$-substituted or unsubstituted heterocycloalkyl, $R^{11}$-substituted or unsubstituted aryl or $R^{11}$-substituted or unsubstituted heteroaryl.

8. The compound of claim 1, or a pharmaceutically acceptable salt thereof, wherein $R^1$ is $R^{11}$-substituted phenyl.

9. The compound of claim 1, or a pharmaceutically acceptable salt thereof, wherein $R^2$ is $R^{14}$-substituted or unsubstituted alkyl.

10. The compound of claim 1, or a pharmaceutically acceptable salt thereof, wherein $R^2$ is unsubstituted $C_1$-$C_6$ alkyl.

11. The compound of claim 1, or a pharmaceutically acceptable salt thereof, wherein each $R^3$ is independently hydrogen.

12. The compound of claim 1, or a pharmaceutically acceptable salt thereof, wherein $R^4$ and $R^5$ are each independently hydrogen.

13. The compound of claim 1, wherein the compound has the Formula (II):

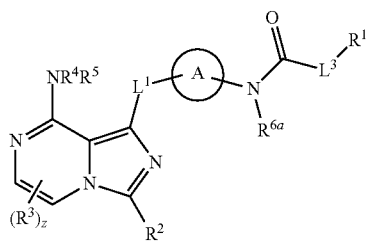

(II)

or a pharmaceutically acceptable salt thereof, wherein:
$L^3$ is —$NR^{6b}$—.

14. The compound of claim 13, wherein the compound has the Formula (III):

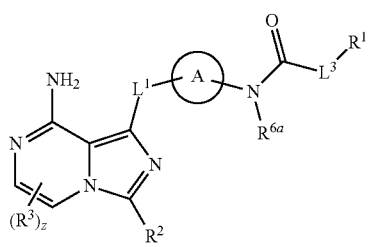

(III)

or a pharmaceutically acceptable salt thereof.

15. The compound of claim 1, or a pharmaceutically acceptable salt thereof, wherein the compound is selected from the group consisting of:

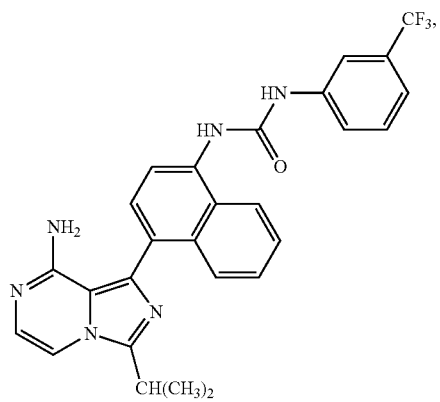

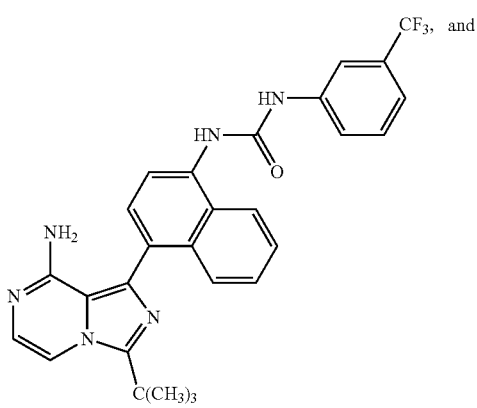

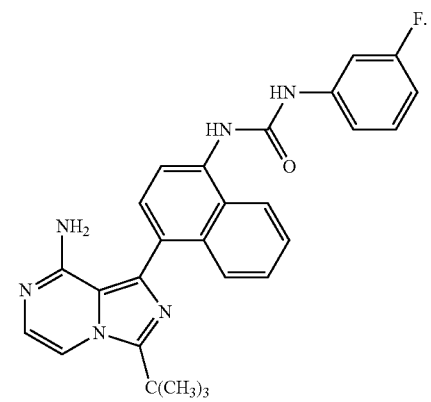

16. A pharmaceutical composition comprising a compound of claim 1, or a pharmaceutically acceptable salt thereof, and a pharmaceutically acceptable excipient.

17. A method for modulating the activity of an inositol-requiring enzyme 1 protein, the method comprising contacting the inositol-requiring enzyme 1 protein with an effective amount a compound of claim 1, or a pharmaceutically acceptable salt thereof.

18. A method for modulating the activity of an inositol-requiring enzyme 1 protein in a subject, the method comprising administering to the subject a therapeutically effective amount a compound of claim 1, or a pharmaceutically acceptable salt thereof.

19. The method of claim 18, wherein the subject suffers from a disease selected from the group consisting of a fibrotic disease, retinitis pigmentosa and diabetes.